(12) United States Patent
Rezania et al.

(10) Patent No.: US 11,708,562 B2
(45) Date of Patent: Jul. 25, 2023

(54) DIFFERENTIATION OF HUMAN EMBRYONIC STEM CELLS

(71) Applicant: Janssen Biotech, Inc., Horsham, PA (US)

(72) Inventors: Alireza Rezania, Wellesley, MA (US); Jean Xu, Skillman, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 820 days.

(21) Appl. No.: 16/598,920

(22) Filed: Oct. 10, 2019

(65) Prior Publication Data

US 2020/0048614 A1     Feb. 13, 2020

Related U.S. Application Data

(60) Continuation of application No. 15/660,823, filed on Jul. 26, 2017, now abandoned, which is a division of application No. 14/217,711, filed on Mar. 18, 2014, now Pat. No. 9,725,699, which is a division of application No. 11/736,908, filed on Apr. 18, 2007, now Pat. No. 8,741,643.

(60) Provisional application No. 60/882,670, filed on Dec. 29, 2006, provisional application No. 60/827,695, filed on Sep. 30, 2006, provisional application No. 60/745,899, filed on Apr. 28, 2006.

(51) Int. Cl.
*C12N 5/071*     (2010.01)
*A61K 35/39*     (2015.01)

(52) U.S. Cl.
CPC ............ *C12N 5/0676* (2013.01); *A61K 35/39* (2013.01); *C12N 5/067* (2013.01); *C12N 2501/115* (2013.01); *C12N 2501/119* (2013.01); *C12N 2501/16* (2013.01); *C12N 2501/385* (2013.01); *C12N 2501/415* (2013.01); *C12N 2501/42* (2013.01); *C12N 2501/70* (2013.01); *C12N 2501/727* (2013.01); *C12N 2506/02* (2013.01); *C12N 2533/90* (2013.01)

(58) Field of Classification Search
CPC .................................................. C12N 5/0678
See application file for complete search history.

(56) References Cited

U.S. PATENT DOCUMENTS

2003/0138948 A1    7/2003   Fisk et al.
2005/0266554 A1*   12/2005   D'Amour ............ C12N 5/0608
                                                      435/366

FOREIGN PATENT DOCUMENTS

| WO | WO 2005/097977 | 10/2005 |
| WO | WO 2005/116073 | 12/2005 |
| WO | WO 2006/016999 | 2/2006 |
| WO | WO 2007/051038 | 5/2007 |
| WO | WO 2009/132083 | 10/2009 |

OTHER PUBLICATIONS

Hebrok et al. (1998, Genes and Development, vol. 12, pp. 1705-1713) (Year: 1998).*
Cai et al., "Generation of Homogeneous PDX1+Pancreatic Progenitors from Human ES Cell-derived Endoderm Cells," *J. Mol. Cell Biol.*, vol. 2:50-60, 2010.
D'Amour et al., "Production of pancreatic hormone-expressing endocrine cells from human embryonic stem cells," *Nat. Biotechnol.*, vol. 24:1392-1401, 2006.
Itkin-Ansari et al., "Cell-Based Therapies for Diabetes: Progress towards a Transplantable Human β Cell Line," *Ann. N.Y. Acad. Sci.*, vol. 1005:138-147, 2003.
Kroon et al., "Pancreatic Endoderm Derived from Human Embryonic Stem Cells Generates Glucose-Responsive Insulin-Secreting Cells in vivo," *Nat. Biotechnol.*, vol. 26:443-452, 2008.
Lee et al., "Human β-cell Precursors Mature into Functional Insulin-producing Cells in an Immunoisolation Device: Implications for Diabetes Cell Therapies," *Transplantation.*, vol. 87:983-991, 2009.
Miralles et al., "Interplay between FGF10 and Notch Signalling is required for the self-renewal of pancreatic progenitors," *Int J Dev Biol*, vol. 50: 17-26, 2006.
Murtaugh et al., "Notch signaling controls multiple steps of pancreatic differentiation," *Proc Natl Acad Sci*, vol. 100(25): 14920-14925, 2003.
Phillips et al., "Directed Differentiation of Human Embryonic Stem Cells into the Pancreatic Endocrine Lineage," *Stem Cells Develop.*, vol. 16:561-578, 2007.
Shim et al., "Directed Differentiation of Human Embryonic Stem Cells towards a Pancreatic Cell Fate," *Diabetologia*, vol. 50:1228-1238, 2007.
Shiraki et al., "Guided Differentiation of Embryonic Stem Cells into Pdx1-Expressing Regional-Specific Definitive Endoderm," *Stem Cells*, vol. 26: 874-885, 2008.

* cited by examiner

*Primary Examiner* — Anoop K Singh
*Assistant Examiner* — David A Montanari
(74) *Attorney, Agent, or Firm* — Klarquist Sparkman, LLP

(57) ABSTRACT

The present invention provides methods to promote the differentiation of pluripotent stem cells. In particular, the present invention provides an improved method for the formation of pancreatic endoderm, pancreatic hormone expressing cells and pancreatic hormone secreting cells. The present invention also provides methods to promote the differentiation of pluripotent stem cells without the use of a feeder cell layer.

18 Claims, 59 Drawing Sheets

GATA4

Sox 17

Sox 7

AFP

Brachyury

Zic 1

Brachyury

CXCR4

Mix1

Sox17

HNF3b

Oct4

Untreated

SOX17

Treated

SOX17/DAPI

Untreated

HNF3β

Treated

HNF3β/DAPI

Untreated

GATA 4

Treated

GATA 4/DAPI

Pdx-1

Glut-2

PDX1

Untreated

PDX1

RA+bFGF

NeuroD1

Ngn3

Nkx2.2

Pdx1

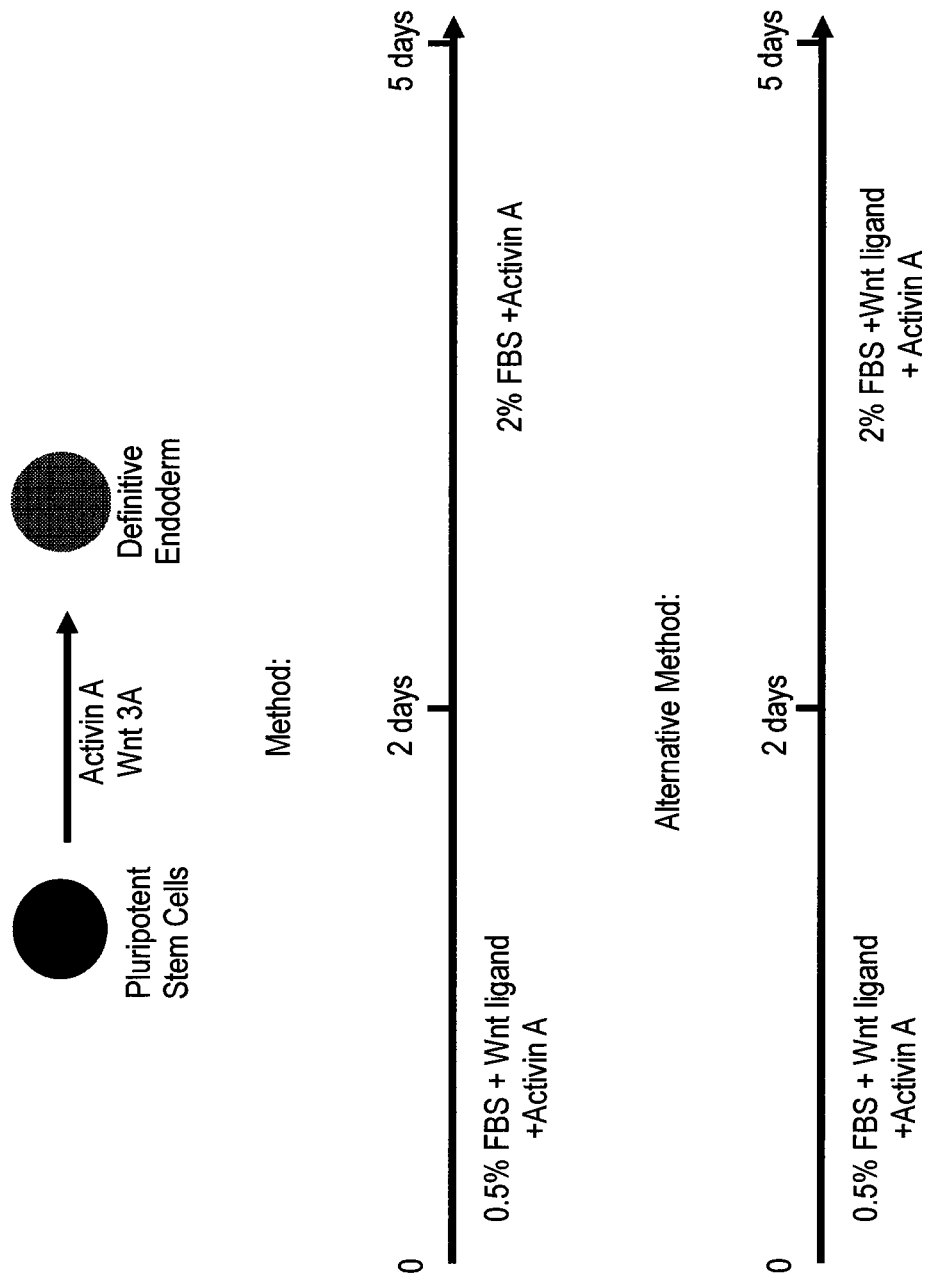

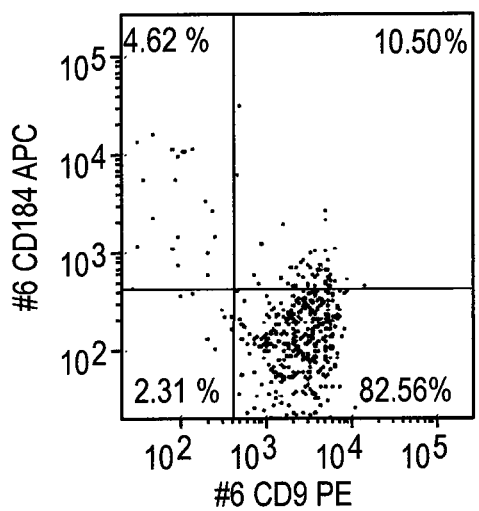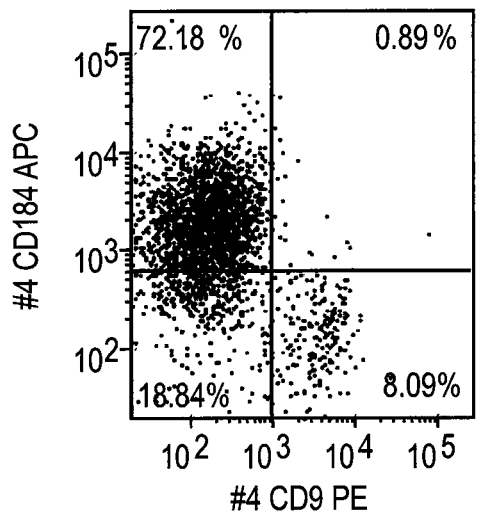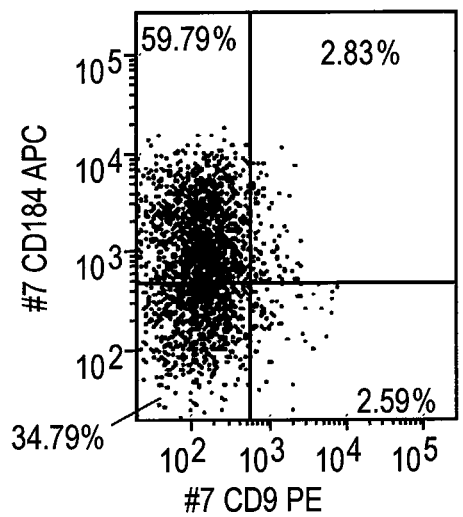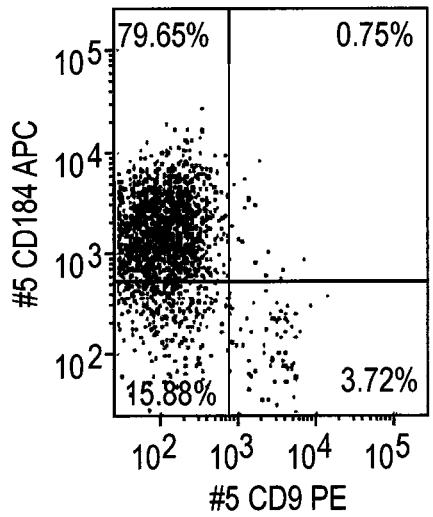

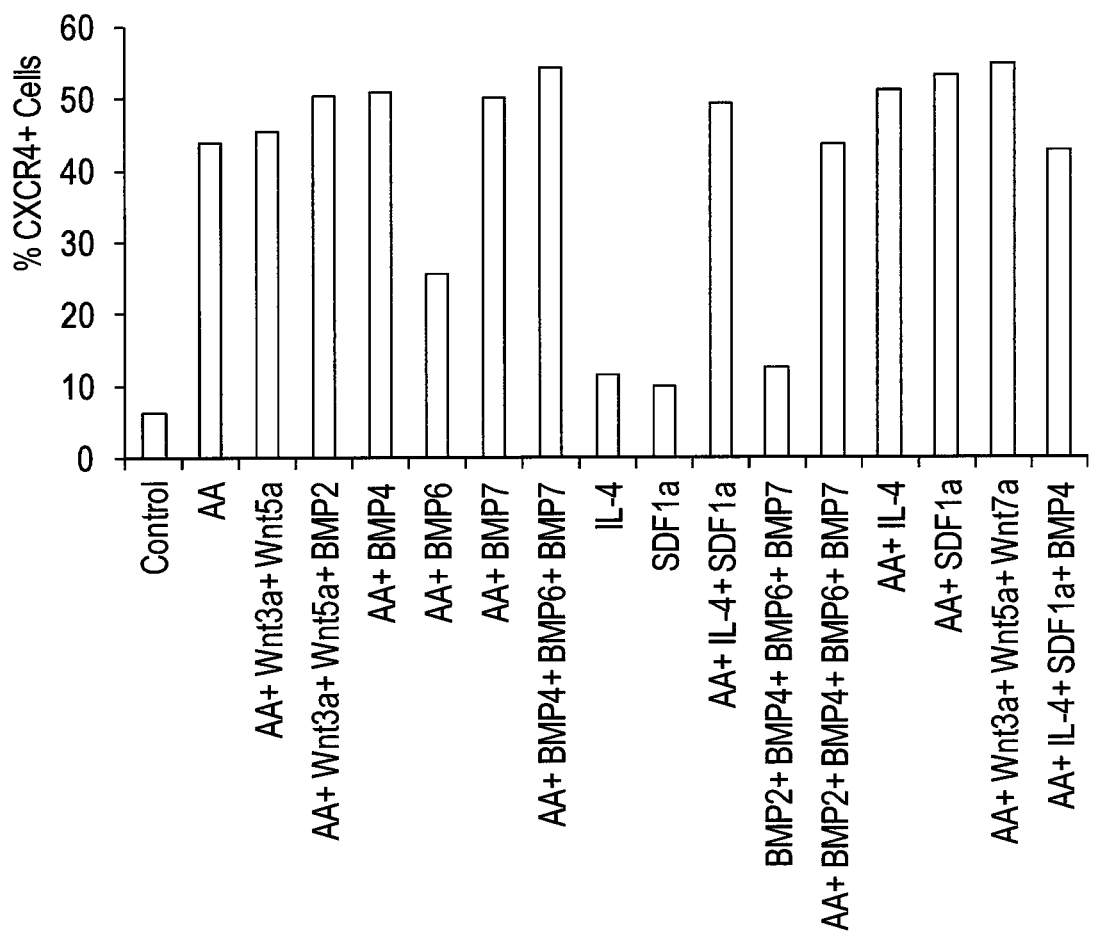

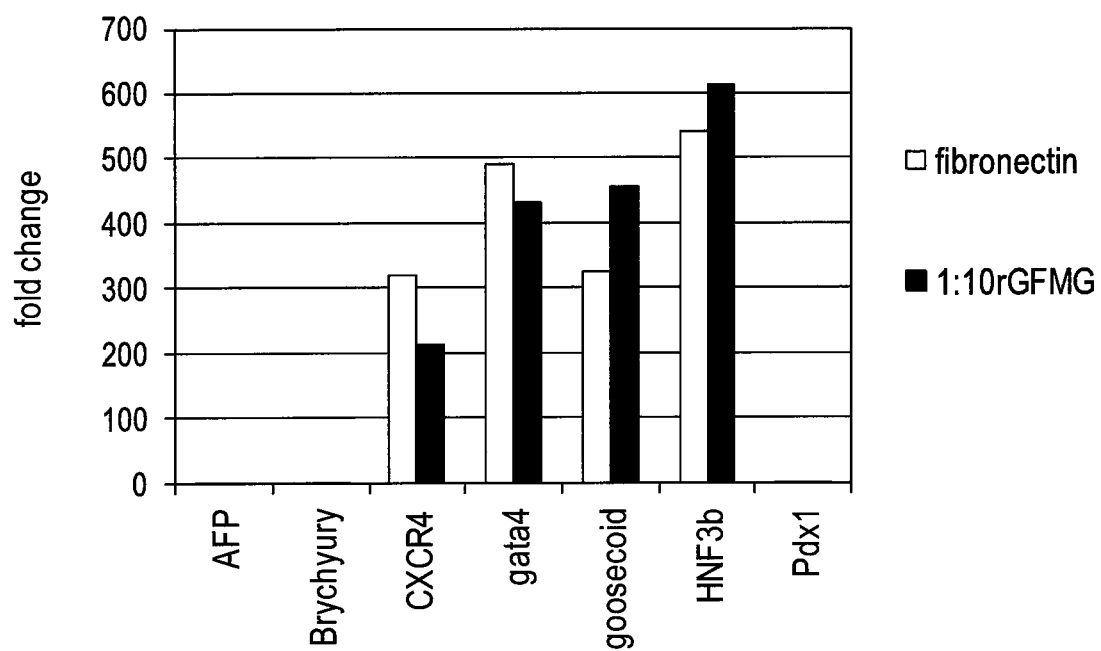

AFP expression following DE protocol at Day 3 and Day 5

Gata4 expression following DE protocol

Gene expression following DE protocol

Gene Expression following DE protocol

Day 3- 100 AA −Wnt3a

Day 3- 100 AA +Wnt3a

Day 5 100 AA−Wnt3a

Day 5-100 AA +Wnt3a

Day 5 −Wnt3a, 10ng/ml AA

Day 5 +Wnt3a, 10ng/ml AA

Gene Expression of cells treated with DE protocol

AFP

Pdx1

DIFFERENTIATION OF HUMAN EMBRYONIC STEM CELLS

FIELD OF THE INVENTION

The present invention provides methods to promote the differentiation of pluripotent stem cells. In particular, the present invention provides an improved method for the formation of pancreatic endoderm, pancreatic hormone expressing cells and pancreatic hormone secreting cells. The present invention also provides methods to promote the differentiation of pluripotent stem cells without the use of a feeder cell layer.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3beta, GATA4, Mix11, CXCR4 and Sox-17.

Formation of the pancreas arises from the differentiation of definitive endoderm into pancreatic endoderm. Cells of the pancreatic endoderm express the pancreatic-duodenal homeobox gene, Pdx1. In the absence of Pdx1, the pancreas fails to develop beyond the formation of ventral and dorsal buds. Thus, Pdx1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form Pdx1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, P48, Pax6, and HNF6 genes in the resulting differentiated cells (Diabetes 53: 1030, 2004).

Skoudy et al. reports that activin A (a member of the TGFβ superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into Pdx1 positive cells. They observed that TGFβ2 reproducibly yielded a higher proportion of Pdx1 positive cells (Genes Cells. 2005 June; 10(6): 503-16.).

Gordon et al. demonstrated the induction of brachyury+/HNF-3beta+ endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (D'Amour K A et al. 2005). Transplanting these cells under the kidney capsule of mice resulted in differentiation into more mature cells with characteristics of some endodermal organs. Human embryonic stem cell-derived definitive endoderm cells can be further differentiated into Pdx1 positive cells after addition of FGF-10 (US 2005/0266554A1).

D'Amour et al. (Nature Biotechnology—24, 1392-1401 (2006)) states "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of n-butyrate and activin A. The cells were then cultured with TGFβ antagonists such as Noggin in combination with EGF or betacellulin to generate Pdx1 positive cells. The terminal differentiation was induced by nicotinamide.

In one example, Benvenistry et al. states: "We conclude that over-expression of Pdx1 enhanced expression of pancreatic enriched genes, induction of insulin expression may require additional signals that are only present in vivo" (Benvenistry et al, Stem Cells 2006; 24:1923-1930).

Therefore, there still remains a significant need to develop conditions for establishing pluripotent stem cell lines that can be expanded to address the current clinical needs, while retaining the potential to differentiate into pancreatic endocrine cells, pancreatic hormone expressing cells, or pancreatic hormone secreting cells. We have taken an alternative approach to improve the efficiency of differentiating human embryonic stem cells toward pancreatic endocrine cells.

SUMMARY

In one embodiment, the present invention provides a method for differentiating pluripotent stem cells, comprising the steps of:
- a. Culturing the pluripotent stem cells, and
- b. Differentiating the pluripotent stem cells into cells expressing markers characteristics of the definitive endoderm lineage,
- c. Differentiating the cells expressing markers characteristics of the definitive endoderm lineage into cells expressing markers characteristics of the pancreatic endoderm lineage, and
- d. Differentiating the cells expressing markers characteristics of the pancreatic endoderm lineage into cells expressing markers characteristics of the pancreatic endocrine lineage.

In one embodiment, cells expressing markers characteristic of the definitive endoderm lineage are differentiated from pluripotent stem cells by treating pluripotent stem cells by any one of the following methods:
- a. Culturing the pluripotent stem cells in medium containing activin A in the absence of serum, then culturing the cells with activin A and serum, and then culturing the cells with activin A and serum of a different concentration, or
- b. Culturing the pluripotent stem cells in medium containing activin A in the absence of serum, then culturing the cells with activin A with serum of another concentration, or
- c. Culturing the pluripotent stem cells in medium containing activin A and a Wnt ligand in the absence of serum, then removing the Wnt ligand and culturing the cells with activin A with serum, or
- d. Culturing the pluripotent stem cells on a tissue culture substrate coated with an extracellular matrix, and culturing the pluripotent stem cells with activin A and a Wnt ligand, or
- e. Culturing the pluripotent stem cells on a tissue culture substrate coated with an extracellular matrix, then culturing the pluripotent stem cells with activin A and a Wnt ligand in a first culture medium containing serum, then culturing the pluripotent stem cells with activin A in a second culture medium containing serum, or
- f. Culturing the pluripotent stem cells on a tissue culture substrate coated with an extracellular matrix, then culturing the pluripotent stem cells with activin A and a Wnt ligand in a first culture medium containing serum, then culturing the pluripotent stem cells with activin A and a Wnt ligand in a second culture medium containing serum of a different concentration.

In one embodiment, cells expressing markers characteristic of the pancreatic endoderm lineage are differentiated from cells expressing markers characteristic of the definitive endoderm lineage by treating cells expressing markers characteristic of the definitive endoderm lineage by any one of the following methods:
- a. Treating the cells expressing markers characteristic of the definitive endoderm lineage with a fibroblast growth factor and a hedgehog signaling pathway inhibitor, then removing the medium containing the fibroblast growth factor and the hedgehog signaling pathway inhibitor and subsequently culturing the cells in medium containing retinoic acid, a fibroblast growth factor and the hedgehog signaling pathway inhibitor, or
- b. Treating the cells expressing markers characteristic of the definitive endoderm lineage with retinoic acid and at least one fibroblast growth factor, or
- c. Treating the cells expressing markers characteristic of the definitive endoderm lineage with retinoic acid, then removing the retinoic acid and subsequently treating the cells with at least one fibroblast growth factor.

In one embodiment, cells expressing markers characteristic of the pancreatic endocrine lineage are differentiated from cells expressing markers characteristic of the pancreatic endoderm lineage by treating cells expressing markers characteristic of the pancreatic endoderm lineage by any one of the following methods:
- a. Culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF, or
- b. Culturing the cells expressing markers characteristic of the pancreatic endoderm lineage in medium containing exendin 4, then removing the medium containing exendin 4 and subsequently culturing the cells in medium containing exendin 1, IGF-1 and HGF, or
- c. Culturing the cells expressing markers characteristic of the pancreatic endoderm lineage in medium containing DAPT and exendin 4, or
- d. Culturing the cells expressing markers characteristic of the pancreatic endoderm lineage in medium containing exendin 4, or
- e. Treating the cells expressing markers characteristic of the pancreatic endoderm lineage with a factor that inhibits the Notch signaling pathway.

In one embodiment, the present invention provides a method for treating a patient suffering from diabetes, comprising the steps of:
- a. Culturing pluripotent stem cells,
- b. Differentiating the pluripotent stem cells into cells expressing markers characteristics of the definitive endoderm lineage,
- c. Differentiating the cells expressing markers characteristics of the definitive endoderm lineage into cells expressing markers characteristics of the pancreatic endoderm lineage,
- d. Differentiating the cells expressing markers characteristics of the pancreatic endoderm lineage into cells of a f-cell lineage, and
- e. Implanting the cells of a β-cell lineage into the patient.

BRIEF DESCRIPTION OF THE DRAWINGS

FIG. 2A shows Sox-17 expression. FIG. 2B shows HNF-3beta expression. FIG. 2C shows Oct3/4 expression.

FIG. 3A shows GATA4 expression. FIG. 3B shows Sox-17 expression. FIG. 3C shows HNF-3beta expression. FIG. 3D shows Mix11 expression. Data points marked 'AA' denote activin A treatment for one (1 d), three (3 d), five (5 d), or seven days (7 d). Data points marked 'UT' denote untreated controls cultured for one (1 d), three (3 d), five (5 d), or seven days (7 d).

FIG. 4A shows the effect of 100 ng/ml activin A on AFP expression. FIG. 4B shows the effect of 100 ng/ml activin A on Sox7 expression. Data points marked 'AA' denote activin A treatment for one (1 d), three (3 d), five (5 d), or seven days (7 d). Data points marked 'UT' denote untreated controls cultured for one (1d), three (3 d), five (5 d), or seven days (7 d).

FIG. 5A shows the effect of 100 ng/ml activin A on Brachyury expression. FIG. 5B shows the effect of 100 ng/ml activin A on Zic1 expression. Data points marked 'AA' denote activin A treatment for one (1 d), three (3 d), five (5 d), or seven days (7 d). Data points marked 'UT' denote untreated controls cultured for one (1 d), three (3 d), five (5 d), or seven days (7 d).

FIGS. 7A and 7B show Sox-17 expression. FIGS. 7C and 7D show HNF-3beta expression. FIGS. 7E and 7F show GATA4 expression. FIGS. 7B, 7D and 7F show counter staining of the nuclei with DAPI. The columns marked 'treated' denote activin A treatment (100 ng/ml) for five days. The columns marked 'untreated' denote untreated controls.

FIG. 8A shows Pdx1 expression. FIG. 8B shows GLUT-2 expression. FIG. 8C shows PTF1a expression.

FIG. 9A shows Pdx1 expression in the untreated control, and FIG. 9B shows Pdx1 expression in the culture treated by the step-wise differentiation protocol.

FIG. 10A shows NeuroD1 expression. FIG. 10B shows Ngn3 expression. FIG. 10C shows insulin expression. FIG. 10D shows Hes-1 expression, the expression level is normalized to pancreatic endoderm cells.

FIG. 11A shows Nkx2.2 expression. FIG. 11B shows Pdx1 expression.

FIG. 13A shows AFP expression. FIG. 13B shows albumin expression.

FIG. 14A shows Oct-4 expression. FIG. 14B shows alkaline phosphatase expression.

FIG. 16 depicts the outline of a differentiation protocol in this invention, where human embryonic stem cells are differentiated into definitive endoderm in a feeder free system.

FIGS. 25B and 25D show the effect of 20 ng/ml of Wnt-3a on CXCR4 expression. FIGS. 25A and 25C show CXCR4 expression in the absence of Wnt-3a. Results were obtained 5 days post treatment.

FIG. 27A depicts CXCR4 expression in the absence of Wnt-3a. FIG. 27B depicts CXCR4 expression following treatment with 10 ng/ml Wnt-3a. FIG. 27C depicts CXCR4 expression following treatment with 20 ng/ml Wnt-3a, and FIG. 27D depicts CXCR4 expression following treatment with 50 ng/ml Wnt-3a.

FIG. 28A shows the effect of 10, 20 and 50 ng/ml Wnt-3a on the expression of definitive endoderm marker genes indicated. FIG. 28B shows the effect of 1, 5 or 10 ng/ml Wnt-3a (x-axis labels: 10, 5, 1) on the expression on goosecoid (■) and CXCR4 (□) expression, at 2 (2 d) and 5 (5 d) days post treatment. FIG. 28C shows the effect of 1, 5 or 10 ng/ml Wnt-3a on cell number, at 2 days (□) or 5 days (■).

FIGS. 29A, 29B, 29C, 29D, 29E, 29F, 29G and 29H depict the expression of CXCR4 in cultures of the human embryonic stem cell line H9 by FACS, following a 5 day treatment with the differentiation protocol disclosed in Example 4. Cells were cultured in the absence of Wnt-3a or GSK-3B inhibitor (FIG. 29A), 20 ng/ml Wnt-3a for the entire 5 day period (FIG. 29B), 1000 nM GSK-3B inhibitor IX for the entire 5 day period (FIG. 29C), 500 nM GSK-3B inhibitor IX for the entire 5 day period (FIG. 29D), 100 nM GSK-3B inhibitor IX for the entire 5 day period (FIG. 29E), 10 nM GSK-3B inhibitor IX for the entire 5 day period (FIG. 29F), 100 nM GSK-3B inhibitor IX for days 1-2 (FIG. 29G), 10 nM GSK-3B inhibitor IX for days 1-2 (FIG. 29H).

FIGS. 30A and 30 B depict the gene expression of definitive endoderm markers by real-time PCR. Results are expressed as fold increase over untreated cells. FIG. 30A shows data obtained from the human embryonic cell line H9 at passage number 48, treated to the definitive endoderm protocol disclosed in Example 4, containing the Wnt-3a or GSK-3B inhibitor at the concentrations and the times indicated.

FIGS. 31A, 31B, 31C and 31D show data obtained from the human embryonic stem cell line H9 at passage number 49. FIGS. 31E and 31F show data obtained from the human embryonic stem cell line H1 at passage number 46. Data was obtained 5 days post treatment. Cells were treated with the following conditions: FIG. 31A: 10 ng/ml activin A for all five days plus 20 ng/ml of Wnt-3a for the first two days; FIG. 31B: 100 ng/ml activin A for all five days plus 20 ng/ml of Wnt-3a for the first two days; FIG. 31C: 100 ng/ml activin A for all five days plus 100 nM of GSK-3B inhibitor IX for the first two days; FIG. 31D: 10 ng/ml activin A for all five days plus 100 nM GSK-3B IX inhibitor for the first two days, FIG. 31 E: 100 ng/ml activin A for all five days plus 20 ng/ml of Wnt-3a for the first two days, and FIG. 31F: 10 ng/ml activin A for all five days plus 20 ng/ml of Wnt-3a for the first two days.

FIGS. 32A and 32B depict the gene expression of definitive endoderm markers, as determined by real-time PCR for cultures of the human embryonic stem cell line H9 at passage 49, treated with 10, 50, or 100 ng/ml of activin A plus 20 ng/ml of Wnt-3a: FIG. 32A: expression of AFP, Bry, CXCR4, GSC, HNF-3B, and POU5F (Oct-4) and FIG. 32B: SOX-17 and GATA4. Results are expressed as fold increase over untreated cells.

FIG. 33A: 100 ng/ml activin A for all five days plus 20 ng/ml of Wnt-3a for the first two days and 25 ng/ml BMP-4 for days 3-5; FIG. 33B: 100 ng/ml activin A for all five days plus 20 ng/ml of Wnt-3a for the first two days; FIG. 33C: 100 ng/ml activin A for all five days plus 100 nM of GSK-3B inhibitor IX for the first two days; FIG. 33D: 20 ng/ml Wnt-3a+25 ng/ml BMP-4 for all five days; FIG. 33E: 100 ng/ml activin A for all five days plus 20 ng/ml of Wnt-3a+ 100 nm GSK-3B inhibitor IX for the first two days, and FIG. 33F: 100 ng/ml activin A+25 ng/ml BMP-4 for all five days. For all the panels, the X-axis represents expression of CD9 and the Y-axis represents expression of CXCR4 (CD184).

FIG. 34A: expression of AFP, Bry, CXCR4, GSC, and POU5F (Oct-4) and FIG. 34B: SOX-17, HNF-3B, and GATA4. Results are expressed as fold increase over untreated cells.

FIG. 35A: expression of AFP, Bry, CXCR4, GSC, HNF-3B, and POU5F (Oct-4) and FIG. 35B: SOX-17 and GATA4. Results are expressed as fold increase over untreated cells.

FIG. 36A: expression of AFP, Bry, CXCR4, GSC, HNF-3B, and SOX7 and FIG. 36B: SOX-17, HNF-3B and GATA4.

FIG. 37 depicts the percentage of CXCR4 expression, determined by FACS, in cultures of the human embryonic stem cell line H9, treated with the conditions listed in Example 22.

FIG. 39 depicts the expression of definitive endoderm markers as determined by real-time PCR in cultures of the human embryonic stem cell line H9, cultured on fibronectin (□) or a 1:10 dilution of growth factor reduced MATRIGEL (■).

FIGS. 41A, 41B, 41C and 41D show real-time PCR data for the genes indicated. FIGS. 41E-1, 41E-2, 41F-1, 41F-2, 41G-1, 41G-2 show FACS data for the conditions indicated.

DETAILED DESCRIPTION

Figure 1A:
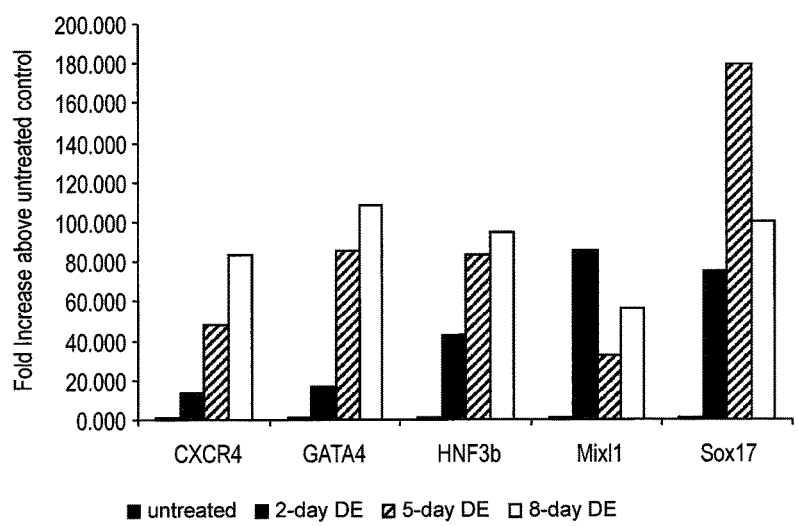
FIG. 1A shows the expression of the definitive endoderm markers CXCR4, GATA4, HNF-3beta, Mix11, Sox-17 in the human embryonic stem cell line H9 following treatment with 100 ng/ml activin A for two, five and eight days. Expression of definitive endoderm markers was assayed at the mRNA level and normalized to expression levels in untreated human embryonic stem cells.

For clarity of disclosure, and not by way of limitation, the detailed description of the invention is divided into subsections that describe or illustrate certain features, embodiments, or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"AFP" or "alpha-fetoprotein protein" as used herein, refers to an antigen produced at the onset of liver development. AFP may also be expressed in extraembryonic cells.

"Albumin" is a soluble monomeric protein that makes up about half of all serum proteins in adults.

"β-cell lineage" refer to cells with positive gene expression for the transcription factor PDX-1 and at least one of the following transcription factors: NGN-3, Nkx2.2, Nkx6.1, NeuroD, Isl-1, HNF-3 beta, MAFA, Pax4, and Pax6. Cells expressing markers characteristic of the β cell lineage include β cells.

"Brachyury", as used herein, is a T-box gene family member. It is the marker for primitive streak and mesoderm cells.

"Cells expressing markers characteristic of the definitive endoderm lineage" as used herein refer to cells expressing at least one of the following markers: SOX-17, GATA-4, HNF-3 beta, GSC, Cer1, Nodal, FGF8, Brachyury, Mix-like homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"c-Kit" and "CD117" both refer to a cell surface receptor tyrosine kinase having a sequence disclosed in Genbank Accession No. X06182, or a naturally occurring variant sequence thereof (e.g., allelic variant).

"CD99" as used herein refers to the protein encoded by the gene with the accession number NM 002414.

"Cells expressing markers characteristic of the pancreatic endoderm lineage" as used herein refer to cells expressing at least one of the following markers: PDX-1, HNF-1beta, PTF-1 alpha, HNF-6, or HB9. Cells expressing markers characteristic of the pancreatic endoderm lineage include pancreatic endoderm cells.

"Cells expressing markers characteristic of the pancreatic endocrine lineage" as used herein refer to cells expressing at least one of the following markers: NGN-3, NeuroD, Islet-1, PDX-1, NKX6.1, Pax-4, Ngn-3, or PTF-1 alpha. Cells expressing markers characteristic of the pancreatic endocrine lineage include pancreatic endocrine cells, pancreatic hormone expressing cells, and pancreatic hormone secreting cells, and cells of the n-cell lineage.

"Cer1" or "Cerebrus" as used herein is a member of the cysteine knot superfamily of proteins.

"CXCR4" as used herein refers to the stromal cell-derived factor 1 (SDF-1) receptor, also known as "LESTR" or "fusin". In the gastrulating mouse embryo, CXCR4 is expressed in the definitive endoderm and mesoderm but not in extraembryonic endoderm.

"Definitive endoderm" as used herein refers to cells which bear the characteristics of cells arising from the epiblast during gastrulation and which form the gastrointestinal tract and its derivatives. Definitive endoderm cells express the following markers: HNF-3 beta, GATA-4, SOX-17, Cerberus, OTX2, goosecoid, C-Kit, CD99, and Mix11.

"Extraembryonic endoderm" as used herein refers to a population of cells expressing at least one of the following markers: SOX-7, AFP, and SPARC.

"FGF-2", "FGF-4" "FGF-8" "FGF-10", and "FGF-17" as used herein, are members of the fibroblast growth factor family.

"GATA-4" and "GATA-6" are members of the GATA transcription factor family. This family of transcription factors is induced by TGF-β signaling, and contribute to the maintenance of early endoderm markers.

"GLUT-2", as used herein, refers to the glucose transporter molecule that is expressed in numerous fetal and adult tissues, including pancreas, liver, intestine, brain, and kidney.

"Goosecoid" or "GSC" as used herein, refers to a homeodomain transcription factor expressed in the dorsal lip of the blastopore.

"HB9" as used herein, refers to the homeobox gene 9.

"HNF-1 alpha", "HNF-1 beta", "HNF-3 beta", and "HNF-6" belong to the hepatic nuclear factor family of transcription factors, which is characterized by a highly conserved DNA binding domain and two short carboxy-terminal domains.

"Islet-1" or "Isl-1" as used herein is a member of the LIM/homeodomain family of transcription factors, and is expressed in the developing pancreas.

"MafA" as used herein is a transcription factor expressed in the pancreas, and controls the expression of genes involved in insulin biosynthesis and secretion.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell" as used herein refers to a cell expressing at least one of the following markers: CD48, eomesodermin (EOMES), SOX-17, DKK4, HNF-3 beta, GSC, FGF17, GATA-6.

"Mix11" as used herein refers to a homeobox gene, which is marker for the cells in the primitive streak, mesoderm, and endoderm.

"NeuroD" as used herein is basic helix-loop-helix (bHLH) transcription factor implicated in neurogenesis.

"NGN-3" as used herein, is a member of the neurogenin family of basic loop-helix-loop transcription factors.

"Nkx-2.2" and "Nkx-6.1" as used herein are members of the Nkx transcription factor family.

"Nodal" as used herein, is a member of the TGF beta superfamily of proteins.

"Oct-4" is a member of the POU-domain transcription factor and is widely regarded as a hallmark of pluripotent stem cells. The relationship of Oct-4 to pluripotent stem cells is indicated by its tightly restricted expression to undifferentiated pluripotent stem cells. Upon differentiation to somatic lineages, the expression of Oct-4 disappears rapidly.

"Pancreatic endocrine cell", or "pancreatic hormone expressing cell" as used herein refers to a cell capable of expressing at least one of the following hormones: insulin, glucagon, somatostatin, and pancreatic polypeptide.

"Pancreatic hormone secreting cell" as used herein refers to a cell capable of secreting at least one of the following hormones: insulin, glucagon, somatostatin, and pancreatic polypeptide.

"Pax-4" and "Pax-6" as used herein are pancreatic β cell specific transcription factors that are implicated in islet development.

"PDX-1" as used herein refers to a homeodomain transcription factor implicated in pancreas development.

"Pre-primitive streak cell" as used herein refers to a cell expressing at least one of the following markers: Nodal, or FGF8

"Primitive streak cell" as used herein refers to a cell expressing at least one of the following markers: Brachyury, Mix-like homeobox protein, or FGF4.

"PTF-1 alpha" as used herein refers to a basic helix-loop-helix protein of 48 kD that is a sequence-specific DNA-binding subunit of the trimeric pancreas transcription factor-1 (PTF1).

"SOX-1", "SOX-2", "SOX-7", and "SOX-17" as used herein, are a members of the SOX transcription factor family, and are implicated in embryogenesis.

"SPARC" as used herein is also known as "secreted protein acidic and rich in cysteine".

"SSEA-1" (Stage Specific Embryonic Antigen-1) is a glycolipid surface antigen present on the surface of murine teratocarcinoma stem cells (EC), murine and human embryonic germ cells (EG), and murine embryonic stem cells (ES).

"SSEA-3" (Stage Specific Embryonic Antigen-3) is a glycolipid surface antigen present on the surface of human teratocarcinoma stem cells (EC), human embryonic germ cells (EG), and human embryonic stem cells (ES).

"SSEA-4" (Stage Specific Embryonic Antigen-4) is a glycolipid surface antigen present on the surface of human teratocarcinoma stem cells (EC), human embryonic germ cells (EG), and human embryonic stem cells (ES).

"TRA1-60" is a keratin sulfate related antigen that is expressed on the surface of human teratocarcinoma stem cells (EC), human embryonic germ cells (EG), and human embryonic stem cells (ES).

"TRA1-81" is a keratin sulfate related antigen that is expressed on the surface of human teratocarcinoma stem cells (EC), human embryonic germ cells (EG), and human embryonic stem cells (ES).

"TRA2-49" is an alkaline phosphatase isozyme expressed on the surface of human teratocarcinoma stem cells (EC) and human embryonic stem cells (ES).

"UTF-1" as used herein, refers a transcriptional coactivator expressed in pluripotent embryonic stem cells and extra-embryonic cells.

"Zic1" as used herein is a member of the Zic transcription factor family. Zic1 regulates the expression of neural and neural crest-specific genes and is expressed in the cells of the dorsal neural tube and the premigratory neural crest.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Rubinoff et al (Nature Biotechnology 18: 399-404 (2000)) and Thompson et al (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al, (Stem Cells 21: 546-556, 2003) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) discloses methods for the long-term growth of human pluripotent stem cells on feeder cell layers derived from human embryonic stem cells.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) discloses a feeder cell layer derived from human foreskin.

In another example, Inzunza et al (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells, in particular, those differentiated and immortalized transgenic hepatocytes, named MMH (Met Murine Hepatocyte)."

In another example, Xu et al (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, a suitable culture substrate is Matrigel® (Becton Dickenson). Matrigel® is a soluble preparation from Engelbreth-Holm-Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; f-mercaptoethanol, Sigma # M7522; human recombinant basic fibroblast growth factor (bFGF), Gibco #13256-029.

Differentiation of Pluripotent Stem Cells into Cells Expressing Markers Characteristic of the Pancreatic Endocrine Lineage Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FoxD3, Connexin43, Connexin45, Oct4, Sox2, Nanog, hTERT, UTF-1, ZFP42, SSEA-3, SSEA-4, Tra1-60, Tra1-81.

Markers characteristic of the definitive endoderm lineage are selected from the group consisting of SOX17, GATA4, Hnf-3beta, GSC, Cer1, Nodal, FGF8, Brachyury, Mix-like homeobox protein, FGF4 CD48, comesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of Pdx1, HNF-1beta, PTF1a, HNF-6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN-3, NeuroD, Islet-1, Pdx-1, NKX6.1, Pax-4, Ngn-3, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the 0 cell lineage. A cell expressing markers characteristic of the 3 cell lineage expresses Pdx1 and at least one of the following transcription factors: NGN-3, Nkx2.2, Nkx6.1, NeuroD, Isl-1, HNF-3 beta, MAFA, Pax4, and Pax6. In one aspect of the present invention, a cell expressing markers characteristic of the β cell lineage is a β cell.

Formation of Cells Expressing Markers
Characteristic of the Definitive Endoderm Lineage Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al, Nature Biotechnology 23, 1534-1541 (2005).

For example, pluripotent stem cells may be differentiated into cells expressing markers characteristic of the definitive endoderm lineage according to the methods disclosed in Shinozaki et al, Development 131, 1651-1662 (2004).

For example, pluripotent stem cells may be differentiated into cells expressing markers characteristic of the definitive endoderm lineage according to the methods disclosed in McLean et al, Stem Cells 25, 29-38 (2007).

For example, pluripotent stem cells may be differentiated into cells expressing markers characteristic of the definitive endoderm lineage according to the methods disclosed in D'Amour et al, Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al, Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

In one aspect of the present invention, pluripotent stem cells may be differentiated into cells expressing markers characteristic of the definitive endoderm lineage by plating the pluripotent stem cells on a tissue culture substrate coated with an extracellular matrix, then culturing the pluripotent stem cells with activin A and a Wnt ligand in a first culture medium containing serum for a period of time, and then culturing the pluripotent stem cells with activin A in a second culture medium containing a greater concentration of serum for about another period of time.

The concentration of serum in the first culture medium disclosed above may be from about zero to about 0.5 percent, and the culture time may be from about one to about three days. The concentration of serum in the second culture medium disclosed above may be from about 0.5 percent to about two percent, and the culture time may be from about one to about four days.

In an alternate embodiment of the present invention, pluripotent stem cells may be differentiated into cells expressing markers characteristic of the definitive endoderm lineage by plating the pluripotent stem cells on a tissue culture substrate coated with an extracellular matrix, then culturing the pluripotent stem cells with activin A and a Wnt ligand in a first culture medium containing serum for about a period of time, and then culturing the pluripotent stem cells with activin A and a Wnt ligand in a second culture medium containing a greater concentration of serum for another period of time.

The concentration of serum in the first culture medium disclosed above may be from about zero to about 0.5 percent, and the culture time may be from about one to about three days. The concentration of serum in the second culture medium disclosed above may be from about 0.5 percent to about two percent, and the culture time may be from about one to about four days.

In one embodiment, the present invention provides a method for differentiating pluripotent stem cells expressing markers characteristic of the definitive endoderm lineage, comprising the steps of:
 a. Plating the pluripotent stem cells on a tissue culture substrate coated with an extracellular matrix, and
 b. Culturing the pluripotent stem cells with activin A and a Wnt ligand.

Culturing the pluripotent stem cells with activin A and a Wnt ligand may be performed in a single culture medium. Alternatively, culturing the pluripotent stem cells with activin A and a Wnt ligand may be performed separately or together in more than one culture media. In one embodiment, culturing the pluripotent stem cells with activin A and a Wnt ligand is performed in two culture media.

Extracellular Matrix

In one aspect of the present invention, the pluripotent stem cells are cultured and differentiated on a tissue culture substrate coated with an extracellular matrix. The extracellular matrix may be a solubilized basement membrane preparation extracted from mouse sarcoma cells (which is sold by BD Biosciences under the trade name MATRIGEL). Alternatively, the extracellular matrix may be growth factor-reduced MATRIGEL. Alternatively, the extracellular matrix may fibronectin. In an alternate embodiment, the pluripotent stem cells are cultured and differentiated on tissue culture substrate coated with human serum.

The extracellular matrix may be diluted prior to coating the tissue culture substrate. Examples of suitable methods for diluting the extracellular matrix and for coating the tissue culture substrate may be found in Kleinman, H. K., et al., Biochemistry 25:312 (1986), and Hadley, M. A., et al., J. Cell. Biol. 101:1511 (1985).

In one embodiment, the extracellular matrix is MATRIGEL. In one embodiment, the tissue culture substrate is coated with MATRIGEL at a 1:10 dilution. In an alternate embodiment, the tissue culture substrate is coated with MATRIGEL at a 1:15 dilution. In an alternate embodiment, the tissue culture substrate is coated with MATRIGEL at a 1:30 dilution. In an alternate embodiment, the tissue culture substrate is coated with MATRIGEL at a 1:60 dilution.

In one embodiment, the extracellular matrix is growth factor-reduced MATRIGEL. In one embodiment, the tissue culture substrate is coated with growth factor-reduced MATRIGEL at a 1:10 dilution. In an alternate embodiment, the tissue culture substrate is coated with growth factor-reduced MATRIGEL at a 1:15 dilution. In an alternate embodiment, the tissue culture substrate is coated with growth factor-reduced MATRIGEL at a 1:30 dilution. In an alternate embodiment, the tissue culture substrate is coated with growth factor-reduced MATRIGEL at a 1:60 dilution.

Differentiation of Pluripotent Stem Cells into Cells Expressing Markers Characteristic of the Definitive Endoderm Lineage on an Extracellular Matrix, Using a Single Culture Medium When a single culture medium is used, it should contain sufficiently low concentrations of certain factors to allow the differentiation of pluripotent stem cells to definitive endoderm, such as, for example insulin and IGF (as disclosed in WO2006020919). This may be achieved by lowing the serum concentration, or alternatively, by using chemically defined media that lacks insulin and IGF. Examples of chemically defined media are disclosed in Wiles et al (Exp Cell Res. 1999 Feb. 25; 247(1): 241-8.).

The culture medium may have a serum concentration in the range of about 0% to about 10%. In an alternate embodiment, the concentration may be in the range of about 0% to about 5%. In an alternate embodiment, the concentration may be in the range of about 0% to about 2%. In an alternate embodiment, the concentration may be about 2%.

The time of culturing with activin A and a Wnt ligand may range from about 1 day to about 7 days. In an alternate embodiment, the time of culturing may range from about 1 day to about 3 days. In an alternate embodiment, the time of culturing may be about 3 days.

Activin A may be used at any concentration suitable to cause differentiation of the pluripotent stem cells. The concentration maybe from about 1 pg/ml to about 100 µg/ml. In an alternate embodiment, the concentration may be about 1 pg/ml to about 1 pg/ml. In another alternate embodiment, the concentration may be about 1 pg/ml to about 100 ng/mi. In another alternate embodiment, the concentration may be about 50 ng/ml to about 100 ng/ml. In another alternate embodiment, the concentration may be about 100 ng/ml.

The choice of the Wnt ligand may be optimized to improve the efficiency of the differentiation process. The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be at a concentration of about 1 ng/ml to about 1000 ng/ml. In an alternate embodiment, the concentration may be about 10 ng/ml to about 100 ng/ml.

The single culture medium may also contain a GSK-3B inhibitor. The GSK-3B inhibitor may be selected from the group consisting of GSK-3B inhibitor IX and GSK-3B inhibitor XI. In one embodiment, the GSK-3B inhibitor is GSK-3B inhibitor IX. I did not see the definitions of IX and XI inhibitors. I did have these in the original WNT patent application.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

The single culture medium may also contain at least one other additional factor that may enhance the formation of cells expressing markers characteristic of the definitive endoderm lineage from pluripotent stem cells. Alternatively, the at least one other additional factor may enhance the proliferation of the ells expressing markers characteristic of the definitive endoderm lineage formed by the methods of the present invention. Further, the at least one other additional factor may enhance the ability of the ells expressing markers characteristic of the definitive endoderm lineage formed by the methods of the present invention to form other cell types, or improve the efficiency of any other additional differentiation steps.

The at least one additional factor may be, for example, nicotinamide, members of the TGF-β family, including TGF-β2, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine 1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), intestinal cell lines such as, for example, FHs 74 (ATCC No: CCL-241), and primary or transformed endothelial cells.

Differentiation of Pluripotent Stem Cells into Cells Expressing Markers Characteristic of the Definitive Endoderm Lineage on an Extracellular Matrix, Using Two Culture Media Differentiation of pluripotent stem cells into cells of a definitive endoderm lineage may be accomplished by culturing the pluripotent stem cells with activin A and a Wnt ligand using two culture media. Thus, the differentiation of the pluripotent stem cells may be accomplished as follows:
  a. Plating the pluripotent stem cells on a tissue culture substrate coated with an extracellular matrix,
  b. Culturing the pluripotent stem cells with activin A and a Wnt ligand in a first culture medium, and
  c. Culturing the pluripotent stem cells with activin A in a second culture medium.

The first culture medium may contain serum at a low concentration, and the second culture medium may contain serum at a higher concentration than the first culture medium.

The second culture medium may contain a Wnt ligand.

First Culture Medium:

The first culture medium should contain sufficiently low concentrations of certain factors to allow the differentiation of pluripotent stem cells into cells expressing markers characteristic of the definitive endoderm lineage, such as, for example insulin and IGF (as disclosed in WO2006020919). This may be achieved by lowing the serum concentration, or alternatively, by using chemically defined media that lacks insulin and IGF. Examples of chemically defined media are disclosed in Wiles et al (Exp Cell Res. 1999 Feb. 25; 247(1):241-8.).

In the first culture medium there may be a lower concentration of serum, relative to the second culture medium. Increasing the serum concentration in the second culture medium increases the survival of the cells, or, alternatively, may enhance the proliferation of the cells. The serum concentration of the first medium may be in the range of about 0% to about 10%. Alternatively, the serum concentration of the first medium may be in the range of about 0% to about 2%. Alternatively, the serum concentration of the first medium may be in the range of about 0% to about 1%. Alternatively, the serum concentration of the first medium may be about 0.5%.

When culturing the pluripotent stem cells with activin A and a Wnt ligand using at least two culture media, the time of culturing in the first culture medium may range from about 1 day to about 3 days.

Activin A may be used at any concentration suitable to cause differentiation of the pluripotent stem cells. The concentration maybe from about 1 pg/ml to about 100 pg/ml. In an alternate embodiment, the concentration may be about 1 pg/ml to about 1 pg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The choice of the Wnt ligand may be optimized to improve the efficiency of the differentiation process. The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be at a concentration of about 1 ng/ml to about 1000 ng/ml. In an alternate embodiment, the concentration may be about 10 ng/ml to about 100 ng/ml.

The first culture medium may also contain a GSK-3B inhibitor. The GSK-3B inhibitor may be added to the first culture medium, to the second culture medium, or to both the first and second culture media.

The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

The first culture medium may also contain at least one other additional factor that may enhance the formation of cells expressing markers characteristic of the definitive endoderm lineage from pluripotent stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and —BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Second Culture Medium:

The second culture medium should contain certain factors, such as, for example, insulin and IGF (as disclosed in WO2006020919), at a sufficient concentration to promote the survival of the cultured cells. This may be achieved by increasing the serum concentration, or, alternatively, by using chemically defined media where the concentrations of insulin and IGF are increased relative to the first culture medium. Examples of chemically defined media are disclosed in Wiles et al (Exp Cell Res. 1999 Feb. 25; 247(1): 241-8.).

In a second culture medium having higher concentrations of serum, the serum concentration of the second culture medium may be in the range about 0.5% to about 10%. Alternatively, the serum concentration of the second culture medium may be in the range of about 0.5% to about 5%. Alternatively, the serum concentration of the second culture medium may be in the range of about 0.5% to about 2%. Alternatively, the serum concentration of the second culture medium may be about 2%. When culturing pluripotent stem cells with the second culture medium, the time of culturing may range from about 1 day to about 4 days.

Similar to the first culture medium, Activin A may be used at any concentration suitable to cause differentiation of the pluripotent stem cells. The concentration maybe from about 1 pg/ml to about 100 μg/ml. In an alternate embodiment, the concentration may be about 1 pg/ml to about 1 μg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The Wnt ligand may be at a concentration of about 1 ng/ml to about 1000 ng/ml. In an alternate embodiment, the concentration may be about 10 ng/ml to about 100 ng/ml.

1 The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The second culture medium may also contain a GSK-3B inhibitor. The GSK-3B inhibitor may be added to the first culture medium, to the second culture medium, or to both the first and second culture media.

The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

Similar to the first culture medium, the second culture medium may also contain at least one other additional factor that may enhance the formation of cells expressing markers characteristic of the definitive endoderm lineage from pluripotent stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and —BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Definitive Endoderm Linage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

For example, characteristics of pluripotent stem cells are well known to those skilled in the art, and additional characteristics of pluripotent stem cells continue to be identified. Pluripotent stem cell markers include, for example, the expression of one or more of the following: ABCG2, cripto, FoxD3, Connexin43, Connexin45, Oct4, Sox2, Nanog, hTERT, UTF-1, ZFP42, SSEA-3, SSEA-4, Tra1-60, Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time. That period of time may be from about one to about six days.

In an alternate aspect of the present invention, cells expressing markers characteristic of the definitive endoderm lineage are further differentiated into cells expressing markers characteristic of the pancreatic endoderm lineage, by treating the cells with retinoic acid for a period of time. That period of time maybe from about one to about three days. The retinoic acid is subsequently removed and the cells are treated with at least one fibroblast growth factor for another period of time. That period of time may be from about one to about three days.

In one embodiment, the present invention provides a method for differentiating cells expressing markers characteristic of the definitive endoderm lineage into cells expressing markers characteristic of the pancreatic endoderm lineage, comprising the steps of:
 a. Culturing cells expressing markers characteristic of the definitive endoderm lineage, and
 b. Treating the cells expressing markers characteristic of the definitive endoderm lineage with retinoic acid and at least one fibroblast growth factor.

Any cell expressing markers characteristic of the definitive endoderm lineage is suitable for differentiating into a cell expressing markers characteristic of the pancreatic endoderm lineage using this method.

In one embodiment, the cells expressing markers characteristic of the definitive endoderm are treated with retinoic acid and at least one fibroblast growth factor for about one to about six days. In one embodiment, the cells expressing markers characteristic of the definitive endoderm are treated with retinoic acid and at least one fibroblast growth factor for about six days.

The at least one fibroblast growth factor is selected from the group consisting of FGF-2, FGF-4 and FGF-10.

Any cell expressing markers characteristic of the definitive endoderm lineage is suitable for differentiating into a cell expressing markers characteristic of the pancreatic endoderm lineage using this method.

In an alternate embodiment, the present invention provides a method for differentiating cells expressing markers characteristic of the definitive endoderm lineage into cells expressing markers characteristic of the pancreatic endoderm lineage, comprising the steps of:
 a. Culturing cells expressing markers characteristic of the definitive endoderm lineage,
 b. Treating the cells expressing markers characteristic of the definitive endoderm lineage treating the cells with retinoic acid, and
 c. Removing the retinoic acid and subsequently treating the cells with at least one fibroblast growth factor.

Any cell expressing markers characteristic of the definitive endoderm lineage is suitable for differentiating into a cell expressing markers characteristic of the pancreatic endoderm lineage using this method.

In one embodiment, the cells expressing markers characteristic of the definitive endoderm are treated with retinoic acid for about one to about three days. In one embodiment, the cells expressing markers characteristic of the definitive endoderm are treated with retinoic acid for about three days. In one embodiment, the cells expressing markers characteristic of the definitive endoderm are treated with at least one fibroblast growth factor for about one to about three days. In one embodiment, the cells expressing markers characteristic of the definitive endoderm are treated with at least one fibroblast growth factor for about three days.

The at least one fibroblast growth factor is selected from the group consisting of FGF-2, FGF-4 and FGF-10.

Any cell expressing markers characteristic of the definitive endoderm lineage is suitable for differentiating into a cell expressing markers characteristic of the pancreatic endoderm lineage using this method.

In one embodiment, the cells expressing markers characteristic of the definitive endoderm lineage are treated with retinoic acid. Alternatively, the cells expressing markers characteristic of the definitive endoderm lineage are treated with FGF-2, or alternatively FGF-4, or alternatively FGF-10. In an alternate embodiment, the cells expressing markers characteristic of the definitive endoderm lineage are treated with at least one of the following factors: retinoic acid, FGF-2, FGF-4 or FGF-10. In an alternate embodiment, the cells expressing markers characteristic of the definitive endoderm lineage are treated with retinoic acid and at least one of the following fibroblast growth factors: FGF-2, FGF-4 or FGF-10. In one embodiment, the cells expressing markers characteristic of the definitive endoderm lineage are treated with retinoic acid and FGF-2. In another embodiment, the cells expressing markers characteristic of the definitive endoderm lineage are treated with retinoic acid and FGF-4. In a further embodiment, the cells expressing markers characteristic of the definitive endoderm lineage are treated with retinoic acid and FGF-10.

Retinoic acid may be used at a concentration from about 1 nM to about 1 mM. In one embodiment, retinoic acid is used at a concentration of 1 µM.

FGF-2 may be used at a concentration from about 50 pg/ml to about 50 pg/ml. In one embodiment, FGF-2 is used at a concentration of 50 ng/ml.

FGF-4 may be used at a concentration from about 50 pg/ml to about 50 g/ml. In one embodiment, FGF-4 is used at a concentration of 50 ng/ml.

FGF-10 may be used at a concentration from about 50 pg/ml to about 50 pg/ml. In one embodiment, FGF-10 is used at a concentration of 50 ng/ml.

Cells expressing markers characteristic of the definitive endoderm lineage may be treated with at least one other additional factor that may enhance the formation of cells expressing markers characteristic of the pancreatic endoderm lineage. Alternatively, the at least one other additional factor may enhance the proliferation of the cells expressing markers characteristic of the pancreatic endoderm lineage formed by the methods of the present invention. Further, the at least one other additional factor may enhance the ability of the cells expressing markers characteristic of the pancreatic endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and —BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Pancreatic Endoderm Linage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, H1xb9, PTF-1a, PDX-1, HNF-6, HNF-1beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

Formation of Cells Expressing Markers of the Pancreatic Endocrine Lineage

Cells expressing markers characteristic of the pancreatic endoderm lineage may be differentiated into cells expressing markers characteristic of the pancreatic endocrine lineage by any method in the art or by any method disclosed in this invention.

For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway. The factor that inhibits the Notch signaling pathway may be an antagonist for the Notch extracellular receptor. Alternatively, the factor may inhibit the biological activity of the Notch receptor. Alternatively, the factor may inhibit or be an antagonist of an element in the Notch signal transduction pathway within a cell.

In one embodiment the factor that inhibits the Notch signaling pathway is a γ-secretase inhibitor. In one embodiment, the γ-secretase inhibitor is 1 SBenzyl-4R-[1-(1S- carbamoyl-2-phenethylcarbamoyl)-1S-3-methylbutylcarbamoyl]-5 2Rhydrozy-5 phenylpentyl] carbamic Acid tert-butyl Ester, also known as L-685,458.

L-685,458 may be used at a concentration from about 0.1 μM to about 100M. In one embodiment, L-685,458 is used at a concentration of about 90 μM. In one embodiment, L-685,458 is used at a concentration of about 80 μM. In one embodiment, L-685,458 is used at a concentration of about 70 μM. In one embodiment, L-685,458 is used at a concentration of about 60 μM. In one embodiment, L-685,458 is used at a concentration of about 50 μM. In one embodiment, L-685,458 is used at a concentration of about 40 μM. In one embodiment, L-685,458 is used at a concentration of about 30 μM. In one embodiment, L-685,458 is used at a concentration of about 20 μM. In one embodiment, L-685,458 is used at a concentration of about 10 μM.

In one embodiment, the present invention provides a method for differentiating cells expressing markers characteristic of the pancreatic endoderm lineage into cells expressing markers characteristic of the pancreatic endocrine lineage, comprising the steps of:
a. Culturing cells expressing markers characteristic of the pancreatic endoderm lineage, and
b. Treating the cells with a factor that inhibits the Notch signaling pathway.

Any cell expressing markers characteristic of the pancreatic endoderm lineage is suitable for differentiating into a cell expressing markers characteristic of the pancreatic endocrine lineage using this method.

In one embodiment, factor that inhibits the Notch signaling pathway is a γ-secretase inhibitor. In one embodiment, the γ-secretase inhibitor is 1S-Benzyl-4R-[1-(1S-carbamoyl-2-phenethylcarbamoyl)-S-3-methylbutylbutylcarbamoyl]-2R-hydrozy-5-phenylpentyl] carbamic Acid tert-butyl Ester, also known as L-685,458.

The cells expressing markers characteristic of the pancreatic endoderm lineage are treated with the factor that inhibits the Notch signaling pathway for about one to about five days. Alternatively, the cells expressing markers characteristic of the pancreatic endoderm lineage are treated with the factor that inhibits the Notch signaling pathway for about three to about five days. Alternatively, the cells expressing markers characteristic of the pancreatic endoderm lineage are treated with the factor that inhibits the Notch signaling pathway for about five days.

In one embodiment, factor that inhibits the Notch signaling pathway is a γ-secretase inhibitor. In one embodiment, the γ-secretase inhibitor is 1S-Benzyl-4R-[1-(1S-carbamoyl-2-phonethylcarbamoyl)-1 S-3-methylbutylcarbamoyl]-2R-hydrozy-5-phenylpentyl] carbamic Acid tert-butyl Ester, also known as L-685,458.

L-685,458 may be used at a concentration from about 0.1 μM to about 100 μM. In one embodiment, L-685,458 is used at a concentration of about 90 μM. In one embodiment, L-685,458 is used at a concentration of about 80 μM. In one embodiment, L-685,458 is used at a concentration of about 70 μM. In one embodiment, L-685,458 is used at a concentration of about 60 μM. In one embodiment, L-685,458 is used at a concentration of about 50 μM. In one embodiment, L-685,458 is used at a concentration of about 40 μM. In one embodiment, L-685,458 is used at a concentration of about 30 μM. In one embodiment, L-685,458 is used at a concentration of about 20 μM. In one embodiment, L-685,458 is used at a concentration of about 10 μM.

Cells expressing markers characteristic of the pancreatic endoderm lineage may be treated with at least one other additional factor that may enhance the formation of cells expressing markers characteristic of the pancreatic endocrine lineage. Alternatively, the at least one other additional factor may enhance the proliferation of the cells expressing markers characteristic of the pancreatic endocrine lineage formed by the methods of the present invention. Further, the at least one other additional factor may enhance the ability of the cells expressing markers characteristic of the pancreatic endocrine lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Pancreatic Endocrine Linage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN-3, NeuroD, Islet-1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristics include the expression of one or more transcription factors such as, for example, Pdx1 (pancreatic and duodenal homeobox gene-1), Nkx2.2, Nkx6.1, Isl1, Pax6, Pax4, NeuroD, Hnf1b, Hnf-6, Hnf-3beta, and MafA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the 0 cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

Therapies

In one aspect, the present invention provides a method for treating a patient suffering from, or at risk of developing, Type 1 diabetes. This method involves culturing pluripotent stem cells, differentiating the pluripotent stem cells in vitro into a β-cell lineage, and implanting the cells of a β-cell lineage into a patient.

In yet another aspect, this invention provides a method for treating a patient suffering from, or at risk of developing, Type 2 diabetes. This method involves culturing pluripotent stem cells, differentiating the cultured cells in vitro into a β-cell lineage, and implanting the cells of a β-cell lineage into the patient.

If appropriate, the patient can be further treated with pharmaceutical agents or bioactives that facilitate the survival and function of the transplanted cells. These agents may include, for example, insulin, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and —BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The pluripotent stem cells may be differentiated into an insulin-producing cell prior to transplantation into a recipient. In a specific embodiment, the pluripotent stem cells are fully differentiated into f-cells, prior to transplantation into a recipient. Alternatively, the pluripotent stem cells may be transplanted into a recipient in an undifferentiated or partially differentiated state. Further differentiation may take place in the recipient.

Definitive endoderm cells or, alternatively, pancreatic endoderm cells, or, alternatively, β cells, may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells, additional factors, such as growth factors, antioxidants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one aspect, this invention provides a method for treating a patient suffering from, or at risk of developing diabetes. This method involves culturing pluripotent stem cells, differentiating the cultured cells in vitro into a -cell lineage, and incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. Nos. 5,770, 417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-31, 2, and 3, bone morphogenic proteins (BMP-2, -3,-4, -5, -6, -7, -11, -12, and -13), fibroblast growth factors-1 and -2, platelet-derived growth factor-AA, and —BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention is further illustrated, but not limited by, the following examples.

EXAMPLES

Example 1

Human Embryonic Stem Cell Culture

The human embryonic stem cell lines H1, H7 and H9 were obtained from WiCell Research Institute, Inc., (Madison, Wis.) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM beta-mercaptoethanol, 2 mM L-glutamine with 4 ng/ml human basic fibroblast growth factor (bFGF) (all from Invitrogen/GIBCO). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 pg/ml mitomycin C (Sigma, St. Louis, Mo.) for 3h to arrest cell division, then trypsinized and plated at $2 \times 10^4/cm^2$ on 0.1% bovine gelatin-coated dishes. MEF cells from passage two through four were used as feeder layers. Human embryonic stem cells plated on MEF cell feeder layers were cultured at 37° C. in an atmosphere of 5% $CO_2$/within a humidified tissue culture incubator. When confluent (approximately 5-7 days after plating), human embryonic stem cells were treated with 1 mg/ml collagenase type IV (Invitrogen/GIBCO) for 5-10 min and then gently scraped off the surface using a 5-ml pipette. Cells were spun at 900 rpm for 5 min, and the pellet was resuspended and re-plated at a 1:3 to 1:4 ratio of cells in fresh culture medium.

Example 2

Formation of Definitive Endoderm

The effects of activin A on the expression of markers of definitive endoderm were examined. Activin A (100 ng/ml) was added to populations of human embryonic stem cells cultured on mouse embryonic fibroblasts. Cells were cultured continuously in the presence of activin A and harvested at the times indicated. The level of expression of definitive endoderm markers was examined by PCR (FIGS. 1A and 1B), FACS (results summarized in Table I), and immunohistochemistry (FIGS. 2A, 2B and 2C).

Figure 1B:
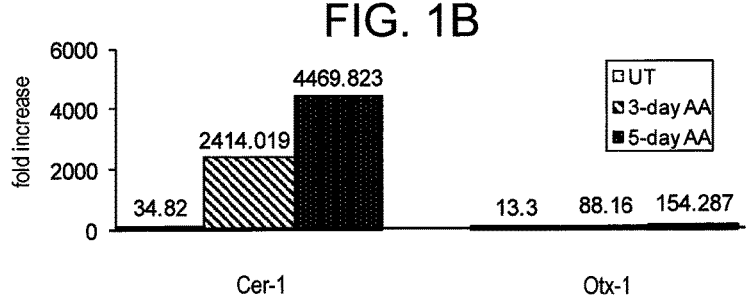
FIG. 1B shows the expression of the anterior endoderm markers Cerberus, Otx-1 and Hex genes in the human embryonic stem cell line H9 following treatment with 100 ng/ml activin A for three and five days.
Figure 2A:
FIGS. 2A, 2B and 2C shows the expression of definitive endoderm markers in the human embryonic stem cell line H9 following treatment with 100 ng/ml activin A for five days. Expression of the definitive endoderm markers was detected by immunohistochemistry.
Figure 2B:
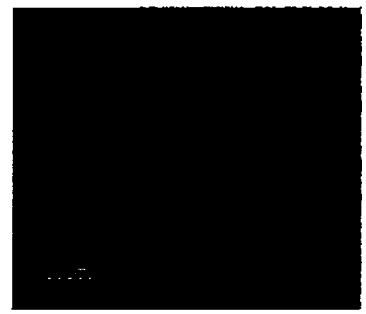
Figure 2C:

Activin A evoked a time-dependent increase in the expression of CXCR4, GATA4, HNF-3beta, Mix11 and Sox-17 mRNA in the H9 line (FIG. 1A). A significant up regulation of anterior endoderm markers, Cerberus, Otx-1 and Hex genes was also observed (FIG. 1B). An increase in CXCR4 protein was observed by FACS analysis following activin A treatment. The expression of E-cadherin and N-cadherin did not change following activin A treatment (Table IIA). CXCR4 positive cells were also highly positive for C-kit, EPCAM, CD99, and negative for CD9. The expression pattern for these markers was consistent among all three hES cell lines examined (Table IIB for H7 and Table IIC for H1). Immunocytochemistry conducted on cells treated with activin A for five days revealed that 30-40% cells in the treated culture were positive for Sox17 and HNF-3beta. In parallel, almost 100% of the differentiated cells were still Oct4 positive (FIGS. 2A, 2B and 2C). With the decrease in expression of surface markers of pluripotency, combined with an increase in the expression of definitive endoderm markers, these data suggest that activin A promotes the differentiation of human embryonic stem cells to definitive endoderm.

Example 3

Formation of Pancreatic Endoderm

Growth factors known to induce the differentiation of human embryonic stem cells to pancreatic endoderm were added to cell cultures. In particular, activin A, bFGF, and retinoic acid, known to induce the formation of pancreatic endoderm, were added to cell cultures.

Figure 3A:
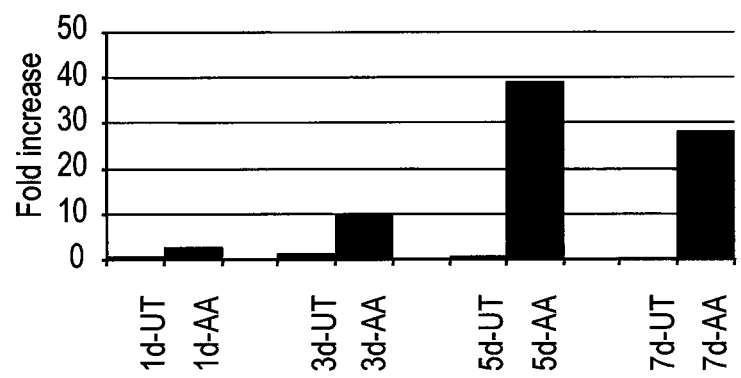
FIGS. 3A, 3B, 3C and 3D show the expression of definitive endoderm markers in the human embryonic stem cell line H9 following a step-wise differentiation protocol. Expression of the definitive endoderm markers was assayed at the mRNA level and normalized to expression levels in untreated human embryonic stem cells.
Figure 3B:
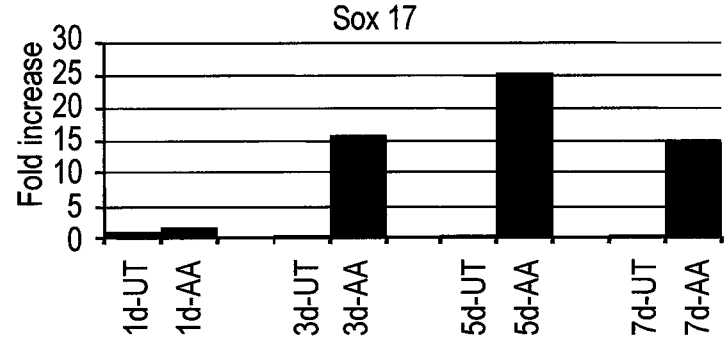
Figure 3C:
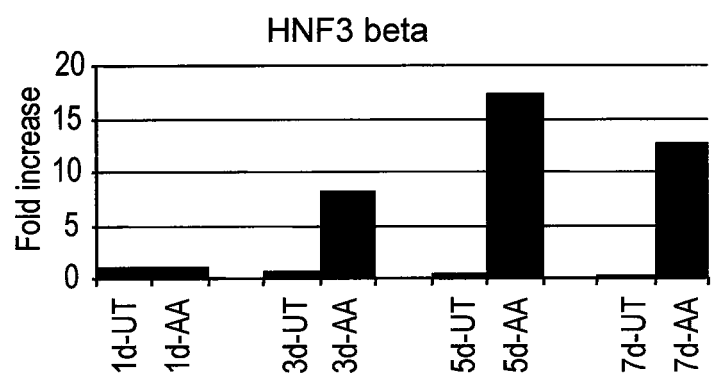
Figure 3D:
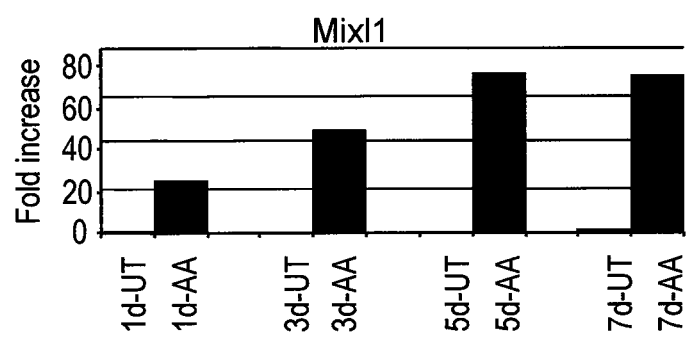

In a first series of experiments, activin A, was added to populations of human embryonic stem cells cultured on mouse embryonic fibroblasts for up to seven days in DMEM/F12 supplemented with 0% to 2% serum and Activin A (100 ng/ml). Cells were harvested at the time points indicated in FIGS. 3A, 3B, 3C and 3D and assayed by PCR for the expression of genes shown (FIGS. 3A, 3B, 3C, 3D, 4A, 4B, 5A and 5B). In FIGS. 3A, 3B, 3C and 3D, PCR analysis indicated that activin treated cells expressed a broad spectrum of genes associated with endoderm development, including GATA4 (FIG. 3A), Sox-17 (FIG. 3B), HNF-3beta (FIG. 3C), and Mix1-1 (FIG. 3D). However, no Pdx1 gene expression was observed. The same expression pattern of endoderm lineage markers was observed in Activin A treated H7 cells (FIGS. 6A, 6B, 6C, 6D, 6E and 6F). At this stage, there was no significant decrease of Oct4 expression.

Figure 4A:
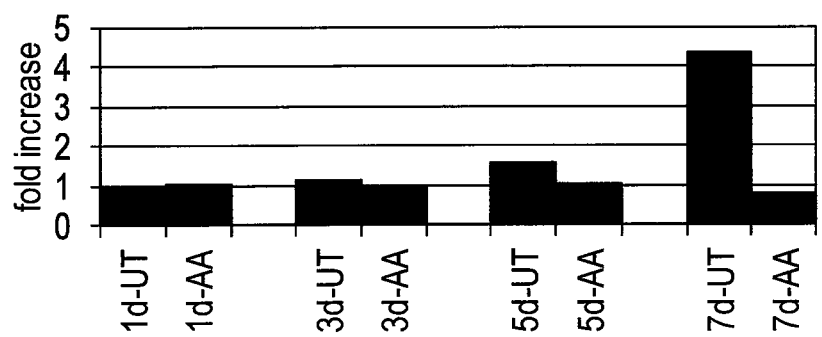
FIGS. 4A and 4B show the expression of extra-embryonic endoderm markers in the human embryonic stem cell line H9 following a step-wise differentiation protocol. Expression of the extraembryonic endoderm markers was assayed at the mRNA level and normalized to expression levels in untreated human embryonic stem cells.
Figure 4B:
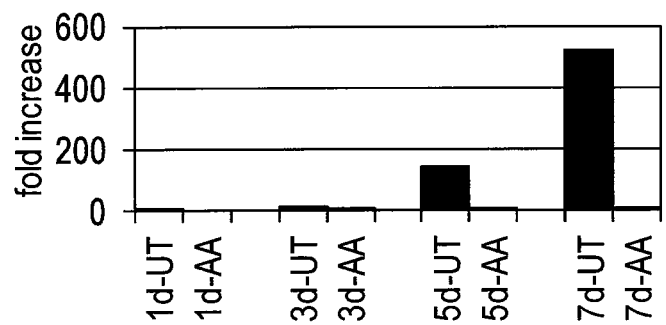
Figure 5A:
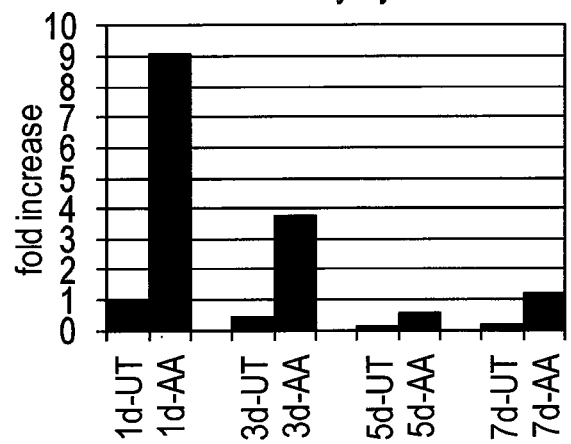
FIGS. 5A and 5B show the expression of mesoderm and ectoderm markers in the human embryonic stem cell line H9 following a step-wise differentiation protocol. Expression of the mesoderm and ectoderm markers was assayed at the mRNA level and normalized to expression levels in untreated human embryonic stem cells.
Figure 5B:
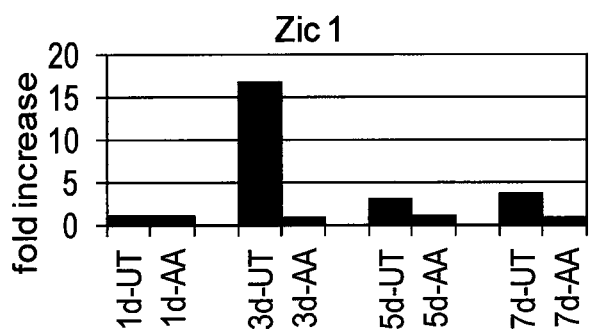
Figure 6A:
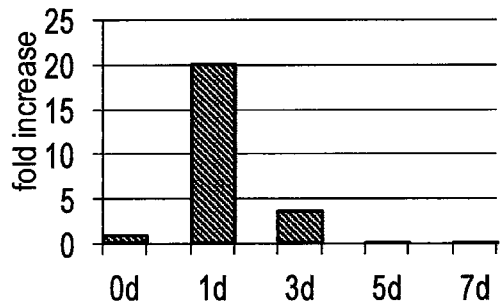
FIGS. 6A, 6B, 6C, 6D, 6E and 6F show the expression of the definitive endoderm markers Brachyury (FIG. 6A) CXCR4 (FIG. 6B), Mix11 (FIG. 6C), Sox17 (FIG. 6D), HNF-3beta (FIG. 6E), Oct4 (FIG. 6F) in the human embryonic stem cell line H7 following treatment with 100 ng/ml activin A for one, three, five and seven days. Expression of definitive endoderm markers was assayed at the mRNA level and normalized to expression levels in untreated human embryonic stem cells.
Figure 6B:
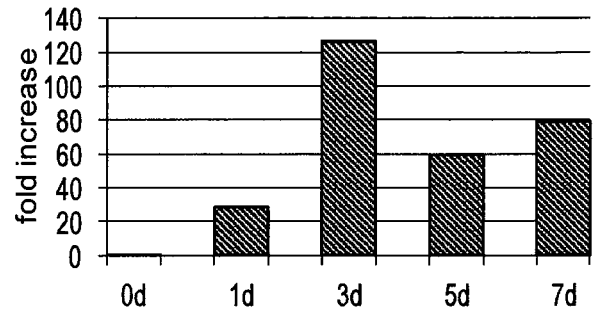
Figure 6C:
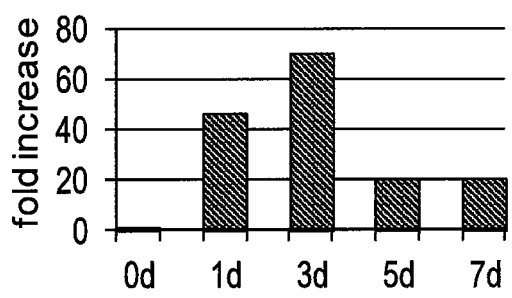
Figure 6D:
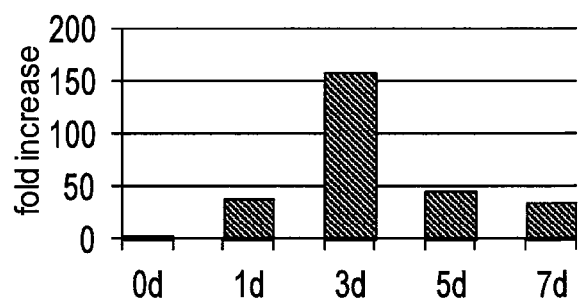
Figure 6E:
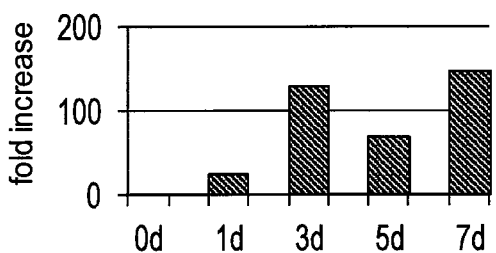
Figure 6F:
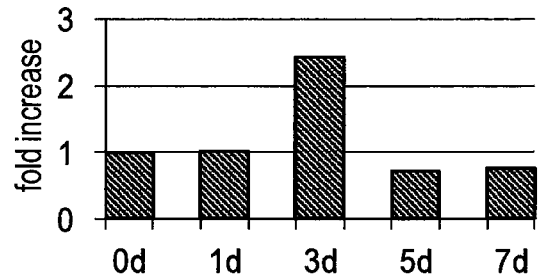
Figure 7A:
FIGS. 7A, 7B, 7C, 7D, 7E and 7F shows the expression of definitive endoderm markers in the human embryonic stem cell line H9 following application of a differentiation protocol. Expression of the definitive endoderm markers was detected by immunohistochemistry.
Figure 7B:
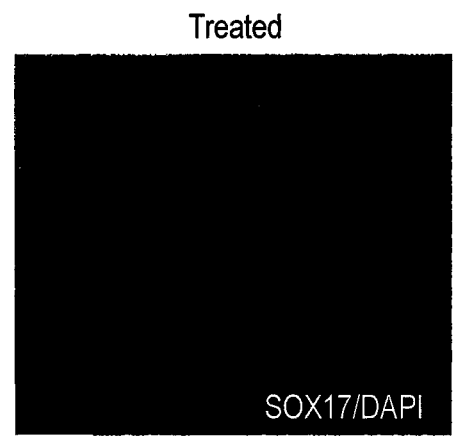
Figure 7C:
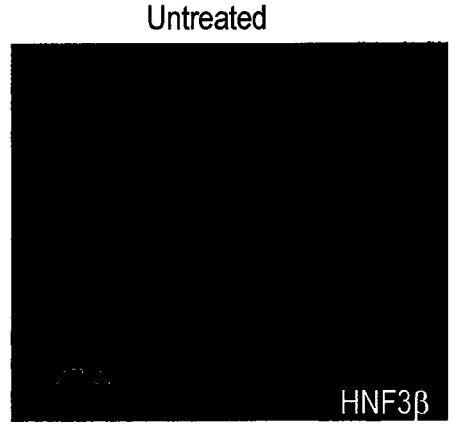
Figure 7D:
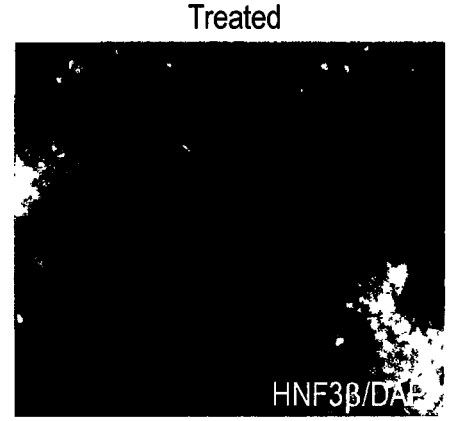
Figure 7E:
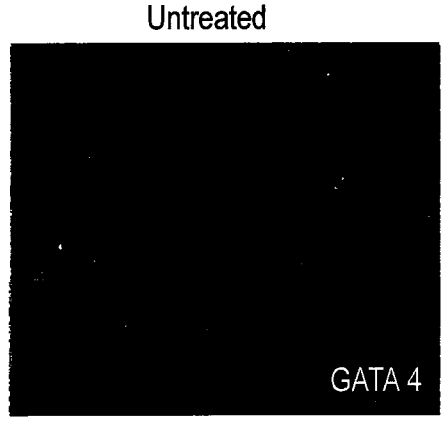
Figure 7F:

Activin A evoked a time-dependent decrease in the expression of the extraembryonic endoderm markers Sox7 (FIG. 4A) and AFP (FIG. 4B). Activin A decreased the expression of Brachyury (FIG. 5A) but had no effect on expression of the neuronal marker Zic1 (FIG. 5B).

Taken together, these data suggest that the increased expression of Sox-17, Mix11, Gata4, and HNF-3beta together with the upregulation of anterior endoderm markers Otx1, Cer1 and Hex genes, corresponds to the formation of definitive endoderm in response to activin A treatment. Analysis of definitive endoderm markers by immunocytochemistry revealed that protein expression for these genes also reflected the trends observed in mRNA expression. Levels of expression for HNF-3beta, Sox-17, and GATA4 were low in untreated cells, approximately 10 to 20% of all cells. Activin A (100 ng/ml) treatment for five days increased the expression of HNF-3beta, Sox-17, and GATA4 to approximately 50% to 90% of all cells (FIGS. 7A, 7B, 7C, 7D, 7E and 7F).

Figure 8A:
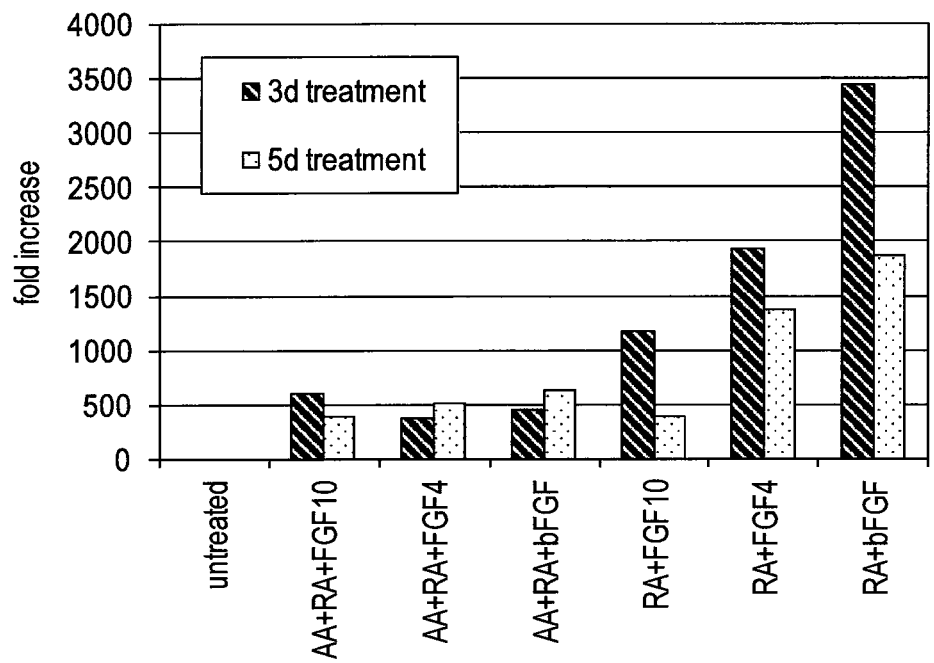
FIGS. 8A, 8B and 8C shows the expression of pancreatic endoderm markers in the human embryonic stem cell line H9 following application of a second differentiation protocol. Expression of the pancreatic endoderm markers was assayed by PCR and normalized to expression levels in activin A treated human embryonic stem cells.
Figure 8B:
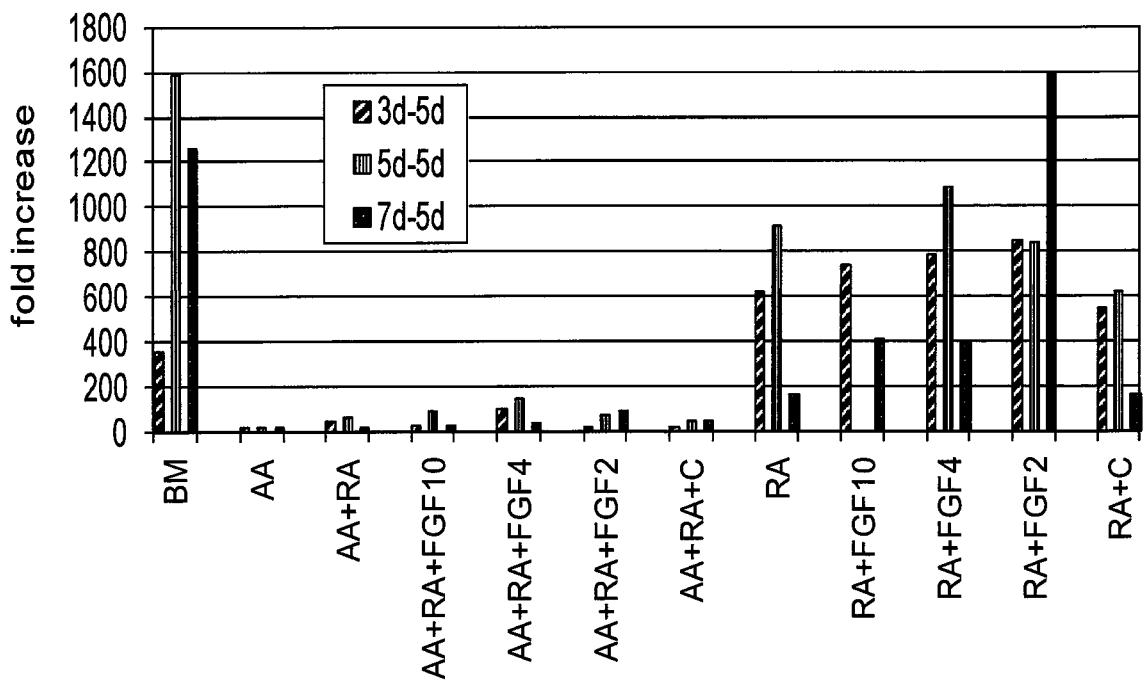
Figure 8C:
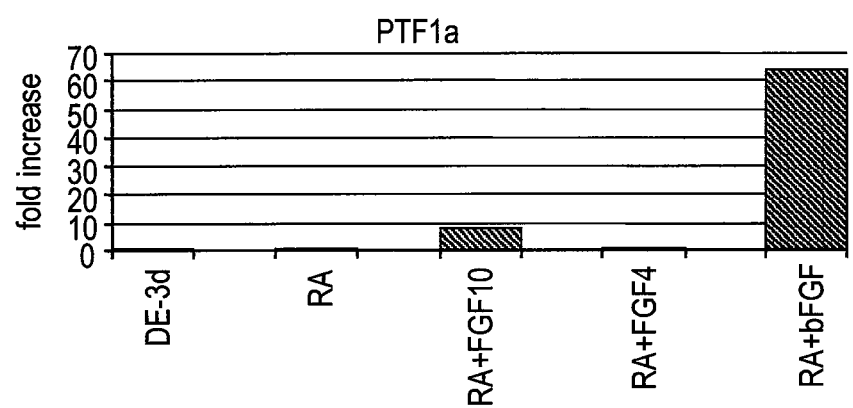

In a second series of experiments, cultures of human embryonic stem cells were maintained in undifferentiated culture conditions for 2-3 days according to the methods described in Example 1. After the cells were 70-80% confluent, the medium was changed to DMEM/F12 with 0 to 2% FBS with addition of activin A at 100 ng/ml and cultured in the presence of activin A for either three, five, or seven days. After this time interval, the cells were then further treated for five to six days with combinations of retinoic acid and bFGF as shown in FIGS. 8A, 8B and 8C. Cultures were harvested and samples of mRNA were collected for analysis. Control cultures consisting of cells treated with activin A alone for five days were also included.

Figure 9A:
FIGS. 9A and 9B show the expression of pancreatic endoderm markers in the human embryonic stem cell line H9 following application of a second differentiation protocol. Expression of the pancreatic endoderm markers was detected by immunohistochemistry.
Figure 9B:

Gene expression analysis revealed that activin A or retinoic acid alone did not induce the expression of Pdx1. Similar results were observed in cultures of cells treated with retinoic acid in combination with FGF and in the presence of activin A (FIG. 8A). However, treatment of cells with retinoic acid and FGF in the absence of activin A increased the expression of Pdx1 still further (FIG. 8A). Cells treated for three days with activin A, then treated for 5 days with 1p M retinoic acid and 50 ng/ml bFGF (also known as FGF-2) in the absence of activin A showed a level of Pdx1 expression that was approximately 3500-fold higher than that observed in samples with activin A treatment alone for 5 days (FIG. 8A). Immunocytochemistry showed that 5 to 20% of all cells expressed Pdx1 (FIGS. 9A and 9B).

Treatment with 1 µM retinoic acid and bFGF in the absence of activin A also caused an increase in the expression of GLUT-2 and PTF1a (FIG. 8C) that was not observed in cells treated in the presence of activin A alone. The largest increase in expression of GLUT-2 and PTF1a was observed in cells treated with 1 µM retinoic acid and 50 ng/ml bFGF. Taken together, these data suggest that the formation of pancreatic endoderm is further enhanced by removal of activin A from cell cultures after definitive endoderm has been formed.

Example 4

Formation of Pancreatic Endocrine Cells

Cultures of human embryonic stem cells were maintained in undifferentiated culture conditions for 3-4 days according to the methods described in Example 1. After the cells were 50-60% confluent, the medium was changed to DMEM/F12 without FBS, containing activin A at 100 ng/ml, and the cells were cultured in this medium for one day. Following the one day culture, the medium was removed and replaced with medium containing 0.5% FBS with 100 ng/ml activin A, and the cells were cultured for one day. Following the second one-day culture, the medium was removed and replaced with medium containing 2% FBS with 100 ng/ml activin A, and the cells were cultured for one day. After this time interval, the cells were then treated for six days with combinations of retinoic acid and FGF as outlined in Example 2, then the culture medium was removed and replaced with medium comprising DMEM/F12 with 2% FBS, containing the γ-secretase inhibitors L-685,458 at 10 µM for three days. Cultures were harvested and samples of mRNA were collected for analysis. Control cultures consisting of cells treated with activin A alone for five days were also included.

Figure 10A:
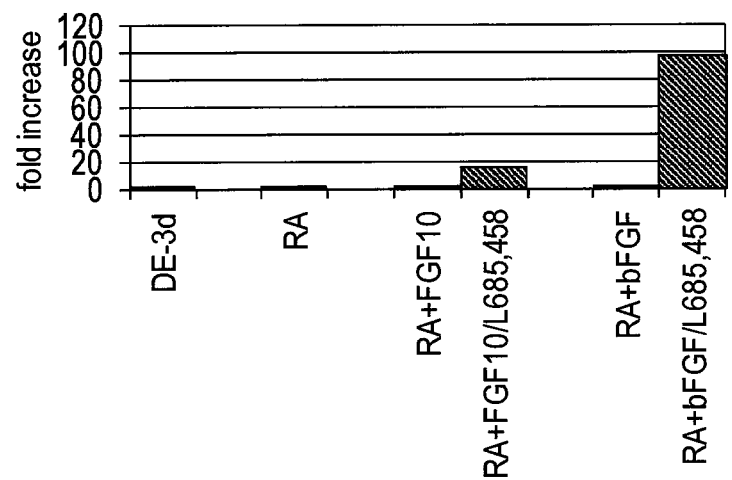
FIGS. 10A, 10B, 10C and 10D show the expression of pancreatic endocrine markers in the human embryonic stem cell line H9 following application of a third differentiation protocol. Expression of the pancreatic endocrine markers was assayed by PCR and normalized to expression levels in activin A treated human embryonic stem cells.
Figure 10B:
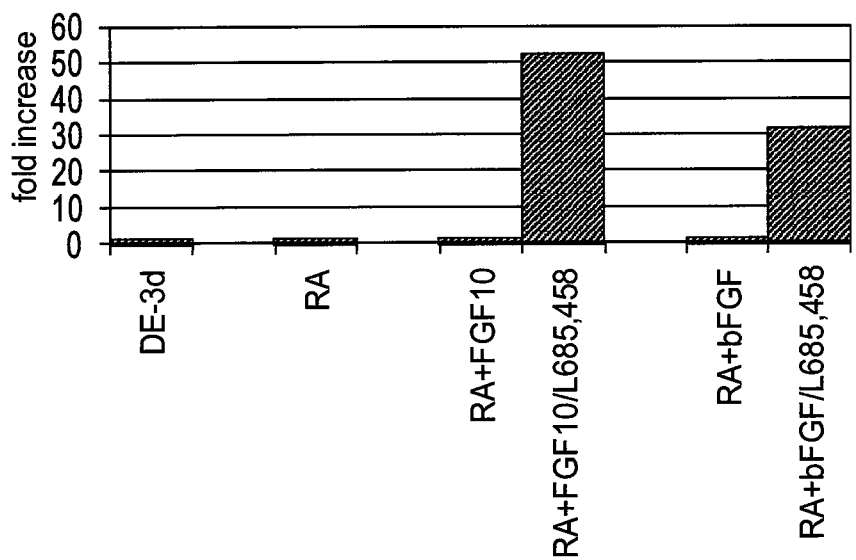
Figure 10C:
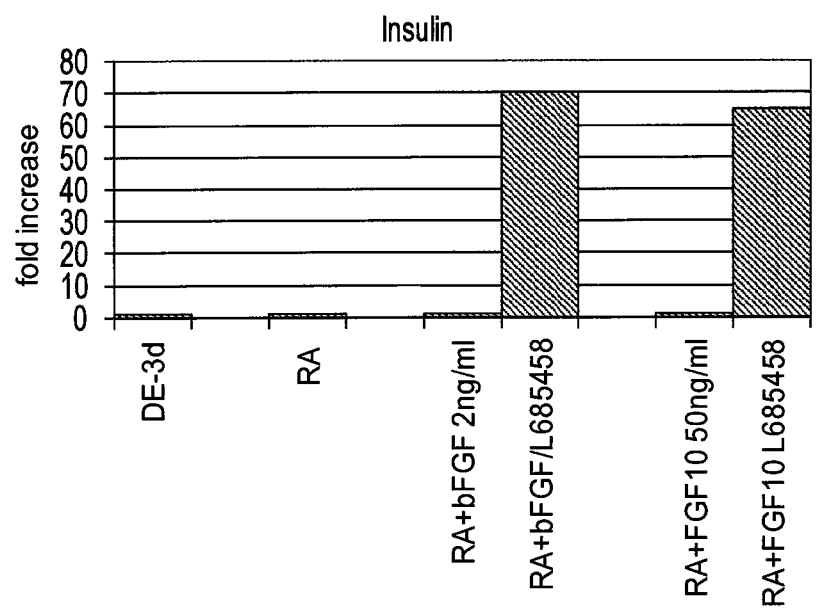
Figure 10D:
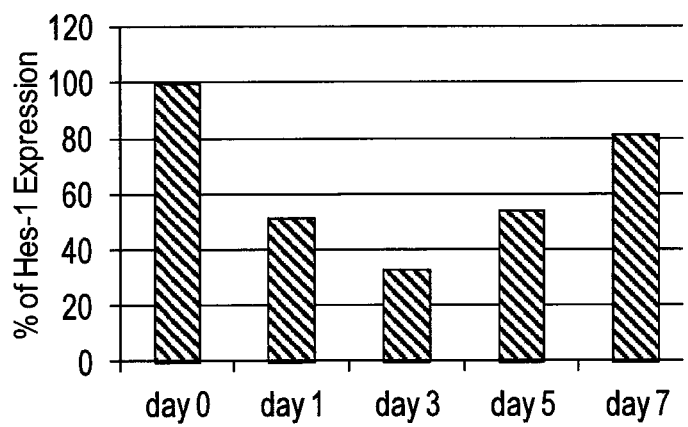

Gene expression analysis revealed that activin A alone or in combination with retinoic acid and FGFs did not induce the expression of Ngn3 or Insulin (FIGS. 10A and 10C). A decrease in the expression of Hes-1 was also observed following treatment with L-685,458. The maximal inhibition was observed on day three post treatment (FIG. 10D). However, treatment of cells with L-685,458 induced the expression of Ngn3 to a level approximately 50-fold higher than that observed in samples treated with activin A alone or retinoic acid with FGFs in combination. A 70-fold increase of insulin expression was observed in samples treated with the γ-secretase inhibitor. NeuroD1 expression was also increased further by the L-685,458 treatment (FIG. 10A). Taken together, these data suggest that the formation of endocrine cells is further enhanced by removal of retinoic acid and FGFs from cell culture and the addition of γ-secretase inhibitors after pancreatic endoderm has been formed.

Example 5

Formation of Pancreatic Endocrine Cells Expressing Nkx2.2

Figure 11A:
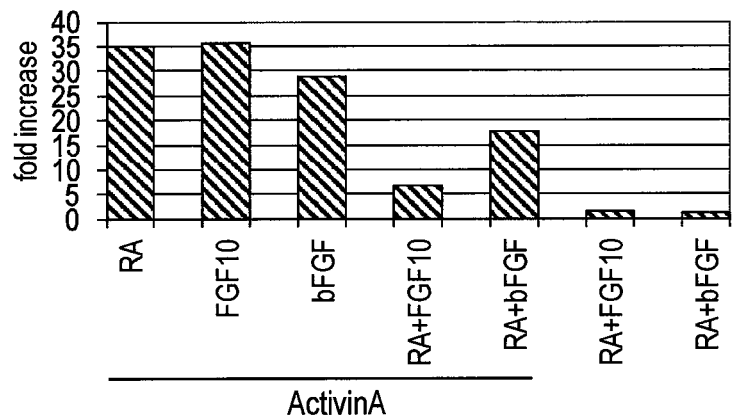
FIGS. 11A and 11B show the expression of pancreatic endoderm markers in the human embryonic stem cell line H9 following application of a differentiation protocol. Expression of the pancreatic endoderm markers was assayed by PCR and normalized to expression levels in activin A treated human embryonic stem cells.
Figure 11B:
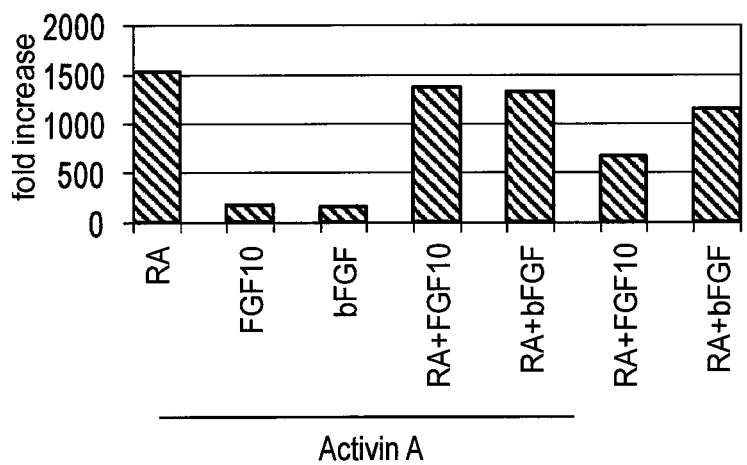

Definitive endoderm cells obtained according to the methods outlined in Example 2 were treated as follows: Cells were cultured in basal medium, comprising DMEM/F12 with 2% FBS plus 50 ng/ml activin A, 50 ng/ml basic FGF and 1 µM of Retinoic Acid for 3 to 5 days. Cells were continuously cultured for another 3 to 5 days in basal medium with retinoic acid at 1 µM, alone or with bFGF. RNA samples were harvested from cells at various time points along this process to help evaluate the directed differentiation of the cells. Furthermore, culture medium and factors were regularly removed and replenished throughout the differentiation protocol. Addition of activin A showed an increase of Nkx2.2 expression about 35-fold compared to samples without activin A. Samples treated with activin A for the first three days of culture maintained Pdx1 expression at a level similar to samples containing no activin A (FIGS. 11A and 11B). Taken together, these data suggest that the expression of the pancreatic endocrine marker Nkx2.2 is further enhanced by adding Activin A to the first three days of retinoic acid and bFGF treatment.

Example 6

Passage and Expansion of Pancreatic Endoderm Cells in Culture

Figure 12:
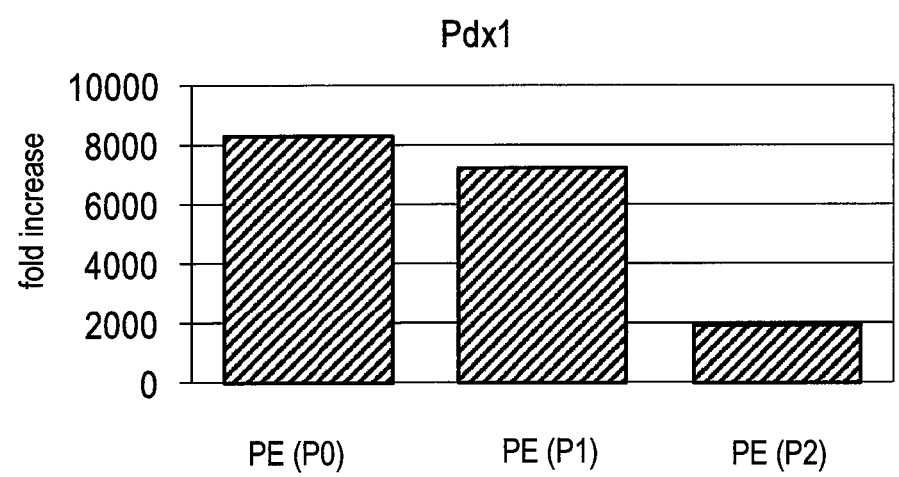
FIG. 12 shows the expression of PDX-1 in cells with each passage (P0, P1 and P2) in culture. Expression of the PDX-1 was assayed by PCR and normalized to expression levels in activin A treated human embryonic stem cells H9.

This example demonstrates that pancreatic endoderm cells derived from human embryonic stem cells herein can be maintained in cell culture and passaged without further differentiation. Pancreatic endoderm cells were differentiated in the presence of 100 ng/ml activin A in low serum DMEM/F12. The low serum DMEM/F12 contained 0% (v/v) fetal bovine serum (FBS) on day 1, 0.5% (v/v) FBS on day two and 2% (v/v) FBS on each day thereafter. After four days of differentiation, the cells were cultured in low serum DMEM/F12 contained 2% (v/v) FBS, 1 µM retinoic acid and 50 ng/ml bFGF for a total of six more days. After the six days of differentiation, the cells were maintained in culture in low serum DMEM/F12 contained 2% (v/v) FBS in the presence of 50 ng/ml FGF10 for a total of 6 days. During the six-day culture period, the pancreatic endoderm cells were passaged twice and cell population-doubling time is about 36 to 48 hours during this 6-day culture. On days 0, 3, and 6 of culture, Q-PCR was used to measure the expression of marker genes indicative of pancreatic endoderm. FIG. 12 shows that cells grown in the presence of 50 ng/ml FGF10 maintained expression of the pancreatic endoderm marker Pdx1 during the 6 day culture period subsequent to their derivation.

Example 7

Derivation of Hepatocytes from Human Embryonic Stem Cells

Figure 13A:
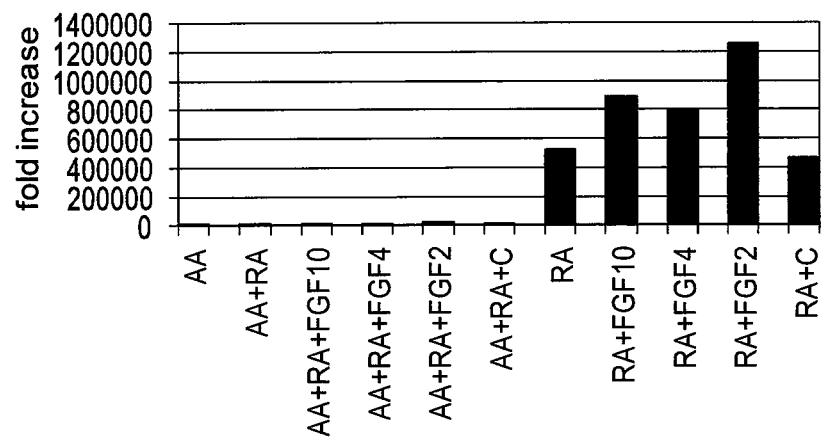
FIGS. 13A and 13B show the expression of hepatocyte markers in the human embryonic stem cell line H9 following application of a third differentiation protocol. Expression of the hepatocyte markers was assayed by PCR and normalized to expression levels in activin A treated human embryonic stem cells.

Cultures of human embryonic stem cells were maintained in undifferentiated culture conditions for 2-3 days according to the methods described in Example 1. After cells were 70-80% confluent, the medium was changed to DMEM/F12 with 2% FBS containing activin A at 100 ng/ml, and cells were cultured in the presence of activin A for seven days. After 7 days treatment with activin A, the cells were then treated for five days with the conditions shown in FIGS. 13A and 13B. After this time, the cells were harvested, and samples of mRNA were collected for analysis.

Figure 13B:
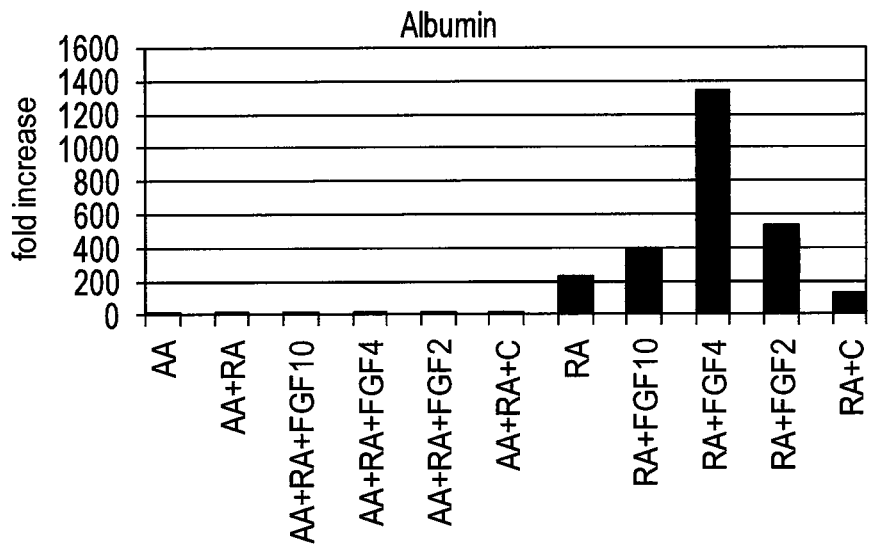

An increase in the expression of α-fetoprotein (AFP) and albumin was observed (FIG. 13A) for cells cultured in the absence of activin A. This was further increased by retinoic acid and FGF-4 (FIG. 13B). Taken together, these data suggest that cultures of human embryonic stem cells are capable of expressing hepatocyte markers following the treatment described above. Furthermore, human embryonic stem cells are capable of being differentiated into cells expressing markers that are characteristic of hepatocytes.

Example 8

Characterization of the H9 Human Embryonic Stem Cell Line

The quality of H9 cells was monitored over time by evaluating expression of several markers expressed by undifferentiated ES cells (Carpenter et al., 2001; Reubinoff et al., 2000; Thomson et al., 1998a). H9 cells exhibited reciprocal expression of stage-specific embryonic antigens (Table III). H9 cells play strong immunoreactivity for SSEA-3, SSEA-4, Tra-1-60, Tra-1-81, AP and CD9 antigens, all of which are characteristic of undifferentiated human embryonic stem cells.

Figure 14A:
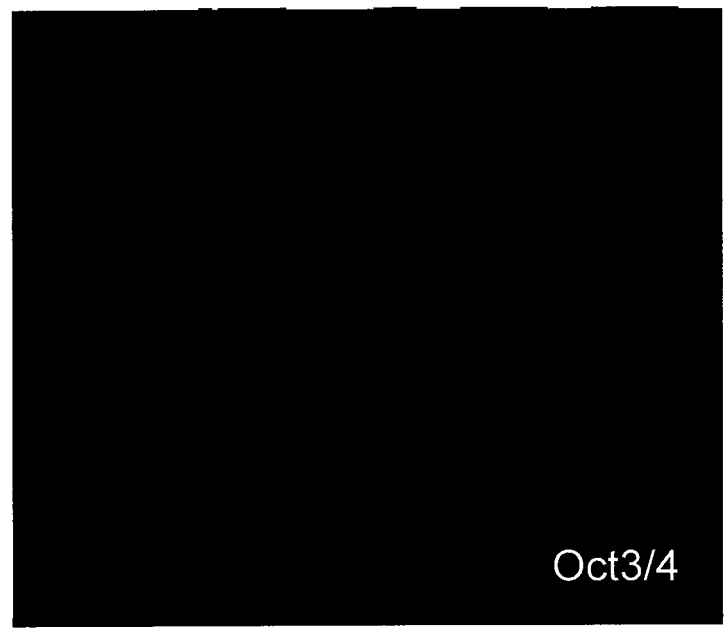
FIGS. 14A and 14B shows the expression of markers of pluripotency in the human embryonic stem cell line H9. Expression of the markers of pluripotency was assayed by immunohistochemistry.
Figure 14B:

RT-PCR was performed to assess the expression of genes characteristic of embryonic stem cells, such as, for example, OCT3/4, SOX-2, UTF-1, REX-1, Cx43, Cx45, ABCG-2 and TERT, confirming that the cells grown in this example appeared similar to previously described undifferentiated embryonic stem cells (Table III). OCT3/4 protein expression and Alkaline Phosphatase activity (Chemicon) were confirmed by immunostaining. A majority of H9 cells were positive for OCT3/4 and AP (FIGS. 14A and 14B). Overall, these results demonstrate that the H9 cells used in this example were not significantly different in morphology, antigen immunostaining, or pluripotency marker expression when compared to reports from other laboratories.

Example 9

Fluorescence-Activated Cell Sorting (FACS) Analysis

Adhered cells were removed from culture plates by five-minute incubation with TrypLE™ Express solution (Invitrogen, CA). Released cells were resuspended in human embryonic stem cell culture medium and recovered by centrifugation, followed by washing and resuspending the cells in a staining buffer consisting of 2% BSA, 0.05% sodium azide in PBS (Sigma, MO). As appropriate, the cells were Fc-receptor blocked for 15 minutes using a 0.1% γ-globulin (Sigma) solution. Aliquots (approximately $10^5$ cells) were incubated with either phycoerytherin (PE) or allophycocyanin (APC) conjugated monoclonal antibodies (5 µl antibody per $10^6$ cells), as indicated in Table I, or with an unconjugated primary antibody. Controls included appropriate isotype matched antibodies, unstained cells, and cells stained only with secondary conjugated antibody. All incubations with antibodies were performed for 30 mins at 4° C. after which the cells were washed with the staining buffer. Samples that were stained with unconjugated primary antibodies were incubated for an additional 30 mins at 4° C. with secondary conjugated PE or -APC labeled antibodies. See Table I for a list of secondary antibodies used. Washed cells were pelleted and resuspended in the staining buffer, and the cell surface molecules were identified using a FACS Array (BD Biosciences) instrument, collecting at least 10,000 events.

Example 10

Immunocytochemistry

Cells seeded on 0.1% Matrigel (BD) coated dishes were fixed with 4% paraformaldehyde for 20 min at room temperature. Fixed cells were blocked for 1 h at room temperature with PBS/0.1% BSA/10% normal chick serum/0.5%

Triton X-100 and then incubated overnight with primary antibodies in PBS/0.1% BSA/10% normal chick serum at 4° C. The list of primary antibodies and their working dilutions are shown in Table IB. After three washes in PBS/0.1% BSA, fluorescent secondary antibodies at a 1:100 dilution in PBS were incubated with cells for 1 h at room temperature to allow binding. Control samples included reactions where the primary antibody was omitted or where the primary antibody was replaced with corresponding matched negative control immunoglobulins at the same concentration as the primary antibodies. Stained samples were rinsed; a drop of PROLONG® (Invitrogen, CA) containing diamidino-2-phenylindole, dihydrochloride (DAPI) was added to each sample to counter-stain the nucleus and to function as an anti-fade reagent. Images were acquired using a Nikon Confocal Eclipse C-1 inverted microscope (Nikon, Japan) and a 10-60× objective.

Example 11

PCR Analysis of Undifferentiated Cells

RNA Extraction, Purification, and cDNA Synthesis.

RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, INC), and high-quality RNA was then eluted in water. Yield and purity were assessed by A260 and A280 readings on a spectrophotometer. cDNA copies were made from purified RNA using an ABI (ABI, CA) high capacity cDNA archive kit.

Real-Time PCR Amplification and Quantitative Analysis.

Unless otherwise stated, all reagents were purchased from Applied Biosystems. Real-time PCR reactions were performed using the ABI PRISM® 7900 Sequence Detection System. TAQMAN® UNIVERSAL PCR MASTER MIX® (ABI, CA) was used with 20 ng of reverse transcribed RNA in a total reaction volume of 20 µl. Each cDNA sample was run in duplicate to correct for pipetting errors. Primers and FAM-labeled TAQMAN® probes were used at concentrations of 200 nM. The level of expression for each target gene was normalized using a human glyceraldehyde-3-phosphate dehydrogenase (GAPDH) endogenous control previously developed by Applied Biosystem. Primer and probe sets are listed as follows: Oct3/4 (Hs00742896), SOX-2 (Hs00602736), UTF-1 (Hs00747497), Rex-1 (Hs00399279), Connexin 43 (Hs00748445), Connexin 45 (Hs00271416), ABCG2 (Hs00184979), Otx-1 (Hs00222238), Cerberus (Hs00193796)m, Albumin (Hs00609411).

After an initial incubation at 50° C. for 2 min followed by 95° C. for 10 min, samples were cycled 40 times in two stages—a denaturation step at 95° C. for 15 sec followed by an annealing/extension step at 60° C. for 1 min. Data analysis was carried out using GENEAMP® 7000 Sequence Detection System software. For each primer/probe set, a C value was determined as the cycle number at which the fluorescence intensity reached a specific value in the middle of the exponential region of amplification. Relative gene expression levels were calculated using the comparative $C_t$ method. Briefly, for each cDNA sample, the endogenous control $C_t$ value was subtracted from the gene of interest $C_t$ to give the delta $C_t$ value ($\Delta C_t$). The normalized amount of target was calculated as $2^{-\Delta Ct}$, assuming amplification to be 100% efficiency. Final data were expressed relative to a calibrator sample.

Example 12

Karyotype Analysis

Figure 15:
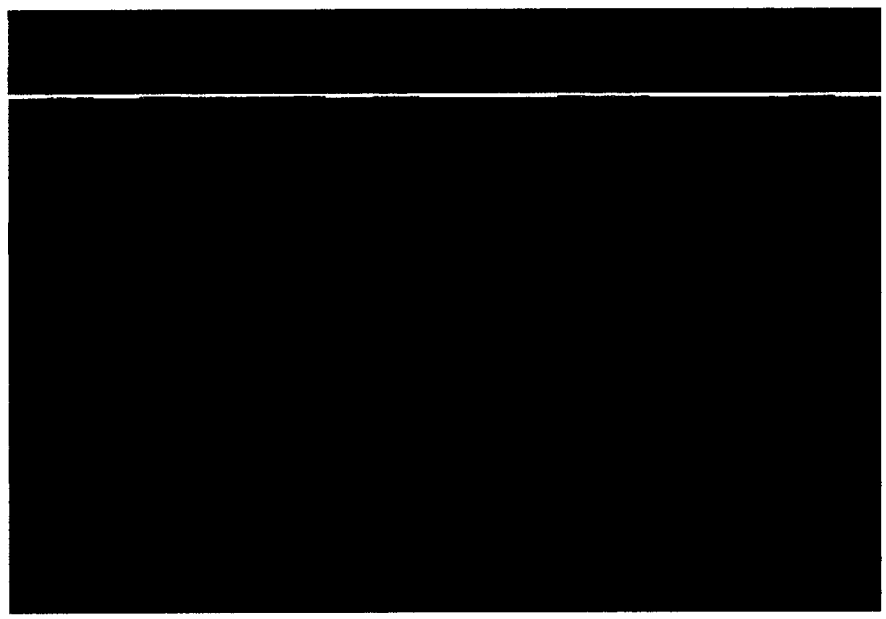
FIG. 15 shows the karyotype of the human embryonic cell line H9. The Karyotype was determined on cells at passage number P36 that were cultured on mouse embryonic fibroblast feeder cells.
Figure 17A:
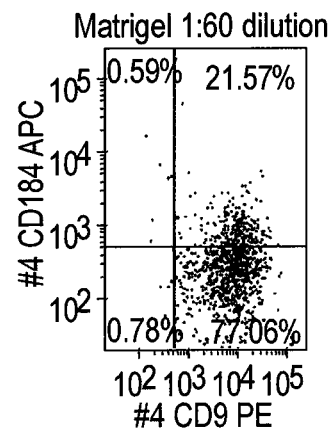
FIGS. 17A, 17B, 17C, 17D, 17E and 17F depict the FACS profile of human embryonic stem cell line H9 at passage number 44, cultured on varying concentrations of MATRIGEL and exposed to (0.5-2%) low serum and high activin A (100 ng/ml) for 5 days. The expression of definite endoderm marker CXCR4 (CD184) is shown on the Y-axis and the expression of ES marker CD9 is shown on the X-axis.
Figure 17B:
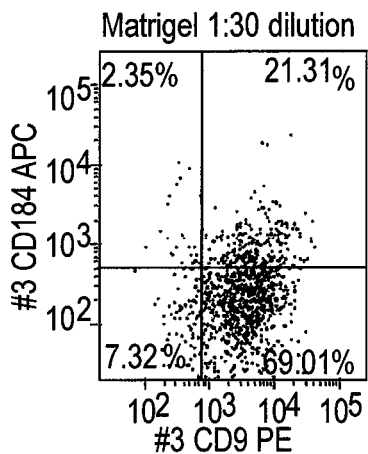
Figure 17C:
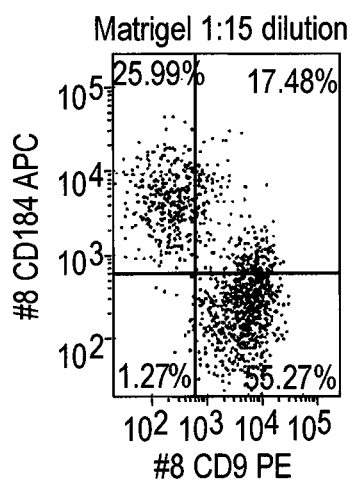
Figure 17D:
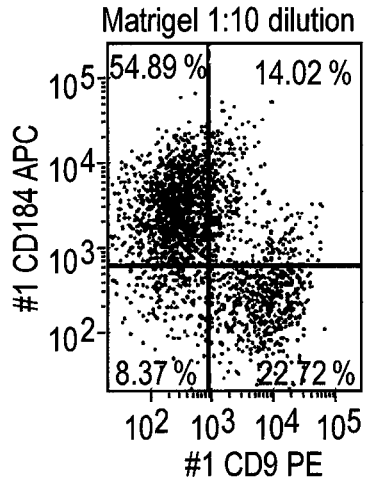
Figure 17E:
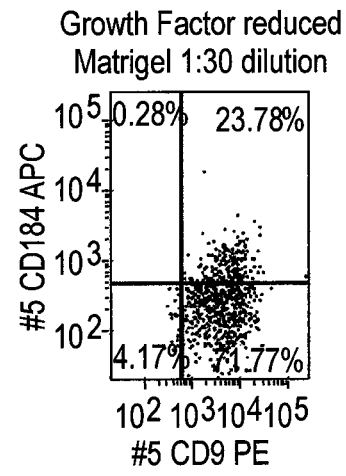
Figure 17F:
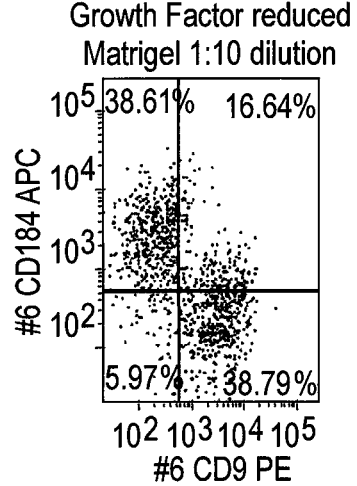

The karyotype of H9 cells was determined by standard G-banding karyotype analysis. A total of 100 metaphase spreads were evaluated (Applied Genetics Laboratories, Inc.). No chromosome aberrations were found in 100 cells analyzed. Cytogenetic analysis showed that the cells had a normal number of autosomes and a modal chromosome number of 46. FIG. 15 depicts a typical karyotype obtained from the human embryonic stem cell line H9.

Example 13

Human Embryonic Stem Cell Culture on Tissue Culture Substrate Coated with Extracellular Matrix The human embryonic stem cell lines H1, H7, and H9 were obtained from WiCell Research Institute, Inc., (Madison, Wis.) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM beta-mercaptoethanol, 2 mM L-glutamine with 4 ng/ml human basic fibroblast growth factor (bFGF). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 pg/ml mitomycin C (Sigma, St. Louis, Mo.) for 3h to arrest cell division, then trypsinized and plated at 2×104/cm2 on 0.1% bovine gelatin-coated dishes. MEF cells from passage two through four were used as feeder layers. Human embryonic stem cells plated on MEF cell feeder layers were cultured at 37° C. in an atmosphere of 5% $CO_2$ within a humidified tissue culture incubator. When confluent (approximately 5 to 7 days after plating), human embryonic stem cells were treated with 1 mg/ml collagenase type IV (Invitrogen/GIBCO) for 5 to 10 min and then gently scraped off the surface using a 5 ml glass pipette. Cells were centrifuged at 900 rpm for 5 min, and the pellet was resuspended and re-plated at a 1:3 to 1:4 ratio of cells on plates coated with a 1:30 dilution of growth factor reduced MATRIGEL™ (BD Biosciences). Cells were subsequently cultured in MEF-conditioned media supplemented with 8 ng/ml bFGF and collagenase passaged on MATRIGEL coated plates for at least five passages. The cells cultured on MATRIGEL™ were routinely passaged with collagenase IV (Invitrogen/GIBCO), Dispase (BD Biosciences) or Liberase enzyme (Roche, IN).

Example 14

Differentiation of Human Embryonic Stem Cells Cultured on Tissue Culture Substrate Coated with Extracellular Matrix to Definitive Endoderm Differentiation of embryonic stem cells to definitive endoderm was carried out as previously described in Nature Biotechnology 23, 1534-1541 (December 2005). Briefly, H9 cultures at approximately 60 to 70% confluency were exposed to DMEM:/F12 medium supplemented with 0.5% FBS and 100 ng/ml activin A for two days, followed by treatment with DMEM/F12 medium supplemented with 2% FBS and 100 ng/ml activin A (AA) for an additional three days. H9 cells were cultured on plates coated with growth factor reduced MATRIGEL at a 1:30 to 1:10 dilution or on regular MATRIGEL at a 1:30 to 1:10 dilution The plates were coated with MATRIGEL for 1 hr at room temperature.

At day 5, the cultures were analyzed by FACS for CXCR4, E-cadherin, CD9, and N-cadherin expression and by real time PCR for SOX-17, SOX-7, Alpha-fetal protein (AFP), CXCR4, Brychyury (Bry), goosecoid (GSC), HNF-3 beta, and GATA4. AFP and SOX-7 are regarded as visceral endoderm markers, while GATA4, HNF-3 beta and SOX-17 represent definite endoderm markers, and GSC, Bry, and CXCR4 represent markers of primitive streak. FIGS. 17A, 17B, 17C, 17D, 17E and 17F depicts the expression of CXCR4 by FACS. There was a significant increase in expression of CXCR4 by cells cultured on plates coated with MATRIGEL at a 1:10 dilution as compared to lower concentrations of MATRIGEL. Furthermore, growth factor reduced MATRIGEL was not as effective in formation of definitive endoderm cells as compared to regular MATRIGEL.

Figure 18:
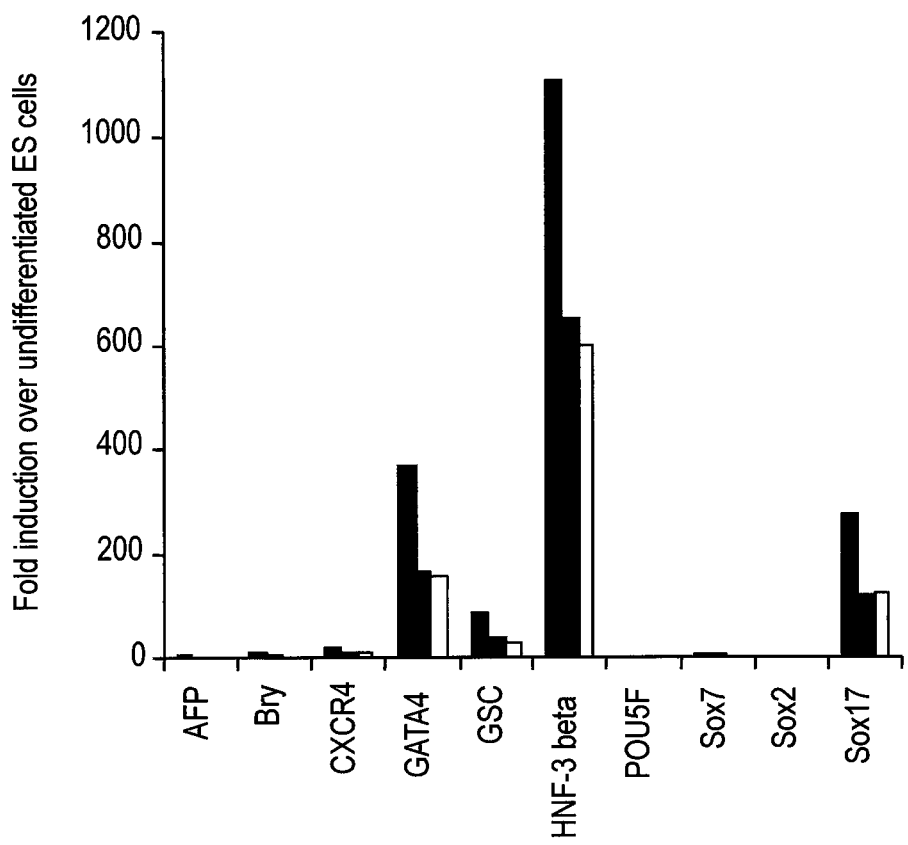
FIG. 18 shows the real-time PCR results for markers of definitive endoderm, from cultures of the human embryonic stem cell line H9 at passage 44 cultured on a 1:10 dilution of MATRIGEL (U), a 1:20 dilution of MATRIGEL (U), or a 1:30 dilution of MATRIGEL (0) and exposed to the differentiation protocol disclosed in Example 14. The fold induction is relative to undifferentiated cells of the human embryonic stem cell line H9, at passage number 44, cultured in medium conditioned using mouse embryonic fibroblasts.

FIG. 18 shows the real-time PCR results verifying that cells cultured on plates coated with a 1:10 dilution of MATRIGEL showed a significant upregulation of definitive endoderm markers as compared to cells cultured on a 1:30 dilution of MATRIGEL.

Example 15

Microarray Analysis of Changes in Gene Expression in Embryonic Stem Cells Following Formation of Definitive Endoderm Total RNA was isolated from the following human embryonic stem cell cultures using an RNeasy mini kit (Qiagen): H9P83 cells cultured on MATRIGEL-coated plates and exposed to DMEM/F12 medium supplemented with 0.5% FBS and 100 ng/ml activin A for two days followed by treatment with DMEM/F12 medium supplemented with 2% FBS and 100 ng/ml Activin A (AA) for an additional three days; H9P44 cells cultured on MEFs and exposed to DMEM/F12 medium supplemented with 0.5% FBS and 100 ng/ml activin A for two days followed by treatment with DMEM/F12 medium supplemented with 2% FBS and 100 ng/ml activin A for an additional three days. Controls for each group included cells plated on MATRIGEL-coated dishes and cultured in MEF-conditioned medium or cells plated on MEFs and cultured in ES medium.

Figure 19A:
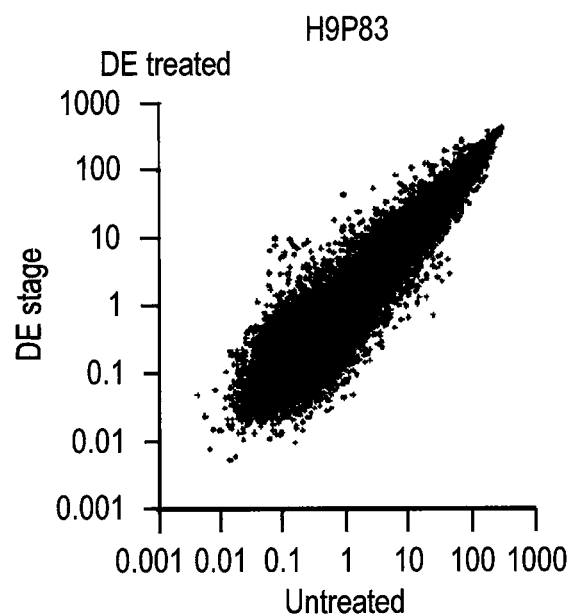
FIGS. 19A and 19B show the scatter plots for global gene expression in undifferentiated pluripotent stem cells and definitive endoderm cells obtained from differentiating pluripotent stem cells. Data shown is from cultures of the human embryonic stem cell line H9 cell line at passage 44 cultured on mouse embryonic fibroblasts (right panel) and passage 83 cultured on MATRIGEL (left panel).
Figure 19B:
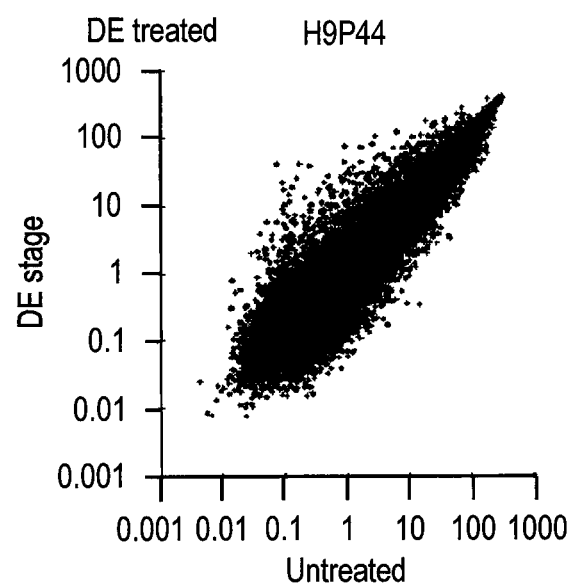

Sample preparation, hybridization, and image analysis were performed according to the Affymetrix Human Genome U133 Plus 2.0 Array. Following normalization and a log transformation, data analysis was performed using OmniViz® software (MA) and GENESIFTER (VizXLabs, WA). The variability within each treatment and among the different treatments was compared using the Pearson correlation coefficient. Variance in gene expression profiles between the different treatments along with the correlation coefficient between the lines are depicted in FIGS. 19A and 19B. Significant differences in gene expression between the samples were evaluated using analysis of variance and an F-test with adjusted P-value (Benjamini and Hochberg correction) of ≤0.05. Only genes with a present call were included in the analysis. Table IV lists the genes that are differentially expressed with a difference at least 5-fold between the various samples. The normalized intensity value of the genes that are significantly expressed along with the standard error of the mean (SEM) for each gene are listed.

Example 16

Differentiation of Human Embryonic Stem Cells Cultured on Tissue Culture Substrate Coated with MATRIGEL™ to Definitive Endoderm Differentiation of embryonic stem cells to definitive endoderm was carried out as previously described in Nature Biotechnology 23, 1534-1541 (December 2005). Briefly, H9, H7, or H1 cells seeded on growth factor reduced MATRIGEL™ (1:30 dilution) cultures at approximately 60 to 70% confluency were exposed to DMEM/F12 medium supplemented with 0.5% FBS and 100 ng/ml activin A (R&D Systems, MN)) for two days followed by treatment with DMEM/F12 media supplemented with 2% FBS and 100 ng/ml activin A (AA) for an additional three days. In all subsequent examples unless otherwise noted, this treatment regimen will be referred to as the definite endoderm (DE) protocol. In parallel, H9, H7, or H1 cells cultured on MEF feeders were also exposed to the same DE protocol outlined above.

At day 5, the cultures were analyzed by FACS for CXCR4, E-cadherin, CD9, CD99, and N-cadherin (CD56) expression and by real time PCR for SOX-17, SOX-7, Alpha-fetal protein (AFP), CXCR4, Brychyury (Bry), goosecoid (GSC), HNF-3 beta, and GATA4. AFP and SOX-7 are regarded as visceral endoderm markers while GATA4, HNF-3beta and SOX-17 represent definite endoderm markers and GSC, Bry, and CXCR4 represent markers of primitive streak.

Figure 20A:
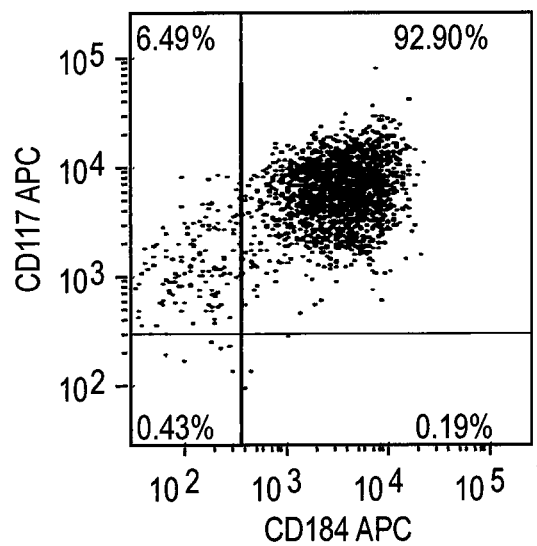
FIGS. 20A, 20B and 20C depict the expression of CXCR4 by FACS at day 5 for the human embryonic stem cell line H1 (FIG. 20A), the human embryonic stem cell line H7 (FIG. 20B), and the human embryonic stem cell line H9 (FIG. 20C) cultured on mouse embryonic fibroblast feeder cells exposed to the definitive endoderm differentiation protocol disclosed in Example 4.
Figure 20B:
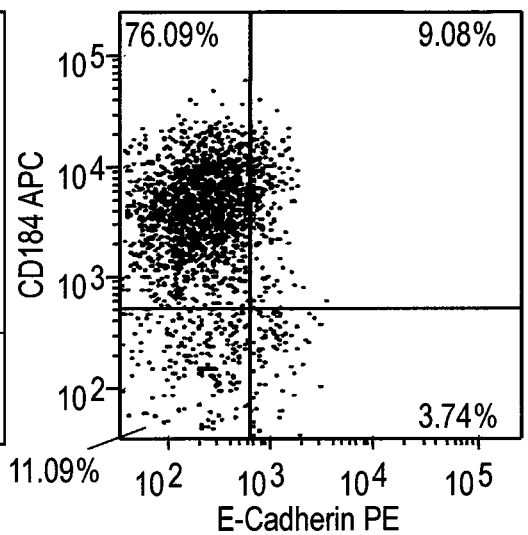
Figure 20C:
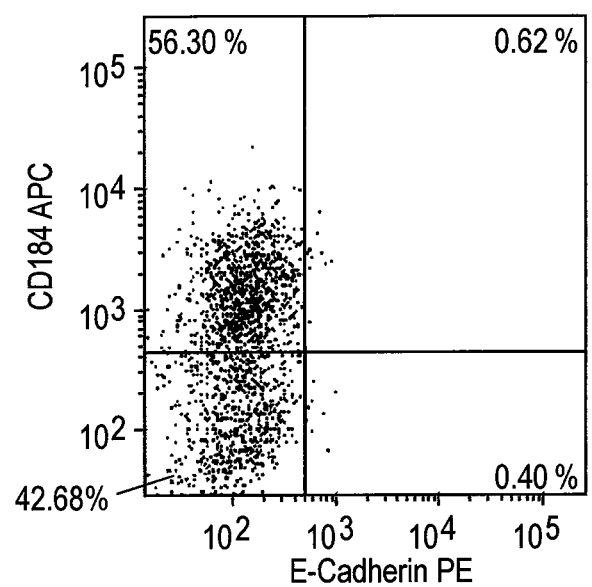
Figure 21A:
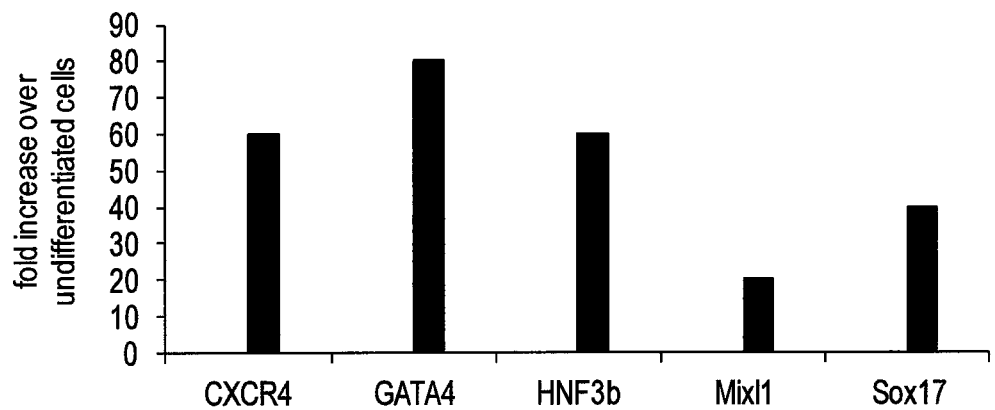
FIGS. 21A and 21B show the real-time PCR results of expression of the indicated definitive endoderm markers in cultures of the human embryonic stem cell line H7 (FIG. 21A) and the human embryonic stem cell line H9 (FIG. 21B) cultured on mouse embryonic fibroblast feeder cells. Results are expressed as fold increase over undifferentiated cells.
Figure 21B:
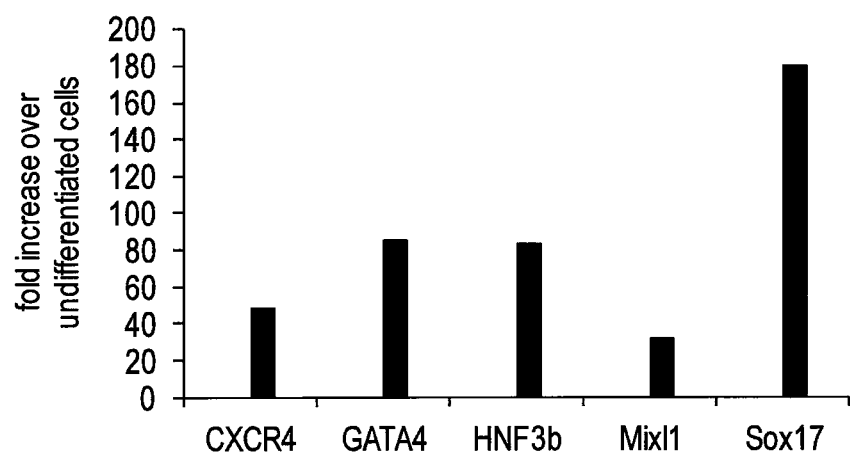
Figure 22A:
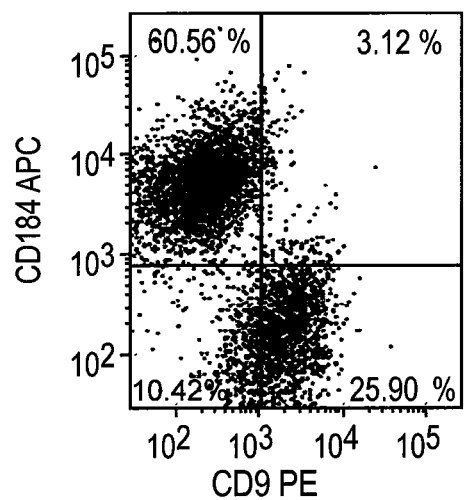
FIGS. 22A, 22B and 22C depict the expression of CXCR4 by FACS at day 5 for the human embryonic stem cell line H1 (FIG. 22A), the human embryonic stem cell line H7 (FIG. 22B), and the human embryonic stem cell line H9 (FIG. 22C) cultured on MATRIGEL (1:30 dilution) and exposed to the definitive endoderm differentiation protocol disclosed in Example 4.
Figure 22B:
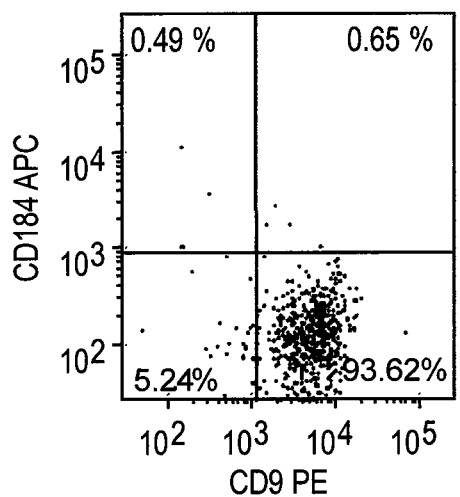
Figure 22C:
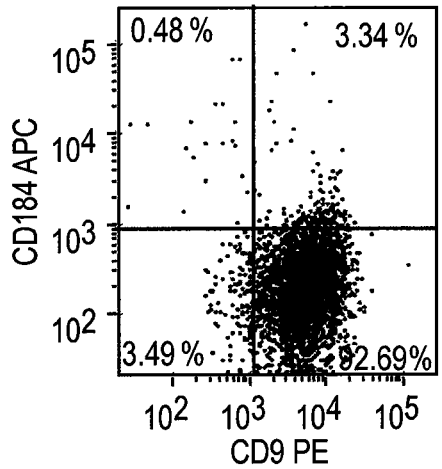

H-lines cultured on mouse feeders and exposed to the DE protocol resulted in a robust expression of DE markers and expression of CXCR4 by FACS (FIGS. 20A, 20B and 20C). There was also a significant decrease in expression of E-cadherin following treatment with the DE protocol. Lastly, the CXCR4+population also stained positive for CD117. FIGS. 21A and 21B shows a significant upregulation of definitive endoderm markers as compared to untreated H7 (FIG. 21A) and H9 cells (FIG. 21B).

Figure 23A:
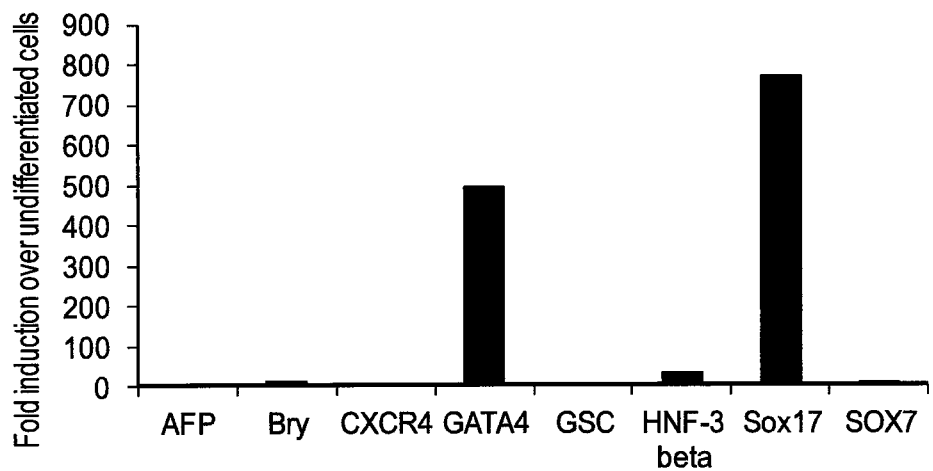
FIGS. 23A, 23B and 23C show the real-time PCR results of the expression of the indicated definitive endoderm markers in cultures of the human embryonic stem cell line H7 (FIG. 23A) and the human embryonic stem cell line H9 (FIG. 23B) and the human embryonic stem cell line H1 (FIG. 23C). Results are expressed as fold increase over undifferentiated cells. Cells were treated according to the methods disclosed in Example 4.
Figure 23B:
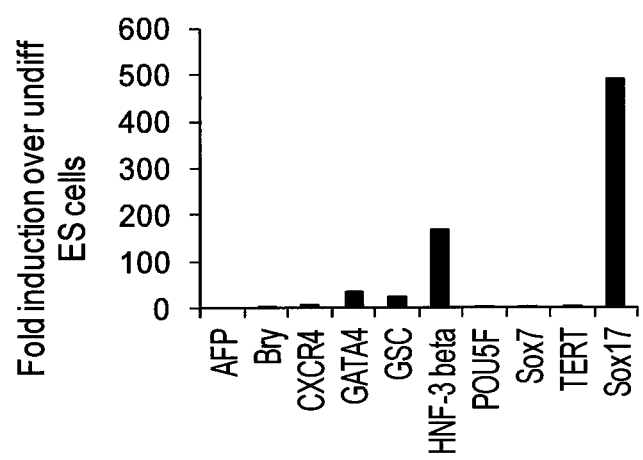
Figure 23C:
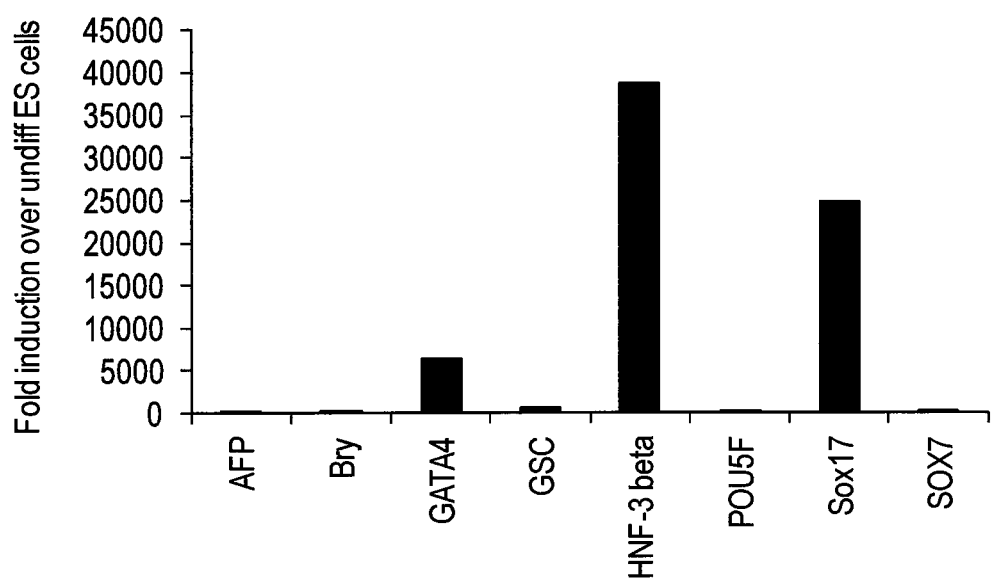

Unlike H-lines cultured on MEF feeders, H-lines cultured on MATRIGEL™ (1:30 dilution) and treated with the definitive endoderm protocol failed to show robust expression of definitive endoderm markers. In particular, the expression of CXCR4 by FACS and by real-time PCR was significantly lower for cells cultured on MATRIGEL™ as compared to cells cultured on mouse embryonic fibroblasts. Expression of definitive endoderm markers follows a general response pattern with H1 being greater than H9, which is greater than H7 (FIGS. 22A, 22B, 22C, 23A, 23B and 23C). From FIGS. 22A, 22B and 22C, H1 cells showed a significant increase in CXCR4 expression as compared to H7 and H9 lines. Note that in all cases, the expression of CXCR4 was lower for cells cultured on MATRIGEL™ (1:30 dilution) as compared to cells cultured on mouse embryonic fibroblasts. FIGS. 23A, 23B, and 23C shows the real-time PCR results showing that there was modest increase in upregulation of definitive endoderm markers in H7 (FIG. 23A) and H9 (FIG. 23B) lines. However, H1 (FIG.

23C) line showed a more robust upregulation of definitive endoderm markers as compared to H7 and H9 lines.

Example 17

Figure 24A:
FIGS. 24A and 24B depict phase contrast images of cultures of the human embryonic stem cell line H9 at passage 46 in the presence of 100 ng/ml of activin A (FIG. 24A) or 100 ng/ml of activin A+20 ng/ml Wnt-3a (FIG. 24B). Cells were treated for five days.
Figure 24B:
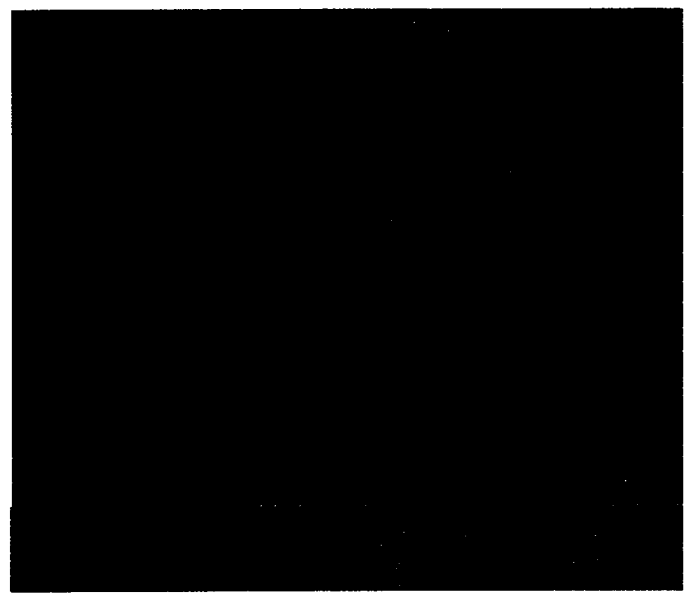
Figure 25A:
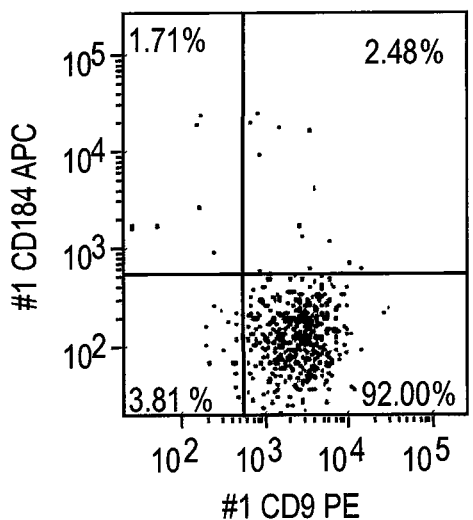
FIGS. 25A, 25B, 25C and 25D depict the expression of CXCR4 by FACS in cultures of the human embryonic stem cell line H7 at passage 44 (FIGS. 25A and 25B) and H9 at passage 46 (FIGS. 25C and 25D), following treatment according to the methods disclosed in Example 4.
Figure 25B:
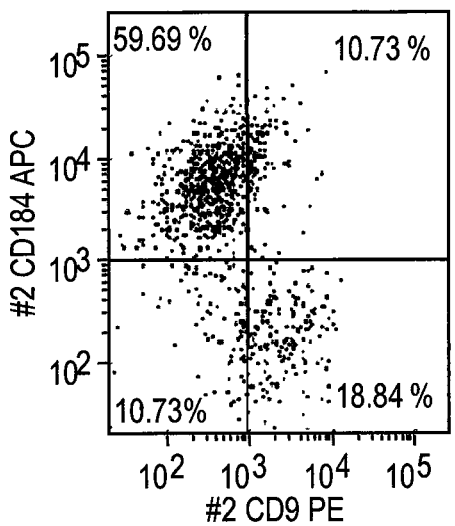
Figure 25C:
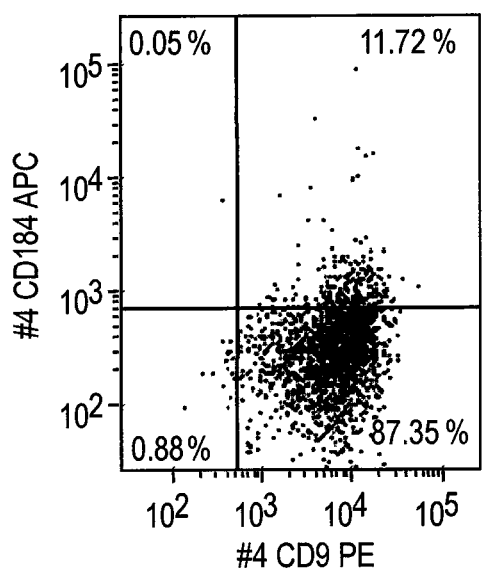
Figure 25D:
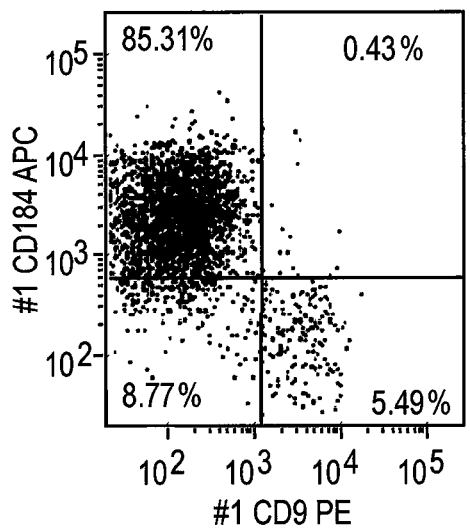
Figure 26A:
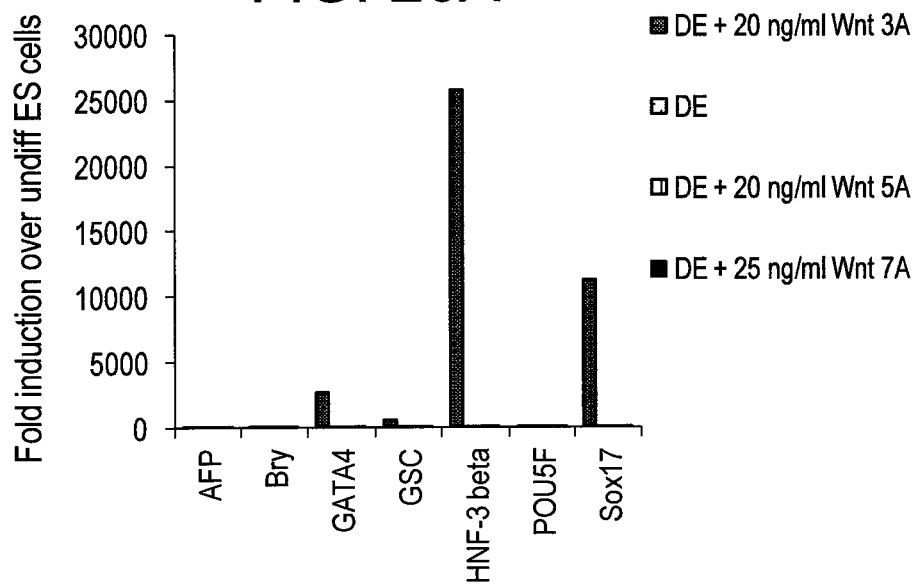
FIGS. 26A and 26B display the real-time PCR data for expression of the genes indicated in cultures of the human embryonic stem cell line H7 (FIG. 26A) and H9 (FIG. 26B). Cultures were treated with the differentiation protocol disclosed in Example 4. The effects of Wnt agonists Wnt-3a (20 ng/ml), Wnt-5a (20 ng/ml) and Wnt-7a (20 ng/ml) were also tested, as indicated in the panels. Cells were treated for 5 days. Results are expressed as fold increase over undifferentiated cells.
Figure 26B:
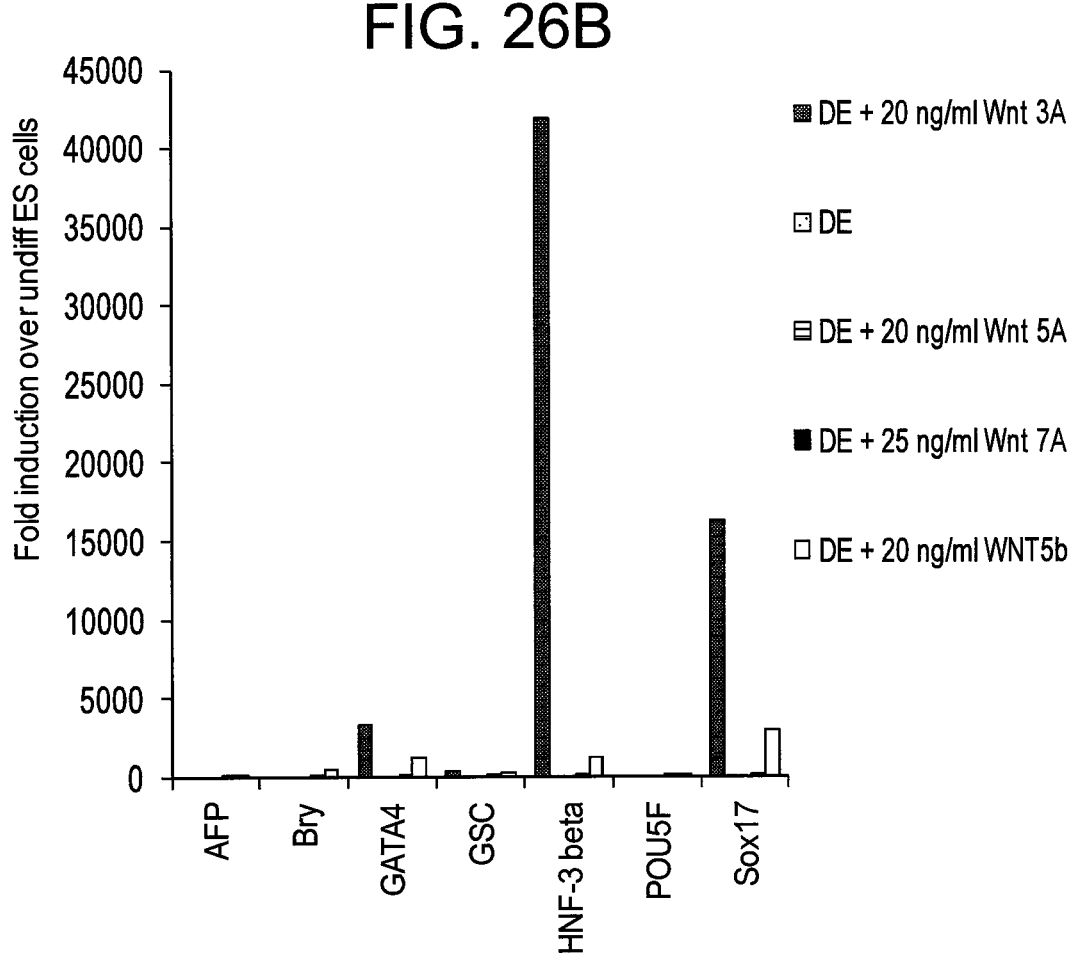

Differentiation of Human Embryonic Stem Cells Cultured on Tissue Culture Substrate Coated with MATRIGEL™ to Definitive Endoderm (DE)-Role of Wnt Ligands H7P44 and H9P46 embryonic stem cells were cultured on MATRIGEL™ (1:10 dilution) coated dishes and exposed to DMEM/F12 medium supplemented with 0.5% FBS, and 100 ng/ml activin A (R&D Systems, MN) for two days followed by treatment with DMEM/F12 media supplemented with 2% FBS and 100 ng/ml activin A (AA) for an additional three days. In some of the cultures 20 ng/ml Wnt-3a (Catalog #1324-WN-002, R&D Systems, MN), 20 ng/ml Wnt-5a (Catalog #654-WN-010, R&D Systems, MN), 25 ng/ml Wnt-7a (Catalog #3008-WN-025, R&D Systems, MN), or 25 ng/ml Wnt-5b (Catalog #3006-WN-025, R&D Systems, MN) was added throughout the five day treatment. FIGS. 24A and 24B depicts phase contrast images of H9P46 definitive endoderm culture in the presence of high concentration of (a) AA or (b) AA+20 ng/ml Wnt-3a. FIGS. 25A, 25B, 25C and 25D depicts the expression of CXCR4 by FACS at day 5 for H7P44, and H9P46 lines cultured on MATRIGEL™ (1:30 dilution) and exposed to the DE protocol+Wnt-3a (FIGS. 25B and 25D) and −Wnt-3a (FIGS. 25A and C). Presence of Wnt-3a in DE cultures resulted in robust expression of CXCR4 (CD184) as compared to DE cultures treated with low serum plus high concentration of AA. FIGS. 26A and 26B displays the real-time PCR data for a) H7 and b) H9 cultures treated with low serum+AA+/−Wnt ligands. For both H-lines, addition of WNT-3a resulted in significant upregulation of definitive endoderm markers. In contrast, Wnt 5a, Wnt-5b and Wnt-7a had minimal impact on expression of definitive endoderm markers.

Example 18

Figure 27A:
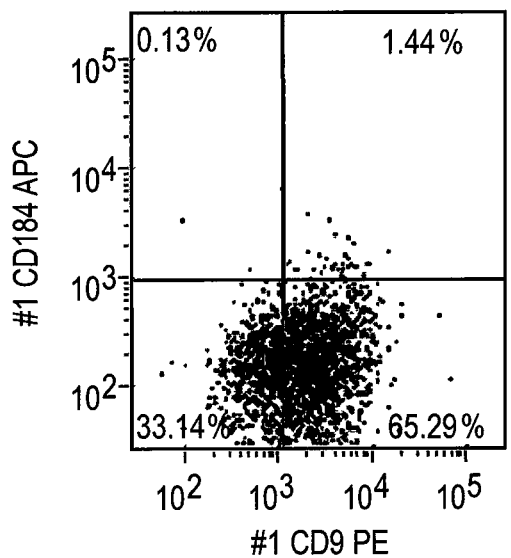
FIGS. 27A, 27B, 27C and 27D depict the expression of CXCR4 in cultures of the human embryonic stem cell line H9 at passage 46, by FACS at five days post treatment.
Figure 27B:
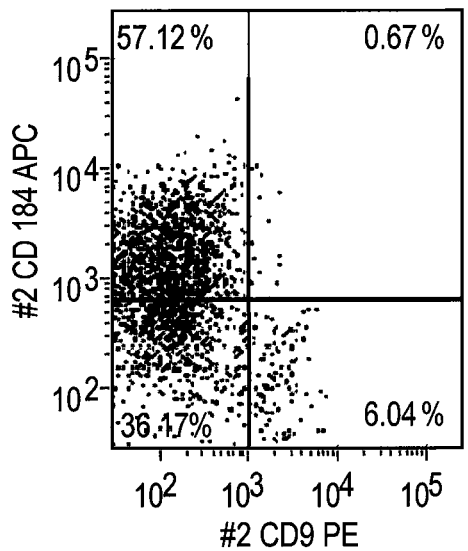
Figure 27C:
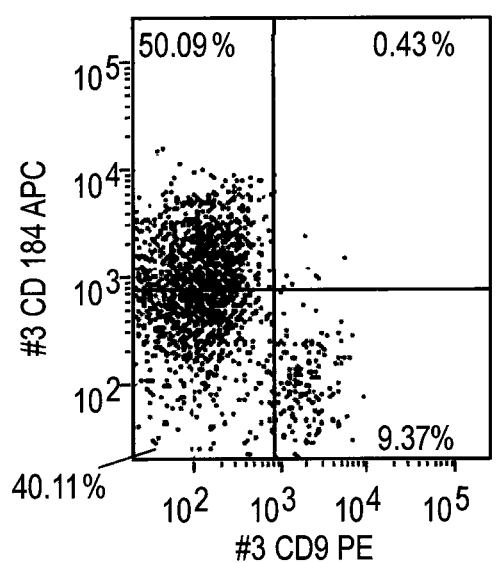
Figure 27D:
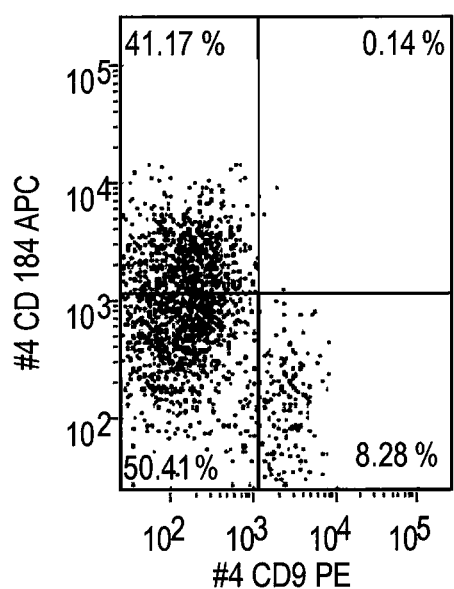
Figure 28A:
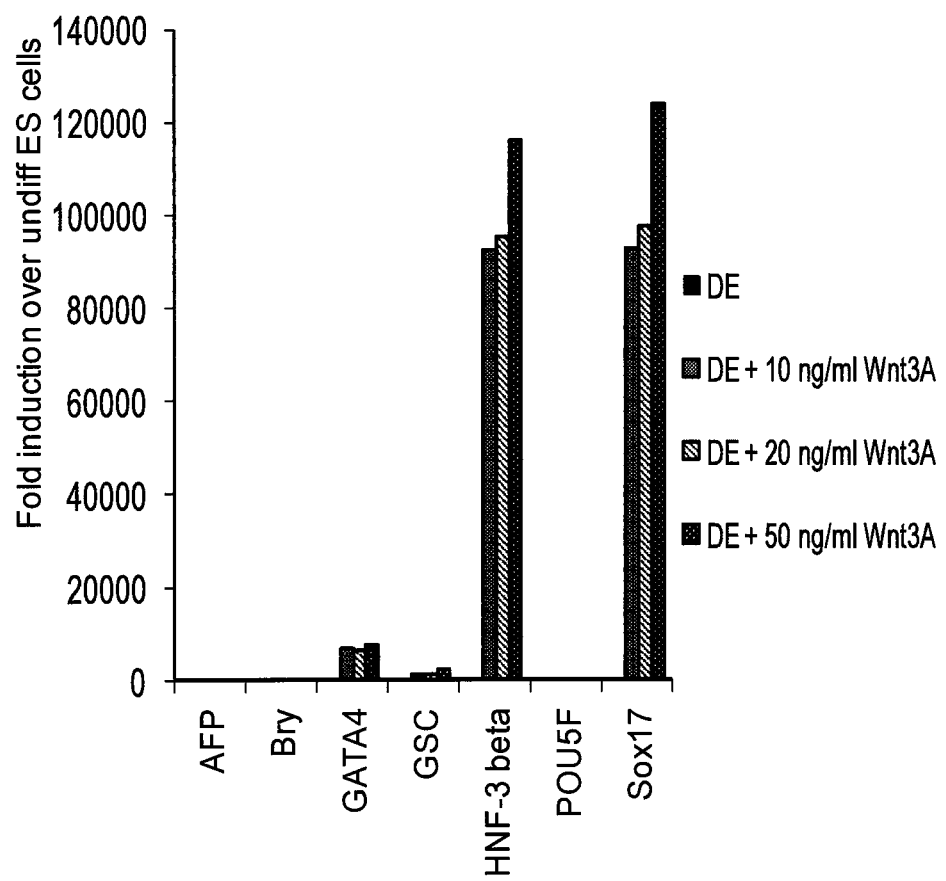
FIGS. 28A, 28B and 28C depict the expression of definitive markers indicated in cultures of the human embryonic stem cell line H9 after 5 days of treatment. Results are shown as fold increase in expression over untreated cells, as determined by real-time PCR.

Differentiation of Human Embryonic Stem Cells Cultured on Tissue Culture Substrate Coated with MATRIGEL™ to Definitive Endoderm: Effective Dose of Wnt-3a H9P46 embryonic stem cells were cultured on MATRIGEL™ coated dishes (1:10 dilution) and exposed to DMEM/F12 medium supplemented with 0.5% FBS, 100 ng/ml Activin A (AA), and 10-50 ng/ml WNt-3a (R&D Systems, MN) for two days followed by treatment with DMEM/F12 media supplemented with 2% FBS, 100 ng/ml activin A (AA), and 10-50 ng/ml Wnt-3a for an additional three days. Control cultures were not treated with Wnt-3a. FIG. 27A depicts the expression of CXCR4 by FACS at day 5 in the absence of Wnt-3a, b) 10 ng/ml Wnt-3a, c) 20 ng/ml Wnt-3a and d) 50 ng/ml Wnt-3a. In the absence of Wnt-3a the expression of CXCR4 was very low. In contrast, addition of 10-50 ng/ml of Wnt-3a significantly increased the number of CXCR4 positive cells. Furthermore, addition of 10 ng/ml of Wnt-3a was as effective as addition of 50 ng/ml of Wnt-3a. Real-time PCR results (FIG. 28A) also confirm this finding.

Figure 28B:
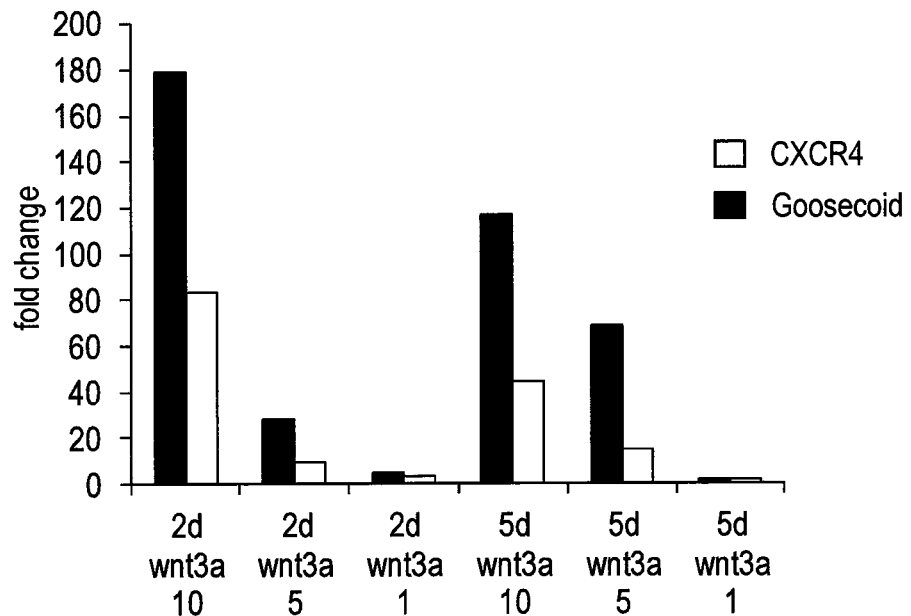
Figure 28C:
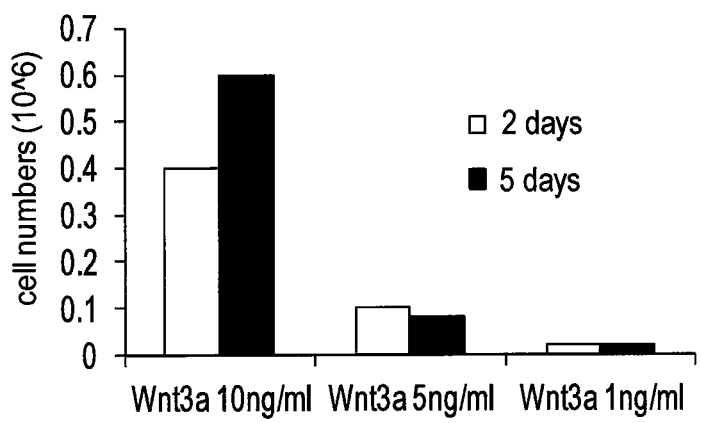

In a separate study, H9p52 cells were plated on 1:30 low growth factor MATRIGEL™. For the first 2 days of the DE protocol a range of Wnt3A doses was used: 10 ng/ml, 5 ng/ml and 1 ng/ml. FIG. 28B shows PCR analysis of the DE markers after 5 days of treatment. The number of cells at the end of the experiment is noted in FIG. 28C. This indicates that cells are proliferating when higher doses of Wnt-3a are used. Extension to 5 days of Wnt3a treatment (5 D) had little effect on DE markers by PCR and did not significantly increase cell numbers (FIG. 28C). These data indicate that 10 ng/ml Wnt3a for 2 days is sufficient to reach optimal cell expansion and definitive endoderm differentiation.

Example 19

Figure 29E:
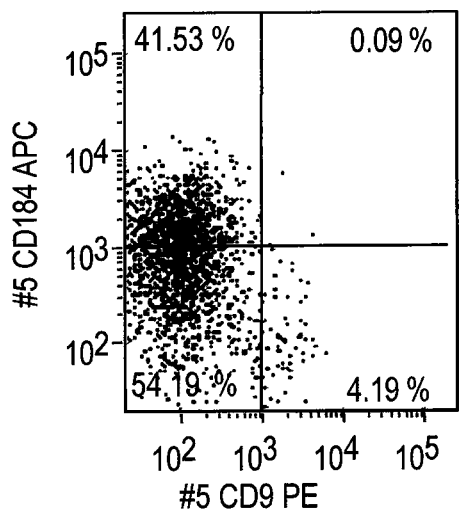
Figure 29F:
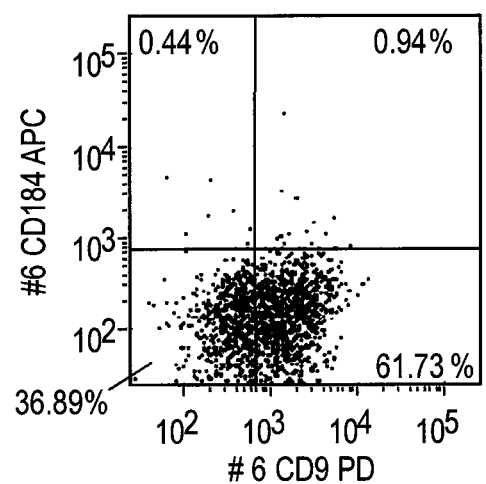
Figure 29G:
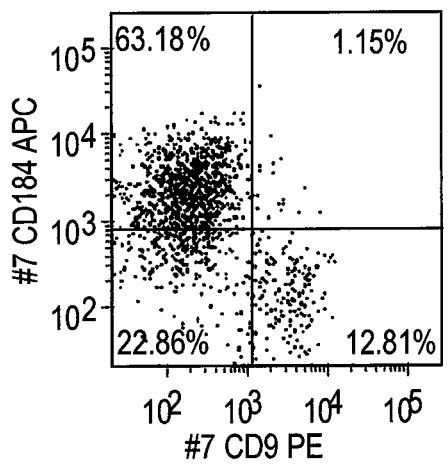
Figure 29H:
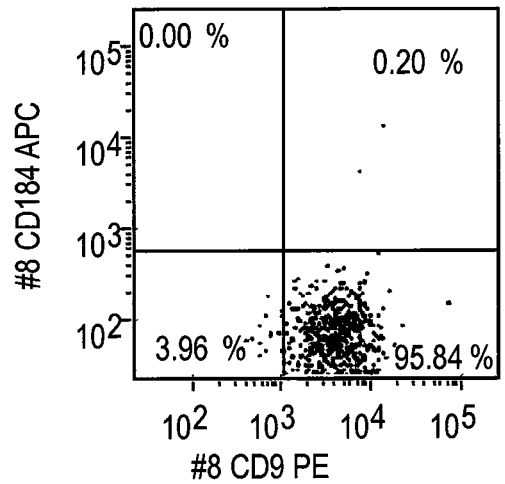

Differentiation of Human Embryonic Stem Cells Cultured on Tissue Culture Substrate Coated with MATRIGEL™ to Definitive Endoderm (DE)-Effect of GSK-3B Inhibitor In order to confirm that the effect of Wnt-3a was through the Wnt pathway, a GSK-3 inhibitor was used to activate the downstream targets of Wnt, such as beta catenin. H9P46-P48 embryonic stem cells were cultured on MATRIGEL™ coated dishes (1:10 dilution) and exposed to DMEM/F12 medium supplemented with 0.5% FBS, 100 ng/ml activin-A (AA), and 10-1000 nM GSK-3B inhibitor IX (Catalog #361550, Calbiochem, CA) for two days followed by treatment with DMEM/F12 media supplemented with 2% FBS, 100 ng/ml activin A (AA), and 0-1000 nM GSK-3B inhibitor IX (Catalog #361550, Calbiochem, CA) for an additional three days. Control cultures were treated with low serum plus high dose of activin A+/−Wnt-3a. FIG. 29A depicts the expression of CXCR4 by FACS at day 5 in the absence of Wnt-3a or GSK-3B inhibitor, b)+20 ng/ml Wnt-3a, c)+1000 nM GSK-3B inhibitor IX, d)+500 nM GSK-3B inhibitor IX, e)+100 nM GSK-3B inhibitor IX, f)+10 nM GSK-3B inhibitor IX, g)+100 nM GSK-3B inhibitor IX for days 1-2, and h)+10 nM GSK-3B inhibitor IX for days 1-2.

Figure 30A:
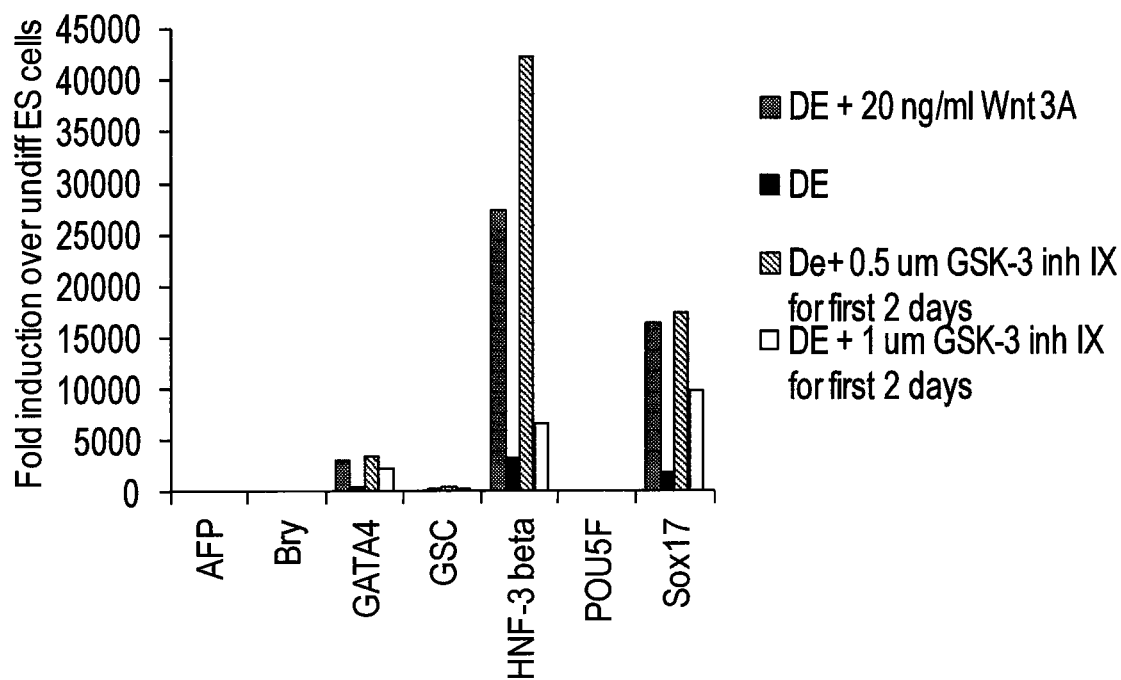
Figure 30B:
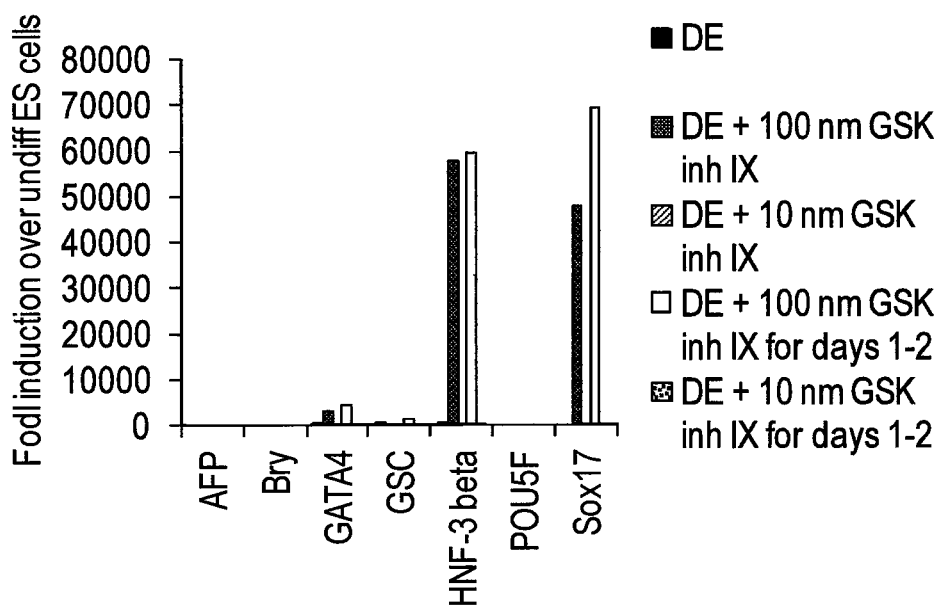
FIG. 30B shows data obtained from the human embryonic cell line H9 at passage number 46, treated to the definitive endoderm protocol disclosed in Example 4, containing the Wnt-3a or GSK-3B inhibitor at the concentrations and the times indicated.

In the absence of Wnt-3a or at 10 nm GSK-3B inhibitor the expression of CXCR4 was very low. In contrast, addition of 20 ng/ml of Wnt-3a or 100-1000 nM GSK-3B inhibitor significantly increased the number of CXCR4 positive cells. Furthermore, addition of 100 nM GSK-3B inhibitor for days 1-2 was as effective as addition of 100 nM GSK-3B inhibitor for the entire five-day period. FIGS. 30A and 30B depicts the gene expression of definitive endoderm markers for (FIG. 30A) H9P48 cells and (FIG. 30B) H9P46 cells.

FIG. 16 depicts the outline of a differentiation protocol in this invention, where embryonic stem cells are differentiated into definitive endoderm in a feeder free system.

Example 20

Figure 31A:
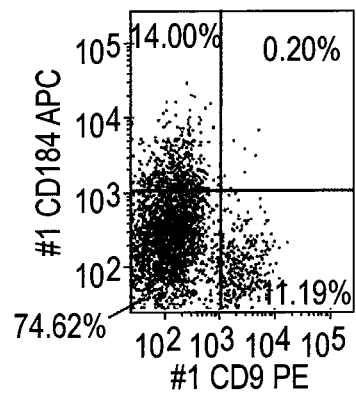
FIGS. 31A, 31B, 31C, 31D, 31E and 31F depict the expression of CXCR4 by FACS for embryonic stem cell lines used in the present invention.
Figure 31B:
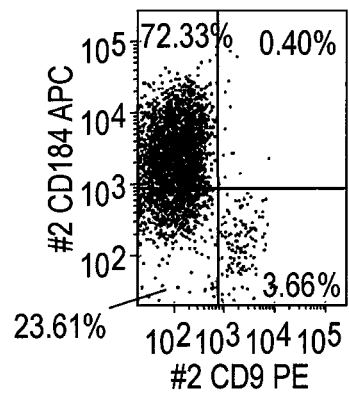
Figure 31C:
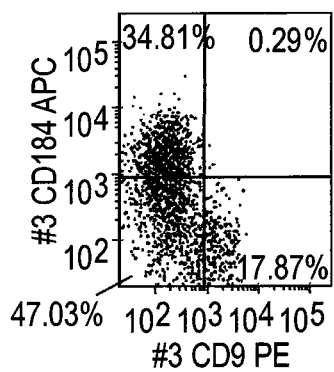
Figure 31D:
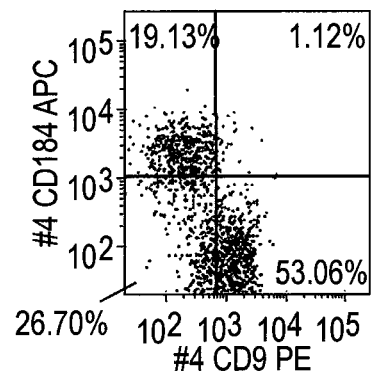
Figure 31E:
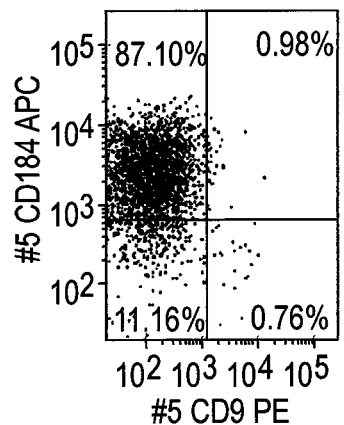
Figure 31F:
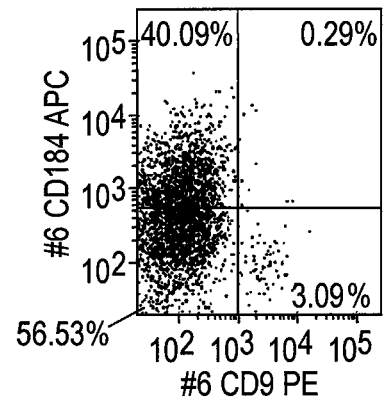
Figure 32A:
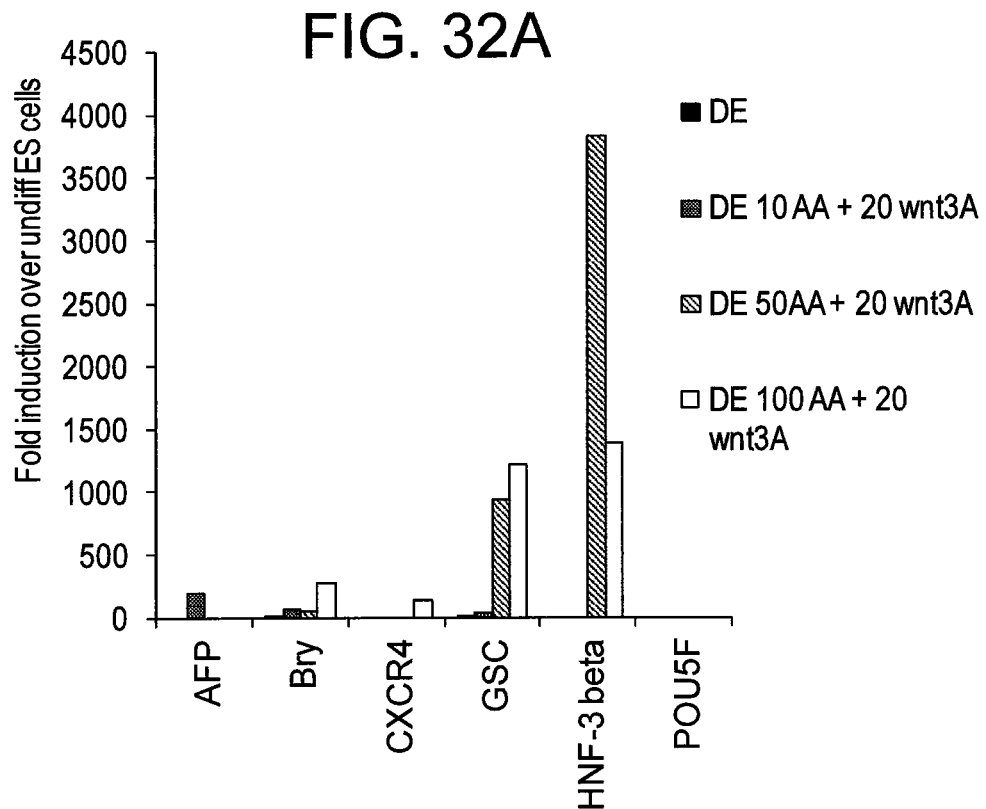
Figure 32B:
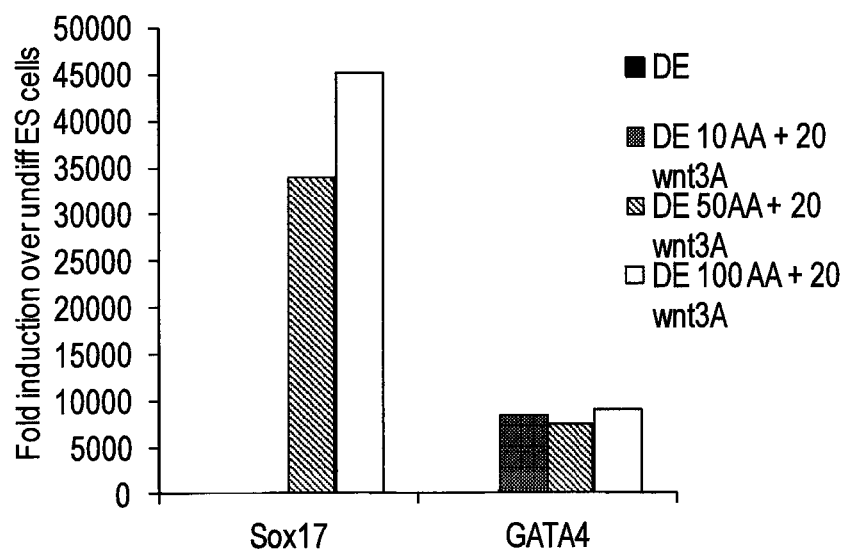
Figure 33A:
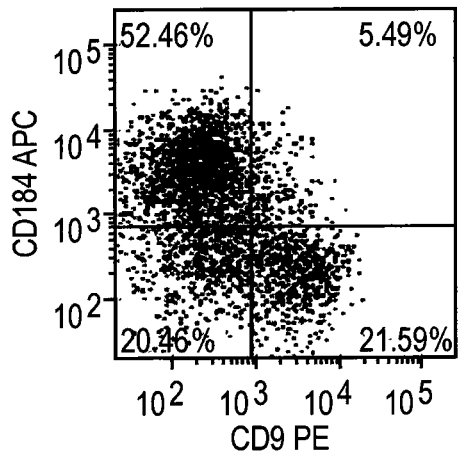
FIGS. 33A, 33B, 33C, 33D, 33E and 33F depict the expression of CXCR4 by FACS for the embryonic stem cell line H9 at passage 53. Data was obtained 5 days post treatment. Cells were treated with the following conditions.
Figure 33B:
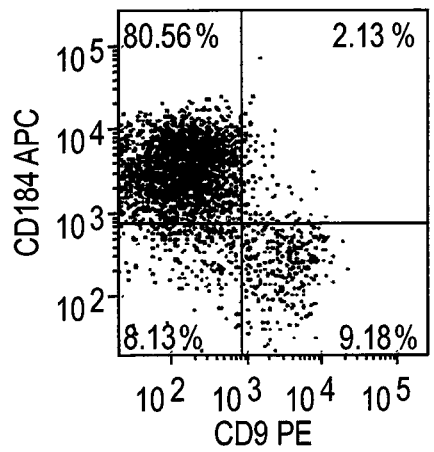
Figure 33C:
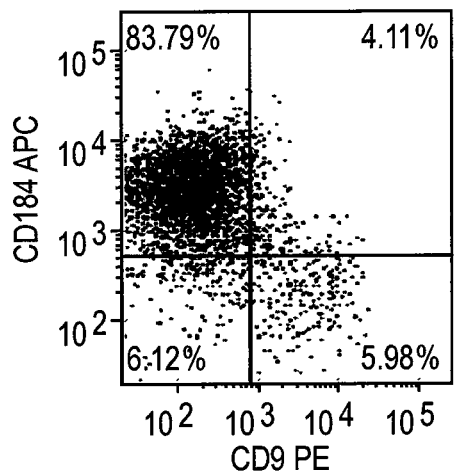
Figure 33D:
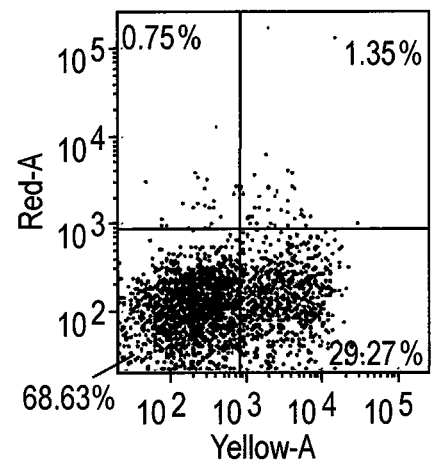
Figure 33E:
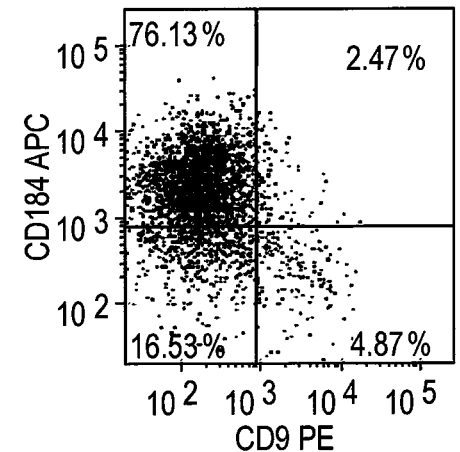
Figure 33F:
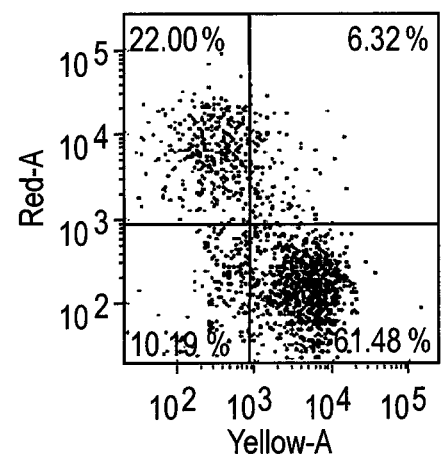

Differentiation of Human Embryonic Stem Cells Cultured on Tissue Culture Substrate Coated with MATRIGEL™ to Definitive Endoderm (DE)-Effective Dose of Activin-A in the Presence of GSK-3B Inhibitor or Wnt-3A H9P49 and H1P46 embryonic stem cells were cultured on MATRIGEL™ coated dishes (1:10 dilution) and exposed to DMEM/F12 medium supplemented with 0.5% FBS, 10-100 ng/ml activin A (AA), and 100 nM GSK-3B inhibitor IX (Catalog #361550, Calbiochem, CA) or 20 ng/ml Wnt-3a for two days followed by treatment with DMEM/F12 media supplemented with 2% FBS, 10-100 ng/ml activin A (AA) for an additional three days. Control cultures were treated with low serum plus 100 ng/ml of activin A. FIGS. 31A, 31B, 31C, 31D, 31E and 31F depicts the expression of CXCR4 by FACS for H9P49 and H1P46 at day 5 with a) 10 ng/ml activin A for all five days plus 20 ng/ml of Wnt-3A for the first two days, b) 100 ng/ml activin A for all five days plus 20 ng/ml of Wnt-3A for the first two days c) 100 ng/ml activin A for all five days plus 100 nM of GSK-3B inhibitor IX for the first two days d) 10 ng/ml activin A for all five days plus 100 nM of GSK-3B inhibitor IX for the first two days, e) 100 ng/ml activin A for all five days plus 20 ng/ml of Wnt-3A for the first two days, and f) 10 ng/ml activin A for all five days plus 20 ng/ml of Wnt-3A for the first two days. FIGS. 31A, 31B, 31C and 31D is for H9P49 cells and FIGS. 31E and 31F is for H1P46 cells. FIGS. 32A and 32B depicts the gene expression of definitive endoderm markers for H9P49 cultures treated with 10, 50, or 100 ng/ml of activin A plus 20 ng/ml of Wnt-3a: FIG. 32A: expression of AFP, Bry, CXCR4, GSC, HNF-3B, and POU5F (Oct-4) and FIG. 32B: SOX-17 and GATA4. This does not add up—It appears to be a problem with figure numbers or it is a cut and paste problem. It appears that robust expression of definitive endoderm markers can be obtained by using 50 ng/ml of AA+20 ng/ml of Wnt-3A or 100 nM GSK-3B inhibitor IX. Lower doses of activin A lead to formation of extraembryonic endoderm.

Example 21

Figure 34A:
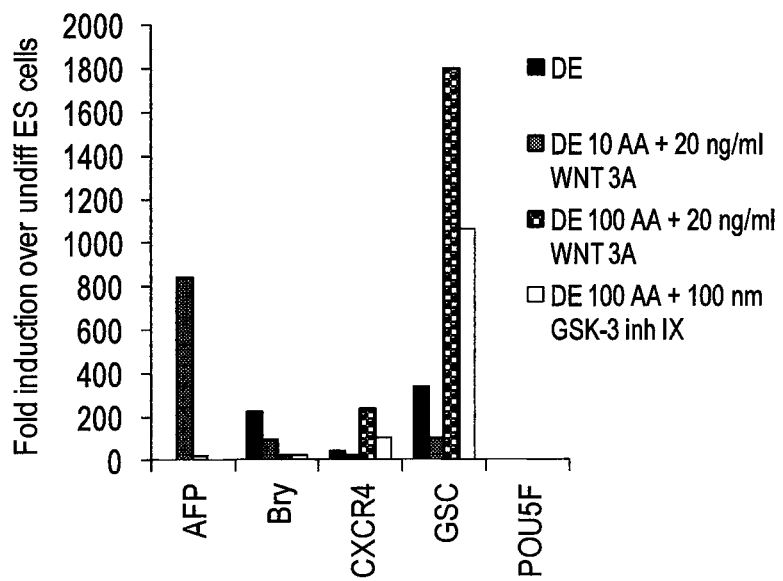
FIGS. 34A and 34B depict the gene expression of definitive endoderm markers, as determined by real-time PCR for cultures of the human embryonic stem cell line H1 at passage 46, treated with 10 or 100 ng/ml of activin A plus 20 ng/ml of Wnt-3a or 100 NM GSK-3B inhibitor.
Figure 34B:
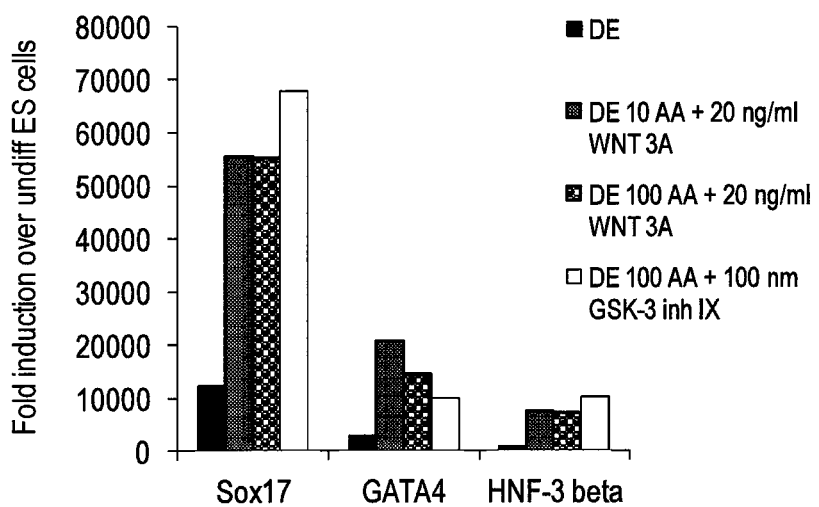
Figure 35A:
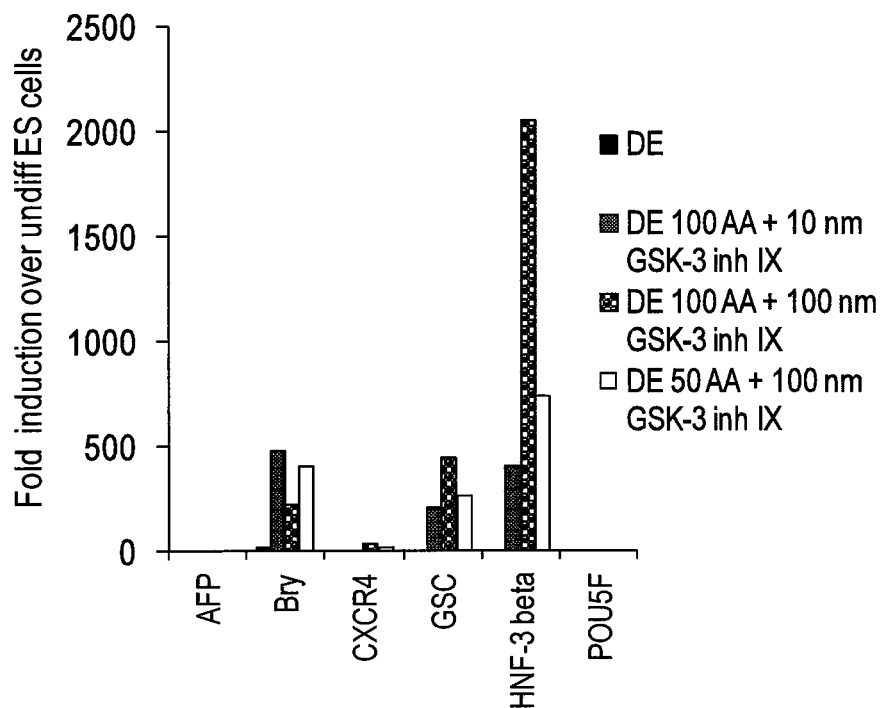
FIGS. 35A and 35B depicts the gene expression of definitive endoderm markers, as determined by real-time PCR for cultures of the human embryonic stem cell line H9 at passage 49, treated with 50 or 100 ng/ml of activin A plus 10 or 100 nM GSK-3B inhibitor.
Figure 35B:
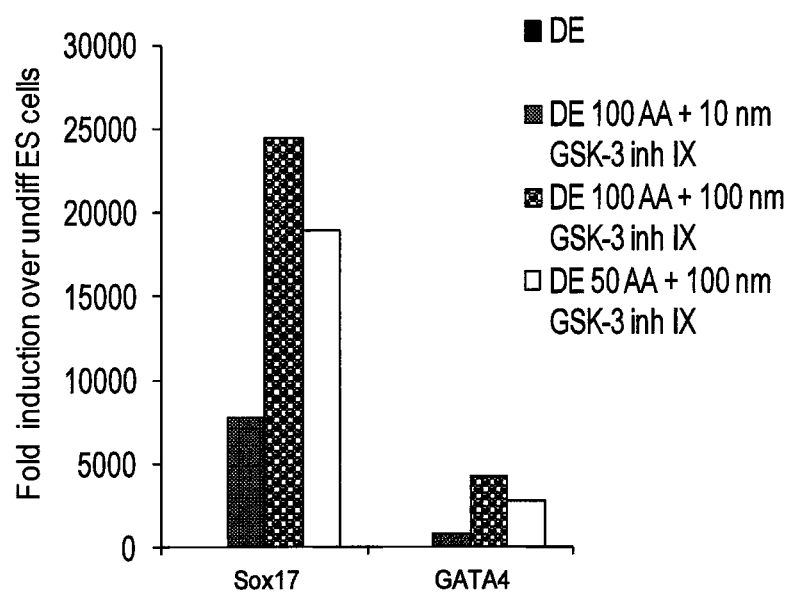
Figure 36A:
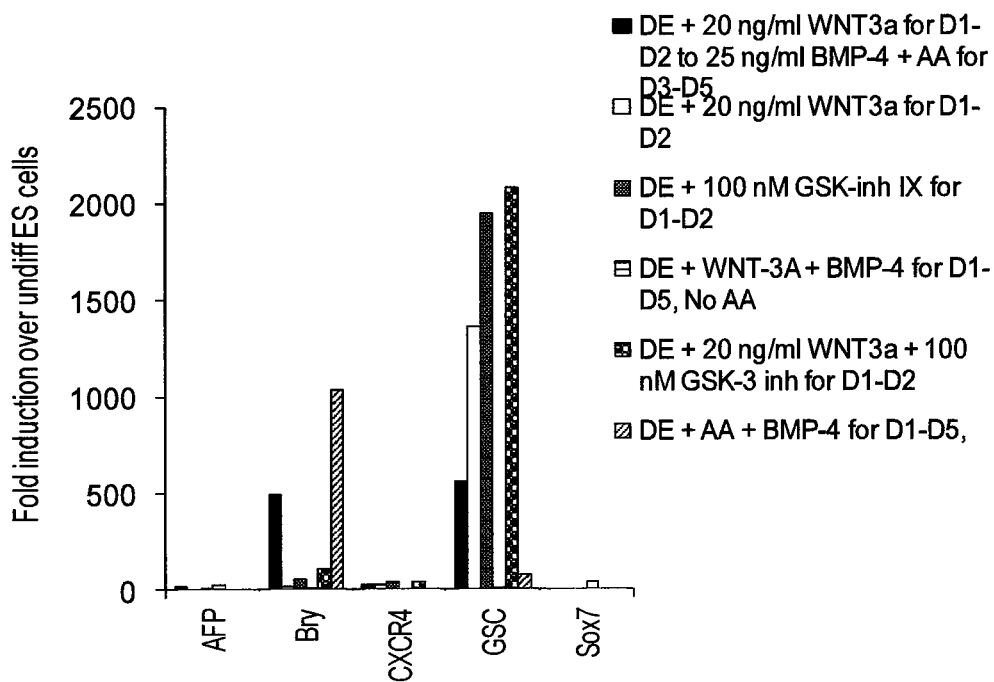
FIGS. 36A and 36B depicts the gene expression of definitive endoderm markers, as determined by real-time PCR for cultures of the human embryonic stem cell line H9 at passage 53, treated with combinations of activin A, Wnt-3a, GSK-3 inhibitor, and BMP-4, for five days.
Figure 36B:
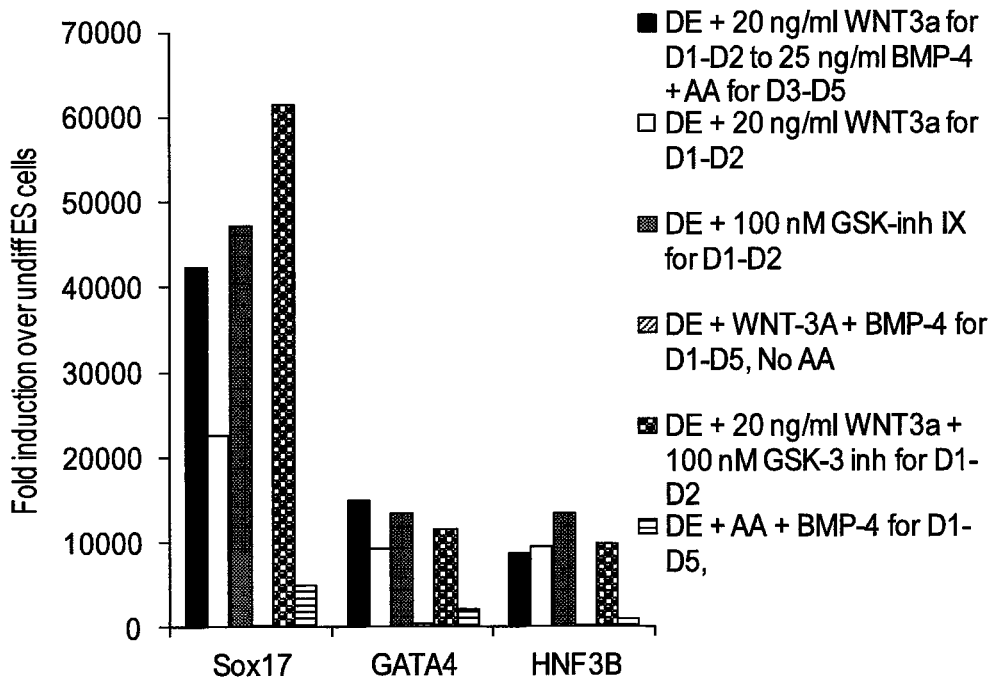

Differentiation of Human Embryonic Stem Cells Cultured on Tissue Culture Substrate Coated with MATRIGEL™ to Definitive Endoderm (DE)-Combination of Wnt-3a and GSK-3B Inhibitor H9P53 embryonic stem cells were cultured on MATRIGEL™ coated dishes (1:30 dilution) and exposed to DMEM/F12 medium supplemented with 0.5% FBS, 100 ng/ml activin A (AA), and 100 nM GSK-3B inhibitor IX (Catalog #361550, Calbiochem, CA)+/−20 ng/ml Wnt-3a for two days followed by treatment with DMEM/F12 media supplemented with 2% FBS, 10-100 ng/ml activin-A (AA) for an additional three days. In parallel, H9P53 cultures were treated with 25 ng/ml BMP-4 (Catalog #314-BP-010, R&D Systems, MN)+/−20 ng/ml Wnt-3A+/−100 ng/ml activin A. Control cultures were treated with low serum plus 100 ng/ml of activin A. FIGS. 33A, 33B, 33C, 33D, 33E, and 33F depicts the expression of CXCR4 by FACS at day 5 with a) 100 ng/ml activin A for all five days plus 20 ng/ml of Wnt-3A for the first two days and 25 ng/ml BMP-4 for days 3-5, b) 100 ng/ml activin A for all five days plus 20 ng/ml of Wnt-3A for the first two days c) 100 ng/ml activin A for all five days plus 100 nM of GSK-3B inhibitor IX for the first two days d) 20 ng/ml Wnt-3a+25 ng/ml BMP-4 for all five days, e) 100 ng/ml activin A for all five days plus 20 ng/ml of Wnt-3A+100 nm GSK-3B inhibitor IX for the first two days, and f) 100 ng/ml activin A+25 ng/ml BMP-4 for all five days. FIGS. 34A and 34B depicts the gene expression of definitive endoderm markers, as determined by real-time PCR for cultures of the human embryonic stem cell line H1 at passage 46, treated with 10 or 100 ng/ml of activin A plus 20 ng/ml of Wnt-3a or 100 NM GSK-3B inhibitor: panel (a): expression of AFP, Bry, CXCR4, GSC, and POU5F (Oct-4) and panel (b): SOX-17, HNF-3B, and GATA4. Results are expressed as fold increase over untreated cells. FIGS. 35A and 35B depicts the gene expression of definitive endoderm markers, as determined by real-time PCR for cultures of the human embryonic stem cell line H9 at passage 49, treated with 50 or 100 ng/ml of activin A plus 10 or 100 nM GSK-3B inhibitor: panel (a): expression of AFP, Bry, CXCR4, GSC, HNF-3B, and POU5F (Oct-4) and panel (b): SOX-17 and GATA4. Results are expressed as fold increase over untreated cells. FIGS. 36A and 36B depicts the gene expression of definitive endoderm markers for H9P53 culture treated with combinations of activin A, Wnt-3a, GSK-3 inhibitor, and BMP-4: a) expression of AFP, Bry, CXCR4, GSC, HNF-3B, and SOX7 and b) SOX-17, HNF-3B and GATA4. Addition of BMP-4 to the DE protocol appears to induce formation of mesoderm marker BRY and combination of Wnt-3A and GSK-4B inhibitor do not lead to significant upregulation of definitive endoderm markers as compared to addition of each agent by itself in the presence of activin A.

Example 22

Differentiation of Human Embryonic Stem Cells Cultured on MEFs to Definitive Endoderm (DE)-Combination of Wnt-3a, Activin a, Wnt-5a, BMP-2, BMP-4, BMP-6, BMP-7, IL-4, and SDF-1 in Low Serum H9P44 cells were plated onto 6 well plates previously coated with mitomycin treated mouse embryonic fibroblasts (MEF). Cells were grown until 70 to 80% confluency in ES cell medium consisting of DMEM/F12 (Invitrogen/GIBCO) supplemented with 20% knockout serum replacement, 100 nM MEM nonessential amino acids, 0.5 mM beta-mercaptoethanol, 2 mM L-glutamine (all from Invitrogen/GIBCO) and 8 ng/ml human basic fibroblast growth factor (bFGF) (R&D Systems).

For DE formation, cells were treated in the presence or absence of Activin A (100 ng/ml) in addition to other growth factors detailed below. Growth factors were added to increasing concentration of FBS in a stepwise manner as indicated in the following regimen:
Day 0: 0% FBS in DMEM/F12
Day 1: 0.5% FBS in DMEM/F12
Day 2: 2% FBS in DMEM/F12.
Day 3: Cells were harvested for FACS analysis and RT-PCR.
All growth factors were purchased from R&D Systems, MN. A detailed description and concentration of growth factors for each treatment group is shown below.
1. Control—No growth factor added
2. Activin A (100 ng/ml)
3. Activin A (100 ng/ml)+Wnt-3a (10 ng/ml)+Wnt5a (10 ng/ml)
4. Activin A (100 ng/ml)+Wnt-3a (10 ng/ml)+Wnt5a (10 ng/ml)+BMP2 (100 ng/ml)
5. Activin A (100 ng/ml)+BMP-4 (100 ng/ml)
6. Activin A (100 ng/ml)+BMP-6 (100 ng/ml)
7. Activin A (100 ng/ml)+BMP-7 (100 ng/ml)
8. Activin A (100 ng/ml)+BMP-4 (100 ng/ml)+BMP-6 (100 ng/ml)+BMP-7 (100 ng/ml)
9. IL-4 (10 ng/ml)
10. SDF1a (20 ng/ml)
11. Activin A (100 ng/ml)+IL-4 (10 ng/ml)+SDF1a (20 ng/ml)
12. BMP2 (100 ng/ml)+BMP-4 (100 ng/ml)+BMP-6 (100 ng/ml)+BMP-7 (100 ng/ml)
13. Activin A (100 ng/ml) BMP-2 (100 ng/ml)+BMP-4 (100 ng/ml)+BMP-6 (100 ng/ml)+BMP-7 (100 ng/ml)
14. Activin A (100 ng/ml)+IL-4 (10 ng/ml)
15. Activin A (100 ng/ml)+(SDF1a (20 ng/ml)
16. Activin A (100 ng/ml)+Wnt-3a (10 ng/ml)+Wnt-5a (10 ng/ml)+Wnt-7a (10 ng/ml)
17. Activin A (100 ng/ml)+IL-4 (10 ng/ml)+SDF1a (20 ng/ml)+BMP-4 (100 ng/ml)

Results:

Cells were harvested on Day 3 of DE protocol treatment. For analysis, an aliquot of treated cells was used for RNA preparation for RT-PCR and the rest of cells used for FACS analysis. The frequency (%) of CXCR4 is shown in FIG. 37. Addition of the above growth factor(s) did not enhance expression of CXCR4 above treatment with 100 ng/ml AA in low serum.

For RT-PCR analysis, cells were analyzed for expression of selected panel of definitive endoderm markers. Results shown were calibrated against cells grown in the base medium but not treated with Activin A or any of the other growth factors. In agreement with the FACS data, Table V shows that there was no significant upregulation of definitive endoderm markers by addition of growth factors, such as Wnt-3a to cultures treated with a high dose of activin A in low serum. This is in contrast to the previous examples showing a significant increase in DE markers for ES cells cultured on feeder-free conditions in the presence of activin A, WNT3A, and low serum.

Example 23

Differentiation of Human Embryonic Stem Cells Cultured on Tissue Culture Substrate Coated with MATRIGEL™ or Human Fibronectin to Definitive Endoderm (DE)

Figure 38A:
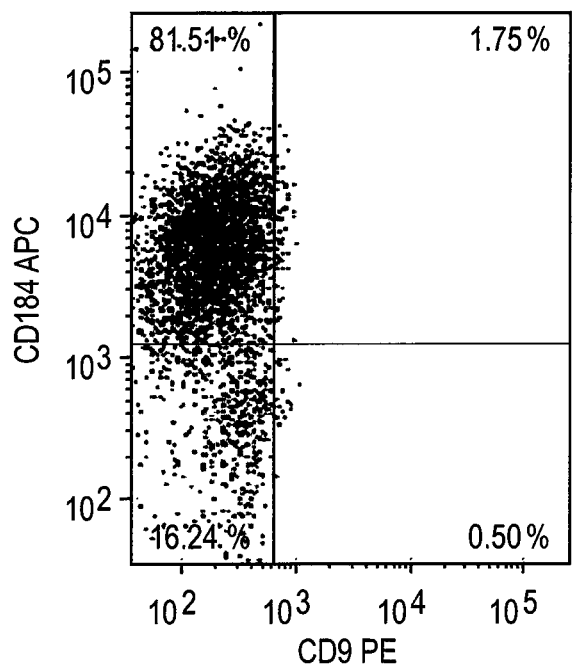
FIGS. 38A and 38B depict the expression of definitive endoderm markers as determined by FACS in cultures of the human embryonic stem cell line H9, cultured on fibronectin (FIG. 38A) or MATRIGEL™ (FIG. 38B).
Figure 38B:
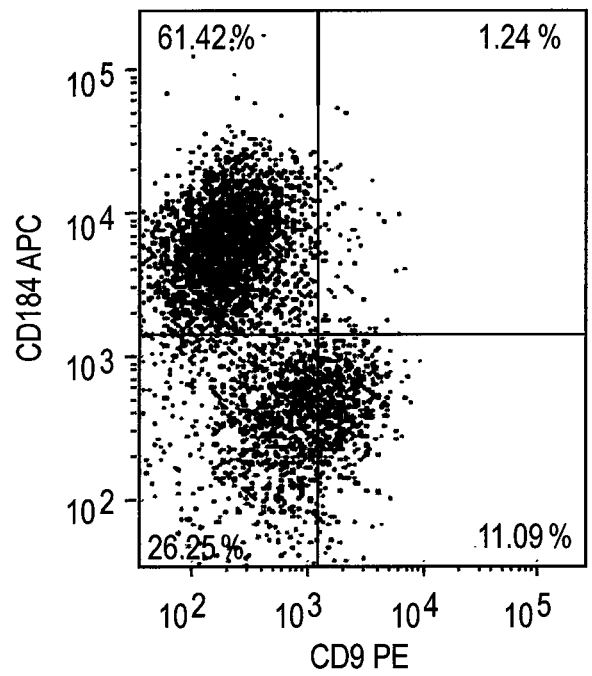

H9P55 cells were grown and differentiated on human fibronectin or regular growth factor MATRIGEL™ (BD Biosciences). 1 ml of DMEM/F12 (Invitrogen/GIBCO) containing 1 ug/ml of human fibronectin (R&D systems, MN) was added to each well of 6 well tissue culture treated dish. Alternatively, regular growth factor MATRIGEL™ was diluted 1:10 in DMEM/F12 and 1 ml of diluted MATRIGEL™ was added to each well of 6 well tissue culture treated dish. Cells were passed with collagenase. After cells reached 80% confluency, there were treated as follows: 2 days 0.5% FBS containing 10 ng/ml mouse recombinant Wnt3a (R&D) and 100 ng/ml Activin A (R&D). This was followed by 3 days 2% FBS plus 100 ng/ml Activin A. FIGS. 38A and 38B depict the expression of CXCR4 by embryonic stem cells cultured on fibronectin and MATRIGEL, respectively. Real-time PCR results (FIG. 39) confirm that formation of definitive endoderm was equivalent on fibronectin and MATRIGEL™ coated plates.

Example 24

Differentiation of Human Embryonic Stem Cells Cultured on Tissue Culture Substrate Coated with Varying Concentrations of MATRIGEL™ to Definitive Endoderm H9 cultures at approximately 60 to 70% confluency were exposed to DMEM/F12 medium supplemented with 0.5% FBS, 20 ng/ml Wnt-3a and 100 ng/ml activin A for two days followed by treatment with DMEM/F12 media supplemented with 2% FBS, 20 ng/ml Wnt-3a and 100 ng/ml activin A (AA) for an additional three days. H9 cells were cultured on plates coated with regular MATRIGEL at a 1:60 to 1:10 dilution. The plates were coated with MATRIGEL for 1 hr at room temperature.

Figure 40:
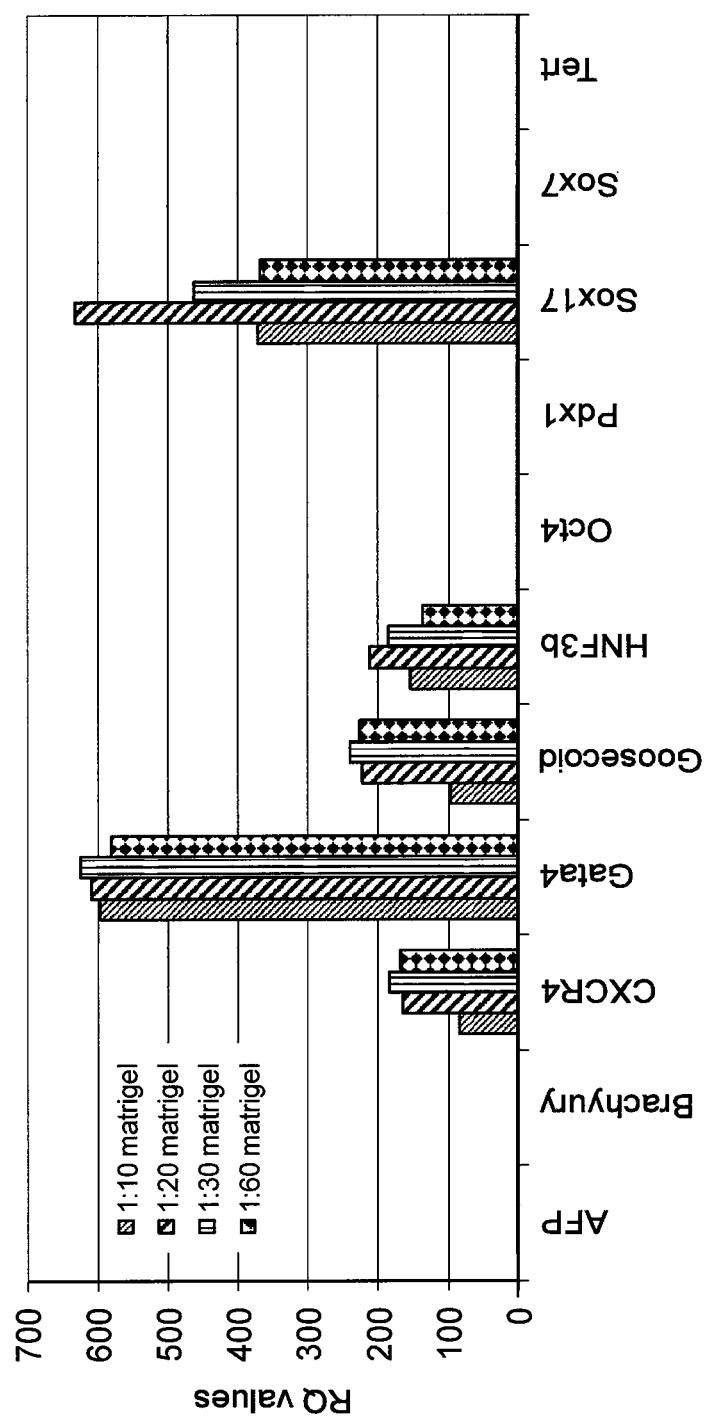
FIG. 40 depicts the effect of various concentrations of MATRIGEL in the presence of low serum, 100 ng/ml of activin A and 20 ng/ml of Wnt-3a on differentiating human embryonic stem cells into definitive endoderm. Cells were treated according to the methods disclosed in Example 4. Results shown are the expression levels of the genes indicated, as determined by real-time PCR.

Real time PCR results are shown in FIG. 40. Treatment of human embryonic stem cells with low serum, Activin A and Wnt3a led to the expression of CXCR4, GATA4, Goosecoid, HNF-3beta, and SOX-17 genes, suggesting that the cells were differentiating to the definitive endoderm stage. However, it does not appear that the in the presence of Wnt-3A concentration of the MATRIGEL™ coating plays an important role in differentiation.

Example 25

Differentiation of Human Embryonic Stem Cells Cultured on Tissue Culture Substrate Coated with Extracellular Matrix and Subsequently Cultured on MEFS and Differentiated to Definitive Endoderm—Role of Wnt-3a Cells from the human embryonic stem cell line H9 cultured on MATRIGEL™ for at least five passages were seeded onto MEF feeders in ES media. When the cells reached 60 to 70% confluency they were exposed to DMEM/F12 medium supplemented with 0.5% FBS and 100 ng/ml activin A for two days followed by treatment with DMEM/F12 media supplemented with 2% FBS and 100 ng/ml activin A (AA) for an additional three days. Additional treatment groups include Wnt-3a at 20 ng/ml for all five days+10-100 ng/ml of activin A.

At day 3 and 5, the cultures were analyzed by real time PCR for SOX-17, SOX-7, Alpha-fetal protein (AFP), CXCR4, Brychyury (Bry), goosecoid (GSC), HNF-3 beta, GATA4, hTERT and Oct4. AFP and SOX-7 are regarded as visceral endoderm markers while GATA4, HNF-3beta and SOX-17 represent definite endoderm markers and GSC, Bry, and CXCR4 represent markers of primitive streak. hTERT and Oct-4 are markers for self renewal and pluripotency respectively. Real time-PCR results are shown in FIGS. 41A, 41B, 41C and 41D. FACS analysis was also performed at day 3 and 5. Expression levels of CXCR-4, and CD9 were analyzed and reported in FIG. 41E.

Figure 41A:
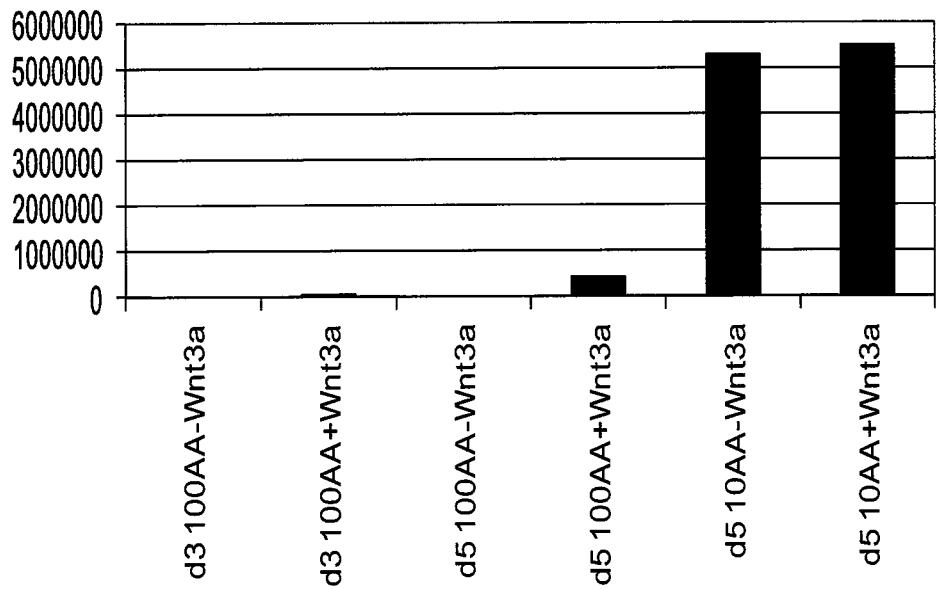
FIGS. 41A, 41B, 41C, 41D, 41E-1, 41E-2, 41F-1, 41F-2, 41G-1, 41G-2 depicts the role of Wnt-3a in definitive endoderm formation by human embryonic stem cells maintained on MATRIGEL, but differentiated on mouse embryonic fibroblasts.
Figure 41B:
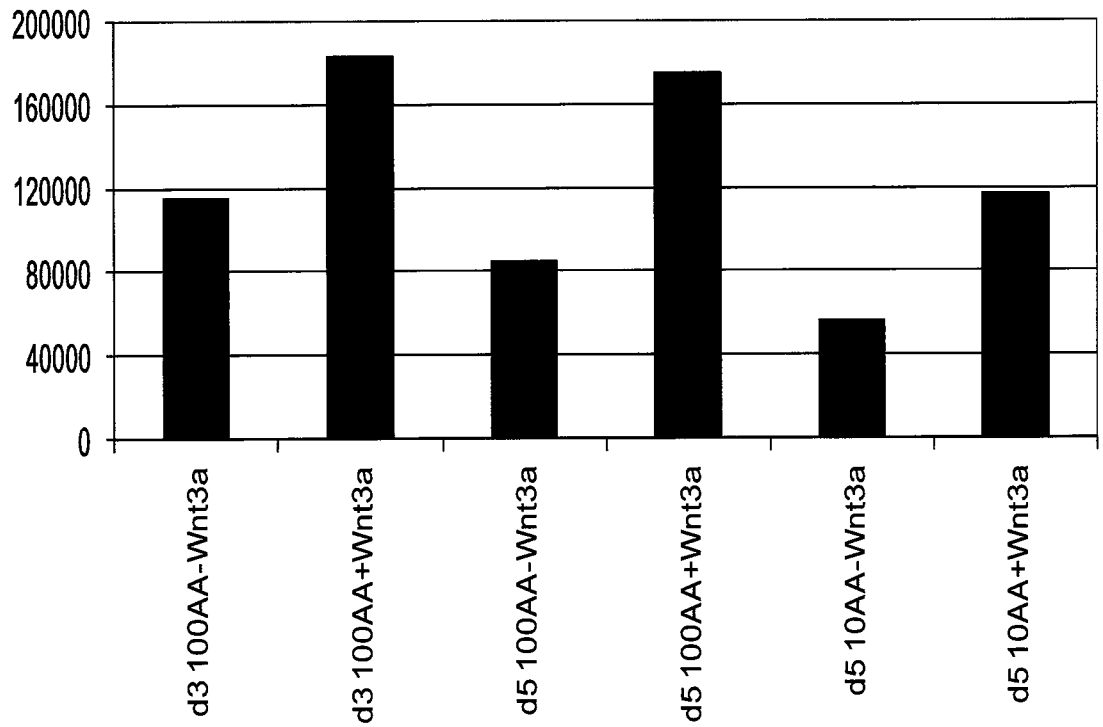
Figure 41C:
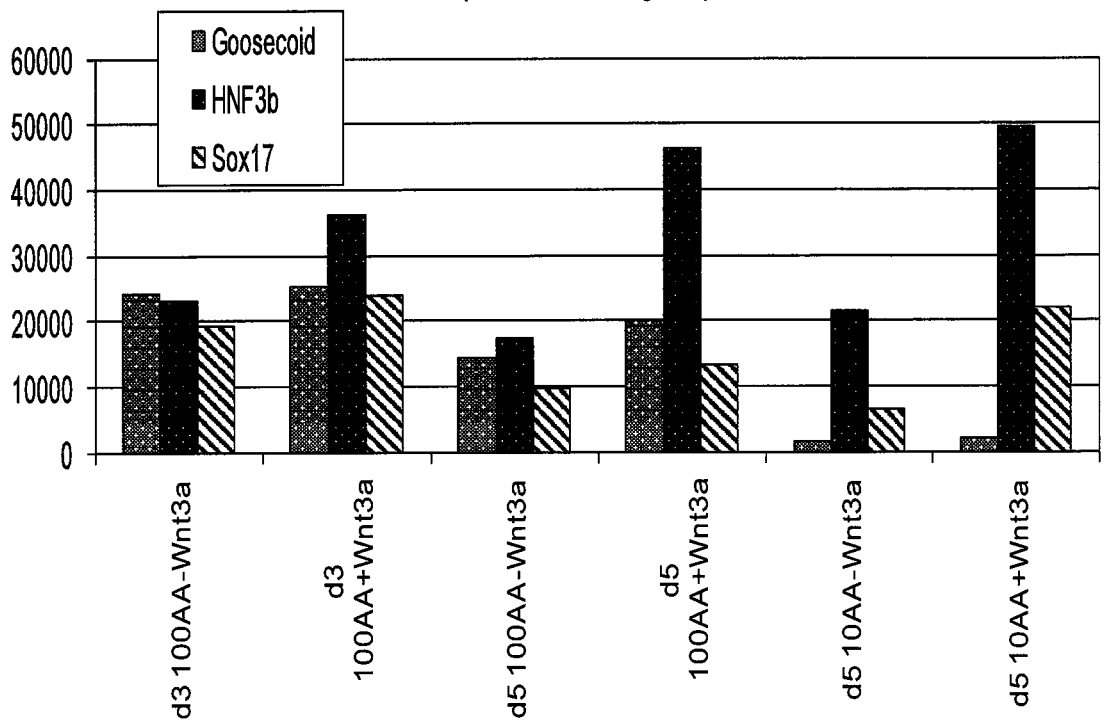
Figure 41D:
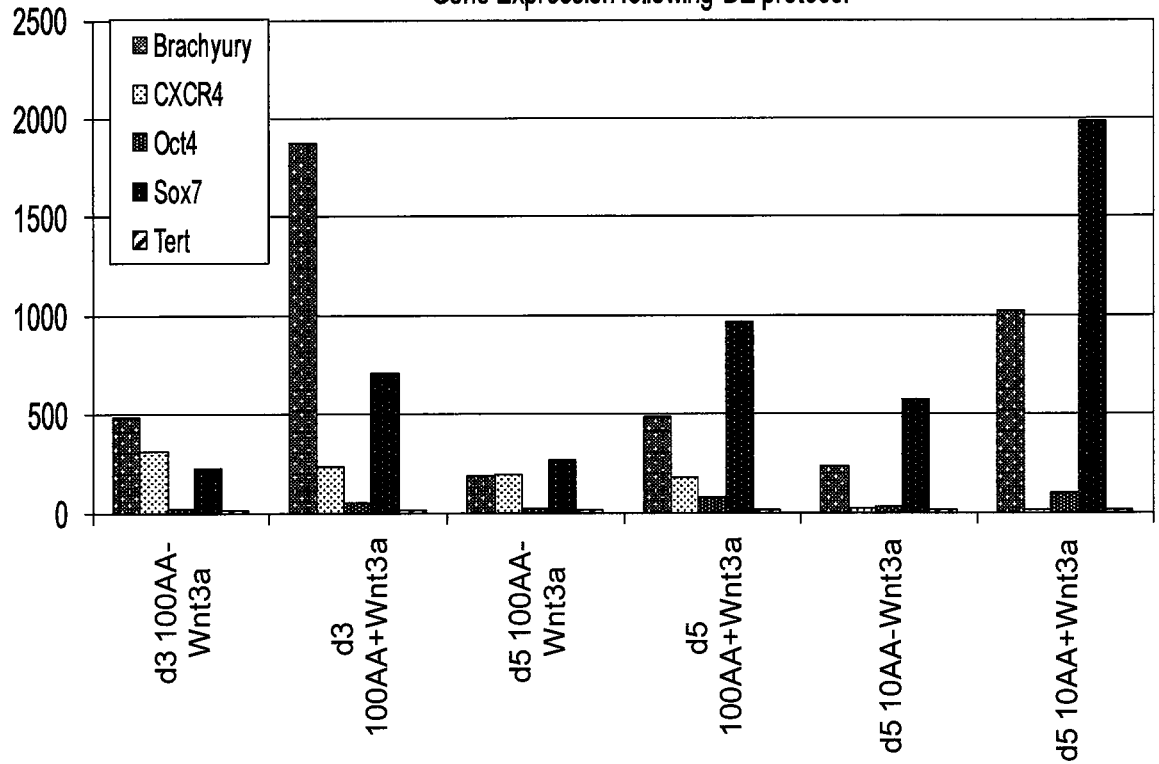

In the absence of Wnt3a, AFP expression levels of cells cultured in 100 ng/ml Activin A are similar to those seen in untreated controls. However, with the addition of Wnt3a to cells cultured in 100 ng/ml activin A, there is an increase in the expression of AFP that increases over time. When a lower concentration of Activin A is used, AFP expression is very high, regardless of the presence of Wnt3a (FIG. 41A). This suggests that a high concentration of Activin A is necessary to keep the cells from differentiating to extra-embryonic tissues.

Figures 1, 41E:
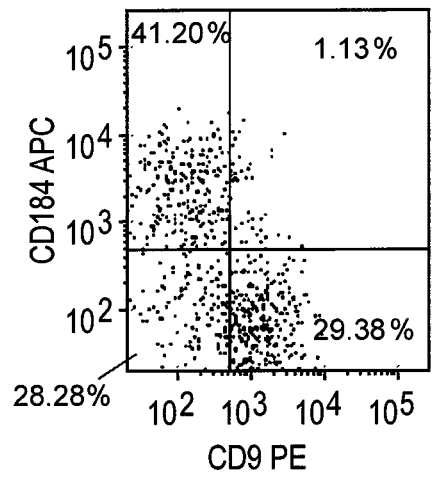
Figures 2, 41E:
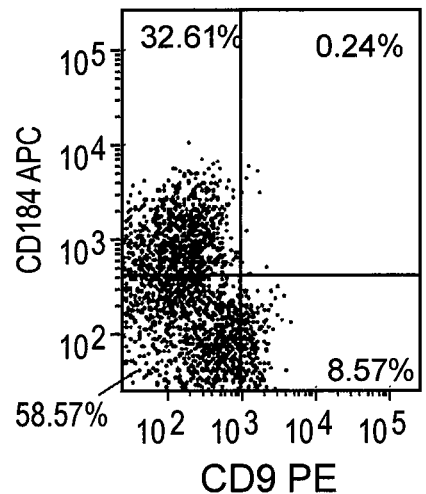
Figures 1, 41F:
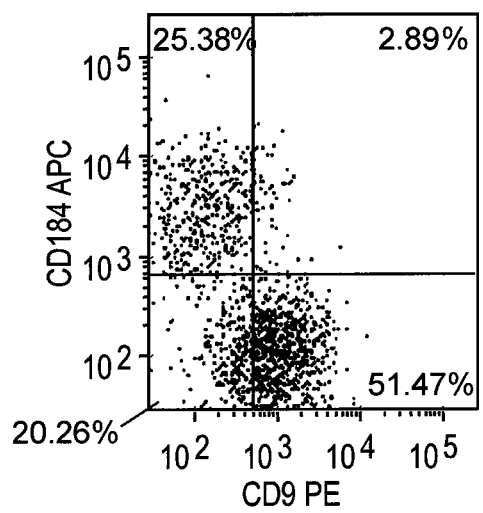
Figures 2, 41F:
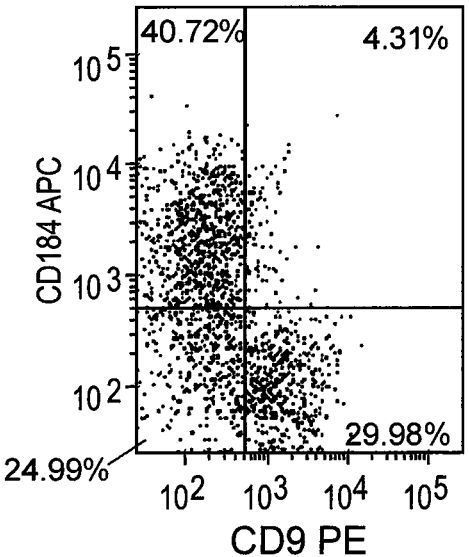
Figures 1, 41G:
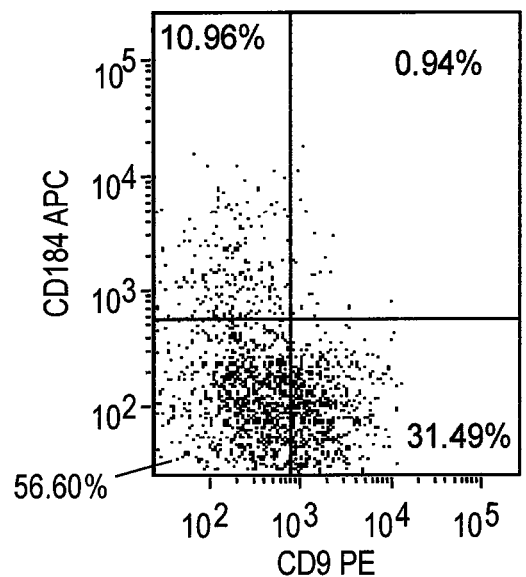
Figures 2, 41G:
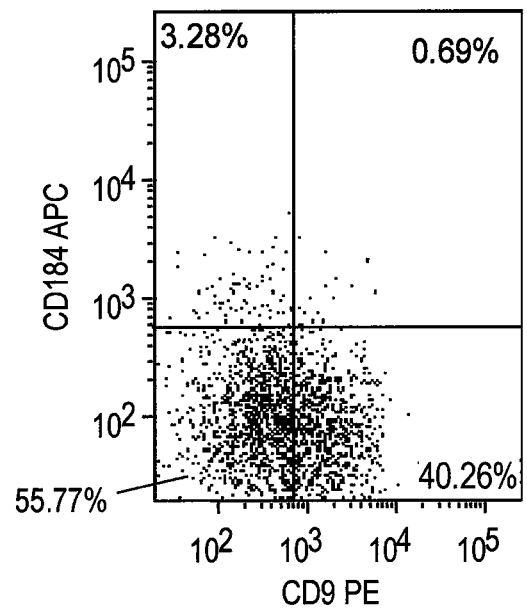

By FACS analysis, CXCR4 positive cells ranged from 32-42% of the population in samples treated with a high concentration of Activin A but not treated with Wnt3a as compared to 23-33% of the population in samples treated with a high concentration of Activin A and Wnt3a at day 3 (FIG. 41E). By day 5 of treatment, 28-32% of cells treated with a high concentration of activin A but not treated with Wnt-3a expressed CXCR4 as compared to 43-51% of cells treated with a high concentration of Activin A and Wnt3a (FIG. 41F). In cells treated with a low concentration of Activin A, there were more CXCR4 positive cells in the treatment group without Wnt3a (11 to 20%) as compared to the Wnt-3a treated group (3 to 4%) (FIG. 41G). Overall, Wnt-3a does not appear to play a significant role in differentiation of human embryonic stem cells, cultured on MEFs, to definitive endoderm. This suggests that the feeder layer is probably secreting sufficient Wnt-3a or analogous ligand to enhance activin A induced definitive endoderm formation.

Example 26

Differentiation of Human Embryonic Stem Cells Cultured on Tissue Culture Substrate Coated with Extracellular Matrix to Definitive Endoderm Following Treatment with a Wnt Inhibitor-DKK-1

To determine if the addition of Wnt-3a was causing the increase in differentiation, an inhibitor of Wnt-3 signaling was added to the cultures. H9 cultures at approximately 60 to 70% confluency were exposed to DMEM/F12 medium supplemented with 0.5% FBS, 20 ng/ml Wnt3a, 100 ng/ml Dikkopf-1 (DKK-1) and 100 ng/ml activin A for two days followed by treatment with DMEM/F12 media supplemented with 2% FBS and 100 ng/ml activin A (AA) for an additional three days. H9 cells were cultured on plates coated with Growth Factor Reduced MATRIGEL at a 1:30 dilution. The plates were coated with MATRIGEL for 1 hr at room temperature.

Figure 42:
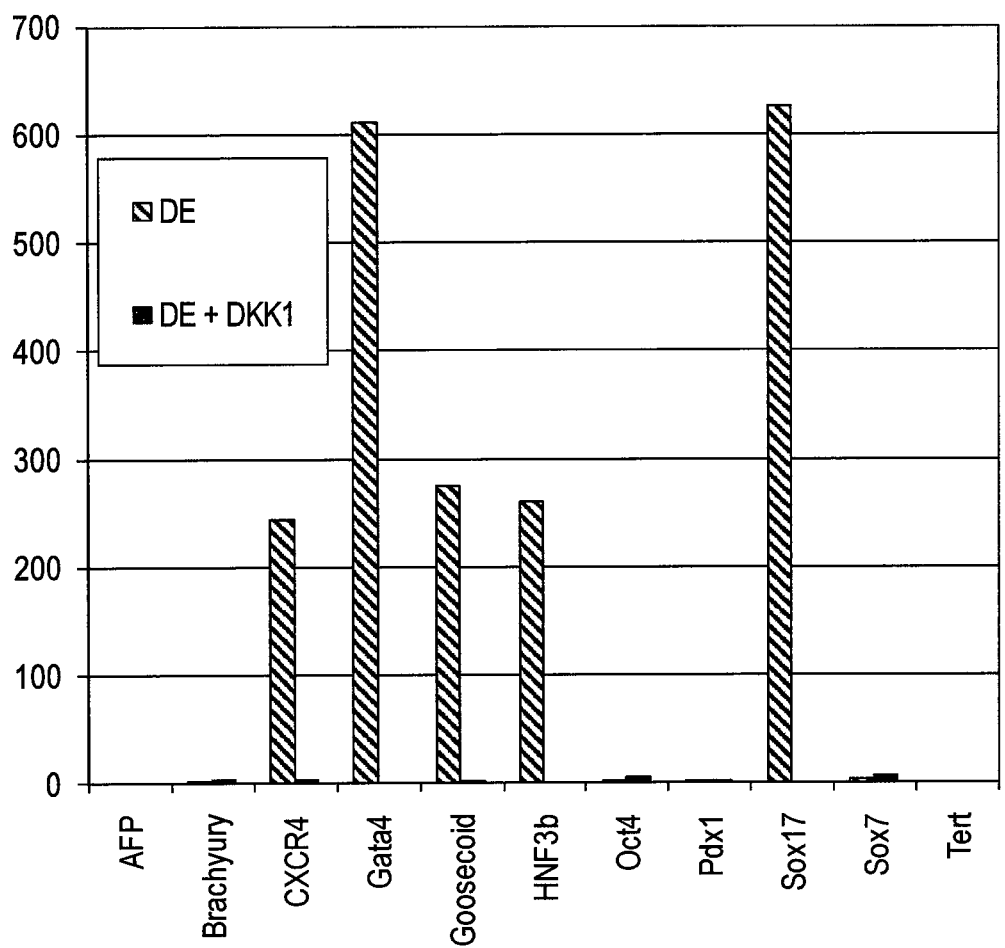
FIG. 42 shows the differentiation of human embryonic stem cells cultured on tissue culture substrate coated with MATRIGEL™ to definitive endoderm following treatment with the Wnt Inhibitor DKK-1. Results shown are the expression of the genes indicated, as determined by real-time PCR in H9 cells treated according to the methods disclosed in Example 4 in the presence of 20 ng/ml of Wnt-3A plus 100 ng/ml of DKK1 (DE+DKK1), or in the absence of DKK1 (DE).

At day 5, the cultures were analyzed by real time PCR for SOX-17, SOX-7, Alpha-fetal protein (AFP), CXCR4, Brychyury (Bry), gooscecoid (GSC), HNF-3 beta, GATA4, hTERT and Oct4. AFP and SOX-7 are regarded as visceral endoderm markers while GATA4, HNF-3beta and SOX-17 represent definite endoderm markers and GSC, Bry, and CXCR4 represent markers of primitive streak. hTERT and Oct-4 are markers for self renewal and pluripotency respectively. Results are shown in FIG. 42.

In the presence of Wnt3a, cells express CXCR4, GATA4, HNF-3beta and SOX17, all markers of definitive endoderm. Markers of primitive streak formation such as goosecoid were also detected at levels higher than that detected in untreated controls. With the addition of DKK1, the expression level of the aforementioned differentiation markers dramatically decrease to levels similar to that of untreated cells.

Example 27

Figure 43A:
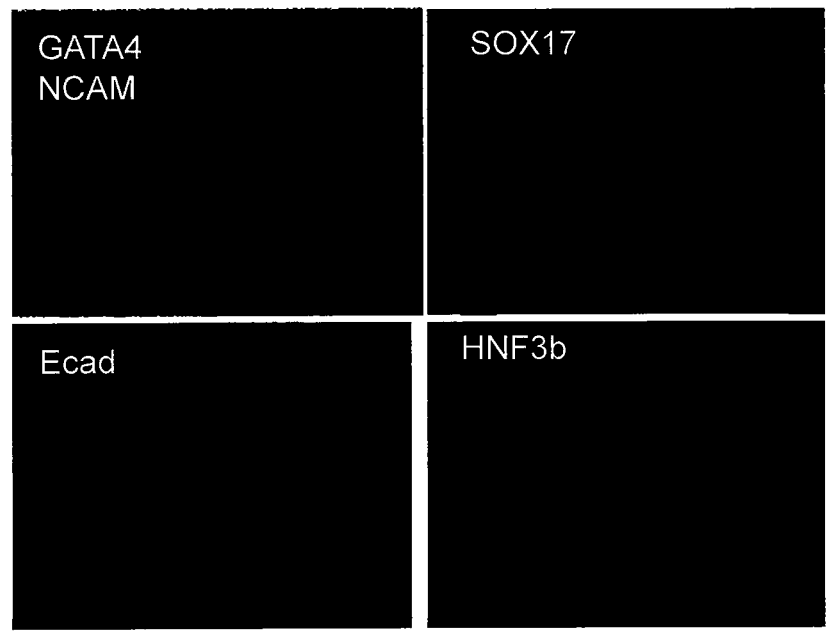
FIGS. 43A and 43B show immunofluorescence staining of definitive endoderm markers in cultures of the human embryonic stem cell line H9 cultured on tissue culture substrate coated with MATRIGEL and differentiated in low serum plus 100 ng/ml of activin-A without (FIG. 43A), or with (FIG. 43B) 20 ng/ml of Wnt-3a. Ecad=E-cadherin, NCAM=N-cadherin.
Figure 43B:
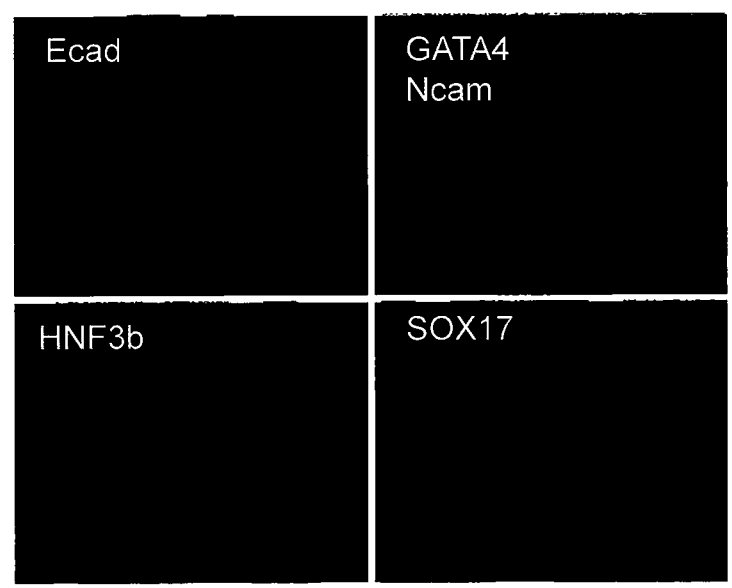

Immunofluorescence Staining of DE Markers for H9 Embryonic Stem Cells Cultured on Tissue Culture Substrate Coated MATRIGEL and Differentiated in Low Serum Plus Activin-a and +/−Wnt-3a Day 5 DE cultures of H9 cells were stained according to Example 10 for SOX-17, HNF-3B, GATA-4, N-cadherin, and E-cadherin. All nuclei were counter stained with DAPI. 20 ng/ml Wnt-3a resulted in significantly larger number of nuclei stained positive for SOX-17, HNF-3beta. and GATA-4 as compared to cultures differentiated in the absence of Wnt-3a. Furthermore, addition of Wnt-3a resulted in significant loss of expression of e-cadherin and enhanced expression of N-cadherin (FIGS. 43A and 43B).

Example 28

Microarray Analysis of Changes in Gene Expression in Embryonic Stem Cells Following Formation of Definitive Endoderm on MEFs Vs MATRIGEL™

Total RNA was isolated from the following embryonic stem cell cultures using an RNeasy mini kit (Qiagen): A) H9P33 cells cultured on MATRIGEL™-coated plates (1:30 dilution) and exposed to DMEM/F12 medium supplemented with 0.5% FBS and 100 ng/ml activin A for two days followed by treatment with DMEM/F12 medium supplemented with 2% FBS and 100 ng/ml activin A (AA) for an additional three days; B) H9P44 cells cultured on MEFs and exposed to DMEM/F12 medium supplemented with 0.5% FBS and 100 ng/ml Activin A for two days followed by treatment with DMEM/F12 medium supplemented with 2% FBS and 100 ng/ml Activin A for an additional three days, and C) H9P48 cells cultured on MATRIGEL™-coated plates (1:30 dilution) and exposed to DMEM/F12 medium supplemented with 0.5% FBS and 100 ng/ml activin A plus 20 ng/ml Wnt-3A for two days followed by treatment with DMEM/F12 medium supplemented with 2% FBS and 100 ng/ml Activin A (AA) for an additional three days. Controls for each group included cells plated on MATRIGEL-coated dishes and cultured in MEF-conditioned medium or cells plated on MEFs and cultured in ES medium. All groups contained three biological replicates and each biological replicate was repeated on two separate gene chips.

Sample preparation, hybridization, and image analysis were performed according to the Affymetrix Human Genome U133 Plus 2.0 Array. Following normalization and a log transformation, data analysis was performed using OmniViz® software (MA) and GENESIFTER (VizXLabs, WA). Significant differences in gene expression between the samples were evaluated using analysis of variance and an F-test with adjusted P-value (Benjamini and Hochberg correction) of ≤0.05. Only genes with a present call in at least one group were included in the analysis. Table VI lists the mean normalized log-transformed signal intensity of genes showing at least 5-fold difference between group A, group B, and group C along with the adjusted P-value for each gene.

Example 29

Differentiation of SA002 ES Line Cultured on Tissue Culture Substrate Coated with MATRIGEL™ to Definitive Endoderm (DE)

Figure 44A:
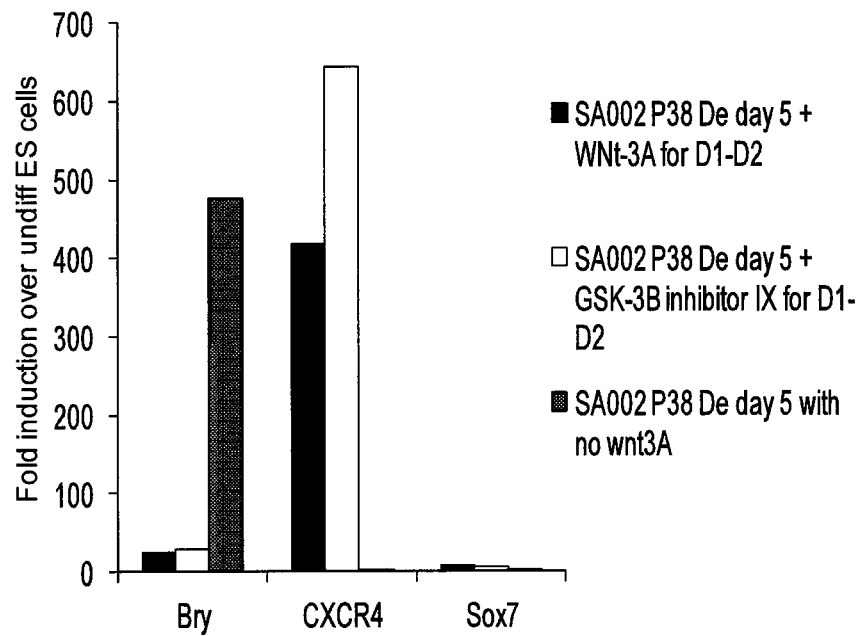
FIGS. 44A and 44B show the differentiation of the human embryonic stem cell line SA002 at passage 38 into definitive endoderm. Cells were treated for five days with the conditions indicated and gene expression was determined by real-time PCR, for the genes indicated in FIGS. 44A and 44B.
Figure 44B:
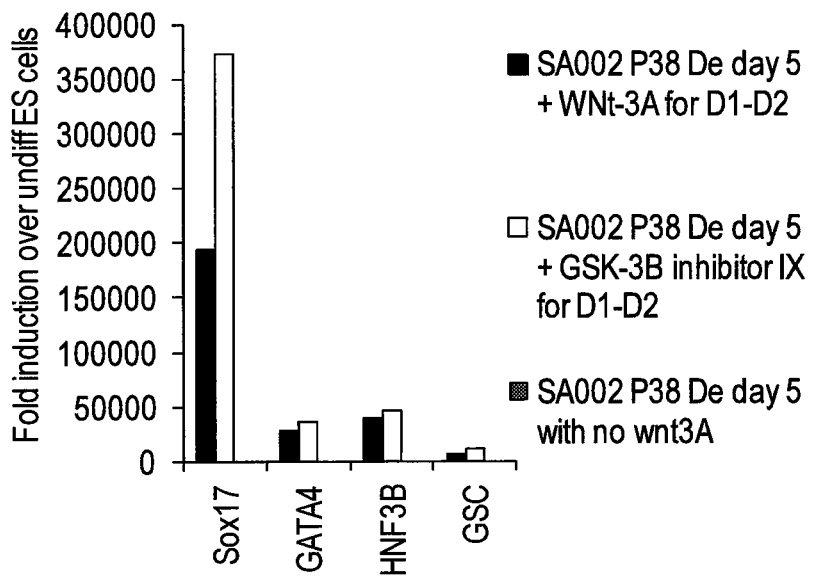
Figure 45A:
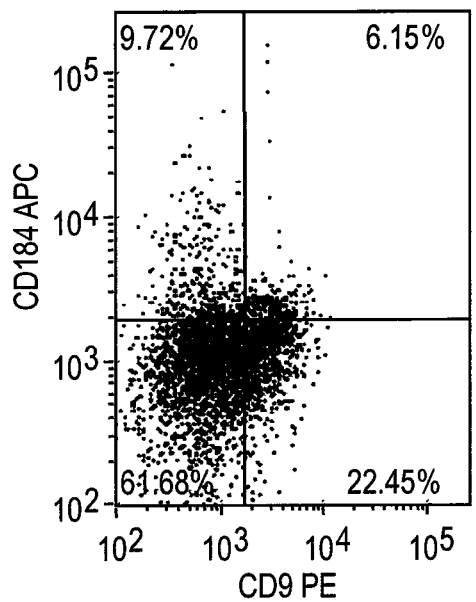
FIGS. 45A, 45B and 45C show the expression of CXCR4 by FACS in the human embryonic stem cell line SA002 at passage 38, following treatment with 100 ng/ml activin A treatment (FIG. 45A), 100 ng/ml activin A+20 ng/ml Wnt-3a (FIG. 45B), or 100 ng/ml activin A+100 nM GSK-3B inhibitor IX (FIG. 45C). Cells were treated for five days.
Figure 45B:
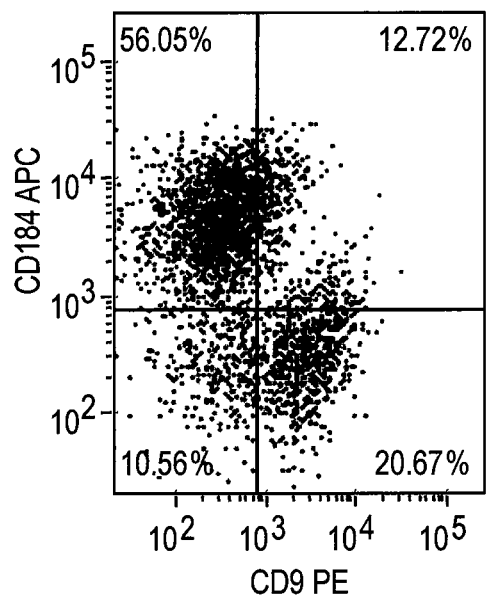
Figure 45C:
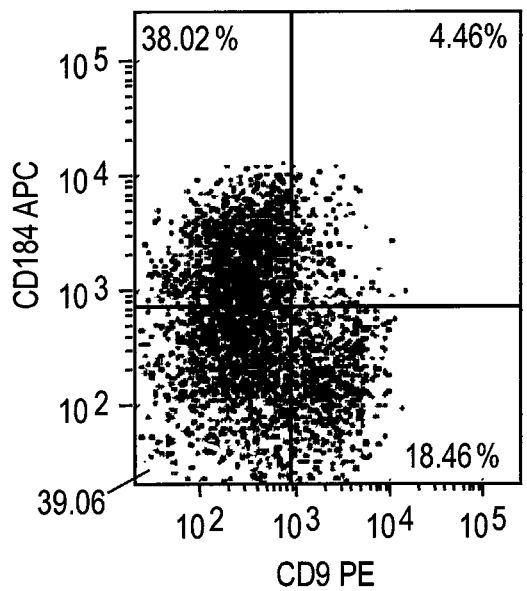

SA002 P38 cells (Cellartis, Sweden) previously cultured for at least three passages on MATRIGEL-coated plates (1:30 dilution) in MEF-CM supplemented with 8 ng/ml of bFGF were exposed to DMEM/F12 medium supplemented with 0.5% FBS, and 100 ng/ml activin A (R&D Systems, MN)+/−20 ng/ml of Wnt-3a or 100 nm GSK-3B IX inhibitor for two days followed by treatment with DMEM/F12 media supplemented with 2% FBS and 100 ng/ml activin A (AA) for an additional three days. Real time PCR results are shown in FIGS. 44A and 44B. Similar to H1, H7, and H9 lines, SA002 line also required addition of Wnt-3A for robust expression of DE markers. Expression of CXCR4 is depicted in FIGS. 45A, 45B and 45C: a) AA treatment b) AA+Wnt-3a c) AA+GSK-3B inhibitor.

Example 30

Differentiation of Human Embryonic Stem Cells Cultured on Tissue Culture Substrate Coated with Human Serum to Definitive Endoderm (DE)

Figure 46A:
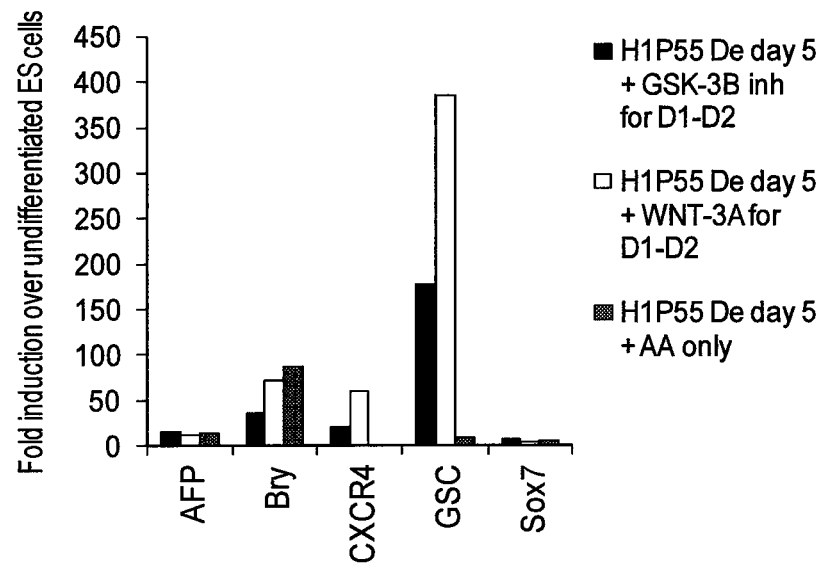
FIGS. 46A and 46B show the differentiation of the human embryonic stem cell line H1 at passage 55 into definitive endoderm on tissue culture substrate coated with human serum. Cells were treated with the conditions indicated and gene expression was determined by real-time PCR, for the genes indicated in FIGS. 46A and 46B.
Figure 46B:
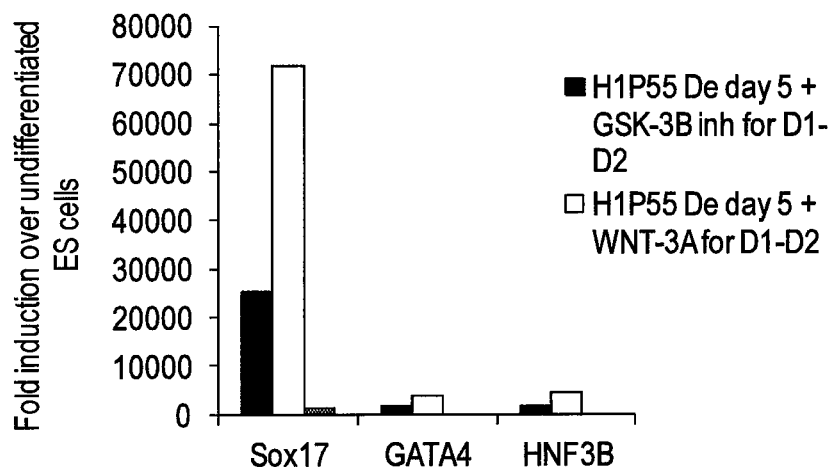

Cultures of the human embryonic stem cell line H1 at passage 55 were grown and differentiated on human serum (Sigma, # H1388, MO) coated plates. 0.5 ml of human serum was added to each well of 6 well tissue culture treated dish, incubated for 1 hr at room temperature, and aspirated before adding human embryonic stem cells. After cells reached 80% confluency, they were treated as follows: 2 days 0.5% FBS containing 10 ng/ml mouse recombinant Wnt3a (R&D) or 100 nM GSK-3B inhibitor IX (Catalog #361550, Calbiochem, CA) and 100 ng/ml Activin A (R&D). This was followed by 3 days 2% FBS plus 100 ng/ml Activin A. Cultures were then analyzed by real-time PCR (FIGS. 46A and 46B). Robust expression of definitive endoderm markers were noted for cells treated with activin A+GSK-3B inhibitor or Wnt-3A as compared to cells treated with activin A only. These findings parallel our findings for human embryonic stem cells cultured on MATRIGEL™ or human fibronectin coated plates.

Example 31

Figure 47A:
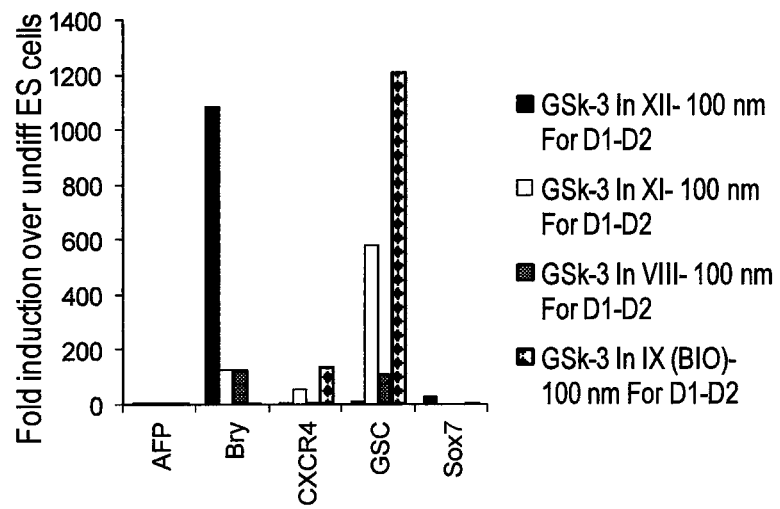
FIGS. 47A and 47B show the differentiation of cultures of the human embryonic stem cell line H1 at P54, on tissue culture substrate coated with MATRIGEL™ to definitive endoderm. The effects of various GSK-B inhibitors were tested following a five-day DE protocol. The following GSK-3B inhibitors were evaluated at 100 nM for the first two days of treatment: GSK-3B VIII, IX, XI, and XII.
Figure 47B:
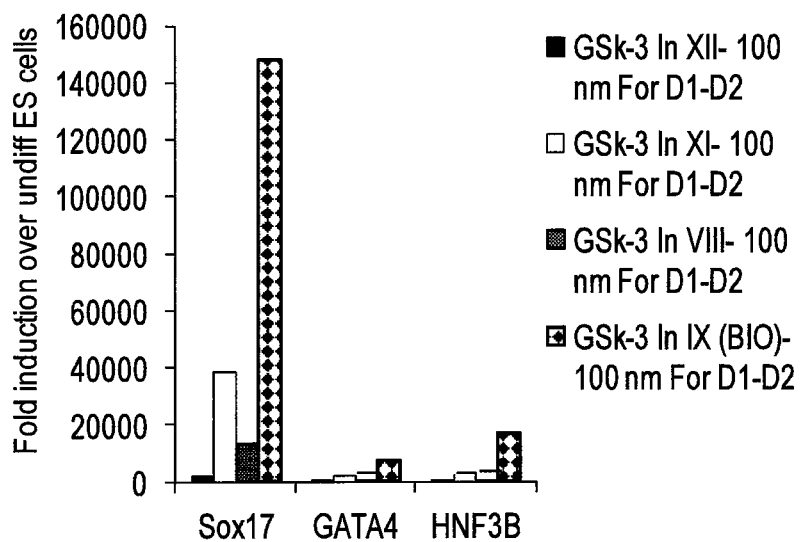
Figure 48A:
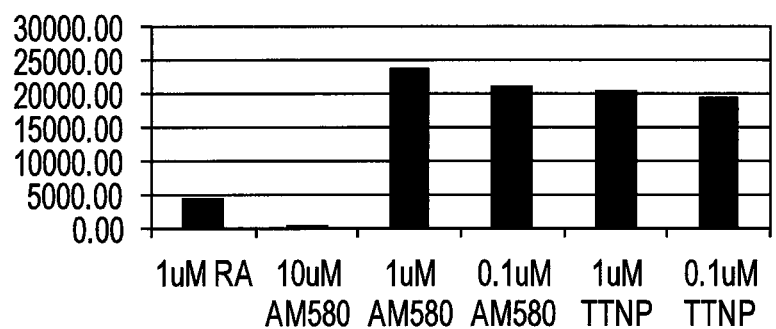
FIGS. 48A, 48B, 48C and 48D show the expression of AFP (FIG. 48A), Pdx-1 (FIG. 48B), Cdx-2 and Glut-2 (FIG. 48C) and HNF-3beta, HNF-6 and somatostatin (FIG. 48D) in cultures of the human embryonic stem cell line H9 at passage 49, cultured and treated according to the methods disclosed in Example 4 in the presence of 20 ng/ml of Wnt-3a for the first two days of treatment. Following the treatment, the cells were treated for three additional days with 2% FBS plus 1 µM retinoic acid, 0.1 to 1 µM TNPB (4-[(E)-2-(5,6,7,8-Tetrahydro-5,5,8,8-tetramethyl-2-naphthalenyl)-1-propenyl]benzoic acid Arotinoid acid), or 0.1-10M AM-580 (4-[(5,6,7,8-Tetrahydro-5,5,8,8-tetramethyl-2-naphthalenyl)carboxamido]benzoic acid). The cells were next treated for three additional days in 2% FBS plus 20 ng/ml of bFGF.
Figure 48B:
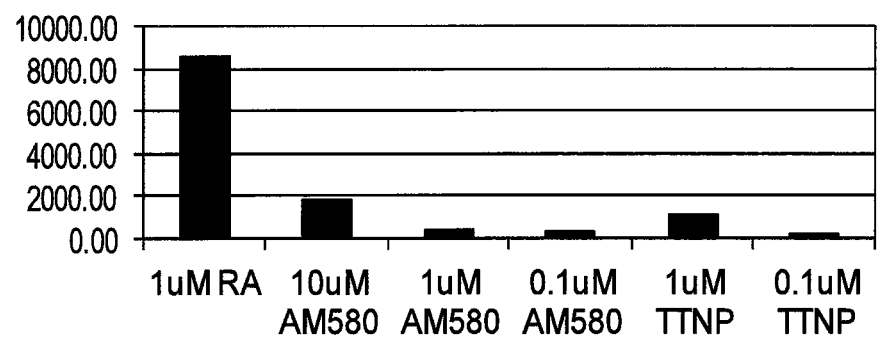
Figure 48C:
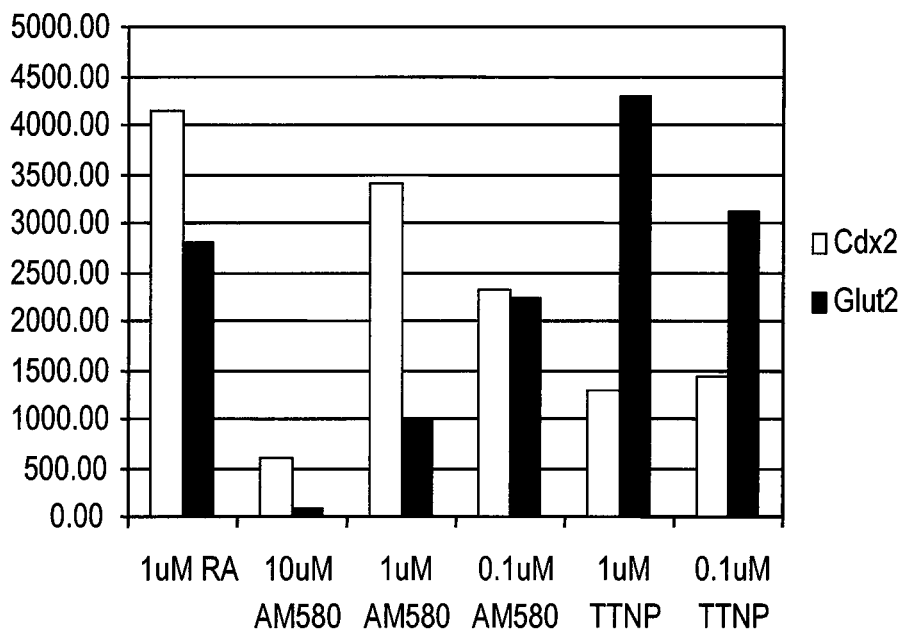
Figure 48D:
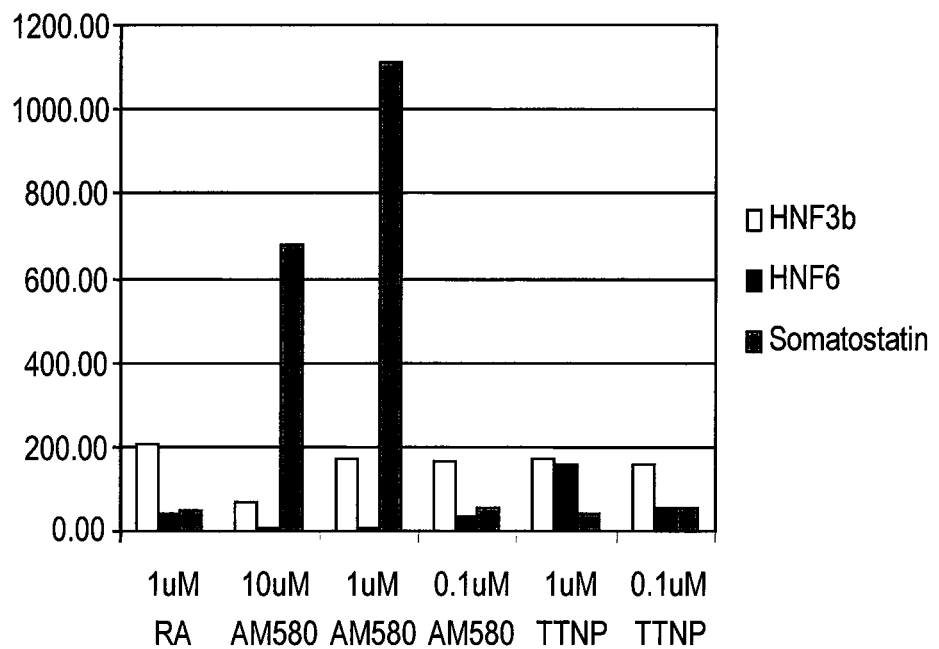

Differentiation of Human Embryonic Stem Cells Cultured on Tissue Culture Substrate Coated with MATRIGEL™ to Definitive Endoderm (DE)-Evaluation of Various GSK-3B Inhibitor The effectiveness of a number of commercially available GSK-3B inhibitors was evaluated in formation of DE from human embryonic stem cells. The following GSK-3B inhibitors were evaluated at 100 nM: GSK-3B inhibitor VIII (Catalog #361549, Calbiochem, CA), GSK-3B inhibitor IX (Catalog #361550, Calbiochem, CA), GSK-3B inhibitor XI (Catalog #361553, Calbiochem, CA), GSK-3B inhibitor XII (Catalog #361554, Calbiochem, CA). H1P54 ES cells were cultured on MATRIGEL™ coated dishes (1:30 dilution) and exposed to DMEM/F12 medium supplemented with 0.5% FBS, 100 ng/ml activin A (AA)+/− various GSK-3B inhibitors for two days followed by treatment with DMEM/F12 media supplemented with 2% FBS, 100 ng/ml activin A (AA) for an additional three days. Control cultures were treated with low serum plus high dose of AA. FIGS. 47A and 47B depicts the gene expression of definitive endoderm markers at day 5. GSK-3B inhibitor IX and XI were both effective in inducing DE formation as compared to GSK-3B inhibitor VIII and XII.

Example 32

Formation of Pancreatic Endoderm by Human Embryonic Stem Cells Cultured Under Feeder-Free Conditions:—Evaluation of Retinoic Add Analogues H9P49 embryonic stem cells were cultured on MATRIGEL™ (1:30 dilution) coated dishes and exposed to DMEM/F12 medium supplemented with 0.5% FBS, 20 ng/ml Wnt-3a (Catalog #1324-WN-002, R&D Systems, MN), and 100 ng/ml activin A (R&D Systems, MN) for two days followed by treatment with DMEM/F12 media supplemented with 2% FBS and 100 ng/ml activin A (AA) for an additional three days. At day 5, cells were collected for evaluation by FACS and real-time PCR. As indicated in previous examples, this protocol resulted in robust upregulation of definitive endoderm markers, such as CXCR4 and SOX-17. The resulting definitive endoderm cells at day 5 were exposed to the following media conditions to induce pancreatic endoderm formation: culturing in DMEM/F12 media supplemented with 2% FBS and 1 µM all-trans retinoic acid (RA) (Catalog # R2625, Sigma, MO), or 0.1-10 µM AM-580 (4-[(5,6,7,8-Tetrahydro-5,5,8,8-tetramethyl-2-naphthalenyl)carboxamido]benzoic acid, Catalog # A8843, Sigma, MO), or 0.1-1 µM TTNPB (4-[(E)-2-(5,6,7,8-Tetrahydro-5,5,8,8-tetramethyl-2-naphthalenyl)-1-propenyl]benzoic acid Arotinoid acid, Catalog # T3757, Sigma, MO) for 3 days. AM-580 and TITNPB are retinoic acid analogs with affinity for retinoic acid receptors. RA treatment was followed by additional three day treatment in DMEM/F12 media supplemented with 2% FBS and 20-50 ng/ml bFGF (Catalog # F0291, Sigma, MO). Cultures were harvested and samples of mRNA were collected for analysis.

Gene expression analysis revealed that (FIGS. 48A, 48B, 48C and 48D) addition of 1 µM RA followed by exposure to bFGF significantly upregulates pancreatic endoderm markers, such as PDX-1. Furthermore, this protocol resulted in robust expression of foregut endoderm markers, such as CDX-2 and AFP. At 1 µM concentration, addition of RA analogs resulted in equivalent pancreatic endoderm and foregut markers. However, addition of 1 µM RA analogs resulted in more robust expression of AFP as compared to all-trans retinoic acid. However, addition of 10 µM AM-580 suppressed AFP and CDX-2 expression while maintaining a high expression of PDX-1.

Example 34

The Effect of Wnt-3a Treatment on Cytokine Expression in Human Embryonic Stem Cells The effect that Wnt-3a treatment has on cytokine expression was analyzed using a protein array. Cells of the human embryonic stem cell line H9 were cultured according to the methods described in Example 15. At passage 54, cells were differentiated in the presence of 100 ng/ml Activin A+/−10 ng/ml Wnt3a for 2 days in 0.5% FBS DMEM/F12. Cells were subsequently cultured for an additional three days in 100 ng/ml Activin A and 2% FBS DMEM/F12. At the end of the 5th day, CXCR4 expression was determined by FACS for each treatment group. Cells treated with Activin A only had 1% of cells expressing CXCR4. Cells treated with Activin A and Wnt3a had 73% of cells positive for CXCR4 expression.

Cell lysates were prepared from cells of each treatment group, with a mammalian cell lysis kit (Sigma-Aldrich, MO). Conditioned media from each treatment group was collected and concentrated. Cytokine array analysis was completed using Cytokine Array panels provided by RayBiotech, GA (http://www.raybiotech.com/). Table VII lists cytokine, growth factor, and receptor expression following normalization of the data and background subtraction. For each panel, positive and negative controls are also included. Th data shown are two independent samples per cell treatment group (1,2).

Noticeable upregulation of Angiogenin, IGFBP-1 and EGF are seen in the Wnt3 treated cell conditioned media. Numerous proteins are upregulated in the Wnt3a treated cell lysates including IGFBP-1, TGFbeta-1 and TGFbeta-3. These upregulated proteins can be added back into the differentiation media to replace or enhance Wnt3a effects on definitive endoderm formation.

Example 35

Differentiation of Human Embryonic Stem Cells Cultured on Tissue Culture Substrate Coated with MATRIGEL™ to Definitive Endoderm: Role of Wnt1

Figure 49A:
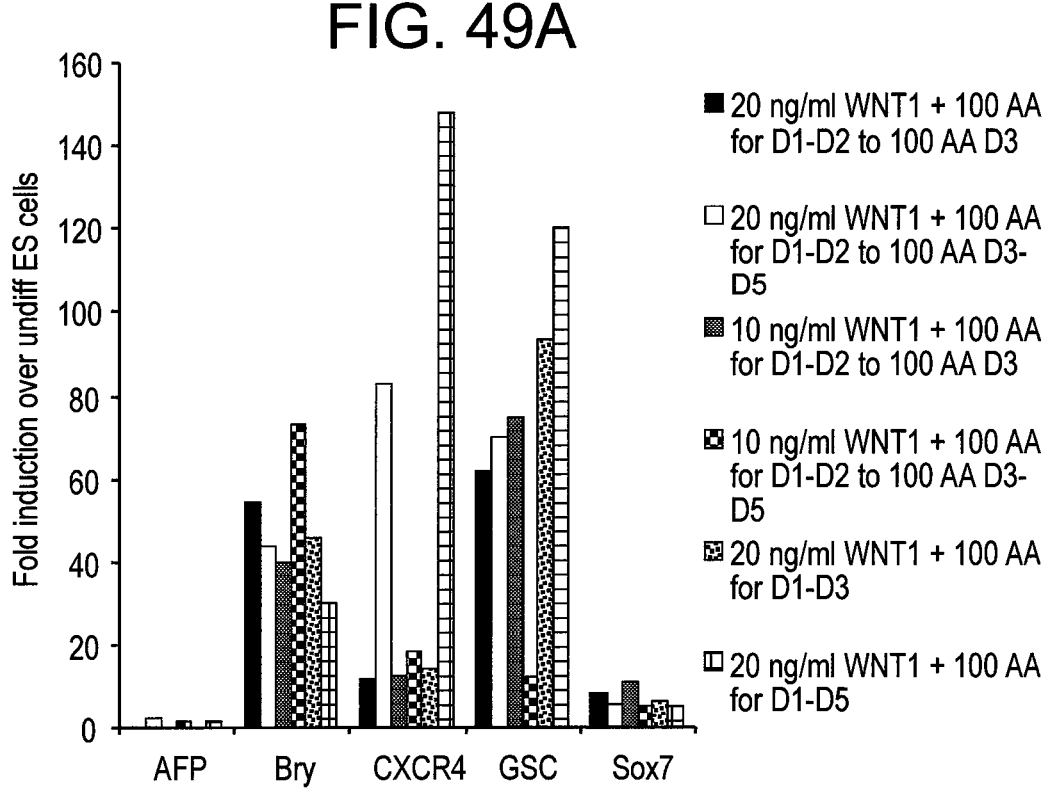
FIGS. 49A and 49B show the real-time PCR results of the expression of the definitive endoderm markers indicated in FIGS. 49A and 49B. in cultures of the human embryonic stem cell line H1 treated with activin A and Wnt-1 for the times and concentrations indicated.
Figure 49B:
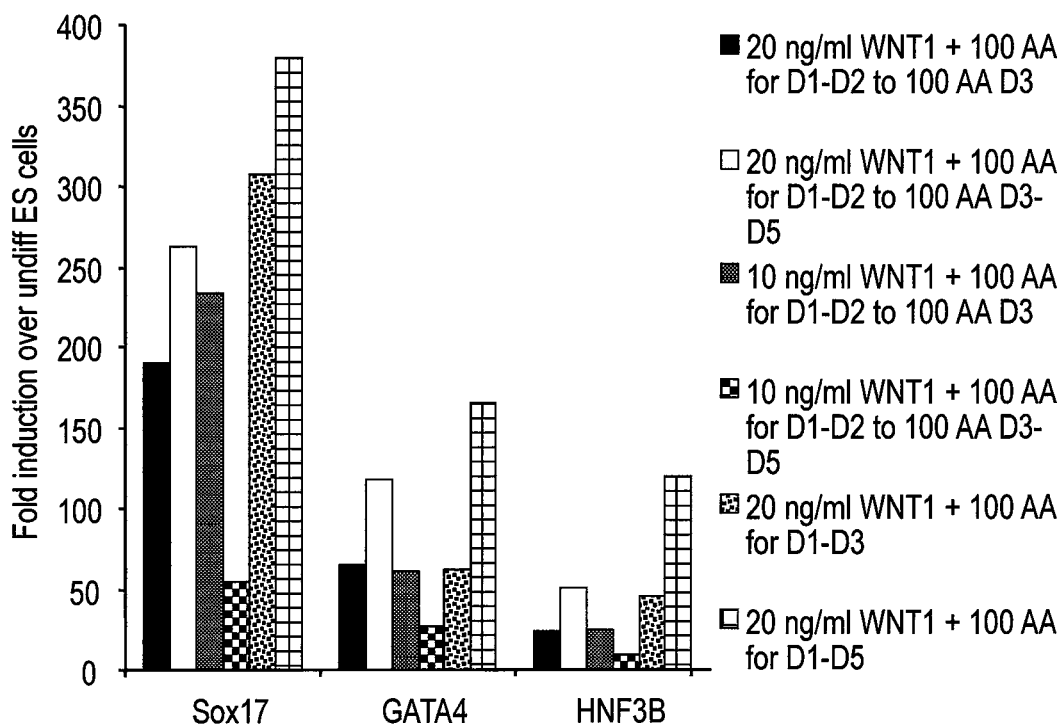

H1P55 ES cells were cultured on MATRIGEL™ (1:30 dilution) coated dishes and exposed to DMEM/F12 medium supplemented with 0.5% FBS, and 100 ng/ml activin A+/− 10-20 ng/ml of WNT-1 (PeproTech, NJ, Catalogue #120-17) for two days followed by treatment with DMEM/F12 media supplemented with 2% FBS, 100 ng/ml activin A (AA) and +/−10 or 20 ng/ml of WNT-1 for an additional three days. The following combinations of WNT1+AA were tested:
a) 20 ng/ml of WNT1+100 ng/ml AA in 0.5% FBS+DM-F12 for days 1-2 followed by 2% FBS+DM-F12+100 ng/ml AA for day three, b) 20 ng/ml of WNT1+100 ng/ml AA in 0.5% FBS+DM-F12 for days 1-2 followed by 2% FBS+DM-F12+ 100 ng/ml AA for days 3-5, c) 10 ng/ml of WNT1+100 ng/ml AA in 0.5% FBS+DM-F12 for days 1-2 followed by 2% FBS+DM-F12+100 ng/ml AA for day three, d) 10 ng/ml of WNT1+100 ng/ml AA in 0.5% FBS+DM-F12 for days 1-2 followed by 2% FBS+DM-F12+100 ng/ml AA for days 3-5, e) 20 ng/ml of WNT1+100 ng/ml AA in 0.5% FBS+ DM-F12 for days 1-2 followed by 2% FBS+DM-F12+100 ng/ml AA+20 ng/ml of WNT1 for day three, f) 20 ng/ml of WNT1+100 ng/ml AA in 0.5% FBS+DM-F12 for days 1-2 followed by 2% FBS+DM-F12+100 ng/ml AA+20 ng/ml of WNT1 for days 3-5. FIGS. 49A and 49B displays the real-time PCR data for definitive endoderm markers following treatment of the H1 cells with low serum, AA and Wnt-1. Addition of 20 ng/ml of Wnt1 in the present of 100 ng/ml of AA resulted in significant upregulation of definitive endoderm markers (Bry, CXCR4, GSC, SOX17, HNF-3B, and GATA-4).

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE IA

LIST OF PRIMARY ANTIBODIES USED FOR FACS AND IMMUNOSTAININGANALYSIS.

| Antibody | Supplier | Isotype | Clone |
|---|---|---|---|
| SSEA-1 | Chemicon (CA) | Mouse IgM | MC-480 |
| SSEA-3 | Chemicon (CA) | Mouse IgG3 | MC-631 |
| SSEA-4 | Chemicon (CA) | Rat IgM | MC-813-70 |
| TRA 1-60 | Chemicon (CA) | Mouse IgM | TRA 1-60 |
| TRA 1-81 | Chemicon (CA) | Mouse IgM | TRA 1-81 |
| TRA 1-85 | Chemicon (CA) | Mouse IgG1 | TRA 1-85 |
| AP | R&D Systems | Mouse IgG1 | B4-78 |
| HNF3β | R&D Systems | Goat IgG | |

TABLE IA-continued

LIST OF PRIMARY ANTIBODIES USED FOR FACS AND IMMUNOSTAININGANALYSIS.

| Antibody | Supplier | Isotype | Clone |
|---|---|---|---|
| PDX1 | Santa Cruz Biotechnology, INC | Goat IgG | A-17 |
| GATA4 | R&D Systems | Goat IgG | |
| Sox 17 | R&D Systems | Goat IgG | |
| CD 9 | BD | Mouse IgG1 | M-L13 |

TABLE IB

LIST OF SECONDARY CONJUGATED ANTIBODIES USED FOR FACS AND IMMUNOSTAININGANALYSIS.

| Secondary Conjugated Antibody | Supplier | Dilution |
|---|---|---|
| Goat Anti-Mouse IgG APC conjugated | Jackson ImmunoResearch (PA) | 1:200 |
| Goat Anti-Mouse IgG PE conjugated | Jackson ImmunoResearch (PA) | 1:200 |
| Donkey anti-rabbit PE or -APC conjugated | Jackson ImmunoResearch (PA) | 1:200 |
| Donkey anti-goat PE or - APC conjugated | Jackson ImmunoResearch (PA) | 1:200 |
| Goat anti-mouse IgM PE | SouthernBiotech (AL) | 1:200 |
| Goat anti-Rat IgM PE | SouthernBiotech (AL) | 1:200 |
| Goat anti-mouse IgG3 PE | SouthernBiotech (AL) | 1:200 |

TABLE IIA

CHANGES IN PROTEIN EXPRESSION IN HUMAN EMBRYONIC STEM CELLS WITH TIME, FOLLOWING ACTIVIN A TREATMENT.

| | 0-DAY | 2-DAY | 5-DAY | 8-DAY |
|---|---|---|---|---|
| SSEA-3 | 98.67% | 92.14% | 42.9% | 22.05% |
| CD9 | 92.64% | 29.42% | 7.27% | 4.1% |
| ECAM | 61.23% | 20.87% | 14.17% | 1.02% |
| NCAM | 7.33% | 5.04% | 21.1% | 8.86% |
| CXCR4 | 8.53% | 20.2% | 55.26% | 56.92% |

TABLE IIB

CHANGES IN PROTEIN EXPRESSION IN HUMAN EMBRYONIC STEM CELLS WITH TIME, FOLLOWING ACTIVIN A TREATMENT.

| | 1-day | | 3-day | | 5-day | |
|---|---|---|---|---|---|---|
| | Untreated | AA 100 ng/ml | Untreated | AA 100 ng/ml | Untreated | AA 100 ng/ml |
| CXCR4+ | 13% | 6% | 7.6% | 38% | 3% | 65.5% |
| CXCR4+ C-Kit+ | 5.32% | 2.97% | 2.9% | 31.56% | 3% | 55.21% |
| CXCR4+ EPCAM+ | 11.5% | 14.58% | 5.26% | 36.67% | 3% | 54.5% |
| CXCR4+ CD9+ | 12.27% | 8.13% | 2.72% | 24.11% | 3% | 2.1% |

TABLE IIC

CHANGES IN PROTEIN EXPRESSION IN HUMAN EMBRYONIC STEM CELLS WITH TIME, FOLLOWING ACTIVIN A TREATMENT.

|  | 5-day AA treatment |
|---|---|
| CXCR4+ | 92.78% |
| CXCR4+/C-kit+ | 92.90% |
| CXCR4+/EPCAM | 87.99% |
| CXCR4+/CD99+ | 88.78% |
| CXCR4+/CD9+ | 7.03% |

TABLE III

EXPRESSION PROFILE OF PLURIPOTENCY MARKERS FOR THE EMBRYONIC STEM CELL USED IN THE PRESENT INVENTION.

| Marker | H9 FACS | H9 RT-PCR | H9 Staining |
|---|---|---|---|
| OCT3/4 |  | + | + |
| SOX-2 |  | + |  |
| UTF-1 |  | + |  |
| REX-1 |  | + |  |
| hTERT |  | + |  |
| Cx 43 |  | + |  |
| Cx 45 |  | + |  |
| ABCG-2 |  | + |  |
| SSEA-1 | ±(36.35%) |  |  |
| SSEA-3 | +(94.38%) |  | + |
| SSEA-4 | +(98.77%) |  | + |
| TRA-1-81 | +(85.85%) |  | + |
| TRA-1-60 | +(78.14%) |  | + |
| TRA-1-85 | +(95.96%) |  |  |
| CD9 | +(92.02%) |  |  |
| AP | +(99%) |  | + |

TABLE IV

DIFFERENTIAL EXPRESSION OF GENES BETWEEN UNDIFFERENTIATED EMBRYONIC STEM CELLS AND DEFINITIVE ENDODERM STAGE CELLS CULTURED ON EITHER MATRIGEL™ OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| D87811 | Homo sapiens mRNA for GATA-6, complete cds. /PROD = GATA-6 /FL = gb: U66075.1 gb: NM_005257.1 gb: D87811.1 | GATA6 | −2.12 | 0.19 | 2.82 | 2.20 | −2.56 | 0.46 | 5.34 | 1.79 |
| AW157548 | insulin-like growth factor binding protein 5 /FL = gb: M65062.1 gb: M62782.1 gb: NM_000599.1 gb: AF055033.1 | IGFBP5 | −3.28 | 0.17 | 3.31 | 2.11 | −3.78 | 0.36 | 5.35 | 2.00 |
| NM_001898 | Homo sapiens cystatin SN (CST1), mRNA. /PROD = cystatin SN /FL = gb: J03870.1 gb: NM_001898.1 | CST4 | −2.15 | 1.26 | 2.54 | 1.95 | −2.71 | 0.98 | 4.64 | 1.63 |
| AK000680 | Homo sapiens cDNA FLJ20673 fis, clone KAIA4464. /FL = gb: AF240634.1 gb: NM_018440.1 | PAG1 | −2.87 | 0.91 | 1.61 | 0.22 | −4.08 | 0.50 | 1.68 | 0.10 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_022642 | Homo sapiens chorionic somatomammotropin hormone 1 (placental lactogen) (CSH1), transcript variant 4, mRNA. /PROD = chorionic somatomammotropin hormone 1, isoform4 /FL = gb: NM_022642.1 | — | −2.24 | 0.12 | 2.97 | 0.42 | −3.78 | 0.07 | 2.51 | 0.44 |
| NM_001317 | Homo sapiens chorionic somatomammotropin hormone 1 (placental lactogen) (CSH1), transcript variant 1, mRNA. /PROD = chorionic somatomammotropin hormone 1, isoform 1precursor /FL = gb: NM_001317.2 gb: J00118.1 | CSH1 | −2.95 | 0.57 | 2.69 | 0.36 | −4.04 | 0.51 | 1.86 | 0.68 |
| BC005921 | Homo sapiens, chorionic somatomammotropin hormone 1 (placental lactogen), clone MGC: 14518, mRNA, complete cds. /PROD = chorionic somatomammotropin hormone 1 (placentallactogen) /FL = gb: BC005921.1 | CSH1 | −2.26 | 0.09 | 3.26 | 0.23 | −2.96 | 0.37 | 2.58 | 0.45 |
| AI796169 | GATA-binding protein 3 /FL = gb: NM_002051.1 gb: M69106.1 gb: BC003070.1 | GATA3 | −4.45 | 0.10 | 0.24 | 1.30 | −4.72 | 0.13 | 0.80 | 2.05 |
| NM_020991 | Homo sapiens chorionic somatomammotropin hormone 2 (CSH2), transcript variant 1, mRNA. | CSH1 | −1.27 | 0.48 | 3.19 | 0.23 | −2.91 | 0.35 | 2.62 | 0.54 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = chorionic somatomammotropin hormone 2, isoform 1precursor /FL = gb: NM_020991.2 gb: BC002717.1 | | | | | | | | | |
| NM_021827 | Homo sapiens hypothetical protein FLJ23514 (FLJ23514), mRNA. /PROD = hypothetical protein FLJ23514 /FL = gb: NM_021827.1 | CCDC81 | −0.37 | 0.35 | 3.16 | 2.05 | −2.02 | 1.27 | 5.25 | 1.98 |
| AB028021 | Cluster Incl. AB028021: Homo sapiens HNF-3beta mRNA for hepatocyte nuclear factor-3 beta, complete cds /cds = (196,1569) /gb = AB028021 /gi = 4958949 /ug = Hs.155651 /len = 1944 | FOXA2 | −2.97 | 0.25 | 0.59 | 3.25 | −3.43 | 0.57 | 4.12 | 2.57 |
| NM_002521 | Homo sapiens natriuretic peptide precursor B (NPPB), mRNA. /PROD = natriuretic peptide precursor B /FL = gb: NM_002521.1 gb: M25296.1 | NPPB | 1.54 | 0.11 | 5.47 | 1.17 | −0.15 | 0.38 | 6.24 | 1.23 |
| AA352113 | ESTs | ST8SIA4 | −4.01 | 1.24 | −0.99 | 2.04 | −4.79 | 1.00 | 1.05 | 1.62 |
| BM128432 | Homo sapiens full length insert cDNA clone YA81B05 | IGFBP5 | −2.73 | 1.11 | 2.31 | 2.30 | −3.48 | 0.56 | 4.45 | 2.02 |
| NM_002770 | Homo sapiens protease, serine, 2 (trypsin 2) (PRSS2), mRNA. /PROD = protease, serine, 2 (trypsin 2) /FL = gb: M27602.1 gb: NM_002770.1 | PRSS1 | −2.77 | 0.33 | 1.59 | 2.68 | −3.13 | 0.48 | 3.88 | 2.95 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_022579 | Homo sapiens chorionic somatomammotropin hormone-like 1 (CSHL1), transcript variant 3, mRNA. /PROD = chorionic somatomammotropin hormone-like 1, isoform 3 precursor /FL = gb: NM_022579.1 | CSH1 | −1.58 | 0.91 | 2.48 | 0.38 | −3.33 | 0.13 | 1.77 | 0.49 |
| NM_005454 | Homo sapiens cerberus 1 (Xenopus laevis) homolog (cysteine knot superfamily) (CER1), mRNA. /PROD = cerberus 1 /FL = gb: NM_005454.1 | CER1 | 2.82 | 0.09 | 5.78 | 1.04 | 1.48 | 0.05 | 6.74 | 1.18 |
| NM_022645 | Homo sapiens chorionic somatomammotropin hormone 2 (CSH2), transcript variant 3, mRNA. /PROD = chorionic somatomammotropin hormone 2, isoform 3precursor /FL = gb: NM_022645.1 | CSH1 | −2.30 | 0.33 | 2.95 | 0.31 | −2.78 | 0.24 | 2.45 | 0.34 |
| AI821586 | ESTs, Moderately similar to JE0284 Mm-1 cell derived transplantability-associated protein 1b (H. sapiens) | LOC440981 | −3.22 | 0.97 | 0.66 | 3.19 | −2.97 | 0.13 | 4.22 | 2.76 |
| AL121722 | Human DNA sequence from clone RP4-788L20 on chromosome 20 Contains the HNF3B (hepatocyte nuclear factor 3, beta) gene. a novel gene based on ESTs, ESTs, STSs, GSSs and CpG Islands | — | −2.95 | 0.36 | −0.01 | 2.69 | −3.43 | 0.38 | 2.95 | 2.66 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_001311 | Homo sapiens cysteine-rich protein 1 (intestinal) (CRIP1), mRNA. /PROD = cysteine-rich protein 1 (intestinal) /FL = gb: U58630.1 gb: BC002738.1 gb: NM_001311.1 gb: U09770.1 | CRIP1 | 1.66 | 0.17 | 1.90 | 0.07 | −2.96 | 0.66 | 1.80 | 0.24 |
| AY177407 | Homo sapiens homeobox protein goosecoid mRNA. complete cds. /PROD = homeobox protein goosecoid /FL = gb: AY177407.1 gb: NM_173849.1 | GSC | −4.59 | 0.18 | −1.08 | 2.89 | −4.64 | 0.06 | 1.89 | 2.79 |
| NM_005442 | Homo sapiens eomesodermin (Xenopus laevis) homolog (EOMES), mRNA. /PROD = eomesodermin (Xenopus laevis) homolog /FL = gb: AB031038.1 gb: NM_005442.1 | EOMES | −0.16 | 0.29 | 2.89 | 1.70 | 0.13 | 0.16 | 4.90 | 1.34 |
| L01639 | Human (clone HSY3RR) neuropeptide Y receptor (NPYR) mRNA, complete cds. /PROD = neuropeptide Y receptor /FL = gb: L06797.1 gb: NM_003467.1 gb: AF025375.1 gb: AF147204.1 gb: M99293.1 gb: L01639.1 | CXCR4 | 0.64 | 0.26 | 3.71 | 1.78 | −0.16 | 0.50 | 5.48 | 1.77 |
| NM_022646 | Homo sapiens chorionic somatomammotropin hormone 2 (CSH2), transcript variant 4, mRNA. | — | −1.57 | 0.60 | 2.67 | 0.26 | −1.88 | 0.98 | 2.22 | 0.35 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = chorionic somatomammotropin hormone 2, isoform4 /FL = gb: NM_022646.1 | | | | | | | | | |
| AW007532 | Human insulin-like growth factor binding protein 5 (IGFBP5) mRNA | IGFBP5 | 0.31 | 0.25 | 4.59 | 1.53 | 0.72 | 0.09 | 6.19 | 1.58 |
| NM_002160 | *Homo sapiens* hexabrachion (tenascin C, cytotactin) (HXB), mRNA. /PROD = hexabrachion (tenascin C, cytotactin) /FL = gb: M55618.1 gb: NM_002160.1 | TNC | −0.24 | 0.29 | 2.23 | 0.80 | −0.81 | 0.81 | 2.85 | 0.82 |
| AA149250 | ESTs, Weakly similar to WDNM RAT WDNM1 PROTEIN PRECURSOR (*R. norvegicus*) | LOC645638 | 1.27 | 0.61 | 4.23 | 1.26 | −0.64 | 0.40 | 2.47 | 1.23 |
| AW977527 | ESTs | — | −0.91 | 0.99 | 1.18 | 0.68 | −2.52 | 1.01 | 1.59 | 0.64 |
| NM_022454 | *Homo sapiens* hypothetical protein FLJ22252 similar to SRY-box containing gene 17 (FLJ22252), mRNA. /PROD = hypothetical protein FLJ22252 similar to SRY-boxcontaining gene 17 /FL = gb: NM_022454.1 | SOX17 | −1.01 | 0.33 | 2.29 | 2.08 | −0.14 | 0.15 | 4.60 | 1.73 |
| AI640307 | protocadherin 10 | PCDH10 | −1.89 | 1.37 | 1.53 | 1.32 | −1.33 | 0.38 | 2.99 | 1.19 |
| AJ224869 | *Homo sapiens* CXCR4 gene encoding receptor CXCR4 | — | 0.98 | 0.18 | 4.22 | 1.88 | 1.34 | 0.17 | 6.36 | 1.49 |
| AI824037 | ESTs, Weakly similar to FCE2 MOUSE LOW AFFINITY | FREM1 | −1.42 | 0.36 | 1.22 | 1.95 | −1.37 | 0.61 | 3.48 | 1.49 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | IMMUNOGLOBULIN EPSILON FC RECEPTOR (*M. musculus*) | | | | | | | | | |
| BE222344 | splicing factor, arginineserine-rich 5 | — | 0.50 | 0.05 | 3.01 | 0.93 | −0.94 | 1.18 | 4.27 | 0.94 |
| NM_001643 | *Homo sapiens* apolipoprotein A-II (APOA2), mRNA. /PROD = apolipoprotein A-II precursor /FL = gb: M29882.1 gb: NM_001643.1 gb: BC005282.1 | APOA2 | −2.25 | 1.05 | 1.72 | 2.60 | −1.20 | 0.44 | 4.47 | 2.42 |
| AI821669 | ESTs | — | −0.94 | 0.79 | 1.71 | 2.19 | −0.89 | 0.21 | 3.91 | 1.94 |
| NM_002608 | *Homo sapiens* platelet-derived growth factor beta polypeptide (simian sarcoma viral (v-sis) oncogene homolog) (PDGFB), mRNA. /PROD = platelet-derived growth factor beta polypeptide (simian sarcoma viral (v-sis) oncogene homolog) /FL = gb: M12783.1 gb: NM_002 | PDGFB | −0.23 | 0.82 | 1.87 | 0.15 | −2.27 | 0.65 | 1.92 | 0.13 |
| AW444761 | ESTs | CDKN2B | −3.35 | 0.90 | 0.39 | 0.52 | −3.11 | 0.88 | 0.80 | 0.25 |
| BF223214 | ESTs | — | −0.48 | 0.08 | 1.69 | 2.04 | −1.51 | 0.25 | 4.09 | 1.98 |
| AF154054 | *Homo sapiens* DRM (DRM) mRNA, complete cds. /PROD = DRM /FL = gb: NM_013372.1 gb: AF110137.2 gb: AF045800.1 gb: AF154054.1 | GREM1 | 1.68 | 0.26 | 4.61 | 0.74 | 0.62 | 0.04 | 3.58 | 0.87 |
| NM_021223 | *Homo sapiens* myosin light chain 2a (LOC58498), mRNA. | MYL7 | 1.81 | 0.05 | 4.28 | 0.81 | 0.17 | 0.08 | 4.87 | 0.96 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = myosin light chain 2a /FL = gb: NM_021223.1 | | | | | | | | | |
| AI817041 | G protein-coupled receptor | CMKOR1 | −0.19 | 0.27 | 2.67 | 1.97 | 0.06 | 0.18 | 5.05 | 1.64 |
| NM_003670 | Homo sapiens basic helix-loop-helix domain containing, class B, 2 (BHLHB2), mRNA. /PROD = differentiated embryo chondrocyte expressed gene1 /FL = gb: AB004066.1 gb: NM_003670.1 | BHLHB2 | 1.09 | 0.08 | 3.85 | 0.10 | −0.11 | 0.17 | 3.46 | 0.03 |
| NM_023915 | Homo sapiens G protein-coupled receptor 87 (GPR87), mRNA. /PROD = G protein-coupled receptor 87 /FL = gb: NM_023915.1 gb: AF237763.1 | GPR87 | −1.70 | 0.61 | 1.64 | 0.18 | −2.99 | 0.06 | 1.40 | 0.23 |
| NM_003867 | Homo sapiens fibroblast growth factor 17 (FGF17), mRNA. /PROD = fibroblast growth factor 17 /FL = gb: NM_003867.1 gb: AB009249.1 | FGF17 | −3.05 | 0.39 | 0.03 | 2.07 | −2.13 | 0.41 | 2.49 | 1.35 |
| NM_024426 | Homo sapiens Wilms tumor 1 (WT1), transcript variant D, mRNA. /PROD = Wilms tumor 1 isoform D /FL = gb: NM_024424.1 gb: NM_024426.1 | WT1 | −3.23 | 0.37 | −1.11 | 0.62 | −4.20 | 0.56 | −2.44 | 1.26 |
| NM_033136 | Homo sapiens fibroblast growth factor 1 (acidic) (FGF1), transcript variant 2, mRNA. | FGF1 | −3.10 | 1.42 | 0.09 | 0.83 | −3.16 | 0.63 | −0.78 | 1.21 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = fibroblast growth factor 1 (acidic) isoform 2precursor /FL = gb: NM_033137.1 gb: NM_033136.1 | | | | | | | | | |
| X99268 | H. sapiens mRNA for B-HLH DNA binding protein. /PROD = B-HLH DNA binding protein /FL = gb: NM_000474.1 | TWIST1 | 0.10 | 0.33 | 3.94 | 0.24 | 0.34 | 0.22 | 3.45 | 0.34 |
| AL524520 | G protein-coupled receptor 49 | LGR5 | −2.27 | 1.43 | 0.76 | 1.40 | −1.58 | 0.40 | 2.51 | 1.35 |
| NM_022557 | Homo sapiens growth hormone 2 (GH2), transcript variant 2, mRNA. /PROD = growth hormone 2, isoform 2 precursor /FL = gb: J03756.1 gb: NM_022557.1 | CSH1 | −0.91 | 0.19 | 1.40 | 0.22 | −2.12 | 0.08 | 1.47 | 0.14 |
| AL544576 | ESTs | TMEM88 | −1.96 | 0.68 | 1.75 | 0.58 | −1.45 | 0.86 | 2.08 | 0.70 |
| NM_022580 | Homo sapiens chorionic somatomammotropin hormone-like 1 (CSHL1), transcript variant 4, mRNA. /PROD = chorionic somatomammotropin hormone-like 1, isoform 4 /FL = gb: NM_022580.1 | CSH1 | −1.20 | 0.86 | 2.30 | 0.39 | −1.78 | 0.64 | 1.55 | 0.63 |
| J03580 | Human, parathyroid-like protein (associated with humoral hypercalcemia of malignancy) mRNA, complete cds. /FL = gb: J03580.1 | PTHLH | −2.72 | 0.33 | −0.80 | 0.40 | −4.05 | 0.41 | −1.42 | 0.73 |
| BC029835 | Homo sapiens, clone IMAGE: 5169759, mRNA. | LOC646867 | −2.66 | 1.12 | 1.01 | 1.85 | −1.40 | 0.41 | 3.03 | 1.61 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AI452798 | ESTs | MYOCD | 0.98 | 0.13 | 3.31 | 0.66 | −0.07 | 0.28 | 2.80 | 0.98 |
| NM_022559 | Homo sapiens growth hormone 1 (GH1), transcript variant 2, mRNA. /PROD = growth hormone 1, isoform 2 precursor /FL = gb: NM_022559.1 | CSH1 | −1.56 | 0.38 | 2.00 | 0.32 | −2.07 | 0.42 | 1.47 | 0.28 |
| NM_001318 | Homo sapiens chorionic somatomammotropin hormone-like 1 (CSHL1), transcript variant 1, mRNA. /PROD = chorionic somatomammotropin hormone-like 1, isoform 1 /FL = gb: NM_001318.2 | CSH1 | 0.15 | 0.41 | 2.83 | 0.40 | −1.30 | 0.34 | 2.37 | 0.50 |
| M65062 | Human insulin-like growth factor binding protein 5 (IGFBP-5) mRNA, complete cds. /PROD = insulin-like growth factor binding protein 5 /FL = gb: M65062.1 gb: M62782.1 gb: NM_000599.1 gb: AF055033.1 | IGFBP5 | −2.80 | 1.17 | 2.19 | 2.00 | −0.99 | 0.23 | 4.11 | 1.81 |
| AF207990 | Homo sapiens fer-1 like protein 3 (FER1L3) mRNA, complete cds. /PROD = fer-1 like protein 3 /FL = gb: AF207990.1 | FER1L3 | 0.49 | 0.40 | 3.00 | 0.81 | −0.16 | 0.09 | 4.02 | 0.92 |
| AI079944 | ESTs | — | −0.78 | 0.22 | 0.08 | 0.59 | −3.56 | 0.24 | −0.13 | 0.73 |
| BC003070 | Homo sapiens, GATA-binding protein 3, clone MGC: 2346, mRNA, complete cds. /PROD = GATA-binding protein 3 | GATA3 | 1.07 | 0.04 | 3.23 | 0.96 | 0.31 | 0.26 | 4.45 | 0.80 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BE877796 | /FL = gb: NM_002051.1 gb: M69106.1 gb: BC003070.1 collagen, type VIII, alpha 1 | COL8A1 | −3.76 | 1.17 | −1.28 | 0.73 | −4.89 | 0.54 | −1.33 | 1.64 |
| NM_022560 | /FL = gb: NM_001850.1 Homo sapiens growth hormone 1 (GH1), transcript variant 3, mRNA. /PROD = growth hormone 1, isoform 3 precursor /FL = gb: NM_022560.1 | CSH1 | −2.23 | 0.74 | 1.95 | 0.08 | −2.01 | 0.51 | 1.47 | 0.31 |
| BE328496 | hypothetical protein PRO2032 /FL = gb: AF116683.1 gb: NM_018615.1 | — | −0.59 | 0.25 | 1.76 | 0.13 | −2.01 | 0.97 | 1.73 | 0.26 |
| NM_022469 | Homo sapiens hypothetical protein FLJ21195 similar to protein related to DAC and cerberus (FLJ21195), mRNA. /PROD = hypothetical protein FLJ21195 similar to proteinrelated to DAC and cerberus /FL = gb: NM_022469.1 | GREM2 | −1.15 | 0.25 | 0.09 | 0.88 | −3.43 | 0.90 | 0.76 | 0.47 |
| NM_001362 | Homo sapiens deiodinase, iodothyronine, type III (DIO3), mRNA. /PROD = thyroxine deiodinase type III /FL = gb: NM_001362.1 gb: S79854.1 | DIO3 | −1.73 | 0.70 | 1.99 | 1.92 | −1.05 | 0.79 | 4.23 | 1.51 |
| NM_022581 | Homo sapiens chorionic somatomammotropin hormone-like 1 (CSHL1), transcript variant 5, mRNA. | CSH1 | −1.56 | 0.67 | 2.08 | 0.42 | −1.63 | 0.80 | 1.47 | 0.53 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = chorionic somatomammotropin hormone-like 1, isoform 5 precursor /FL = gb: NM_022581.1 | | | | | | | | | |
| NM_013372 | Homo sapiens cysteine knot superfamily 1, BMP antagonist 1 (CKTSF1B1), mRNA. /PROD = cysteine knot superfamily 1, BMP antagonist 1 /FL = gb: NM_013372.1 gb: AF110137.2 gb: AF045800.1 gb: AF154054.1 | GREM1 | 1.61 | 0.07 | 4.15 | 0.64 | 0.91 | 0.15 | 3.20 | 0.81 |
| NM_022561 | Homo sapiens growth hormone 1 (GH1), transcript variant 4, mRNA. /PROD = growth hormone 1, isoform 4 precursor /FL = gb: NM_022561.1 | CSH1 | −1.32 | 0.60 | 1.91 | 0.25 | −1.66 | 0.46 | 1.57 | 0.22 |
| NM_022659 | Homo sapiens hypothetical protein FLJ11500 similar to EBF2 (FLJ11500), mRNA. /PROD = hypothetical protein FLJ11500 similar to EBF2 /FL = gb: NM_022659.1 | — | −1.58 | 0.75 | −1.24 | 1.79 | −3.62 | 0.20 | −1.81 | 1.25 |
| AF006060 | Homo sapiens placental growth hormone 20 kDa isoform (hGH-V) mRNA, complete cds. /PROD = placental growth hormone 20 kDa isoform /FL = gb: AF006060.1 gb: NM_022556.1 | CSH1 | −1.21 | 0.06 | 1.13 | 0.05 | −3.08 | 0.63 | 0.50 | 0.17 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AI688418 | plexin A2 | PLXNA2 | −0.18 | 0.14 | 0.84 | 1.58 | −1.28 | 0.53 | 2.74 | 0.96 |
| M86849 | *Homo sapiens* connexin 26 (GJB2) mRNA, complete cds. /PROD = connexin 26 /FL = gb: NM__004004.1 gb: M86849.2 | — | −5.08 | 0.26 | 0.54 | 0.47 | −1.64 | 0.19 | −0.09 | 0.44 |
| N71923 | fibronectin leucine rich transmembrane protein 3 /FL = gb: AF169677.1 gb: NM__013281.1 | — | 0.30 | 0.24 | 2.83 | 1.46 | 0.53 | 0.12 | 4.38 | 1.46 |
| NM__013281 | *Homo sapiens* fibronectin leucine rich transmembrane protein 3 (FLRT3), mRNA. /PROD = fibronectin leucine rich transmembrane protein3 /FL = gb: AF169677.1 gb: NM__013281.1 | FLRT3 | −0.20 | 0.33 | 2.14 | 1.61 | 0.00 | 0.15 | 3.96 | 1.39 |
| AI601101 | *Homo sapiens* cDNA: FLJ21410 fis, clone COL03938 | FAM84A | 0.46 | 0.38 | 3.07 | 0.46 | −0.32 | 0.46 | 3.82 | 0.48 |
| NM__000325 | *Homo sapiens* paired-like homeodomain transcription factor 2 (PITX2), mRNA. /PROD = paired-like homeodomain transcription factor 2 /FL = gb: NM__000325.1 gb: U69961.1 gb: AF048720.1 | PITX2 | 1.37 | 0.17 | 3.51 | 0.47 | 0.89 | 0.16 | 4.02 | 0.47 |
| AI692659 | heat shock 90 kD protein 1, alpha | PRDM1 | 0.21 | 0.25 | 1.67 | 0.77 | −0.67 | 0.17 | 2.61 | 0.80 |
| NM__000602 | *Homo sapiens* serine (or cysteine) proteinase inhibitor, clade E | SERPINE1 | 2.97 | 0.16 | 4.75 | 1.89 | 1.55 | 0.22 | 2.75 | 1.87 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | (nexin, plasminogen activator inhibitor type 1), member 1 (SERPINE1), mRNA. /PROD = serine (or cysteine) proteinase inhibitor, cladeE (nexin, plasminogen activator inhibitor type 1), membe | | | | | | | | | |
| NM_001480 | Homo sapiens galanin receptor 1 (GALR1), mRNA. /PROD = galanin receptor 1 /FL = gb: NM_001480.2 gb: U23854.1 gb: L34339.1 gb: U53511.1 | GALR1 | −1.90 | 0.68 | 0.04 | 0.73 | −2.42 | 0.72 | −0.34 | 0.73 |
| NM_000393 | Homo sapiens collagen, type V, alpha 2 (COL5A2), mRNA. /PROD = collagen, type V, alpha 2 /FL = gb: NM_000393.1 | COL5A2 | 4.29 | 0.14 | 5.25 | 0.21 | 2.62 | 0.02 | 5.48 | 0.13 |
| N63706 | ESTs | — | 0.06 | 0.18 | 1.73 | 1.89 | −0.74 | 0.13 | 3.75 | 1.75 |
| AF132818 | Homo sapiens colon Kruppel-like factor (CKLF) mRNA, complete cds. /PROD = colon Kruppel-like factor /FL = gb: AF132818.1 gb: AF287272.1 gb: AB030824.1 gb: NM_001730.1 gb: D14520.1 | KLF5 | 0.63 | 0.11 | 3.16 | 0.50 | 0.07 | 0.42 | 3.40 | 0.44 |
| X59065 | H. sapiens FGF gene, exon 3 /FL = gb: NM_000800.1 gb: M13361.1 | — | −1.17 | 1.11 | −0.39 | 1.06 | −2.61 | 0.26 | −0.96 | 1.01 |
| R73554 | Human insulin-like growth factor binding protein 5 (IGFBP5) mRNA | IGFBP5 | −0.12 | 0.15 | 2.63 | 1.41 | −0.69 | 0.16 | 4.00 | 1.65 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_002149 | Homo sapiens hippocalcin-like 1 (HPCAL1), mRNA. /PROD = hippocalcin-like 1 /FL = gb: NM_002149.1 gb: D16227.1 | HPCAL1 | −0.18 | 0.28 | 1.81 | 0.44 | −1.98 | 0.86 | 1.18 | 0.22 |
| AI093327 | ESTs | — | 0.69 | 0.11 | 3.09 | 0.58 | 0.45 | 0.07 | 2.29 | 0.85 |
| NM_003240 | Homo sapiens endometrial bleeding associated factor (left-right determination, factor A; transforming growth factor beta superfamily) (EBAF), mRNA. /PROD = transforming growth factor, beta 4 /FL = gb: U81523.1 gb: NM_003240.1 gb: AF081513.1 | PYCR2 | 6.22 | 0.16 | 6.97 | 0.60 | 4.16 | 0.07 | 7.51 | 0.68 |
| AI263909 | ras homolog gene family, member B /FL = gb: NM_004040.1 | RHOB | 3.89 | 0.16 | 5.88 | 0.13 | 3.01 | 0.15 | 5.64 | 0.10 |
| NM_001792 | Homo sapiens cadherin 2, type 1, N-cadherin (neuronal) (CDH2), mRNA. /PROD = cadherin 2, type 1, N-cadherin (neuronal) /FL = gb: NM_001792.1 gb: M34064.1 | CDH2 | 3.83 | 0.17 | 6.01 | 0.11 | 2.85 | 0.13 | 5.74 | 0.17 |
| NM_003897 | Homo sapiens immediate early response 3 (IER3), mRNA. /PROD = immediate early response 3 /FL = gb: BC005080.1 gb: BC000844.1 gb: AF083421.1 gb: NM_003897.1 | IER3 | 5.45 | 0.15 | 6.97 | 0.17 | 4.33 | 0.11 | 6.75 | 0.27 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF278532 | Homo sapiens beta-netrin mRNA, complete cds. /PROD = beta-netrin /FL = gb: AF119916.1 gb: AF297711.1 gb: NM_021229.1 gb: AF278532.1 | NTN4 | −0.16 | 0.30 | 1.70 | 0.91 | −0.67 | 0.48 | 2.66 | 0.74 |
| AF348491 | Homo sapiens chemokine receptor CXCR4 mRNA, complete cds. /PROD = chemokine receptor CXCR4 /FL = gb: AF348491.1 | CXCR4 | 1.39 | 0.21 | 4.05 | 1.58 | 1.45 | 0.07 | 5.67 | 1.65 |
| NM_030781 | Homo sapiens scavenger receptor with C-type lectin (SRCL), mRNA. /PROD = scavenger receptor with C-type lectin /FL = gb: NM_030781.1 | COLEC12 | 1.93 | 0.13 | 3.64 | 1.66 | 1.96 | 0.18 | 5.68 | 1.51 |
| NM_000599 | Homo sapiens insulin-like growth factor binding protein 5 (IGFBP5), mRNA. /PROD = insulin-like growth factor binding protein 5 /FL = gb: M65062.1 gb: M62782.1 gb: NM_000599.1 gb: AF055033.1 | IGFBP5 | −0.31 | 0.34 | 3.03 | 1.85 | 0.12 | 0.24 | 4.51 | 1.75 |
| AI348094 | KIAA0882 protein | TBC1D9 | 0.13 | 0.26 | 3.21 | 1.13 | 0.96 | 0.13 | 4.67 | 1.08 |
| BG287862 | AHNAK nucleoprotein (desmoyokin) | AHNAK | 1.47 | 0.20 | 3.72 | 0.51 | 1.37 | 0.17 | 4.34 | 0.58 |
| AI676059 | ESTs | FOXQ1 | −0.32 | 0.55 | 3.08 | 1.63 | 0.50 | 0.17 | 4.81 | 1.47 |
| AI127440 | ESTs | — | −0.85 | 0.36 | 0.60 | 1.22 | −0.65 | 0.27 | 2.13 | 1.13 |
| AL574210 | serine (or cysteine) proteinase inhibitor, clade E (nexin, plasminogen | SERPINE1 | 2.81 | 0.24 | 5.07 | 0.88 | 2.13 | 0.15 | 3.96 | 0.86 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | activator inhibitor type 1), member 1 /FL = gb: NM_000602.1 gb: M16006.1 | | | | | | | | | |
| AB037810 | Homo sapiens mRNA for KIAA1389 protein, partial cds. /PROD = KIAA1389 protein | SIPA1L2 | 3.88 | 0.04 | 5.66 | 0.08 | 3.18 | 0.11 | 5.85 | 0.11 |
| NM_001394 | Homo sapiens dual specificity phosphatase 4 (DUSP4), mRNA. /PROD = dual specificity phosphatase 4 /FL = gb: NM_001394.2 gb: BC002671.1 gb: U48807.1 gb: U21108.1 | DUSP4 | 0.22 | 0.37 | 2.88 | 1.09 | 0.50 | 0.14 | 4.12 | 0.99 |
| BC029442 | Homo sapiens, Similar to immunity associated protein 1, clone MGC: 32707 IMAGE: 4618467, mRNA, complete cds. /PROD = Similar to immunity associated protein 1 /FL = gb: BC029442.1 | — | 2.04 | 0.20 | 3.80 | 0.74 | 1.18 | 0.05 | 4.50 | 0.65 |
| NM_000700 | Homo sapiens annexin A1 (ANXA1), mRNA. /PROD = annexin I /FL = gb: BC001275.1 gb: NM_000700.1 | ANXA1 | 5.00 | 0.18 | 6.27 | 1.28 | 3.67 | 0.05 | 4.96 | 1.25 |
| BC000740 | Homo sapiens, cholecystokinin B receptor, clone MGC: 2199, mRNA, complete cds. /PROD = cholecystokinin B receptor /FL = gb: L07746.1 gb: L08112.1 gb: S70057.1 gb: BC000740.1 gb: L04473.1 gb: NM_000731.1 | CCKBR | 1.08 | 0.36 | 3.93 | 1.84 | 1.93 | 0.03 | 5.86 | 1.82 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| N36408 | hypothetical protein FLJ23306 /FL = gb: NM_024530.1 | FOSL2 | −0.09 | 0.40 | 2.07 | 0.04 | −0.85 | 0.24 | 1.71 | 0.28 |
| AF072242 | Homo sapiens methyl-CpG binding protein MBD2 (MBD2) mRNA, complete cds. /PROD = methyl-CpG binding protein MBD2 /FL = gb: NM_003927.2 gb: AF072242.1 | MBD2 | −3.98 | 0.38 | −0.59 | 0.27 | −3.07 | 0.22 | −1.70 | 0.68 |
| AF211891 | Homo sapiens Mix-like homeobox protein 1 (MILD1) mRNA, complete cds. /PROD = Mix-like homeobox protein 1 /FL = gb: AF211891.1 | MIXL1 | −0.63 | 0.38 | 0.77 | 0.95 | −2.29 | 0.44 | 0.92 | 1.71 |
| BF063186 | ESTs | CALD1 | 1.16 | 0.19 | 2.03 | 0.42 | −1.20 | 1.02 | 1.65 | 0.27 |
| NM_000362 | Homo sapiens tissue inhibitor of metalloproteinase 3 (Sorsby fundus dystrophy, pseudoinflammatory) (TIMP3), mRNA. /PROD = tissue inhibitor of metalloproteinase 3precursor /FL = gb: NM_000362.2 gb: U14394.1 gb: U67195.1 gb: U02571.1 | TIMP3 | 0.08 | 0.32 | 1.98 | 0.09 | −0.34 | 0.33 | 1.80 | 0.26 |
| AK022852 | Homo sapiens cDNA FLJ12790 fis, clone NT2RP2001985, weakly similar to Homo sapiens high-risk human papilloma viruses E6 oncoproteins | SIPA1L2 | 2.87 | 0.12 | 4.50 | 0.09 | 1.87 | 0.01 | 4.55 | 0.09 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | targeted protein E6TP1 alpha mRNA. | | | | | | | | | |
| BE500942 | *Homo sapiens* mRNA; cDNA DKFZp761M0111 (from clone DKFZp761M0111) | C6orf155 | 3.23 | 0.10 | 4.68 | 0.86 | 1.95 | 0.03 | 3.77 | 0.96 |
| AW665892 | paternally expressed 3 | MFAP5 | −1.82 | 0.54 | 0.37 | 0.60 | −1.54 | 0.39 | −0.01 | 0.28 |
| AK025063 | *Homo sapiens* cDNA: FLJ21410 fis, clone COL03938. | FAM84A | −1.34 | 0.84 | 0.75 | 0.45 | −2.35 | 0.85 | 1.01 | 0.53 |
| NM_001828 | *Homo sapiens* Charot-Leyden crystal protein (CLC), mRNA. /PROD = Charot-Leyden crystal protein /FL = gb: NM_001828.3 gb: L01664.1 | CLC | 2.17 | 0.21 | 3.53 | 1.07 | 0.45 | 0.08 | 2.11 | 1.27 |
| M15329 | Human interleukin 1-alpha (IL1A) mRNA, complete cds. /PROD = interleukin 1-alpha /FL = gb: M15329.1 | IL1A | 0.85 | 0.32 | 2.72 | 0.30 | −0.88 | 0.60 | 2.20 | 0.22 |
| BC002671 | *Homo sapiens*, dual specificity phosphatase 4, clone MGC: 3713, mRNA, complete cds. /PROD = dual specificity phosphatase 4 /FL = gb: NM_001394.2 gb: BC002671.1 gb: U48807.1 gb: U21108.1 | DUSP4 | 1.79 | 0.03 | 4.30 | 1.39 | 2.10 | 0.10 | 5.60 | 1.22 |
| AA524250 | deleted in liver cancer 1 | DLC1 | 1.02 | 0.05 | 2.35 | 0.98 | 0.10 | 0.38 | 3.26 | 0.96 |
| BC001211 | *Homo sapiens*, kinesin family member C3, clone MGC: 3226, mRNA, | KIFC3 | −1.53 | 0.72 | 0.81 | 0.38 | −2.08 | 0.42 | 0.75 | 0.16 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | complete cds. /PROD = kinesin family member C3 /FL = gb: BC001211.1 gb: NM_005550.1 gb: AF004426.1 | | | | | | | | | |
| NM_004560 | Homo sapiens receptor tyrosine kinase-like orphan receptor 2 (ROR2), mRNA. /PROD = receptor tyrosine kinase-like orphan receptor 2 /FL = gb: M97639.1 gb: NM_004560.1 | ROR2 | 0.76 | 0.08 | 2.20 | 0.81 | 0.08 | 0.14 | 3.06 | 0.95 |
| BC000125 | Homo sapiens, Similar to transforming growth factor, beta 1, clone MGC: 3119, mRNA, complete cds. /PROD = Similar to transforming growth factor, beta 1 /FL = gb: M38449.1 gb: BC001180.1 gb: BC000125.1 gb: NM_000660.1 | TGFB1 | 1.16 | 0.18 | 3.43 | 0.08 | 0.72 | 0.14 | 3.30 | 0.16 |
| NM_016931 | Homo sapiens NADPH oxidase 4 (NOX4), mRNA. /PROD = NADPH oxidase 4 /FL = gb: AF261943.1 gb: NM_016931.1 gb: AF254621.1 gb: AB041035.1 | NOX4 | 1.83 | 0.06 | 3.31 | 1.29 | 1.20 | 0.14 | 2.28 | 1.27 |
| BC001830 | Homo sapiens, Similar to transforming growth factor beta 1 induced transcript 1, clone MGC: 4078, mRNA, complete cds. | TGFB1I1 | 0.95 | 0.17 | 3.59 | 0.73 | 1.52 | 0.09 | 2.74 | 0.69 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = Similar to transforming growth factor beta 1induced transcript 1 /FL = gb: NM_015927.1 gb: BC001830.1 gb: AF116343.1 | | | | | | | | | |
| NM_024576 | Homo sapiens hypothetical protein FLJ21079 (FLJ21079), mRNA. /PROD = hypothetical protein FLJ21079 /FL = gb: NM_024576.1 | OGFRL1 | 3.15 | 0.13 | 4.49 | 0.82 | 1.63 | 0.06 | 3.30 | 0.98 |
| NM_001963 | Homo sapiens epidermal growth factor (beta-urogastrone) (EGF), mRNA. /PROD = epidermal growth factor (beta-urogastrone) /FL = gb: NM_001963.2 | EGF | 0.12 | 0.22 | 1.82 | 1.15 | −0.62 | 0.36 | 2.68 | 1.23 |
| BE620374 | ESTs | C6orf155 | 1.97 | 0.05 | 3.35 | 1.01 | 0.59 | 0.17 | 2.10 | 1.05 |
| AL359062 | Homo sapiens mRNA full length insert cDNA clone EUROIMAGE 1913076. | COL8A1 | −1.31 | 0.25 | 2.32 | 0.94 | 0.03 | 0.12 | 3.51 | 1.02 |
| AL117653 | Homo sapiens mRNA; cDNA DKFZp586C0224 (from clone DKFZp586C0224). | MITF | −0.12 | 0.61 | 2.32 | 0.10 | 0.21 | 0.13 | 2.56 | 0.06 |
| AL021977 | Cluster Incl. AL021977: bK447C4.1 (novel MAFF (v-maf musculoapo neurotic fibrosarcoma (avian) oncogene family, protein F) LIKE protein) /cds = (0.494) /gb = AL021977 /gi = 4914526 /ug = Hs.51305 /len = 2128 | — | 1.92 | 0.14 | 4.53 | 0.43 | 2.15 | 0.12 | 4.66 | 0.22 |
| NM_003564 | Homo sapiens transgelin 2 | TAGLN2 | 5.43 | 0.12 | 6.76 | 0.06 | 3.48 | 0.27 | 6.69 | 0.04 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | (TAGLN2), mRNA. /PROD = transgelin 2 /FL = gb: D21261.1 gb: NM_003564.1 | | | | | | | | | |
| BC005107 | Homo sapiens, clone IMAGE: 3840937, mRNA, partial cds. /PROD = Unknown (protein for IMAGE: 3840937) | — | 7.08 | 0.07 | 6.42 | 0.26 | 2.60 | 0.07 | 6.93 | 0.22 |
| NM_001124 | Homo sapiens adrenomedullin (ADM), mRNA. /PROD = adrenomedullin /FL = gb: NM_001124.1 gb: D14874.1 | ADM | 4.70 | 0.22 | 7.61 | 0.19 | 5.21 | 0.06 | 7.58 | 0.21 |
| AF280545 | Homo sapiens neuropilin-2b(5) (NRP2) mRNA, complete cds, alternatively spliced. /PROD = neuropilin-2b(5) /FL = gb: AF280544.1 gb: AF280545.1 | NRP2 | −0.29 | 0.33 | 1.40 | 0.30 | −1.67 | 0.61 | 1.22 | 0.33 |
| NM_014624 | Homo sapiens S100 calcium-binding protein A6 (calcyclin) (S100A6), mRNA. /PROD = S100 calcium-binding protein A6 /FL = gb: NM_014624.2 gb: BC001431.1 | S100A6 | 3.08 | 0.38 | 3.10 | 0.18 | −0.57 | 0.37 | 3.24 | 0.19 |
| AB030824 | Homo sapiens mRNA for transcription factor BTEB2, complete cds. /PROD = transcription factor BTEB2 /FL = gb: AF132818.1 gb: AF287272.1 gb: AB030824.1 gb: NM_001730.1 gb: D14520.1 | KLF5 | 0.57 | 0.24 | 2.16 | 0.49 | −0.41 | 0.05 | 2.53 | 0.17 |
| NM_015675 | Homo sapiens growth arrest | GADD45B | 2.47 | 0.22 | 4.44 | 0.46 | 2.02 | 0.09 | 4.64 | 0.33 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | and DNA-damage-inducible, beta (GADD45B), mRNA. /PROD = DKFZP566B133 protein /FL = gb: NM_015675.1 gb: AF090950.1 | | | | | | | | | |
| BF347089 | tissue inhibitor of metalloproteinase 3 (Sorsby fundus dystrophy, pseudoinflammatory) /FL = gb: NM_000362.2 gb: U14394.1 gb: U67195.1 gb: U02571.1 | TIMP3 | 0.57 | 0.13 | 2.01 | 0.29 | −0.19 | 0.20 | 2.09 | 0.44 |
| BF056473 | ESTs | — | −0.64 | 0.87 | 1.79 | 0.10 | −0.73 | 0.34 | 1.57 | 0.23 |
| AA809487 | *Homo sapiens* cDNA: FLJ21715 fis, clone COL10287, highly similar to AF071569 *Homo sapiens* multifunctional calciumcalmodulin-dependent protein kinase II delta2 isoform mRNA | — | 0.52 | 0.22 | 3.68 | 0.43 | 1.39 | 0.22 | 3.89 | 0.48 |
| AL575735 | collagen, type V, alpha 2 /FL = gb: NM_000393.1 | — | 5.54 | 0.11 | 6.65 | 0.14 | 4.57 | 0.08 | 6.68 | 0.07 |
| AF003934 | *Homo sapiens* prostate differentiation factor mRNA, complete cds. /PROD = prostate differentiation factor /FL = gb: U88323.1 gb: BC000529.1 gb: AF003934.1 gb: NM_004864.1 gb: AF019770.1 gb: AB000584.1 | GDF15 | 2.74 | 0.20 | 4.01 | 0.41 | 0.72 | 0.17 | 4.34 | 0.50 |
| NM_000313 | *Homo sapiens* protein S (alpha) (PROS1), mRNA. /PROD = protein S (alpha) /FL = gb: M15036.1 gb: NM_000313.1 | PROS1 | −1.54 | 0.10 | 0.98 | 0.83 | −0.62 | 0.09 | 1.79 | 0.86 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
| --- | --- | --- | --- | --- | --- | --- | --- | --- | --- | --- |
| NM_016651 | *Homo sapiens* heptacellular carcinoma novel gene-3 protein (LOC51339), mRNA. /PROD = heptacellular carcinoma novel gene-3 protein /FL = gb: NM_016651.2 gb: AF251079.2 | DACT1 | 2.37 | 0.26 | 4.79 | 0.67 | 2.46 | 0.14 | 3.92 | 0.78 |
| NM_020129 | *Homo sapiens* placental protein 13-like protein (LOC56891), mRNA. /PROD = placental protein 13-like protein /FL = gb: NM_020129.1 gb: AF267852.1 | LGALS14 | 1.38 | 0.30 | 3.15 | 0.70 | 0.79 | 0.04 | 2.47 | 0.66 |
| NM_013451 | *Homo sapiens* fer-1 (*C. elegans*)-like 3 (myoferlin) (FER1L3), mRNA. /PROD = fer-1 (*C. elegans*)-like 3 (myoferlin) /FL = gb: NM_013451.1 gb: AF182316.1 | FER1L3 | 1.75 | 0.15 | 4.02 | 0.97 | 1.59 | 0.13 | 5.14 | 0.82 |
| R72286 | microfibrillar-associated protein 4 | MFAP4 | −1.15 | 0.60 | −1.76 | 0.61 | −2.37 | 0.22 | −0.60 | 0.72 |
| AI417362 | ESTs, Moderately similar to ALU1_HUMAN ALU SUBFAMILY J SEQUENCE CONTAMINATION WARNING ENTRY (*H. sapiens*) | FUT1 | 2.42 | 0.14 | 2.32 | 0.72 | −0.46 | 0.53 | 1.70 | 0.59 |
| NM_001553 | *Homo sapiens* insulin-like growth factor binding protein 7 (IGFBP7), mRNA. /PROD = insulin-like growth factor binding protein 7 /FL = gb: NM_001553.1 gb: L19182.1 | IGFBP7 | 3.41 | 0.19 | 4.63 | 1.07 | 1.65 | 0.10 | 3.34 | 1.16 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BG285011 | Homo sapiens mRNA; cDNA DKFZp586N012 (from clone DKFZp586N012) | ARID5B | 0.05 | 0.22 | 1.79 | 0.21 | −0.95 | 0.42 | 1.16 | 0.55 |
| BE967311 | Homo sapiens mRNA; cDNA DKFZp762O1615 (from clone DKFZp762O1615) | — | 1.99 | 0.06 | 4.08 | 0.92 | 2.28 | 0.17 | 5.01 | 0.87 |
| BC005047 | Homo sapiens, clone MGC: 12852, mRNA, complete cds. /PROD = Unknown (protein for MGC: 12852) /FL = gb: NM_001946.1 gb: AB013382.1 gb: BC003562.1 gb: BC003143.1 gb: BC005047.1 | DUSP6 | 2.50 | 0.32 | 4.04 | 0.67 | 1.56 | 0.16 | 2.94 | 0.84 |
| AW005572 | putative 47 kDa protein | ANKS1B | −0.59 | 0.12 | 0.19 | 0.70 | −1.59 | 0.07 | 0.86 | 0.92 |
| AW294092 | ESTs | RERG | 0.54 | 0.16 | −0.68 | 1.55 | −2.78 | 0.92 | −0.58 | 0.97 |
| NM_001899 | Homo sapiens cystatin S (CST4), mRNA. /PROD = cystatin S /FL = gb: NM_001899.1 | CST4 | 0.14 | 0.52 | 2.46 | 1.59 | 0.53 | 0.14 | 3.87 | 1.40 |
| AI917371 | ESTs | — | −1.47 | 0.95 | 0.18 | 1.43 | −1.24 | 0.33 | 2.21 | 1.17 |
| NM_000515 | Homo sapiens growth hormone 1 (GH1), transcript variant 1, mRNA. /PROD = growth hormone 1, isoform 1 precursor /FL = gb: NM_000515.2 | CSH1 | −2.36 | 0.29 | 1.92 | 0.10 | −0.73 | 0.57 | 1.37 | 0.21 |
| NM_004414 | Homo sapiens Down syndrome critical region gene 1 (DSCR1), mRNA. /PROD = Down syndrome critical region protein 1 /FL = gb: U28833.2 gb: NM_004414.2 | DSCR1 | 2.14 | 0.03 | 3.85 | 0.26 | 1.74 | 0.16 | 3.34 | 0.36 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AI355441 | sprouty (*Drosophila*) homolog 4 | — | 0.24 | 0.48 | 1.72 | 0.50 | −1.12 | 0.40 | 2.03 | 0.61 |
| AB032953 | *Homo sapiens* mRNA for KIAA1127 protein, partial cds. /PROD = KIAA1127 protein | ODZ2 | 0.00 | 0.14 | 0.65 | 0.35 | −1.74 | 0.74 | 0.88 | 0.03 |
| BE048571 | ESTs | MGC16121 | −1.66 | 0.78 | 1.44 | 1.00 | −1.31 | 0.21 | 0.10 | 1.22 |
| AW471145 | ESTs | PRSS23 | 0.87 | 0.10 | 3.46 | 0.35 | 1.13 | 0.11 | 3.37 | 0.53 |
| BF196943 | ESTs | USP53 | 1.43 | 0.03 | 3.24 | 0.92 | 0.85 | 0.26 | 2.32 | 0.88 |
| AF498927 | *Homo sapiens* Rho GDP dissociation inhibitor beta (ARHGDIB) mRNA, complete cds. /PROD = Rho GDP dissociation inhibitor beta /FL = gb: AF498927.1 | ARHGDIB | −0.03 | 0.19 | 0.04 | 0.96 | −3.00 | 0.54 | −0.85 | 0.93 |
| AF329092 | *Homo sapiens* GPBP-interacting protein 90 mRNA, complete cds. /PROD = GPBP-interacting protein 90 /FL = gb: AF329092.1 | DOC1 | −2.38 | 0.45 | 1.00 | 0.19 | −1.62 | 0.74 | 0.75 | 0.11 |
| BG250721 | *Homo sapiens* mRNA; cDNA DKFZp564C2063 (from clone DKFZp564C2063) | — | 2.48 | 0.04 | 4.54 | 0.95 | 2.63 | 0.14 | 5.31 | 0.83 |
| N69091 | ESTs | PCDH17 | 0.59 | 0.10 | 1.49 | 0.88 | −1.11 | 0.69 | 2.49 | 0.78 |
| BF589359 | ESTs | PAG1 | −1.11 | 0.52 | −0.09 | 0.43 | −1.54 | 0.12 | 0.50 | 0.13 |
| BF968270 | ESTs | SLC35F3 | 0.37 | 0.02 | 1.84 | 0.30 | 0.10 | 0.17 | 2.46 | 0.36 |
| NM_006183 | *Homo sapiens* neurotensin (NTS), mRNA. /PROD = neurotensin precursor /FL = gb: NM_006183.2 gb: U91618.1 | NTS | 4.77 | 0.15 | 4.73 | 1.45 | 3.01 | 0.19 | 3.21 | 1.47 |
| D28124 | Cluster Incl. D28124: Human mRNA for unknown product, complete cds | NBL1 | 2.90 | 0.03 | 4.24 | 0.37 | 2.09 | 0.08 | 4.44 | 0.38 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
| --- | --- | --- | --- | --- | --- | --- | --- | --- | --- | --- |
| AW129593 | /cds = (61,603) /gb = D28124 /gi = 641821 /ug = Hs.76307 /len = 1929 tudor repeat associator with PCTAIRE 2 | TDRD7 | 1.19 | 0.19 | 2.40 | 0.87 | 0.92 | 0.04 | 3.27 | 0.89 |
| BE675435 | core promoter element binding protein /FL = gb: AF001461.1 gb: BC000311.1 gb: NM_001300.2 gb: AB017493.1 gb: BC004301.1 | KLF6 | 0.29 | 0.30 | 2.91 | 1.02 | 0.54 | 0.24 | 3.68 | 0.94 |
| AI202327 | ESTs | CPEB2 | 1.88 | 0.09 | 3.42 | 0.07 | 0.99 | 0.10 | 3.36 | 0.03 |
| NM_002228 | *Homo sapiens* v-junavian sarcoma virus 17 oncogene homolog (JUN), mRNA. /PROD = v-junavian sarcoma virus 17 oncogene homolog /FL = gb: NM_002228.2 gb: BC002646.1 | JUN | 2.12 | 0.16 | 4.09 | 0.56 | 1.62 | 0.13 | 4.53 | 0.41 |
| AF005775 | *Homo sapiens* caspase-like apoptosis regulatory protein 2 (clarp) mRNA, alternatively spliced, complete cds. /PROD = caspase-like apoptosis regulatory protein 2 /FL = gb: AF005775.1 | CFLAR | 2.88 | 0.18 | 3.70 | 1.56 | 0.35 | 0.17 | 5.22 | 1.69 |
| NM_007173 | *Homo sapiens* protease, serine, 23 (SPUVE), mRNA. /PROD = protease, serine, 23 /FL = gb: BC001278.1 gb: AF193611.1 gb: AF015287.1 gb: AL136914.1 gb: NM_007173.1 | PRSS23 | 3.02 | 0.10 | 5.11 | 0.21 | 2.90 | 0.05 | 5.22 | 0.23 |
| NM_012413 | *Homo sapiens* glutaminyl- | QPCT | 1.44 | 0.09 | 0.97 | 0.85 | −2.46 | 0.65 | 0.19 | 1.10 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | peptide cyclotransferase (glutaminyl cyclase) (QPCT), mRNA. /PROD = glutaminyl-peptide cyclotransferase precursor /FL = gb: NM_012413.2 | | | | | | | | | |
| BU683415 | Homo sapiens, clone IMAGE: 4096273, mRNA | KLF6 | 3.40 | 0.06 | 5.28 | 0.85 | 3.46 | 0.09 | 6.01 | 0.85 |
| AV729634 | DnaJ (Hsp40) homolog, subfamily B, member 6 /FL = gb: AB007942.1 gb: NM_014787.1 | DNAJC6 | 0.62 | 0.20 | 2.59 | 0.79 | 0.99 | 0.19 | 3.35 | 0.65 |
| BC038556 | Homo sapiens, clone IMAGE: 3446976, mRNA. | — | −0.79 | 0.40 | 0.12 | 0.99 | −2.17 | 0.62 | −0.08 | 0.38 |
| NM_014942 | Homo sapiens KIAA0957 protein (KIAA0957), mRNA. /PROD = KIAA0957 protein /FL = gb: AB023174.1 gb: NM_014942.1 | ANKRD6 | 0.62 | 0.04 | 2.17 | 1.11 | 0.59 | 0.23 | 3.30 | 1.07 |
| AF260333 | Homo sapiens AD036 mRNA, complete cds. /PROD = AD036 /FL = gb: AF260333.1 | C4orf18 | −1.58 | 0.10 | 0.21 | 1.21 | −3.19 | 1.07 | 1.60 | 1.12 |
| AA448956 | Homo sapiens cDNA: FLJ21715 fis, clone COL10287, highly similar to AF071569 Homo sapiens multifunctional calciumcalmodulin-dependent protein kinase II delta2 isoform mRNA /FL = gb: AF071569.1 | CAMK2D | 1.47 | 0.18 | 2.75 | 0.42 | 0.21 | 0.21 | 2.97 | 0.39 |
| BE349115 | ESTs | COL22A1 | −0.02 | 0.52 | 2.04 | 0.25 | 0.24 | 0.06 | 2.38 | 0.22 |
| BF209337 | Homo sapiens cDNA FLJ10934 | LOC541471 | 4.83 | 0.17 | 5.80 | 0.73 | 3.13 | 0.02 | 4.84 | 0.81 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AB019695 | fis, clone OVARC1000640 Homo sapiens mRNA for thioredoxin reductase II beta, complete cds. /PROD = thioredoxin reductase II beta /FL = gb: AB019695.1 | — | 2.43 | 0.01 | 4.15 | 0.40 | 1.42 | 0.05 | 3.50 | 0.29 |
| AK090497 | Homo sapiens cDNA FLJ33178 fis, clone ADRGL2002753. | LOC284576 | −3.78 | 0.56 | −2.87 | 1.42 | −4.94 | 0.07 | −4.74 | 0.53 |
| NM_006763 | Homo sapiens BTG family, member 2 (BTG2), mRNA. /PROD = BTG family, member 2 /FL = gb: U72649.1 gb: NM_006763.1 | BTG2 | 2.30 | 0.10 | 3.28 | 0.62 | 0.85 | 0.25 | 3.84 | 0.74 |
| BC002616 | Homo sapiens, transgelin 2, clone MGC: 2989, mRNA, complete cds. /PROD = transgelin 2 /FL = gb: BC002616.1 | TAGLN2 | 5.61 | 0.20 | 5.56 | 0.17 | 2.91 | 0.18 | 5.40 | 0.12 |
| AF078077 | Homo sapiens growth arrest and DNA-damage-inducible protein GADD45beta mRNA, complete cds. /PROD = growth arrest and DNA-damage-inducible protein GADD45beta /FL = gb: AF087853.1 gb: AF078077.1 | GADD45B | 1.30 | 0.17 | 3.41 | 0.31 | 0.61 | 0.12 | 3.05 | 0.29 |
| NM_001854 | Homo sapiens collagen, type XI, alpha 1 (COL11A1), mRNA. /PROD = collagen, type XI, | COL11A1 | 2.90 | 0.02 | 4.06 | 1.44 | 1.87 | 0.06 | 2.68 | 1.43 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | alpha 1 /FL = gb: J04177.1 gb: NM_001854.1 | | | | | | | | | |
| AI830201 | ESTs | KIAA0773 | −0.75 | 0.82 | 1.24 | 0.22 | −1.87 | 0.51 | 0.40 | 0.22 |
| N95437 | ESTs | LMCD1 | 0.74 | 0.12 | 2.72 | 0.57 | 0.39 | 0.14 | 3.05 | 0.42 |
| BC002511 | *Homo sapiens*, carbonyl reductase 1, clone MGC: 1920, mRNA, complete cds. /PROD = carbonyl reductase 1 /FL = gb: BC002511.1 gb: NM_001757.1 gb: J04056.1 | CBR1 | 3.72 | 0.02 | 1.03 | 2.43 | −4.10 | 0.16 | −1.64 | 2.36 |
| AV682252 | HIV-1 rev binding protein 2 | — | −0.33 | 0.15 | 1.78 | 1.36 | −0.24 | 0.17 | 0.41 | 1.29 |
| AW263497 | ESTs | SYTL5 | −1.05 | 0.25 | 1.44 | 0.38 | −0.55 | 0.41 | 2.11 | 0.47 |
| AF130095 | *Homo sapiens* clone FLC0562 PRO2841 mRNA, complete cds. /PROD = PRO2841 /FL = gb: AF130095.1 | — | 5.80 | 0.14 | 6.80 | 0.49 | 4.54 | 0.10 | 7.35 | 0.36 |
| H92988 | tyrosine 3-monooxygenasetryptophan 5-monooxygenase activation protein, eta polypeptide | C9orf19 | 2.00 | 0.06 | 3.54 | 0.91 | 1.93 | 0.14 | 4.61 | 0.81 |
| X02761 | Human mRNA for fibronectin (FN precursor). /PROD = fibronectin precursor | FN1 | 5.67 | 0.17 | 6.65 | 0.54 | 4.52 | 0.21 | 7.21 | 0.42 |
| AI016316 | ESTs | — | 0.24 | 0.18 | 1.19 | 1.17 | −0.33 | 0.18 | 0.25 | 1.18 |
| NM_006622 | *Homo sapiens* serum-inducible kinase (SNK), mRNA. /PROD = serum-inducible kinase /FL = gb: AF059617.1 gb: NM_006622.1 gb: AF223574.1 | PLK2 | 4.64 | 0.14 | 5.88 | 0.45 | 3.50 | 0.06 | 5.19 | 0.47 |
| NM_013238 | *Homo sapiens* DNAJ domain-containing (MCJ), mRNA. /PROD = DNAJ domain- | DNAJC15 | −2.27 | 0.60 | 3.79 | 2.03 | 4.07 | 0.09 | 5.58 | 2.31 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | containing /FL = gb: NM_013238.1 gb: AF126743.1 | | | | | | | | | |
| AK026737 | Homo sapiens cDNA: FLJ23084 fis, clone LNG06602, highly similar to HSFIB1 Human mRNA for fibronectin (FN precursor). | FN1 | 5.86 | 0.14 | 6.85 | 0.49 | 4.66 | 0.08 | 7.39 | 0.37 |
| NM_001458 | Homo sapiens filamin C, gamma (actin-binding protein-280) (FLNC), mRNA. /PROD = gamma filamin /FL = gb: AF089841.1 gb: NM_001458.1 | FLNC | 3.28 | 0.17 | 4.17 | 0.70 | 2.11 | 0.17 | 3.39 | 0.64 |
| AK025843 | Homo sapiens cDNA: FLJ22190 fis, clone HRC01053. /FL = gb: AF151909.1 gb: AF077041.1 gb: NM_016081.1 | PALLD | 1.58 | 0.31 | 3.38 | 0.15 | 1.03 | 0.20 | 3.29 | 0.19 |
| BC005858 | Homo sapiens, clone MGC: 3255, mRNA, complete cds. /PROD = Unknown (protein for MGC: 3255) /FL = gb: BC005858.1 | FN1 | 5.86 | 0.10 | 6.86 | 0.49 | 4.70 | 0.19 | 7.37 | 0.36 |
| BG491844 | v-jun avian sarcoma virus 17 oncogene homolog /FL = gb: NM_002228.2 gb: BC002646.1 | JUN | 3.53 | 0.08 | 5.45 | 0.47 | 3.42 | 0.11 | 5.91 | 0.34 |
| AA284532 | tyrosine 3-monooxygenasetryptophan 5-monooxygenase activation protein, eta polypeptide | C9orf19 | 2.19 | 0.11 | 4.12 | 0.84 | 2.43 | 0.08 | 4.93 | 0.90 |
| AA192306 | triadin /FL = gb: U18985.1 gb: NM_006073.1 | TRDN | −2.54 | 0.69 | 0.02 | 0.61 | −1.99 | 0.31 | 0.57 | 0.63 |
| AF116676 | Homo sapiens PRO1957 mRNA, | — | 1.50 | 0.18 | 3.31 | 1.11 | 1.37 | 0.15 | 4.23 | 1.05 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_003033 | complete cds. /PROD = PRO1957 /FL = gb: AF116676.1 Homo sapiens sialyltransferase 4A (beta-galactosidase alpha-2,3-sialyltransferase) (SIAT4A), mRNA. /PROD = sialyltransferase 4A (beta-galactosidasealpha-2,3-sialyltransferase) /FL = gb: L13972.1 gb: L29555.1 gb: NM_003033.1 | ST3GAL1 | −0.08 | 0.18 | 1.68 | 1.04 | 0.20 | 0.16 | 2.74 | 0.74 |
| AI222435 | ESTs | — | −4.14 | 1.52 | −0.73 | 0.32 | −2.33 | 0.62 | −0.33 | 0.12 |
| NM_001924 | Homo sapiens growth arrest and DNA-damage-inducible, alpha (GADD45A), mRNA. /PROD = growth arrest and DNA-damage-inducible, alpha /FL = gb: M60974.1 gb: NM_001924.2 | GADD45A | 3.59 | 0.09 | 5.04 | 0.44 | 3.06 | 0.17 | 5.38 | 0.48 |
| NM_001425 | Homo sapiens epithelial membrane protein 3 (EMP3), mRNA. /PROD = epithelial membrane protein 3 /FL = gb: U52101.1 gb: NM_001425.1 gb: U87947.1 | EMP3 | 2.76 | 0.18 | 3.90 | 0.64 | 1.51 | 0.06 | 3.13 | 0.57 |
| AB017493 | Homo sapiens mRNA for DNA-binding zinc finger (GBF), complete cds. /PROD = DNA-binding zinc finger (GBF) /FL = gb: AF001461.1 gb: BC000311.1 gb: NM_001300.2 gb: AB017493.1 gb: BC004301.1 | KLF6 | 1.69 | 0.20 | 4.02 | 1.01 | 1.80 | 0.08 | 4.87 | 0.87 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| X58851 | Human MLC1emb gene for embryonic myosin alkaline light chain, promoter and exon 1 | — | 0.99 | 0.16 | 2.75 | 1.28 | 1.12 | 0.15 | 4.04 | 1.14 |
| BE327172 | v-jun avian sarcoma virus 17 oncogene homolog | — | 0.86 | 0.15 | 2.94 | 0.51 | 1.14 | 0.08 | 3.57 | 0.45 |
| U37283 | Human microfibril-associated glycoprotein-2 MAGP-2 mRNA, complete cds. /PROD = microfibril-associated glycoprotein-2 MAGP-2 /FL = gb: NM_003480.1 gb: U37283.1 | MFAP5 | 0.48 | 0.19 | 1.87 | 0.26 | 0.15 | 0.35 | 1.36 | 0.47 |
| AI819043 | ESTs | CREB5 | 0.92 | 0.26 | 2.63 | 0.73 | 0.65 | 0.15 | 1.80 | 0.79 |
| NM_001511 | *Homo sapiens* GRO1 oncogene (melanoma growth stimulating activity, alpha) (GRO1), mRNA. /PROD = GRO1 oncogene (melanoma growth stimulatingactivity, alpha) /FL = gb: NM_001511.1 | CXCL1 | 1.01 | 0.13 | 2.95 | 0.35 | 0.31 | 0.08 | 2.39 | 0.27 |
| NM_006736 | *Homo sapiens* heat shock protein, neuronal DNAJ-like 1 (HSJ1), mRNA. /PROD = heat shock protein, neuronal DNAJ-like 1 /FL = gb: NM_006736.1 | DNAJB2 | 2.23 | 0.04 | 3.46 | 0.44 | 1.10 | 0.02 | 3.75 | 0.41 |
| AA534817 | ESTs, Weakly similar to ALU8_HUMAN ALU SUBFAMILY SX SEQUENCE CONTAMINATION | EDG3 | 2.32 | 0.06 | 3.28 | 1.04 | 2.08 | 0.04 | 4.58 | 1.04 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| U82164 | WARNING ENTRY (*H. sapiens*) Human transmembrane protein CD99 type II mRNA, complete cds. /PROD = CD99 typeII /FL = gb: BC002584.1 gb: NM_002414.1 gb: M16279.1 gb: BC003147.1 gb: U82164.1 | CD99 | 4.73 | 0.15 | 5.69 | 0.73 | 3.19 | 0.07 | 6.36 | 0.93 |
| NM_000389 | *Homo sapiens* cyclin-dependent kinase inhibitor 1A (p21, Cip1) (CDKN1A), mRNA. /PROD = cyclin-dependent kinase inhibitor 1A (p21, Cip1) /FL = gb: U03106.1 gb: BC000275.1 gb: BC001935.1 gb: L25610.1 gb: U09579.1 gb: NM_000389.1 gb: L26165.1 | CDKN1A | 4.03 | 0.02 | 4.20 | 0.12 | 1.81 | 0.07 | 4.16 | 0.05 |
| NM_001299 | *Homo sapiens* calponin 1, basic, smooth muscle (CNN1), mRNA. /PROD = calponin 1, basic, smooth muscle /FL = gb: U37019.1 gb: NM_001299.1 gb: D17408.1 | CNN1 | 3.75 | 0.15 | 5.75 | 0.50 | 3.47 | 0.11 | 5.14 | 0.43 |
| M36172 | Human embryonic myosin alkali light chain (MLC1) mRNA, complete cds. /FL = gb: M36172.1 gb: M24121.1 gb: NM_002476.1 | MYL4 | 1.55 | 0.21 | 3.30 | 1.05 | 1.21 | 0.13 | 4.11 | 1.06 |
| AB033831 | *Homo sapiens* hSCDGF mRNA for spinal cord-derived | PDGFC | 0.48 | 0.21 | 0.63 | 0.15 | −1.87 | 0.96 | 0.21 | 0.16 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | growth factor, complete cds. /PROD = spinal cord-derived growth factor /FL = gb: NM_016205.1 gb: AB033831.1 gb: AF091434.1 gb: AF244813.1 | | | | | | | | | |
| NM_014333 | *Homo sapiens* immunoglobulin superfamily, member 4 (IGSF4), mRNA. /PROD = immunoglobulin superfamily, member 4 /FL = gb: NM_014333.1 gb: AF132811.1 | IGSF4 | 3.11 | 0.09 | 4.12 | 0.27 | 1.85 | 0.06 | 3.79 | 0.24 |
| AF345910 | *Homo sapiens* NYD-SP14 mRNA, complete cds. /PROD = NYD-SP14 /FL = gb: AF345910.1 | TTC29 | 0.35 | 0.26 | 1.53 | 0.93 | −0.51 | 0.52 | 0.91 | 0.72 |
| NM_004297 | *Homo sapiens* guanine nucleotide binding protein (G protein), alpha 14 (GNA14), mRNA. /PROD = guanine nucleotide binding protein (G protein), alpha 14 /FL = gb: AF105201.1 gb: NM_004297.1 | GNA14 | 4.59 | 0.06 | 4.52 | 1.59 | 1.95 | 0.11 | 2.95 | 1.50 |
| AK057525 | *Homo sapiens* cDNA FLJ32963 fis, clone TESTI2008405. | — | 3.60 | 0.08 | 4.45 | 0.44 | 2.00 | 0.16 | 4.80 | 0.46 |
| BC000893 | *Homo sapiens*, H2B histone family, member A, clone MGC: 5132, mRNA, complete cds. | HIST1H2BK | 2.80 | 0.06 | 3.99 | 0.90 | 2.48 | 0.09 | 4.81 | 0.82 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = H2B histone family, member A /FL = gb: BC000893.1 | | | | | | | | | |
| NM_007038 | *Homo sapiens* a disintegrin-like and metalloprotease (reprolysin type) with thrombospondin type 1 motif, 5 (aggrecanase-2) (ADAMTS5), mRNA. /PROD = a disintegrin and metalloprotease withthrombospondin motifs-5 preproprotein /FL = gb: NM_007038.1 gb: AF14209 | ADAMTS5 | 0.23 | 0.17 | 1.80 | 0.48 | 0.45 | 0.28 | 1.11 | 0.73 |
| AW241910 | ESTs, Weakly similar to JX0369 collagen alpha 1(XIX) chain precursor (*H. sapiens*) | COL22A1 | −0.21 | 0.12 | 1.15 | 0.47 | −0.57 | 0.18 | 1.90 | 0.51 |
| AI860150 | ESTs, Weakly similar to A49134 Ig kappa chain V-I region (*H. sapiens*) | FOSL2 | −0.43 | 0.55 | 1.59 | 0.37 | −0.34 | 0.10 | 1.08 | 0.20 |
| NM_005902 | *Homo sapiens* MAD (mothers against decapentaplegic, *Drosophila*) homolog 3 (MADH3), mRNA. /PROD = MAD (mothers against decapentaplegic, *Drosophila*) homolog 3 /FL = gb: U68019.1 gb: U76622.1 gb: NM_005902.1 | SMAD3 | 1.09 | 0.41 | 1.49 | 0.25 | −1.10 | 0.89 | 1.73 | 0.10 |
| AA777512 | *Homo sapiens* cDNA: FLJ21715 fis, clone COL10287, highly similar | CAMK2D | 2.27 | 0.15 | 3.67 | 0.47 | 1.67 | 0.08 | 3.99 | 0.51 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | to AF071569 Homo sapiens multifunctional calciumcalmodulin-dependent protein kinase II delta2 isoform mRNA | | | | | | | | | |
| AI130705 | ESTs, Weakly similar to A46302 PTB-associated splicing factor, long form (*H. sapiens*) | FAM89A | 0.80 | 0.00 | 1.96 | 0.99 | 0.43 | 0.18 | 2.70 | 0.97 |
| NM_007061 | *Homo sapiens* serum constituent protein (MSE55), mRNA. /PROD = serum constituent protein /FL = gb: M88338.1 gb: NM_007061.1 | CDC42EP1 | 1.86 | 0.11 | 2.51 | 0.29 | 0.16 | 0.27 | 2.00 | 0.17 |
| NM_003407 | *Homo sapiens* zinc finger protein homologous to Zfp-36 in mouse (ZFP36), mRNA. /PROD = zinc finger protein homologous to Zfp-36 inmouse /FL = gb: NM_003407.1 gb: M92843.1 gb: M63625.1 | ZFP36 | 2.55 | 0.14 | 3.53 | 0.55 | 1.49 | 0.28 | 3.98 | 0.47 |
| BC033088 | *Homo sapiens*, Similar to lamin AC, clone MGC: 45654 IMAGE: 3623265, mRNA, complete cds. /PROD = Similar to lamin AC /FL = gb: BC033088.1 | LMNA | 2.03 | 0.22 | 2.89 | 0.45 | 0.69 | 0.24 | 1.79 | 0.50 |
| U97075 | *Homo sapiens* FLICE-like inhibitory protein short | CFLAR | 2.50 | 0.09 | 3.39 | 1.45 | 0.73 | 0.08 | 4.93 | 1.54 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | form mRNA, complete cds. /PROD = FLICE-like inhibitory protein short form /FL = gb: U97075.1 | | | | | | | | | |
| AF133207 | *Homo sapiens* protein kinase (H11) mRNA, complete cds. /PROD = protein kinase /FL = gb: AF133207.1 | HSPB8 | 2.54 | 0.07 | 4.47 | 0.62 | 2.22 | 0.04 | 4.88 | 0.58 |
| NM_005979 | *Homo sapiens* S100 calcium-binding protein A13 (S100A13), mRNA. /PROD = S100 calcium-binding protein A13 /FL = gb: BC000632.1 gb: NM_005979.1 | S100A13 | 4.10 | 0.11 | 5.67 | 1.17 | 3.92 | 0.02 | 6.81 | 1.20 |
| AL040178 | ESTs | PEAR1 | −0.87 | 0.08 | 0.51 | 0.36 | −1.16 | 0.30 | 0.48 | 0.26 |
| AL117523 | *Homo sapiens* mRNA; cDNA DKFZp434H0350 (from clone DKFZp434H0350); partial cds. /PROD = hypothetical protein | SAMD4A | 0.47 | 0.06 | 1.59 | 0.61 | −0.24 | 0.30 | 1.28 | 0.53 |
| AB051826 | *Homo sapiens* hG28K mRNA for GTP-binding protein like 1, complete cds. /PROD = GTP-binding protein like 1 /FL = gb: AF282258.1 gb: NM_021205.1 gb: AB051826.1 | RHOU | 0.55 | 0.23 | 2.18 | 0.61 | 0.17 | 0.29 | 2.73 | 0.65 |
| BC005961 | *Homo sapiens*, parathyroid hormone-like hormone, clone MGC: 14611, mRNA, complete cds. | PTHLH | −3.33 | 0.69 | −0.88 | 0.81 | −2.86 | 0.77 | −1.97 | 1.36 |

TABLE IV-continued

DIFFERENTIAL EXPRESSION OF GENES BETWEEN UNDIFFERENTIATED EMBRYONIC STEM CELLS AND DEFINITIVE ENDODERM STAGE CELLS CULTURED ON EITHER MATRIGELTM OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = parathyroid hormone-like hormone /FL = gb: BC005961.1 | | | | | | | | | |
| AI670948 | ESTs | NODAL | 2.13 | 0.04 | 2.37 | 0.22 | 0.42 | 0.13 | 2.78 | 0.38 |
| AI685060 | caldesmon 1 /FL = gb: M64110.1 gb: NM_004342.2 | CALD1 | 4.34 | 0.33 | 6.42 | 0.73 | 4.45 | 0.09 | 5.63 | 0.82 |
| BF797381 | *Homo sapiens* cDNA: FLJ21715 fis, clone COL10287, highly similar to AF071569 *Homo sapiens* multifunctional calciumcalmodulin-dependent protein kinase II delta2 isoform mRNA | CAMK2D | 3.16 | 0.13 | 4.91 | 0.65 | 3.10 | 0.10 | 5.49 | 0.61 |
| AF026219 | *Homo sapiens* HP protein (HP) mRNA, complete cds. /PROD = HP protein /FL = gb: AF026219.1 gb: AF035119.1 gb: NM_006094.2 | DLC1 | 1.16 | 0.07 | 2.28 | 1.13 | 0.61 | 0.09 | 3.52 | 0.84 |
| AK024480 | *Homo sapiens* mRNA for FLJ00074 protein, partial cds. /PROD = FLJ00074 protein | LOC126917 | 1.64 | 0.11 | 2.86 | 0.24 | 1.19 | 0.06 | 2.58 | 0.25 |
| N29837 | ESTs | LIX1 | −1.43 | 0.15 | −0.11 | 0.33 | −1.50 | 0.45 | −0.22 | 0.22 |
| AK001022 | *Homo sapiens* cDNA FLJ10160 fis, clone HEMBA1003545, highly similar to INSULIN GENE ENHANCER PROTEIN ISL-2. | ISL2 | 0.41 | 0.34 | 2.14 | 0.39 | 0.32 | 0.08 | 1.57 | 0.49 |
| NM_000047 | *Homo sapiens* arylsulfatase E (chondrodysplasia punctata 1) (ARSE), mRNA. /PROD = arylsulfatase E precursor /FL = gb: X83573.1 gb: NM_000047.1 | ARSE | 1.37 | 0.11 | 2.45 | 1.03 | 0.59 | 0.05 | 3.18 | 1.23 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
| --- | --- | --- | --- | --- | --- | --- | --- | --- | --- | --- |
| NM_006379 | Homo sapiens sema domain, immunoglobulin domain (Ig), short basic domain, secreted, (semaphorin) 3C (SEMA3C), mRNA. /PROD = sema domain, immunoglobulin domain (Ig), shortbasic domain, secreted, (semaphorin) 3C /FL = gb: NM_006379.1 gb: AB000220.1 | SEMA3C | 0.24 | 0.25 | 1.08 | 0.00 | −0.34 | 0.05 | 0.86 | 0.18 |
| NM_007127 | Homo sapiens villin 1 (VIL1), mRNA. /PROD = villin 1 /FL = gb: NM_007127.1 | VIL1 | 0.31 | 0.30 | 1.92 | 0.49 | 0.02 | 0.22 | 2.54 | 0.68 |
| U76549 | Human cytokeratin 8 mRNA, complete cds. /PROD = cytokeratin 8 /FL = gb: BC000654.1 gb: U76549.1 gb: NM_002273.1 gb: M26324.1 gb: M34225.1 | KRT8 | 5.41 | 0.16 | 5.87 | 0.56 | 3.79 | 0.05 | 6.34 | 0.57 |
| NM_004904 | Homo sapiens cAMP response element-binding protein CRE-BPa (H_GS165L15.1), mRNA. /PROD = cAMP response element-binding protein CRE-BPa /FL = gb: NM_004904.1 gb: L05911.1 | CREB5 | 0.92 | 0.23 | 1.84 | 0.37 | 0.00 | 0.06 | 1.21 | 0.80 |
| AW082836 | ESTs, Weakly similar to B34087 hypothetical protein (H. sapiens) | WNK4 | −1.17 | 0.26 | 0.98 | 0.38 | −0.97 | 0.20 | 0.05 | 0.86 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BE568134 | death receptor 6 /FL = gb: NM_014452.1 gb: AF068868.1 | TNFRSF21 | 4.76 | 0.06 | 5.90 | 0.54 | 3.94 | 0.08 | 6.28 | 0.58 |
| NM_002845 | Homo sapiens protein tyrosine phosphatase, receptor type, M (PTPRM), mRNA. /PROD = protein tyrosine phosphatase, receptor type, mupolypeptide /FL = gb: NM_002845.1 | PTPRM | 2.50 | 0.10 | 3.43 | 0.46 | 1.34 | 0.19 | 3.76 | 0.50 |
| AI949419 | ESTs | — | −0.11 | 0.21 | 1.72 | 0.64 | −0.47 | 0.01 | 2.39 | 0.77 |
| AK024680 | Homo sapiens cDNA: FLJ21027 fis, clone CAE07110. /FL = gb: NM_018534.1 | NRP2 | 0.42 | 0.02 | 2.65 | 0.17 | 0.98 | 0.09 | 2.86 | 0.17 |
| BE542563 | ESTs | LOC643277 | 2.20 | 0.10 | 0.54 | 1.49 | −3.73 | 0.40 | −1.74 | 1.96 |
| AW005572 | putative 47 kDa protein | ANKS1B | −1.21 | 0.52 | −0.24 | 0.82 | −1.19 | 0.55 | 1.05 | 0.64 |
| AW665892 | paternally expressed 3 | MFAP5 | −3.87 | 0.82 | −1.56 | 1.24 | −2.40 | 0.24 | −3.49 | 2.10 |
| NM_006206 | Homo sapiens platelet-derived growth factor receptor, alpha polypeptide (PDGFRA), mRNA. /PROD = platelet-derived growth factor receptor, alphapolypeptide /FL = gb: NM_006206.1 gb: M21574.1 | PDGFRA | 0.92 | 0.18 | 2.34 | 0.74 | 0.72 | 0.09 | 3.18 | 0.62 |
| NM_002425 | Homo sapiens matrix metalloproteinase 10 (stromelysin 2) (MMP10), mRNA. /PROD = matrix metalloproteinase 10 preproprotein /FL = gb: BC002591.1 gb: NM_002425.1 | MMP10 | −1.21 | 0.70 | 1.21 | 0.88 | −0.37 | 0.28 | 0.52 | 0.45 |
| NM_004338 | Homo sapiens chromosome 18 open reading frame 1 | C18orf1 | −0.79 | 0.22 | −0.09 | 0.39 | −1.57 | 0.43 | 0.50 | 0.02 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | (C18ORF1), mRNA. /PROD = chromosome 18 open reading frame 1 /FL = gb: NM_004338.1 gb: AF009426.1 | | | | | | | | | |
| AF052094 | *Homo sapiens* clone 23698 mRNA sequence. /FL = gb: U51626.1 gb: U81984.1 gb: NM_001430.1 | EPAS1 | 0.75 | 0.12 | 2.28 | 0.19 | 0.42 | 0.21 | 1.74 | 0.33 |
| BF126155 | ESTs | S100A10 | −0.32 | 0.25 | 1.24 | 0.28 | −0.65 | 0.33 | 1.02 | 0.44 |
| AI860212 | phosphoprotein associated with GEMs /FL = gb: AF240634.1 gb: NM_018440.1 | PAG1 | −0.17 | 0.22 | 1.37 | 0.28 | −0.40 | 0.23 | 1.25 | 0.13 |
| AL110298 | *Homo sapiens* mRNA; cDNA DKFZp564K1672 (from clone DKFZp564K1672); partial cds. /PROD = hypothetical protein | SLC2A14 | 5.13 | 0.06 | 6.03 | 0.58 | 3.97 | 0.24 | 6.33 | 0.73 |
| AY048775 | *Homo sapiens* mandaselin long form mRNA, complete cds. /PROD = mandaselin long form /FL = gb: AY048775.1 | MANEA | −0.47 | 0.40 | 0.71 | 0.90 | −0.69 | 0.35 | 1.23 | 0.81 |
| M99436 | Cluster Incl. M99436: Human transducin-like enhancer protein (TLE2) mRNA, complete cds /cds = (25,2256) /gb = M99436 /gi = 307511 /ug = Hs.173063 /len = 2271 | TLE2 | 2.65 | 0.07 | 4.05 | 0.66 | 1.95 | 0.13 | 4.76 | 0.61 |
| NM_014061 | *Homo sapiens* APR-1 protein (APR-1), mRNA. /PROD = APR-1 protein /FL = gb: AF320912.1 gb: AF143235.3 gb: NM_014061.1 | MAGEH1 | 2.04 | 0.23 | 3.84 | 1.17 | 1.08 | 0.24 | 4.86 | 1.12 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AL577531 | caldesmon 1 /FL = gb: M64110.1 gb: NM_004342.2 | CALD1 | 5.79 | 0.06 | 6.06 | 0.75 | 4.07 | 0.06 | 5.13 | 0.77 |
| AI082237 | proprotein convertase subtilisinkexin type 7 | TAGLN | 1.38 | 0.21 | 3.20 | 0.33 | 1.55 | 0.15 | 2.74 | 0.44 |
| BF055171 | acyl-Coenzyme A oxidase 3, pristanoyl /FL = gb: NM_003501.1 | ACOX3 | 0.88 | 0.22 | 2.52 | 0.83 | 1.27 | 0.06 | 3.73 | 0.81 |
| AF231124 | *Homo sapiens* testican-1 mRNA, complete cds. /PROD = testican-1 /FL = gb: NM_004598.1 gb: AF231124.1 | SPOCK1 | 2.84 | 0.09 | 4.17 | 0.95 | 2.71 | 0.07 | 5.38 | 1.00 |
| AA588092 | ESTs | SLC40A1 | −1.53 | 0.23 | −0.94 | 0.51 | −2.42 | 0.33 | 0.27 | 0.27 |
| AK094809 | *Homo sapiens* cDNA FLJ37490 fis, clone BRAWH2014934, highly similar to GUANINE NUCLEOTIDE RELEASING PROTEIN. | RASGRF2 | 3.20 | 0.05 | 3.64 | 0.77 | 1.95 | 0.24 | 2.95 | 0.74 |
| NM_013959 | *Homo sapiens* neuregulin 1 (NRG1), transcript variant SMDF, mRNA. /PROD = neuregulin 1 isoform SMDF /FL = gb: L41827.1 gb: NM_013959.1 | NRG1 | 1.50 | 0.20 | 3.22 | 0.68 | 1.34 | 0.13 | 3.78 | 0.75 |
| NM_004887 | *Homo sapiens* small inducible cytokine subfamily B (Cys-X-Cys), member 14 (BRAK) (SCYB14), mRNA. /PROD = small inducible cytokine subfamily B(Cys-X-Cys), member 14 | CXCL14 | 0.70 | 0.07 | 1.70 | 0.37 | −0.15 | 0.11 | 2.36 | 0.63 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | (BRAK) /FL = gb: AF144103.1 gb: AF106911.1 gb: AF073957.1 gb: BC003513.1 gb: NM_004887.1 | | | | | | | | | |
| T77995 | Homo sapiens cDNA FLJ13392 fis, clone PLACE1001280 | — | −0.20 | 0.16 | 0.82 | 0.50 | −1.70 | 0.24 | 1.17 | 0.06 |
| NM_030971 | Homo sapiens similar to rat tricarboxylate carrier-like protein (BA108L7.2), mRNA. /PROD = similar to rat tricarboxylate carrier-likeprotein /FL = gb: NM_030971.1 | SFXN3 | −0.43 | 0.59 | −0.01 | 0.78 | −1.92 | 0.17 | −1.25 | 0.43 |
| H25097 | KIAA1350 protein | USP53 | 3.25 | 0.05 | 4.57 | 0.20 | 2.96 | 0.04 | 4.47 | 0.13 |
| NM_004932 | Homo sapiens cadherin 6, type 2, K-cadherin (fetal kidney) (CDH6), mRNA. /PROD = cadherin 6, type 2, K-cadherin (fetal kidney) /FL = gb: D31784.1 gb: NM_004932.1 | CDH6 | −3.58 | 1.16 | −1.12 | 0.51 | −2.14 | 0.63 | −0.88 | 0.39 |
| N21426 | hypothetical protein FLJ20163 | SYTL2 | 2.41 | 0.09 | 3.44 | 1.22 | 1.70 | 0.06 | 2.02 | 1.21 |
| AA234096 | KIAA0963 protein | MGC16121 | 0.38 | 0.16 | 1.74 | 0.63 | −0.13 | 0.04 | 1.10 | 0.65 |
| AV734843 | hypothetical protein FLJ22833 | OBFC2A | 0.62 | 0.06 | 1.62 | 0.79 | 0.09 | 0.02 | 1.25 | 0.73 |
| AL519710 | immunoglobulin superfamily, member 4 /FL = gb: NM_014333.1 gb: AF132811.1 | IGSF4 | 3.86 | 0.02 | 4.95 | 0.26 | 3.22 | 0.12 | 4.66 | 0.27 |
| N32834 | HIV-1 rev binding protein 2 | — | −0.28 | 0.36 | 1.58 | 0.97 | −0.23 | 0.18 | 0.33 | 1.17 |
| AF132811 | Homo sapiens nectin-like protein 2 (NECL2) mRNA, complete cds. | IGSF4 | 2.23 | 0.07 | 3.85 | 0.28 | 2.17 | 0.10 | 3.58 | 0.34 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = nectin-like protein 2 /FL = gb: NM_014333.1 gb: AF132811.1 | | | | | | | | | |
| J04177 | Cluster Incl. J04177: Human alpha-1 type XI collagen (COL11A1) mRNA, complete cds /cds = (161,5581) /gb = J04177 /gi = 179729 /ug = Hs.82772 /len = 6158 | COL11A1 | 3.28 | 0.22 | 4.44 | 1.22 | 2.32 | 0.03 | 3.03 | 1.31 |
| AI982754 | clusterin (complement lysis inhibitor, SP-40,40, sulfated glycoprotein 2, testosterone-repressed prostate message 2, apolipoprotein J) | CLU | 0.17 | 0.14 | 1.86 | 0.94 | 0.39 | 0.13 | 0.97 | 0.83 |
| NM_003501 | *Homo sapiens* acyl-Coenzyme A oxidase 3, pristanoyl (ACOX3), mRNA. /PROD = acyl-Coenzyme A oxidase 3, pristanoyl /FL = gb: NM_003501.1 | ACOX3 | 0.43 | 0.32 | 2.10 | 0.91 | 0.79 | 0.08 | 3.19 | 0.95 |
| AF144103 | *Homo sapiens* NJAC protein (NJAC) mRNA, complete cds. /PROD = NJAC protein /FL = gb: AF144103.1 gb: AF106911.1 gb: AF073957.1 gb: BC003513.1 gb: NM_004887.1 | CXCL14 | 1.69 | 0.13 | 2.16 | 0.55 | 0.40 | 0.21 | 2.73 | 0.69 |
| NM_005451 | *Homo sapiens* enigma (LIM domain protein) (ENIGMA), mRNA. /PROD = enigma protein /FL = gb: BC001093.1 gb: NM_005451.2 gb: AF265209.1 | PDLIM7 | 2.58 | 0.12 | 3.12 | 0.50 | 1.30 | 0.16 | 2.65 | 0.37 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_004472 | Homo sapiens forkhead box D1 (FOXD1), mRNA. /PROD = fork head box D1 /FL = gb: U59832.1 gb: NM_004472.1 | FOXD1 | −0.85 | 0.80 | 2.04 | 0.55 | 0.71 | 0.23 | 1.70 | 0.74 |
| AF332197 | Homo sapiens adult SIX2 (SIX2) mRNA, complete cds. /PROD = SIX2 /FL = gb: AF332197.1 gb: NM_016932.1 gb: AF136940.1 | SIX2 | 0.36 | 0.24 | 0.72 | 0.12 | −0.44 | 0.35 | 1.05 | 0.15 |
| AB046817 | Homo sapiens mRNA for KIAA1597 protein, partial cds. /PROD = KIAA1597 protein | SYTL2 | 2.88 | 0.17 | 4.09 | 1.09 | 2.50 | 0.05 | 3.12 | 1.03 |
| AK093435 | Homo sapiens cDNA FLJ36116 fis, clone TESTI2022338. | FLJ36116 | 4.75 | 0.02 | 4.59 | 1.53 | 2.46 | 0.18 | 6.15 | 1.46 |
| NM_004815 | Homo sapiens PTPL1-associated RhoGAP 1 (PARG1), mRNA. /PROD = PTPL1-associated RhoGAP 1 /FL = gb: U90920.1 gb: NM_004815.1 | ARHGAP29 | 2.18 | 0.02 | 3.18 | 0.82 | 1.69 | 0.03 | 4.15 | 0.69 |
| BG028597 | ESTs | COL11A1 | 0.19 | 0.02 | 1.61 | 1.02 | −0.11 | 0.38 | 0.48 | 1.09 |
| AB019562 | Homo sapiens mRNA expressed only in placental villi, clone SMAP41. | SPP1 | 0.58 | 0.14 | 2.79 | 1.07 | 1.10 | 0.02 | 1.21 | 1.06 |
| NM_002346 | Homo sapiens lymphocyte antigen 6 complex, locus E (LY6E), mRNA. /PROD = lymphocyte antigen 6 complex, locus E /FL = gb: U42376.1 gb: NM_002346.1 gb: U56145.1 | LY6E | 3.54 | 0.06 | 3.92 | 1.16 | 1.81 | 0.23 | 4.93 | 1.39 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BF589515 | ESTs | TMEM16D | 0.63 | 0.24 | 1.94 | 0.85 | 0.90 | 0.20 | 1.47 | 0.75 |
| AL037401 | nuclear receptor subfamily 2, group F, member 2 /FL = gb: M64497.1 | NR2F2 | −2.00 | 0.30 | 0.58 | 0.67 | −2.19 | 0.13 | 0.82 | 0.66 |
| NM_000783 | Homo sapiens cytochrome P450, subfamily XXVIA, polypeptide 1 (CYP26A1), mRNA. /PROD = cytochrome P450, subfamily XXVIA, polypeptide 1 /FL = gb: NM_000783.1 gb: AF005418.1 | CYP26A1 | 3.92 | 0.27 | 6.28 | 1.06 | 6.29 | 0.09 | 7.31 | 0.98 |
| U16307 | Human glioma pathogenesis-related protein (GliPR) mRNA, complete cds. /PROD = glioma pathogenesis-related protein /FL = gb: NM_006851.1 gb: U16307.1 | GLIPR1 | −0.11 | 0.03 | 1.16 | 0.95 | −0.46 | 0.77 | 0.35 | 0.77 |
| NM_001233 | Homo sapiens caveolin 2 (CAV2), mRNA. /PROD = caveolin 2 /FL = gb: AF035752.1 gb: BC005256.1 gb: NM_001233.1 | CAV2 | 4.07 | 0.07 | 4.42 | 0.90 | 2.82 | 0.08 | 3.44 | 0.85 |
| AA211909 | ESTs | C20orf100 | 0.62 | 0.17 | 1.93 | 1.00 | −0.21 | 0.11 | 0.72 | 0.99 |
| AK057525 | Homo sapiens cDNA FLJ32963 fis, clone TESTI2008405. | — | 2.17 | 0.13 | 2.97 | 0.77 | 0.97 | 0.08 | 3.68 | 0.60 |
| BF344237 | Homo sapiens mRNA; cDNA DKFZp564N1116 (from clone DKFZp564N1116) | — | −2.82 | 0.20 | −0.92 | 0.64 | −0.73 | 0.67 | −1.25 | 1.03 |
| NM_014481 | Homo sapiens apurinicapyrimidinic endonuclease | APEX2 | 2.76 | 0.15 | 3.18 | 0.80 | 1.57 | 0.11 | 3.91 | 0.93 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | (APEX nuclease)-like 2 protein (APEXL2), mRNA. /PROD = apurinicapyrimidinic endonuclease (APEXnuclease)-like 2 protein /FL = gb: AB049211.1 gb: NM_014481.1 gb: BC002959.1 gb: AB021260.1 gb: AF119046.1 | | | | | | | | | |
| AI912583 | HIV-1 rev binding protein 2 | KRR1 | 1.10 | 0.23 | 2.68 | 1.04 | 1.31 | 0.06 | 1.53 | 1.01 |
| BI254089 | Homo sapiens full length insert cDNA clone ZD50E03 | ADAMTS5 | −1.40 | 0.26 | −0.01 | 0.31 | −1.71 | 0.64 | −0.79 | 0.52 |
| BF197655 | caveolin 2 /FL = gb: AF035752.1 gb: BC005256.1 gb: NM_001233.1 | CAV2 | 3.51 | 0.10 | 3.54 | 0.94 | 2.32 | 0.09 | 2.70 | 0.85 |
| NM_001955 | Homo sapiens endothelin 1 (EDN1), mRNA. /PROD = endothelin 1 /FL = gb: NM_001955.1 | EDN1 | 2.84 | 0.15 | 2.97 | 0.95 | 1.01 | 0.14 | 1.75 | 1.03 |
| NM_003319 | Homo sapiens titin (TTN), mRNA. /PROD = titin /FL = gb: NM_003319.1 | TTN | 1.28 | 0.19 | 0.62 | 0.86 | −0.92 | 0.42 | 2.00 | 0.55 |
| BE965029 | Homo sapiens cDNA: FLJ22463 fis, clone HRC10126 | MICAL2 | 0.60 | 0.21 | 1.95 | 0.64 | 0.21 | 0.19 | 0.83 | 0.78 |
| AI452457 | ESTs | C1orf168 | −1.48 | 0.53 | 0.02 | 0.93 | −1.87 | 0.07 | 1.05 | 0.94 |
| AI733465 | collagen, type IX, alpha 2 /FL = gb: NM_001852.1 | COL9A2 | 0.96 | 0.13 | 1.99 | 1.00 | 1.17 | 0.14 | 2.94 | 0.86 |
| NM_006103 | Homo sapiens epididymis-specific, whey-acidic protein type, four-disulfide core; putative ovarian carcinoma marker (HE4), mRNA. /PROD = epididymis-specific, whey-acidic protein type, four- | WFDC2 | 4.02 | 0.11 | 5.11 | 1.05 | 3.39 | 0.04 | 6.19 | 1.10 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | disulfide core; putative ovarian carcinoma marker /FL = gb: NM_00610 | | | | | | | | | |
| NM_017540 | *Homo sapiens* hypothetical protein DKFZp586H0623 (DKFZp586H0623), mRNA. /PROD = hypothetical protein DKFZp586H0623 /FL = gb: NM_017540.1 | GALNT10 | 1.46 | 0.18 | 2.68 | 0.78 | 0.97 | 0.23 | 3.47 | 0.82 |
| W72527 | phosphoserine aminotransferase | SLC1A4 | −0.65 | 0.09 | 0.38 | 0.80 | −0.63 | 0.62 | −0.72 | 0.09 |
| NM_003468 | *Homo sapiens* frizzled (*Drosophila*) homolog 5 (FZD5), mRNA. /PROD = frizzled 5 /FL = gb: NM_003468.1 gb: U43318.1 | FZD5 | 1.35 | 0.26 | 3.43 | 1.21 | 1.45 | 0.10 | 4.43 | 1.16 |
| H15920 | ESTs, Weakly similar to RTA RAT PROBABLE G PROTEIN-COUPLED RECEPTOR RTA (*R. norvegicus*) | MRGPRF | 2.34 | 0.18 | 3.62 | 1.02 | 2.11 | 0.11 | 2.87 | 0.84 |
| U83508 | Human angiopoietin-1 mRNA, complete cds. /PROD = angiopoietin-1 /FL = gb: NM_001146.1 gb: D13628.1 gb: U83508.1 | ANGPT1 | 1.06 | 0.11 | 1.49 | 0.44 | −0.32 | 0.27 | 0.32 | 0.79 |
| AF043179 | *Homo sapiens* T cell receptor beta chain (TCRBV13S1-TCRBJ2S1) mRNA, complete cds. /PROD = T cell receptor beta chain /FL = gb: AF043179.1 | PRSS1 | 2.42 | 0.12 | 3.07 | 0.81 | 1.71 | 0.10 | 2.30 | 0.60 |
| AU157541 | hypothetical protein FLJ22833 /FL = gb: NM_022837.1 | — | 1.39 | 0.08 | 2.12 | 0.42 | 0.55 | 0.18 | 1.41 | 0.77 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF114264 | Homo sapiens clone HH409 unknown mRNA. /PROD = unknown | NEXN | 1.37 | 0.21 | 2.86 | 0.51 | 1.72 | 0.16 | 1.96 | 0.76 |
| BE965029 | Homo sapiens cDNA: FLJ22463 fis, clone HRC10126 | MICAL2 | 1.58 | 0.19 | 2.58 | 0.51 | 1.32 | 0.13 | 1.40 | 0.74 |
| AB028976 | Homo sapiens mRNA for KIAA1053 protein, partial cds. /PROD = KIAA1053 protein | SAMD4A | 2.89 | 0.08 | 3.65 | 0.66 | 2.04 | 0.17 | 2.78 | 0.81 |
| AI670862 | ESTs, Weakly similar to A49134 Ig kappa chain V-I region (H. sapiens) | FOSL2 | 0.17 | 0.21 | 2.05 | 0.57 | 0.45 | 0.16 | 1.18 | 0.65 |
| L03203 | Human peripheral myelin protein 22 (GAS3) mRNA, complete cds. /PROD = peripheral myelin protein 22 /FL = gb: L03203.1 | PMP22 | 0.37 | 0.24 | 1.95 | 0.84 | 0.31 | 0.26 | 2.77 | 0.91 |
| AI571798 | Rho GDP dissociation inhibitor (GDI) alpha | ARHGDIA | 0.89 | 0.06 | −0.54 | 0.26 | −3.00 | 0.89 | −2.58 | 0.87 |
| X57348 | Cluster Incl. X57348: H. sapiens mRNA (clone 9112) /cds = (165,911) /gb = X57348 /gi = 23939 /ug = Hs.184510 /len = 1407 | — | 2.94 | 0.04 | 4.07 | 0.41 | 2.70 | 0.08 | 3.69 | 0.41 |
| AF051851 | Homo sapiens supervillin mRNA, complete cds. /PROD = supervillin /FL = gb: AF051851.1 gb: NM_003174.2 gb: AF051850.1 | SVIL | 2.03 | 0.18 | 2.28 | 0.62 | 1.13 | 0.20 | 1.71 | 0.69 |
| M95929 | Human homeobox protein (PHOX1) mRNA, 3 end. /PROD = homeobox protein | — | 0.07 | 0.43 | 1.27 | 0.58 | −0.02 | 0.19 | 0.64 | 0.61 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BG251266 | FOS-like antigen-1 /FL = gb: NM_005438.1 | FOSL1 | 1.94 | 0.06 | 2.41 | 0.46 | 1.25 | 0.05 | 1.93 | 0.36 |
| AW298375 | ESTs | — | −0.40 | 0.30 | 0.46 | 0.63 | −0.09 | 0.20 | −0.58 | 1.07 |
| NM_004362 | *Homo sapiens* calmegin (CLGN), mRNA. /PROD = calmegin /FL = gb: NM_004362.1 gb: D86322.1 | CLGN | 0.90 | 0.30 | 1.95 | 0.96 | 0.69 | 0.11 | 3.11 | 1.01 |
| AF001540 | calcineurin-binding protein calsarcin-1 | — | 0.10 | 0.15 | 2.84 | 0.70 | 0.42 | 0.44 | 1.64 | 0.39 |
| NM_001191 | *Homo sapiens* BCL2-like 1 (BCL2L1), mRNA. /PROD = BCL2-like 1 /FL = gb: NM_001191.1 | BCL2L1 | 1.21 | 0.22 | 0.58 | 0.35 | −1.89 | 0.35 | −1.09 | 1.03 |
| NM_003316 | *Homo sapiens* tetratricopeptide repeat domain 3 (TTC3), mRNA. /PROD = tetratricopeptide repeat domain 3 /FL = gb: D84295.1 gb: NM_003316.1 | TTC3 | 3.90 | 0.15 | 5.15 | 0.98 | 3.68 | 0.12 | 6.19 | 0.97 |
| L16895 | Human lysyl oxidase (LOX) gene, exon 7 | — | −0.66 | 0.24 | 0.53 | 0.14 | −0.63 | 0.15 | 0.14 | 0.19 |
| AI912976 | ESTs | RASGRF2 | 3.13 | 0.08 | 4.05 | 0.56 | 2.66 | 0.16 | 3.54 | 0.64 |
| NM_012242 | *Homo sapiens* dickkopf (*Xenopus laevis*) homolog 1 (DKK1), mRNA. /PROD = dickkopf (*Xenopus laevis*) homolog 1 /FL = gb: AF177394.1 gb: NM_012242.1 gb: AF127563.1 | DKK1 | 0.47 | 0.29 | 0.73 | 0.04 | 0.49 | 0.51 | 1.09 | 0.23 |
| AL096776 | Human DNA sequence from clone RP4-646B12 on chromosome 1q42.11-42.3. Contains an FTH1 (ferritin, heavy polypeptide 1) (FTHL6) pseudogene, | — | 1.94 | 0.07 | 3.41 | 0.16 | 2.40 | 0.07 | 3.40 | 0.14 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
| --- | --- | --- | --- | --- | --- | --- | --- | --- | --- | --- |
| | the gene for a novel Ras family protein, ESTs, STSs, GSSs and a putative CpG island /FL = gb: AF282258.1 gb: NM_0212 | | | | | | | | | |
| BC005997 | *Homo sapiens*, clone MGC: 14801, mRNA, complete cds. /PROD = Unknown (protein for MGC: 14801) /FL = gb: BC005997.1 | — | 1.12 | 0.25 | 0.95 | 0.44 | 2.04 | 0.07 | 1.51 | 0.22 |
| AF074979 | *Homo sapiens* regulator of G protein signaling-Z (RGSZ1) mRNA, complete cds. /PROD = regulator of G protein signaling /FL = gb: AF060877.2 gb: AF074979.1 gb: NM_003702.2 | RGS20 | −0.52 | 0.18 | −0.04 | 0.38 | −1.30 | 0.09 | −0.34 | 0.13 |
| BF060767 | ESTs | ADAMTS5 | −0.36 | 0.15 | 0.80 | 0.33 | 0.22 | 0.14 | 0.40 | 0.56 |
| AU151151 | *Homo sapiens* cDNA FLJ13536 fis, clone PLACE1006521 | LEPR | 1.72 | 0.18 | 2.38 | 0.80 | 1.85 | 0.10 | 1.71 | 0.69 |
| L27624 | *Homo sapiens* tissue factor pathway inhibitor-2 mRNA, complete cds. /PROD = tissue factor pathway inhibitor-2 /FL = gb: D29992.1 gb: L27624.1 gb: NM_006528.1 gb: BC005330.1 | TFPI2 | 3.77 | 0.06 | 3.57 | 0.77 | 2.59 | 0.11 | 2.44 | 0.89 |
| NM_003174 | *Homo sapiens* supervillin (SVIL), transcript variant 1, mRNA. /PROD = supervillin, isoform 1 /FL = gb: AF051851.1 | SVIL | 3.15 | 0.09 | 3.68 | 0.44 | 2.91 | 0.01 | 3.27 | 0.46 |

TABLE IV-continued

DIFFERENTIAL EXPRESSION OF GENES BETWEEN UNDIFFERENTIATED EMBRYONIC STEM CELLS AND DEFINITIVE ENDODERM STAGE CELLS CULTURED ON EITHER MATRIGEL™ OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF052127 | gb: NM_003174.2 gb: AF051850.1 Homo sapiens clone 23850 mRNA sequence. | RELN | −3.13 | 1.04 | −1.36 | 0.26 | −0.88 | 0.17 | −0.40 | 0.11 |
| AL031290 | Human DNA sequence from clone 774I24 on chromosome 1q24.1-24.3 Contains protein similar to pregnancy-associated plasma protein A precursor neuronal migration protein astrotactin, ESTs, STS and GSS | — | 0.38 | 0.06 | 1.39 | 0.46 | 0.40 | 0.05 | 0.95 | 0.44 |
| AI129628 | ESTs | SAMD3 | −0.30 | 0.18 | −0.01 | 0.25 | 0.72 | 0.06 | 0.17 | 0.21 |
| NM_016206 | Homo sapiens colon carcinoma related protein (LOC51159), mRNA. /PROD = colon carcinoma related protein /FL = gb: NM_016206.1 gb: AF099505.1 | VGLL3 | −0.39 | 0.36 | 0.05 | 1.03 | −0.31 | 0.29 | −1.05 | 1.01 |
| BE348291 | ESTs | — | 1.62 | 0.06 | −0.19 | 0.98 | −3.65 | 0.10 | −2.75 | 1.84 |
| AW242720 | Homo sapiens cDNA FLJ10561 fis, clone NT2RP2002672 | LOC143381 | −1.62 | 0.34 | −1.20 | 0.94 | −0.08 | 0.24 | −0.08 | 0.77 |
| NM_001146 | Homo sapiens angiopoietin 1 (ANGPT1), mRNA. /PROD = angiopoietin 1 /FL = gb: NM_001146.1 gb: D13628.1 gb: U83508.1 | ANGPT1 | 1.86 | 0.06 | 2.09 | 0.81 | 1.10 | 0.16 | 0.87 | 1.05 |
| AU152579 | Homo sapiens cDNA FLJ13034 fis, clone NT2RP3001232 | PCSK5 | 2.41 | 0.14 | 2.47 | 0.86 | 2.04 | 0.15 | 1.11 | 1.20 |
| NM_006200 | Homo sapiens proprotein convertase subtilisinkexin type 5 | PCSK5 | 3.01 | 0.21 | 2.88 | 0.92 | 2.28 | 0.11 | 1.52 | 1.25 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | (PCSK5), mRNA. /PROD = proprotein convertase subtilisinkexin type 5 /FL = gb: U56387.2 gb: NM_006200.1 | | | | | | | | | |
| BF342661 | KIAA0036 gene product | MAP2 | −0.77 | 0.30 | −0.19 | 0.44 | 0.12 | 0.17 | −2.21 | 1.64 |
| AF063824 | *Homo sapiens* trp-related protein 4 truncated variant delta mRNA, complete cds. /PROD = trp-related protein 4 truncated variant delta /FL = gb: AF063824.1 | TRPC4 | −3.03 | 0.39 | 0.05 | 0.49 | 1.28 | 0.17 | 0.21 | 0.92 |
| AA723810 | cDNA for differentially expressed CO16 gene /FL = gb: BC001291.1 | LY6K | 0.07 | 0.20 | −0.13 | 1.23 | 0.15 | 0.14 | −0.38 | 1.27 |
| N29877 | interleukin 14 | — | 1.94 | 0.13 | 0.51 | 0.48 | 0.78 | 0.64 | −1.57 | 0.65 |
| NM_007287 | *Homo sapiens* membrane metallo-endopeptidase (neutral endopeptidase, enkephalinase, CALLA, CD10) (MME), transcript variant 1bis, mRNA. /PROD = membrane metallo-endopeptidase /FL = gb: NM_007288.1 gb: NM_007287.1 gb: J03779.1 | MME | 2.59 | 0.03 | 1.81 | 0.40 | 1.89 | 0.21 | 2.14 | 0.30 |
| AB050856 | *Homo sapiens* beta3GalNAcT-1 mRNA for globoside synthase, complete cds, clone: type 2. /PROD = globoside synthase /FL = gb: AB050856.1 | B3GALNT1 | 1.39 | 0.05 | 0.20 | 0.22 | −0.13 | 0.21 | −0.10 | 0.17 |
| AI827455 | *Homo sapiens* cDNA: FLJ21042 fis, clone CAE11204 | BCL6B | 0.65 | 0.31 | 0.62 | 0.21 | 1.07 | 0.24 | 0.90 | 0.29 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF017987 | *Homo sapiens* secreted apoptosis related protein 2 (SARP2) mRNA, complete cds. /PROD = secreted apoptosis related protein 2 /FL = gb: AF056087.1 gb: NM_003012.2 gb: AF017987.1 gb: AF001900.1 | SFRP1 | 4.15 | 0.22 | 4.37 | 1.24 | 6.02 | 0.06 | 5.74 | 1.01 |
| AL117451 | *Homo sapiens* mRNA; cDNA DKFZp586E2317 (from clone DKFZp586E2317). | C1orf108 | −0.73 | 0.20 | 0.68 | 0.24 | 1.06 | 0.05 | 0.82 | 0.21 |
| AW268357 | ESTs, Highly similar to AF155116 1 NY-REN-60 antigen (*H. sapiens*) | USP32 | 0.73 | 0.20 | 0.36 | 0.19 | 0.70 | 0.03 | 0.09 | 0.18 |
| BE465243 | ESTs | ARFGEF1 | 0.50 | 0.23 | 0.16 | 0.32 | 1.03 | 0.08 | 0.47 | 0.06 |
| AA993400 | ESTs | ADAL | 0.89 | 0.22 | 0.48 | 0.28 | 0.83 | 0.10 | 0.29 | 0.43 |
| AI970898 | Cluster Incl. AI970898: wr 21c03.x1 *Homo sapiens* cDNA, 3 end /clone = IMAGE-2488324 /clone_end = 3 /gb = AI970898 /gi = 5767724 /ug = Hs.234898 /len = 382 | ACACB | 0.69 | 0.15 | 0.51 | 0.53 | 1.46 | 0.11 | −0.87 | 0.83 |
| BG026457 | ESTs, Weakly similar to ALU5_HUMAN ALU SUBFAMILY SC SEQUENCE CONTAMINATION WARNING ENTRY (*H. sapiens*) | KIAA1909 | 0.60 | 0.07 | 0.23 | 0.59 | 0.98 | 0.03 | −2.11 | 1.28 |
| BC041933 | *Homo sapiens*, clone IMAGE: 5300703, mRNA. | UBE3C | 0.83 | 0.23 | 0.11 | 0.51 | 0.55 | 0.05 | 0.41 | 0.92 |
| AI638611 | KIAA1373 protein | STAMBPL1 | 2.20 | 0.17 | 1.37 | 0.58 | 2.32 | 0.08 | −0.39 | 1.24 |
| AI341686 | ESTs, Highly similar to RF1M_HUMAN | MTRF1 | 1.36 | 0.14 | 0.45 | 0.48 | 1.43 | 0.09 | −1.09 | 0.99 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | MITOCHONDRIAL PEPTIDE CHAIN RELEASE FACTOR 1 PRECURSOR (*H. sapiens*) | | | | | | | | | |
| NM_003182 | *Homo sapiens* tachykinin, precursor 1 (substance K, substance P, neurokinin 1, neurokinin 2, neuromedin L, neurokinin alpha, neuropeptide K, neuropeptide gamma) (TAC1), transcript variant beta, mRNA. /PROD = tachykinin 2 precursor, isoform beta /FL = gb: U3 | TAC1 | 1.89 | 0.20 | 1.65 | 0.13 | 2.46 | 0.09 | 1.48 | 0.26 |
| M80634 | Human keratinocyte growth factor receptor mRNA, complete cds. /PROD = keratinocyte growth factor receptor /FL = gb: M80634.1 gb: NM_022969.1 gb: M97193.1 | FGFR2 | 3.63 | 0.06 | 2.25 | 0.39 | 2.79 | 0.19 | 2.07 | 0.84 |
| AK021452 | *Homo sapiens* cDNA FLJ11390 fis, clone HEMBA1000561, weakly similar to ZINC FINGER PROTEIN 91. | ZNF521 | −0.20 | 0.16 | −1.15 | 1.12 | 1.31 | 0.05 | 0.36 | 0.18 |
| AA541622 | ESTs | SYNPO2 | −0.49 | 0.30 | −0.90 | 0.06 | 0.35 | 0.09 | −2.58 | 0.93 |
| N50714 | ESTs | — | −1.13 | 0.13 | −1.34 | 0.52 | 0.10 | 0.12 | −0.21 | 0.28 |
| NM_002674 | *Homo sapiens* pro-melanin-concentrating hormone (PMCH), mRNA. /PROD = pro-melanin-concentrating hormone /FL = gb: NM_002674.1 gb: M57703.1 | PMCH | 0.62 | 0.24 | 1.10 | 0.48 | 1.64 | 0.03 | 0.09 | 0.80 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BM666010 | Homo sapiens cDNA FLJ23803 fis, clone HEP22811. | LOC200169 | 1.36 | 0.16 | 0.45 | 0.74 | 1.49 | 0.12 | −1.65 | 1.41 |
| AI343467 | Homo sapiens cDNA FLJ11041 fis, clone PLACE1004405 | — | −0.44 | 0.08 | −1.50 | 0.82 | 1.11 | 0.19 | −0.64 | 0.20 |
| AA046424 | ESTs, Weakly similar to YZ28_HUMAN HYPOTHETICAL PROTEIN ZAP128 (H. sapiens) | ACOT4 | 0.58 | 0.27 | −0.94 | 0.66 | −1.08 | 0.38 | −1.09 | 0.25 |
| R38389 | olfactomedin related ER localized protein | OLFM1 | 4.27 | 0.11 | 3.02 | 0.76 | 4.53 | 0.07 | 2.17 | 0.96 |
| BF724270 | ESTs | — | 2.03 | 0.22 | 0.72 | 0.42 | 2.36 | 0.06 | 0.01 | 0.97 |
| NM_001819 | Homo sapiens chromogranin B (secretogranin 1) (CHGB), mRNA. /PROD = chromogranin B precursor /FL = gb: BC000375.1 gb: NM_001819.1 | CHGB | 1.40 | 0.18 | 0.50 | 0.75 | 1.66 | 0.05 | −0.74 | 1.03 |
| AK026387 | Homo sapiens cDNA: FLJ22734 fis, clone HUV00109. | — | 0.03 | 0.28 | −0.05 | 0.52 | 1.23 | 0.26 | 0.52 | 0.67 |
| BF062139 | polymerase (RNA) III (DNA directed) (32 kD) /FL = gb: NM_006467.1 gb: U93868.1 | — | 5.23 | 0.06 | 4.31 | 0.74 | 5.80 | 0.07 | 3.37 | 0.86 |
| BG540454 | ESTs | SCGB3A2 | 4.64 | 0.02 | 2.91 | 0.84 | 4.13 | 0.07 | 1.72 | 0.83 |
| AI659533 | ArgAbl-interacting protein ArgBP2 | SORBS2 | 0.02 | 0.12 | 1.12 | 0.71 | 2.17 | 0.05 | −1.08 | 1.48 |
| AA531287 | ESTs | — | 2.94 | 0.27 | 1.32 | 0.72 | 2.57 | 0.04 | 0.22 | 0.90 |
| NM_013243 | Homo sapiens secretogranin III (SCG3), mRNA. /PROD = secretogranin III /FL = gb: AF078851.1 gb: NM_013243.1 | SCG3 | 3.30 | 0.20 | 2.13 | 0.95 | 3.67 | 0.19 | 0.87 | 1.06 |
| AI307586 | Homo sapiens mRNA; | C10orf95 | 0.34 | 0.22 | −1.15 | 0.24 | −0.49 | 0.16 | −3.61 | 0.99 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BC032004 | cDNA DKFZp566H0124 (from clone DKFZp566H0124) Homo sapiens, Similar to glutamate receptor, ionotrophic, AMPA 3, clone IMAGE: 4753474, mRNA. | GRIA3 | −0.02 | 0.23 | −0.15 | 0.33 | 0.47 | 0.04 | 0.17 | 0.07 |
| AW205739 | ESTs, Weakly similar to ORF YGL050w (S. cerevisiae) | TYW3 | 0.47 | 0.01 | 0.81 | 1.35 | 3.72 | 0.18 | 2.46 | 1.15 |
| NM_153262 | Homo sapiens hypothetical protein FLJ34198 (FLJ34198), mRNA. /FL = gb: NM_153262.1 | SYT14 | −0.01 | 0.17 | −0.84 | 0.51 | 0.00 | 0.18 | −3.88 | 1.64 |
| AA156873 | albumin | PELO | 0.77 | 0.12 | −0.23 | 0.93 | 0.65 | 0.14 | −2.33 | 1.01 |
| BC012375 | Homo sapiens, Similar to KIAA1001 protein, clone MGC: 8996 IMAGE: 3882163, mRNA, complete cds. /PROD = Similar to KIAA1001 protein /FL = gb: AB023218.1 gb: NM_014960.1 gb: BC012375.1 | ARSG | −0.46 | 0.48 | −0.78 | 0.42 | 0.57 | 0.22 | −0.41 | 0.55 |
| AA843242 | ESTs | BNC2 | 2.12 | 0.37 | 1.03 | 0.47 | 2.89 | 0.06 | 0.43 | 0.80 |
| BF792954 | ESTs | HDLBP | −1.53 | 1.04 | −2.75 | 0.91 | 0.30 | 0.16 | −0.72 | 0.26 |
| AA780067 | heparan sulfate (glucosamine) 3-O-sulfotransferase 3B1 | HS3ST3B1 | 0.41 | 0.19 | 0.30 | 0.61 | 2.61 | 0.18 | 0.78 | 0.60 |
| AA909330 | ESTs | RP1-32F7.2 | 0.98 | 0.17 | −1.67 | 0.51 | 0.79 | 0.02 | −0.38 | 0.12 |
| AF141339 | Homo sapiens LYST-interacting protein LIP3 mRNA, partial cds. /PROD = LYST-interacting protein LIP3 | ZNF521 | −0.41 | 0.12 | −0.97 | 0.93 | 1.67 | 0.11 | −0.31 | 0.80 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BF435123 | bromodomain and PHD finger containing, 3 | — | 2.28 | 0.17 | 1.31 | 0.51 | 2.70 | 0.12 | 1.30 | 1.00 |
| AK056212 | *Homo sapiens* cDNA FLJ31650 fis, clone NT2RI2004079. | — | 1.03 | 0.14 | 0.14 | 0.27 | 1.10 | 0.07 | −1.41 | 0.51 |
| NM_001446 | *Homo sapiens* fatty acid binding protein 7, brain (FABP7), mRNA. /PROD = fatty acid binding protein 7, brain /FL = gb: U81235.1 gb: D88648.1 gb: U51338.1 gb: NM_001446.1 gb: D50373.1 | FABP7 | 2.07 | 0.15 | 0.74 | 0.29 | 2.20 | 0.04 | 1.08 | 0.16 |
| AW051591 | ESTs, Moderately similar to unnamed protein product (*H. sapiens*) | RNF175 | 1.41 | 0.32 | 0.22 | 0.10 | 2.60 | 0.06 | 0.96 | 0.20 |
| BC041970 | *Homo sapiens*, clone IMAGE: 5302687, mRNA. | C9orf122 | 0.74 | 0.03 | −0.35 | 0.49 | 0.76 | 0.06 | −2.31 | 1.25 |
| BC013077 | *Homo sapiens*, clone IMAGE: 3459334, mRNA. | — | 2.51 | 0.11 | 0.80 | 1.15 | 2.85 | 0.06 | 0.08 | 0.89 |
| AW572379 | ESTs | — | 1.80 | 0.03 | 0.60 | 0.84 | 1.45 | 0.07 | 1.88 | 0.53 |
| BE644917 | nuclear receptor subfamily 1, group I, member 3 | XIST | −3.88 | 1.26 | −0.54 | 1.28 | 1.94 | 0.13 | −0.20 | 1.94 |
| NM_171999 | *Homo sapiens* sal-like 3 (*Drosophila*) (SALL3), mRNA. /PROD = sal-like 3 /FL = gb: NM_171999.1 | SALL3 | 2.97 | 0.18 | 2.04 | 0.71 | 3.79 | 0.08 | 1.02 | 0.74 |
| AI654224 | ESTs | — | 0.46 | 0.36 | 0.14 | 0.44 | 1.03 | 0.07 | −0.81 | 0.85 |
| AA167449 | nuclear receptor subfamily 1, group I, member 3 | XIST | −3.08 | 0.10 | −0.47 | 2.59 | 4.59 | 0.07 | 2.80 | 1.86 |
| BF977837 | KIAA0527 protein | SUSD5 | 1.64 | 0.02 | 0.50 | 0.68 | 1.96 | 0.16 | −1.52 | 1.66 |
| BC029425 | *Homo sapiens*, Similar to KIAA1275 | FILIP1 | −0.83 | 0.45 | −0.03 | 0.62 | 0.76 | 0.20 | −0.29 | 0.44 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | protein, clone IMAGE: 4616553, mRNA. | | | | | | | | | |
| AI978754 | ESTs | — | 2.76 | 0.14 | 1.54 | 0.57 | 3.57 | 0.06 | 2.31 | 0.69 |
| AA628440 | nuclear receptor subfamily 1, group I, member 3 | XIST | 0.18 | 0.13 | 1.42 | 1.52 | 4.80 | 0.02 | 3.01 | 1.50 |
| L36861 | L36861 /FEATURE = expanded_cds /DEFINITION = HUMGCAPB *Homo sapiens* guanylate cyclase activating protein (GCAP) gene exons 1-4, complete cds | — | 2.75 | 0.17 | 2.01 | 0.82 | 3.63 | 0.09 | 3.00 | 0.97 |
| AW023227 | ESTs | MKX | −0.91 | 0.60 | −1.31 | 0.06 | 0.27 | 0.13 | −2.90 | 0.52 |
| NM_021614 | *Homo sapiens* potassium intermediate small conductance calcium-activated channel, subfamily N, member 2 (KCNN2), mRNA. /PROD = potassium intermediate small conductance calcium-activated channel, subfamily N, member 2 /FL = gb: NM_021614.1 gb: AF239613.1 | KCNN2 | 3.45 | 0.13 | 2.52 | 0.83 | 4.40 | 0.14 | 1.54 | 0.80 |
| NM_000956 | *Homo sapiens* prostaglandin E receptor 2 (subtype EP2), 53 kD (PTGER2), mRNA. /PROD = prostaglandin E receptor 2 (subtype EP2), 53 kD /FL = gb: U19487.1 gb: NM_000956.1 | PTGER2 | −0.71 | 0.71 | −0.73 | 0.57 | 0.63 | 0.33 | −2.38 | 0.61 |
| NM_013381 | *Homo sapiens* thyrotropin-releasing hormone degrading | TRHDE | 1.96 | 0.16 | 0.25 | 0.36 | 1.81 | 0.03 | 0.82 | 0.23 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | ectoenzyme (TRHDE), mRNA. /PROD = thyrotropin-releasing hormone degradingectoenzyme /FL = gb: AF126372.1 gb: NM_013381.1 | | | | | | | | | |
| NM_016354 | *Homo sapiens* solute carrier family 21 (organic anion transporter), member 12 (SLC21A12), mRNA. /PROD = organic anion transporter OATP-E /FL = gb: AB031051.1 gb: NM_016354.1 gb: AF205072.1 gb: AF187817.1 | SLCO4A1 | 2.18 | 0.06 | 1.01 | 0.37 | 2.35 | 0.05 | −0.91 | 1.23 |
| BC028359 | *Homo sapiens*, clone IMAGE: 4828836, mRNA. | ZNF141 | −1.05 | 0.39 | −0.59 | 0.65 | 1.25 | 0.17 | −1.48 | 0.72 |
| AI193252 | ESTs, Weakly similar to AF133270 1 SLIT2 (*H. sapiens*) | LRRN6A | 4.38 | 0.11 | 2.47 | 0.43 | 4.23 | 0.11 | 1.90 | 0.37 |
| H09780 | Human (clone CTG-A4) mRNA sequence | — | 2.04 | 0.19 | 0.56 | 0.07 | 2.50 | 0.11 | 0.12 | 0.40 |
| BC040605 | *Homo sapiens*, clone IMAGE: 5271039, mRNA. | — | 2.64 | 0.16 | 1.61 | 1.08 | 3.59 | 0.09 | 0.45 | 1.14 |
| AW057589 | ESTs | — | −0.96 | 0.26 | −2.77 | 0.81 | 0.25 | 0.24 | −1.21 | 0.35 |
| M31213 | Human papillary thyroid carcinoma-encoded protein mRNA, complete cds. /FL = gb: M31213.1 | RET | 0.42 | 0.10 | −1.86 | 0.83 | 1.77 | 0.12 | −0.64 | 0.15 |
| Z92546 | Human DNA sequence from clone CTA-65A6 on chromosome 22q11-12 Contains the 3 part of the gene for the | — | 0.58 | 0.13 | −1.16 | 0.54 | 1.07 | 0.12 | −1.27 | 0.14 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AA974416 | ortholog of rat CAIN (KIAA0330), the gene for a novel Sushi domain (SCR repeat) containing protein similar to Mucins, ESTs, an STS, GSSs and two . . . protein phosphatase 2 (formerly 2A), regulatory subunit B (PR 52), beta isoform | PPP2R2B | 4.02 | 0.16 | 3.52 | 0.23 | 5.22 | 0.07 | 3.12 | 0.15 |
| AW138143 | ESTs | SORBS2 | 3.44 | 0.16 | 2.89 | 0.88 | 4.47 | 0.10 | 1.88 | 1.15 |
| NM_014862 | *Homo sapiens* KIAA0307 gene product (KIAA0307), mRNA. /PROD = KIAA0307 gene product /FL = gb: AB002305.1 gb: NM_014862.1 | ARNT2 | 1.29 | 0.08 | −0.68 | 0.97 | 2.00 | 0.08 | 0.02 | 0.24 |
| AI765540 | ESTs | — | 1.28 | 0.22 | 0.07 | 0.39 | 1.50 | 0.07 | −0.11 | 0.26 |
| NM_018013 | *Homo sapiens* hypothetical protein FLJ10159 (FLJ10159), mRNA. /PROD = hypothetical protein FLJ10159 /FL = gb: NM_018013.1 | FLJ10159 | 1.30 | 0.21 | 0.38 | 0.39 | 2.89 | 0.02 | 0.62 | 0.21 |
| BF382322 | ESTs, Weakly similar to unnamed protein product (*H. sapiens*) | — | −0.40 | 0.09 | −2.09 | 0.67 | −0.12 | 0.08 | −1.73 | 0.50 |
| AV699347 | nuclear receptor subfamily 1, group I, member 3 | XIST | −1.37 | 0.38 | 0.45 | 1.69 | 4.28 | 0.02 | 2.25 | 1.53 |
| BC011549 | *Homo sapiens*, clone MGC: 19945 IMAGE: 4554461, mRNA, complete cds. | ATP5S | 0.69 | 0.19 | 0.96 | 0.68 | 2.57 | 0.29 | −0.02 | 0.52 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_001889 | /PROD = Unknown (protein for MGC: 19945) /FL = gb: BC011549.1 Homo sapiens crystallin, zeta (quinone reductase) (CRYZ), mRNA. /PROD = crystallin, zeta (quinone reductase) /FL = gb: NM_001889.1 gb: L13278.1 gb: S58039.1 | CRYZ | −1.68 | 0.26 | 0.23 | 1.38 | 3.75 | 0.07 | 1.78 | 1.11 |
| BC002665 | Homo sapiens, proteolipid protein (Pelizaeus-Merzbacher disease, spastic paraplegia 2, uncomplicated), clone MGC: 3940, mRNA, complete cds. /PROD = proteolipid protein (Pelizaeus-Merzbacherdisease, spastic paraplegia 2, uncomplicated) /FL = gb: BC002665.1 | PLP1 | 4.57 | 0.15 | 2.95 | 0.64 | 4.70 | 0.06 | 2.32 | 0.52 |
| NM_001243 | Homo sapiens tumor necrosis factor receptor superfamily, member 8 (TNFRSF8), mRNA. /PROD = CD30 antigen (Ki-1 antigen) /FL = gb: NM_001243.1 gb: D86042.1 gb: M83554.1 | TNFRSF8 | 3.75 | 0.03 | 1.45 | 0.35 | 3.24 | 0.11 | 0.89 | 0.46 |
| NM_001195 | Homo sapiens beaded filament structural protein 1, filensin (BFSP1), mRNA. /PROD = filensin /FL = gb: AF039655.1 | BFSP1 | 0.57 | 0.33 | −1.65 | 1.30 | 0.60 | 0.14 | −0.86 | 0.73 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_024582 | gb: NM_001195.2 gb: Y16717.2 Homo sapiens hypothetical protein FLJ23056 (FLJ23056), mRNA. /PROD = hypothetical protein FLJ23056 /FL = gb: NM_024582.1 | FAT4 | 2.16 | 0.27 | −0.49 | 0.30 | 1.54 | 0.28 | −1.35 | 1.01 |
| NM_000767 | Homo sapiens cytochrome P450, subfamily IIB (phenobarbital-inducible), polypeptide 6 (CYP2B6), mRNA. /PROD = cytochrome P450, subfamily IIB(phenobarbital-inducible), polypeptide 6 /FL = gb: NM_000767.2 gb: AF182277.1 gb: M29874.1 | CYP2B6 | 2.60 | 0.18 | 0.87 | 0.96 | 1.47 | 0.12 | −0.69 | 1.03 |
| AW665509 | ESTs | MGC42174 | −0.10 | 0.33 | −0.87 | 0.72 | 1.20 | 0.08 | −2.60 | 1.40 |
| NM_001104 | Homo sapiens actinin, alpha 3 (ACTN3), mRNA. /PROD = skeletal muscle specific actinin, alpha 3 /FL = gb: M86407.1 gb: NM_001104.1 | ACTN3 | 2.12 | 0.13 | 1.64 | 0.28 | 3.35 | 0.03 | 1.67 | 0.36 |
| NM_021069 | Homo sapiens ArgAbl-interacting protein ArgBP2 (ARGBP2), transcript variant 2, mRNA. /PROD = Arg Abl-interacting protein 2, isoform 2 /FL = gb: AB018320.1 gb: NM_021069.1 | SORBS2 | −0.49 | 0.43 | 0.30 | 1.36 | 2.03 | 0.07 | −1.13 | 1.15 |
| T65020 | ESTs | — | 0.51 | 0.16 | −0.84 | 0.26 | 1.10 | 0.15 | −1.50 | 0.38 |
| NM_152647 | Homo sapiens hypothetical protein FLJ32800 (FLJ32800), mRNA. /FL = gb: NM_152647.1 | GALK2 | 0.08 | 0.56 | −1.42 | 0.52 | 0.03 | 0.17 | −2.34 | 0.91 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BC036917 | *Homo sapiens*, clone MGC: 46457 IMAGE: 5201433, mRNA, complete cds. /PROD = Unknown (protein for MGC: 46457) /FL = gb: BC036917.1 | C6orf141 | −0.82 | 0.30 | −1.18 | 0.40 | 0.88 | 0.11 | −2.18 | 0.62 |
| AI969112 | *Homo sapiens*, clone IMAGE: 5260603, mRNA, partial cds | PHIP | −1.07 | 0.13 | −2.88 | 0.91 | −0.37 | 0.02 | −2.23 | 0.33 |
| AW449813 | KIAA0918 protein | SLITRK5 | 0.32 | 0.26 | −1.89 | 0.50 | 0.46 | 0.10 | −0.57 | 0.13 |
| AW044658 | ESTs | — | 0.16 | 0.16 | −1.47 | 0.25 | 0.90 | 0.14 | −0.89 | 0.16 |
| AI694300 | ESTs | — | −0.52 | 0.02 | −1.34 | 0.52 | 0.27 | 0.08 | −1.00 | 0.08 |
| NM_017631 | *Homo sapiens* hypothetical protein FLJ20035 (FLJ20035), mRNA. /PROD = hypothetical protein FLJ20035 /FL = gb: NM_017631.1 | FLJ20035 | 1.35 | 0.13 | 0.05 | 0.19 | 1.51 | 0.17 | 0.32 | 0.15 |
| AF298547 | *Homo sapiens* nucleotide-binding site protein 1 mRNA, complete cds. /PROD = nucleotide-binding site protein 1 /FL = gb: AF298547.1 | NALP2 | 1.54 | 0.08 | 1.22 | 1.61 | 5.04 | 0.05 | 3.23 | 1.36 |
| NM_030631 | *Homo sapiens* oxodicarboxylate carrier (ODC1), mRNA. /PROD = oxodicarboxylate carrier /FL = gb: NM_030631.1 | SLC25A21 | 1.96 | 0.25 | 0.33 | 0.81 | 2.47 | 0.11 | −0.28 | 0.63 |
| BF196255 | ESTs | — | 2.94 | 0.05 | 1.18 | 0.43 | 3.15 | 0.08 | 0.54 | 0.57 |
| NM_003247 | *Homo sapiens* thrombospondin 2 (THBS2), mRNA. /PROD = thrombospondin 2 /FL = gb: NM_003247.1 gb: L12350.1 | THBS2 | 2.62 | 0.20 | 1.04 | 0.28 | 2.70 | 0.04 | 0.27 | 0.45 |
| NM_001446 | *Homo sapiens* fatty acid binding protein 7, brain (FABP7), mRNA. | FABP7 | 0.95 | 0.09 | −0.75 | 0.37 | 0.20 | 0.22 | −1.73 | 0.99 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | /PROD = fatty acid binding protein 7, brain /FL = gb: U81235.1 gb: D88648.1 gb: U51338.1 gb: NM_001446.1 gb: D50373.1 | | | | | | | | | |
| AW004016 | ESTs | ST6GAL2 | 1.57 | 0.14 | 0.89 | 0.32 | 3.30 | 0.07 | 1.48 | 0.43 |
| AW072790 | contactin 1 | CNTN1 | 0.50 | 0.20 | 0.18 | 0.98 | 1.84 | 0.10 | 1.01 | 1.39 |
| AL512686 | Homo sapiens mRNA; cDNA DKFZp761I177 (from clone DKFZp761I177). | GNAO1 | 2.16 | 0.50 | −0.28 | 1.03 | 1.67 | 0.18 | −1.12 | 0.37 |
| AI638063 | ESTs | CBX5 | 0.49 | 0.16 | −0.34 | 0.34 | 0.98 | 0.11 | −2.71 | 1.22 |
| AU157049 | Homo sapiens cDNA FLJ14284 fis, clone PLACE1005898 | LOC153346 | 2.24 | 0.20 | 0.34 | 0.47 | 2.24 | 0.09 | −0.44 | 0.96 |
| NM_002738 | Homo sapiens protein kinase C, beta 1 (PRKCB1), mRNA. /PROD = protein kinase C, beta 1 /FL = gb: NM_002738.1 | PRKCB1 | 0.99 | 0.28 | −0.15 | 0.45 | 1.42 | 0.08 | −1.02 | 1.04 |
| AI185136 | ESTs | DYDC2 | 0.12 | 0.31 | −0.80 | 0.08 | 0.72 | 0.08 | −0.60 | 0.09 |
| AI928037 | ESTs | RPIB9 | −0.55 | 0.55 | −2.71 | 0.74 | 0.49 | 0.12 | −0.89 | 0.27 |
| NM_016179 | Homo sapiens transient receptor potential channel 4 (TRPC4), mRNA. /PROD = transient receptor potential 4 /FL = gb: NM_016179.1 gb: AF175406.1 | TRPC4 | −1.51 | 0.85 | −1.87 | 1.42 | 1.71 | 0.11 | −0.13 | 1.23 |
| AW138143 | ESTs | SORBS2 | 3.29 | 0.13 | 2.35 | 1.05 | 4.28 | 0.10 | 1.32 | 1.07 |
| NM_001876 | Homo sapiens carnitine palmitoyltransferase I, liver (CPT1A), nuclear gene encoding mitochondrial protein, mRNA. /PROD = liver carnitine palmitoyltransferase I /FL = gb: L39211.1 gb: NM_001876.1 | CPT1A | 1.63 | 0.18 | −0.15 | 0.21 | 1.32 | 0.07 | −0.20 | 0.33 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AA903862 | ESTs | C20orf54 | 1.61 | 0.15 | −1.17 | 0.30 | 0.68 | 0.21 | −1.49 | 0.23 |
| AI670947 | phosphatidylinositol-4-phosphate 5-kinase, type I, beta | — | 3.91 | 0.05 | 0.55 | 1.54 | 3.33 | 0.10 | 1.17 | 0.68 |
| AV648405 | polymerase (RNA) III (DNA directed) (32 kD) | — | −0.01 | 0.11 | 0.23 | 0.52 | 1.73 | 0.14 | −1.23 | 1.15 |
| BF435123 | bromodomain and PHD finger containing, 3 | — | 1.80 | 0.13 | −1.35 | 1.01 | 1.14 | 0.03 | 0.37 | 0.24 |
| NM_016582 | *Homo sapiens* peptide transporter 3 (LOC51296), mRNA. /PROD = peptide transporter 3 /FL = gb: NM_016582.1 gb: AB020598.1 | SLC15A3 | 1.77 | 0.16 | −0.88 | 1.35 | 1.30 | 0.23 | −2.04 | 1.23 |
| AI830490 | glycerol kinase | GK | 0.61 | 0.01 | −0.65 | 0.79 | 1.25 | 0.20 | −0.38 | 0.33 |
| AW134979 | HSPC156 protein | STXBP6 | 2.28 | 0.03 | 0.55 | 0.28 | 2.05 | 0.03 | 0.30 | 0.44 |
| AI354636 | ESTs | — | 2.81 | 0.11 | 0.68 | 1.17 | 3.02 | 0.20 | 0.19 | 0.76 |
| BE672659 | ESTs | — | 0.20 | 0.64 | −0.43 | 0.61 | 1.98 | 0.12 | −0.69 | 0.45 |
| AF284095 | *Homo sapiens* alpha-2A adrenergic receptor mRNA, complete cds. /PROD = alpha-2A adrenergic receptor /FL = gb: AF284095.1 gb: NM_000681.1 | ADRA2A | 0.63 | 0.21 | −0.74 | 0.98 | 1.85 | 0.03 | 0.55 | 0.31 |
| NM_021136 | *Homo sapiens* reticulon 1 (RTN1), mRNA. /PROD = reticulon 1 /FL = gb: L10333.1 gb: L10334.1 gb: NM_021136.1 | RTN1 | −0.30 | 0.03 | −1.39 | 0.35 | 0.80 | 0.07 | −1.23 | 0.39 |
| NM_014729 | *Homo sapiens* KIAA0808 gene product (KIAA0808), mRNA. /PROD = KIAA0808 gene product /FL = gb: AB018351.1 gb: NM_014729.1 | TOX | 0.34 | 0.03 | −0.46 | 0.12 | 0.90 | 0.18 | −1.86 | 0.40 |
| BE674118 | ESTs | — | 0.78 | 0.07 | −1.32 | 0.73 | 0.28 | 0.19 | −0.96 | 0.74 |
| BC026969 | *Homo sapiens,* clone | WDR67 | 2.95 | 0.11 | 0.75 | 0.92 | 3.08 | 0.08 | 0.45 | 0.61 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF131783 | IMAGE: 5116073, mRNA, partial cds. Homo sapiens clone 25181 mRNA sequence. | PAP2D | −0.42 | 0.26 | −2.00 | 1.05 | 0.31 | 0.22 | −1.56 | 0.70 |
| U11058 | Homo sapiens large conductance calcium- and voltage-dependent potassium channel alpha subunit (MaxiK) mRNA, complete cds. /PROD = large conductance calcium- and voltage-dependentpotassium channel alpha subunit /FL = gb: U23767.1 gb: NM_002247.1 | KCNMA1 | 1.56 | 0.09 | −0.16 | 1.08 | 2.29 | 0.18 | −0.79 | 0.86 |
| BF510715 | gb: AF025999 fibroblast growth factor 4 (heparin secretory transforming protein 1, Kaposi sarcoma oncogene) /FL = gb: M17446.1 gb: NM_002007.1 | — | 2.67 | 0.27 | 0.84 | 0.17 | 3.29 | 0.01 | 0.64 | 0.51 |
| BE897866 | ESTs | ACADSB | 1.41 | 0.23 | 0.08 | 0.34 | 3.10 | 0.10 | −0.27 | 0.88 |
| AI735586 | ESTs | LOC152573 | 0.60 | 0.13 | 0.00 | 1.14 | 2.84 | 0.07 | 1.12 | 1.30 |
| AL573058 | complement component 1, r subcomponent | C1R | 0.92 | 0.14 | −1.67 | 0.38 | 0.73 | 0.02 | −0.96 | 0.77 |
| AF429305 | Homo sapiens C23up NCRMS mRNA, partial sequence; alternatively spliced. | RMST | −0.48 | 0.03 | −2.49 | 0.51 | −0.25 | 0.20 | −1.89 | 0.27 |
| BF195118 | ESTs, Weakly similar to ALU7_HUMAN ALU SUBFAMILY SQ SEQUENCE CONTAMINATION WARNING | ATP5J | 0.09 | 0.13 | −0.92 | 0.42 | 1.57 | 0.16 | −0.53 | 0.08 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_005460 | Homo sapiens synuclein, alpha interacting protein (synphilin) (SNCAIP), mRNA. /PROD = synuclein alpha interacting protein /FL = gb: AF076929.1 gb: NM_005460.1 | SNCAIP | 1.76 | 0.16 | −0.84 | 0.52 | 1.61 | 0.19 | −0.92 | 0.88 |
| NM_024893 | Homo sapiens hypothetical protein FLJ14220 (FLJ14220), mRNA. /PROD = hypothetical protein FLJ14220 /FL = gb: NM_024893.1 | C20orf39 | 1.16 | 0.29 | −0.56 | 0.42 | 2.36 | 0.15 | −0.06 | 0.17 |
| NM_022034 | Homo sapiens estrogen regulated gene 1 (ERG-1), mRNA. /PROD = estrogen regulated gene 1 /FL = gb: AF305835.1 gb: NM_022034.1 | CUZD1 | 1.31 | 0.08 | 0.80 | 0.28 | 2.78 | 0.07 | 0.24 | 0.58 |
| NM_014788 | Homo sapiens KIAA0129 gene product (KIAA0129), mRNA. /PROD = KIAA0129 gene product /FL = gb: D50919.1 gb: NM_014788.1 | TRIM14 | 3.12 | 0.09 | 1.22 | 0.59 | 3.54 | 0.08 | 1.02 | 0.45 |
| AV646597 | ESTs, Weakly similar to ALU7_HUMAN ALU SUBFAMILY SQ SEQUENCE CONTAMINATION WARNING ENTRY (H. sapiens) | XIST | −0.77 | 0.18 | 0.06 | 1.55 | 3.78 | 0.25 | 2.28 | 0.98 |
| BF062629 | DKFZP586E1621 protein | TMEM158 | 4.00 | 0.19 | 2.41 | 0.27 | 4.87 | 0.00 | 1.93 | 0.19 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AW440492 | ATPase, Na+K+ transporting, alpha 2 (+) polypeptide /FL = gb: NM_000702.1 | ATP1A2 | 1.33 | 0.07 | −2.12 | 1.07 | 1.27 | 0.06 | −0.53 | 0.11 |
| AF283777 | *Homo sapiens* clone TCBAP0702 mRNA sequence. | CD72 | −0.08 | 0.45 | −1.88 | 1.19 | 0.41 | 0.24 | −1.42 | 1.13 |
| NM_005375 | *Homo sapiens* v-myb avian myeloblastosis viral oncogene homolog (MYB), mRNA. /PROD = v-myb avian myeloblastosis viral oncogenehomolog /FL = gb: NM_005375.1 gb: AF104863.1 gb: M15024.1 | MYB | 2.11 | 0.17 | −0.52 | 0.18 | 2.24 | 0.03 | 0.10 | 0.08 |
| NM_017671 | *Homo sapiens* hypothetical protein FLJ20116 (FLJ20116), mRNA. /PROD = hypothetical protein FLJ20116 /FL = gb: NM_017671.1 | C20orf42 | 3.19 | 0.12 | 0.97 | 0.70 | 3.26 | 0.07 | 0.16 | 0.94 |
| BG283790 | ESTs | MATR3 | 2.27 | 0.11 | 0.95 | 0.57 | 3.53 | 0.04 | 0.89 | 0.51 |
| NM_000702 | *Homo sapiens* ATPase, Na+K+ transporting, alpha 2 (+) polypeptide (ATP1A2), mRNA. /PROD = ATPase, Na+K+ transporting, alpha 2 (+)polypeptide /FL = gb: NM_000702.1 | ATP1A2 | 2.12 | 0.17 | 0.76 | 0.38 | 2.93 | 0.16 | 0.51 | 0.12 |
| NM_025135 | *Homo sapiens* hypothetical protein FLJ22297 (KIAA1695), mRNA. /PROD = hypothetical protein KIAA1695 /FL = gb: NM_025135.1 | FHOD3 | 1.02 | 0.18 | 0.80 | 0.40 | 2.34 | 0.10 | −0.77 | 0.72 |
| NM_012281 | *Homo sapiens* potassium | KCND2 | 1.67 | 0.30 | 0.05 | 0.15 | 2.70 | 0.09 | −0.26 | 0.38 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | voltage-gated channel, Shal-related subfamily, member 2 (KCND2), mRNA. /PROD = potassium voltage-gated channel, Shal-relatedsubfamily, member 2 /FL = gb: NM_012281.1 gb: AB028967.1 gb: AF121104.1 | | | | | | | | | |
| BF449063 | collagen, type XIV, alpha 1 (undulin) | COL14A1 | 1.61 | 0.15 | 0.30 | 0.38 | 2.68 | 0.17 | −0.33 | 0.68 |
| AA280904 | ESTs | C9orf39 | 0.23 | 0.21 | −1.58 | 1.26 | 1.13 | 0.14 | −0.78 | 0.42 |
| NM_022467 | Homo sapiens N-acetylgalactosamine-4-O-sulfotransferase (GALNAC-4-ST1), mRNA. /PROD = N-acetylgalactosamine-4-O-sulfotransferase /FL = gb: NM_022467.1 gb: AF300612.1 | CHST8 | 2.11 | 0.20 | −0.51 | 0.30 | 2.17 | 0.10 | 0.48 | 0.02 |
| BE468066 | ESTs | RMST | 3.26 | 0.09 | 1.49 | 0.10 | 3.80 | 0.09 | 1.63 | 0.08 |
| AL120674 | ESTs | — | 1.00 | 0.11 | −1.35 | 1.73 | 1.55 | 0.15 | −2.20 | 0.86 |
| NM_133329 | Homo sapiens potassium voltage-gated channel, subfamily G, member 3 (KCNG3), transcript variant 1, mRNA. /PROD = potassium voltage-gated channel, subfamily G, member 3 isoform 1 /FL = gb: AF454548.1 gb: AF348982.1 gb: AB070604.1 gb: NM_133329.4 | KCNG3 | 2.18 | 0.27 | 0.74 | 0.29 | 3.67 | 0.01 | 0.26 | 0.28 |
| AI742043 | ESTs | — | 0.94 | 0.34 | −0.76 | 0.37 | 1.77 | 0.10 | −1.45 | 0.52 |
| NM_005103 | Homo sapiens fasciculation and elongation protein zeta 1 (zygin I) | FEZ1 | 2.80 | 0.11 | 2.08 | 0.25 | 4.98 | 0.06 | 2.20 | 0.26 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | (FEZ1), transcript variant 1, mRNA. /PROD = zygin 1, isoform 1 /FL = gb: U60060.1 gb: U69139.1 gb: NM_005103.2 | | | | | | | | | |
| NM_000277 | Homo sapiens phenylalanine hydroxylase (PAH), mRNA. /PROD = phenylalanine hydroxylase /FL = gb: U49897.1 gb: NM_000277.1 | PAH | 0.65 | 0.11 | −1.08 | 0.08 | 1.46 | 0.18 | −0.42 | 0.12 |
| BF698797 | ESTs | — | 0.93 | 0.10 | −0.74 | 0.11 | 2.07 | 0.10 | −0.40 | 0.44 |
| BF437747 | ESTs, Weakly similar to ALU7_HUMAN ALU SUBFAMILY SQ SEQUENCE CONTAMINATION WARNING ENTRY (*H. sapiens*) | C20orf118 | 4.26 | 0.07 | 1.99 | 0.45 | 4.57 | 0.09 | 1.75 | 0.39 |
| NM_003020 | Homo sapiens secretory granule, neuroendocrine protein 1 (7B2 protein) (SGNE1), mRNA. /PROD = secretory granule, neuroendocrine protein 1 (7B2protein) /FL = gb: BC005349.1 gb: NM_003020.1 | SCG5 | 4.03 | 0.14 | 2.53 | 0.32 | 5.01 | 0.12 | 3.11 | 0.24 |
| NM_002800 | Homo sapiens proteasome (prosome, macropain) subunit, beta type, 9 (large multifunctional protease 2) (PSMB9), mRNA. /PROD = proteasome (prosome, macropain) subunit, betatype, 9 (large multifunctional protease 2) /FL = gb: U01025.1 gb: NM_002800.1 | PSMB9 | 1.38 | 0.10 | 0.27 | 0.34 | 2.05 | 0.07 | −1.43 | 1.14 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGEL™ OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BE972639 | ESTs | LOC646326 | 0.00 | 0.15 | −2.71 | 0.55 | 0.33 | 0.22 | −2.24 | 0.61 |
| BC044830 | Homo sapiens, Similar to RIKEN cDNA 1700011F14 gene, clone MGC: 35062 IMAGE: 5166167, mRNA, complete cds. /PROD = Similar to RIKEN cDNA 1700011F14 gene /FL = gb: BC044830.1 | C10orf96 | 1.38 | 0.12 | −0.32 | 0.82 | 2.28 | 0.06 | −1.39 | 0.90 |
| AI961231 | KIAA0808 gene product /FL = gb: AB018351.1 | TOX | 3.28 | 0.13 | 1.23 | 0.06 | 4.00 | 0.01 | 1.13 | 0.37 |
| U17496 | gb: NM_014729.1 Human proteasome subunit LMP7 (allele LMP7B) mRNA, complete cds. /PROD = proteasome subunit LMP7 /FL = gb: U17497.1 gb: U17496.1 | PSMB8 | 3.43 | 0.21 | 0.46 | 1.17 | 3.30 | 0.06 | 0.09 | 0.64 |
| N23651 | ESTs | SDK2 | −1.16 | 0.31 | −2.65 | 0.42 | 1.27 | 0.09 | −2.07 | 0.75 |
| NM_007015 | Homo sapiens chondromodulin I precursor (CHM-I), mRNA. /PROD = chondromodulin I precursor /FL = gb: NM_007015.1 gb: AB006000.1 | LECT1 | 4.83 | 0.12 | 2.27 | 0.84 | 5.36 | 0.09 | 1.83 | 0.69 |
| NM_015474 | Homo sapiens DKFZP564A032 protein (DKFZP564A032), mRNA. /PROD = DKFZP564A032 protein /FL = gb: AF228421.1 gb: AL050267.1 gb: AB013847.1 gb: NM_015474.1 | SAMHD1 | 2.63 | 0.17 | 0.57 | 0.33 | 2.89 | 0.09 | 0.29 | 0.22 |
| AF147427 | Homo sapiens full length insert cDNA clone YP80A10. | SAMHD1 | 1.33 | 0.03 | −0.99 | 0.88 | 1.35 | 0.08 | −2.30 | 0.97 |
| NM_004688 | Homo sapiens N-myc (and STAT) | NMI | 3.54 | 0.04 | 0.96 | 0.07 | 3.80 | 0.07 | 1.13 | 0.34 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | interactor (NMI), mRNA. /PROD = N-myc and STAT interactor /FL = gb: BC001268.1 gb: NM_004688.1 gb: U32849.1 | | | | | | | | | |
| AB040812 | *Homo sapiens* mRNA for protein kinase PAK5, complete cds. /PROD = protein kinase PAK5 /FL = gb: AB040812.1 | PAK7 | −1.37 | 0.60 | −3.89 | 1.62 | −0.49 | 0.07 | −4.18 | 0.12 |
| AI985987 | ESTs, Moderately similar to ALU1_HUMAN ALU SUBFAMILY J SEQUENCE CONTAMINATION WARNING ENTRY (*H. sapiens*) | SCNN1G | −0.28 | 0.31 | −0.99 | 0.35 | 0.12 | 0.19 | −2.70 | 0.59 |
| NM_001877 | *Homo sapiens* complement component (3dEpstein Barr virus) receptor 2 (CR2), mRNA. /PROD = complement component (3dEpstein Barr virus)receptor 2 /FL = gb: NM_001877.1 gb: M26004.1 | CR2 | 1.50 | 0.13 | −0.43 | 1.05 | 2.35 | 0.14 | −1.44 | 1.51 |
| NM_001351 | *Homo sapiens* deleted in azoospermia-like (DAZL), mRNA. /PROD = deleted in azoospermia-like /FL = gb: U66726.2 gb: NM_001351.1 gb: U65918.1 gb: U66078.1 | DAZL | 1.69 | 0.24 | −0.81 | 0.76 | 1.93 | 0.12 | −0.73 | 0.06 |
| NM_022168 | *Homo sapiens* melanoma differentiation | IFIH1 | −2.03 | 1.08 | −2.76 | 0.83 | −0.10 | 0.15 | −2.15 | 0.40 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | associated protein-5 (MDA5), mRNA. /PROD = melanoma differentiation associated protein-5 /FL = gb: AY017378.1 gb: NM_022168.1 gb: AF095844.1 | | | | | | | | | |
| AF052108 | Homo sapiens clone 23687 mRNA sequence. | LOC157627 | 1.49 | 0.33 | 0.22 | 1.02 | 2.26 | 0.40 | −1.33 | 1.19 |
| AI056877 | Human DNA sequence from clone RP4-530I15 on chromosome 20. Contains the 3 end of the PTPN1 gene for protein tyrosine phosphatase, non-receptor type 1 (EC 3.1.3.48), the gene for a novel protein similar to placental protein DIFF40, an RPL36 (60S Ribos | LOC200230 | 0.11 | 0.30 | −2.37 | 0.94 | 1.15 | 0.18 | −1.35 | 0.75 |
| NM_002522 | Homo sapiens neuronal pentraxin I (NPTX1), mRNA. /PROD = neuronal pentraxin I precursor /FL = gb: NM_002522.1 gb: U61849.1 | NPTX1 | 2.35 | 0.25 | −0.48 | 0.19 | 2.17 | 0.09 | −1.19 | 0.83 |
| N21096 | ESTs | STXBP6 | 2.42 | 0.16 | 0.99 | 0.08 | 3.69 | 0.09 | 1.14 | 0.04 |
| AI693516 | ESTs | COL14A1 | 0.39 | 0.23 | −1.63 | 0.96 | 0.96 | 0.17 | −1.81 | 0.67 |
| NM_018043 | Homo sapiens hypothetical protein FLJ10261 (FLJ10261), mRNA. /PROD = hypothetical protein FLJ10261 /FL = gb: NM_018043.1 | TMEM16A | −0.90 | 0.37 | −1.93 | 0.70 | 0.25 | 0.43 | −3.93 | 0.49 |
| AF110400 | Homo sapiens fibroblast growth factor 19 (FGF19) | FGF19 | 2.12 | 0.14 | −0.08 | 0.34 | 2.18 | 0.04 | −0.91 | 0.18 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| | mRNA, complete cds. /PROD = fibroblast growth factor 19 /FL = gb: AF110400.1 gb: NM_005117.1 gb: AB018122.1 | | | | | | | | | |
| AK098525 | *Homo sapiens* cDNA FLJ25659 fis, clone TST00427, highly similar to Mus musculus hedgehog-interacting protein (Hip) mRNA. | HHIP | 1.76 | 0.14 | −0.57 | 0.63 | 3.32 | 0.06 | −0.11 | 0.15 |
| AV715309 | ESTs, Weakly similar to ALU7_HUMAN ALU SUBFAMILY SQ SEQUENCE CONTAMINATION WARNING ENTRY (*H. sapiens*) | C20orf118 | 4.28 | 0.13 | 1.89 | 0.39 | 4.76 | 0.10 | 1.48 | 0.42 |
| U96136 | *Homo sapiens* delta-catenin mRNA, complete cds. /PROD = delta-catenin /FL = gb: NM_001332.1 gb: U72665.1 gb: AB013805.1 gb: U96136.1 gb: AF035302.1 | CTNND2 | 0.78 | 0.11 | −1.33 | 0.87 | 1.18 | 0.12 | −1.17 | 0.67 |
| NM_002590 | *Homo sapiens* protocadherin 8 (PCDH8), mRNA. /PROD = protocadherin 8 /FL = gb: NM_002590.2 gb: AF061573.2 | PCDH8 | −0.80 | 0.34 | −0.83 | 0.82 | 2.18 | 0.02 | 0.12 | 0.33 |
| AF107846 | *Homo sapiens* neuroendocrine-specific Golgi protein p55 (XLalphas) gene, exon XL2 and complete cds | — | 0.44 | 0.20 | −0.25 | 0.12 | 2.12 | 0.14 | −2.56 | 0.81 |
| BG169832 | adenylate kinase 5 /FL = gb: NM_012093.1 gb: AF062595.1 | AK5 | 0.62 | 0.36 | −2.79 | 0.50 | 1.03 | 0.36 | −1.94 | 0.32 |

TABLE IV-continued

DIFFERENTIAL EXPRESSION OF GENES BETWEEN
UNDIFFERENTIATED EMBRYONIC STEM CELLS AND
DEFINITIVE ENDODERM STAGE CELLS CULTURED ON EITHER
MATRIGELTM OR MOUSE EMBRYONIC FIBROBLASTS AFTER 5
DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BE968806 | ESTs, Weakly similar to ALU4_HUMAN ALU SUBFAMILY SB2 SEQUENCE CONTAMINATION WARNING ENTRY (*H. sapiens*) | ATP5S | −1.15 | 0.14 | −3.03 | 0.71 | −0.34 | 0.15 | −4.73 | 0.74 |
| BU729850 | hypothetical protein LOC153469 | JAKMIP2 | 2.30 | 0.07 | 0.43 | 1.78 | 3.86 | 0.04 | −1.56 | 1.92 |
| AL832535 | *Homo sapiens* mRNA; cDNA DKFZp547J1816 (from clone DKFZp547J1816). | LOC157627 | 2.25 | 0.18 | −0.04 | 1.00 | 3.14 | 0.25 | −1.50 | 1.19 |
| NM_000439 | *Homo sapiens* proprotein convertase subtilisinkexin type 1 (PCSK1), mRNA. /PROD = proprotein convertase subtilisinkexin type 1 /FL = gb: NM_000439.2 gb: M90753.1 | PCSK1 | −0.63 | 0.18 | −2.68 | 0.53 | 0.69 | 0.30 | −3.19 | 1.03 |
| M34455 | Human interferon-gamma-inducible indoleamine 2,3-dioxygenase (IDO) mRNA, complete cds. /FL = gb: NM_002164.1 gb: M34455.1 | INDO | 4.39 | 0.23 | 1.58 | 0.09 | 5.44 | 0.08 | 1.69 | 0.13 |
| AB014737 | *Homo sapiens* mRNA for SMAP-2b, complete cds. /PROD = SMAP-2b /FL = gb: AB014737.1 | SMOC2 | 1.25 | 0.12 | −2.04 | 0.48 | 1.94 | 0.06 | −2.27 | 1.12 |
| BM682352 | *Homo sapiens* cDNA FLJ37204 fis, clone BRALZ2006976. | HCN1 | −0.41 | 0.14 | −4.38 | 1.19 | 0.35 | 0.31 | −3.88 | 0.32 |

TABLE V

RELATIVE EXPRESSION OF DEFINITE ENDODERM MARKERS FOR CONDITIONS OUTLINED IN EXAMPLE 10. ALL VALUES WERE NORMALIZED TO GROUP 1 (CONTROL).

|  | Sox17 | CXCR4 | Goosecoid | HNF-3B | SOX-2 | Oct-4 |
|---|---|---|---|---|---|---|
| Group 1-control | 1 | 1 | 1 | 1 | 1 | 1 |
| Group 2 | 45 | 19.5 | 2.8 | 0.64 | 0.91 | 1.1 |
| Group 3 | 45 | 30 | 2.9 | 0.74 | 0.70 | 0.76 |
| Group 4 | 8 | 14 | 2.7 | 1.11 | 0.18 | 0.36 |
| Group 5 | 23 | 16 | 3.1 | 1.76 | 0.16 | 0.41 |
| Group 6 | 41 | 5.8 | 3.0 | 1.87 | 0.61 | 0.57 |
| Group 7 | 25 | 19.5 | 2.7 | 0.62 | 0.34 | 0.48 |
| Group 8 | 6 | 15.9 | 2.9 | 2.0 | 0.13 | 0.43 |
| Group 9 | 1 | 1.4 | 0.9 | 0.89 | 1.2 | 0.85 |
| Group 10 | 22 | 1.5 | 1.4 | 1.20 | 1.36 | 0.68 |
| Group 11 | 54 | 23 | 2.5 | 0.71 | 0.66 | 0.65 |
| Group 12 | 68 | 0.7 | 0.9 | 1.51 | 0.02 | 0.30 |
| Group 13 | 13.9 | 12.7 | 3.0 | 2.1 | 0.11 | 0.30 |
| Group 14 | 52.6 | 20.6 | 2.9 | 0.82 | 0.69 | 0.70 |
| Group 15 | 68 | 27.7 | 2.9 | 0.68 | 0.68 | 0.85 |
| Group 16 | 13.9 | 21 | 2.4 | 0.79 | 0.46 | 0.72 |
| Group 17 | 52 | 14.9 | 3.5 | 2.12 | 0.22 | 0.44 |

TABLE VI

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | −4.82708 | 2.63968 | −4.26995 | 8.62E−05 |
| microfibrillar-associated protein 4 | 0.063791 | 5.16358 | −0.60091 | 3.48E−03 |
| *Homo sapiens*, alpha-1 (VI) collagen | −3.66187 | 2.36459 | −2.26934 | 1.45E−04 |
| ESTs | −3.43712 | 2.14508 | −2.6475 | 0.00E+00 |
| *Homo sapiens* cystatin SN (CST1), mRNA. /PROD = cystatin SN /FL = gb: J03870.1 gb: NM_001898.1 | 0.072931 | 7.53908 | 4.63955 | 4.46E−03 |
| solute carrier family 16 (monocarboxylic acid transporters), member 3 /FL = gb: U81800.1 gb: NM_004207.1 | −0.066405 | 5.23572 | 0.279005 | 4.27E−04 |
| *Homo sapiens* fibroblast growth factor 17 (FGF17), mRNA. /PROD = fibroblast growth factor 17 /FL = gb: NM_003867.1 gb: AB009249.1 | −0.894644 | 5.75417 | 2.4872 | 4.93E−03 |
| Human link protein mRNA, complete cds. /PROD = link protein /FL = gb: NM_001884.1 gb: U43328.1 | −1.93991 | 3.31348 | −1.26346 | 1.14E−02 |
| *Homo sapiens* solute carrier family 16 (monocarboxylic acid transporters), member 3 (SLC16A3), mRNA. /PROD = solute carrier family 16 (monocarboxylic acidtransporters), member 3 /FL = gb: U81800.1 gb: NM_004207.1 | 0.710321 | 6.12971 | 1.72403 | 0.00E+00 |
| *Homo sapiens* apolipoprotein A-I (APOA1), mRNA. /PROD = apolipoprotein A-I precursor /FL = gb: M27875.1 gb: M11791.1 gb: NM_000039.1 gb: BC005380.1 | −1.47073 | 5.37558 | 2.46891 | 5.07E−03 |
| *Homo sapiens* cytidine deaminase (CDA), mRNA. /PROD = cytidine deaminase /FL = gb: L27943.1 gb: NM_001785.1 | −3.89129 | 2.05822 | −1.67035 | 2.23E−03 |
| ESTs, Moderately similar to JE0284 Mm-1 cell derived transplantability-associated protein 1b (*H. sapiens*) | −2.37712 | 5.75671 | 4.22227 | 2.56E−02 |
| ESTs | −0.04716 | 5.28231 | 0.966974 | 0.00E+00 |
| glycophorin B (includes Ss blood group) | −2.85201 | 3.32812 | −0.12969 | 1.45E−04 |
| *Homo sapiens* homeobox protein goosecoid mRNA, complete cds. /PROD = homeobox protein goosecoid /FL = gb: AY177407.1 gb: NM_173849.1 | −4.42042 | 3.55326 | 1.89424 | 2.50E−02 |
| MCP-1 = monocyte chemotactic protein (human, aortic endothelial cells, mRNA, 661 nt). /PROD = MCP-1 | −2.27571 | 5.13499 | 2.95543 | 2.92E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* Mix-like homeobox protein 1 (MILD1) mRNA, complete cds. /PROD = Mix-like homeobox protein 1 /FL = gb: AF211891.1 | −1.54648 | 4.47601 | 0.921971 | 2.01E−02 |
| ESTs | −4.93603 | 2.17917 | −0.23735 | 1.12E−04 |
| *Homo sapiens* lumican (LUM), mRNA. /PROD = lumican /FL = gb: NM_002345.1 gb: U18728.1 gb: U21128.1 | −4.05726 | 3.21064 | 0.948822 | 3.39E−02 |
| *Homo sapiens* HNF-3beta mRNA for hepatocyte nuclear factor-3 beta, complete cds. /PROD = hepatocyte nuclear factor-3 beta /FL = gb: AB028021.1 gb: NM_021784.1 | −2.71785 | 4.68666 | 2.82506 | 3.71E−02 |
| *Homo sapiens* reserved (KCNK12), mRNA. /PROD = tandem pore domain potassium channel THIK-2 /FL = NM_022055.1 gb: AF287302.1 | −0.468745 | 6.28184 | 3.77969 | 1.97E−02 |
| *Homo sapiens* atrophin-1 interacting protein 1; activin receptor interacting protein 1 (KIAA0705), mRNA. /PROD = atrophin-1 interacting protein 1; activinreceptor interacting protein 1 /FL = gb: NM_012301.1 gb: AF038563.1 | −4.30828 | 1.80825 | −1.32021 | 9.63E−03 |
| ESTs | −2.33636 | 2.25176 | −2.32124 | 5.26E−04 |
| *Homo sapiens* glutamate decarboxylase 1 (brain, 67 kD) (GAD1), transcript variant GAD25, mRNA. /PROD = glutamate decarboxylase 1, isoform GAD25 /FL = gb: NM_013445.1 gb: AF178853.1 gb: BC002815.1 | −2.424 | 2.31908 | −1.87965 | 4.07E−04 |
| *Homo sapiens* cardiac ventricular troponin C mRNA, complete cds. /PROD = cardiac ventricular troponin C /FL = gb: NM_003280.1 gb: AF020769.1 | −0.549728 | 4.89072 | 1.4377 | 2.99E−03 |
| ESTs | −2.89554 | 3.42817 | 0.926036 | 2.62E−02 |
| *Homo sapiens* fibroblast growth factor 8 (androgen-induced) (FGF8), mRNA. /PROD = fibroblast growth factor 8 (androgen-induced) /FL = gb: U36223.1 gb: U46212.1 gb: NM_006119.1 | −4.32791 | 2.19561 | 0.015827 | 5.91E−03 |
| ESTs | −3.09818 | 1.66254 | −2.20564 | 8.62E−05 |
| *Homo sapiens* haptoglobin-related protein (HPR), mRNA. /PROD = haptoglobin-related protein /FL = gb: NM_020995.1 | −2.6068 | 2.38009 | −1.19632 | 6.95E−03 |
| collagen, type VI, alpha 1 | −1.418 | 3.85952 | 0.604245 | 1.21E−02 |
| Human (clone 8B1) Br-cadherin mRNA, complete cds. /PROD = Br-cadherin /FL = gb: L34057.1 gb: L33477.1 gb: NM_004061.1 | −2.17941 | 2.59894 | −1.02624 | 1.24E−02 |
| ESTs | −1.40092 | 2.57297 | −1.82509 | 1.45E−04 |
| *Homo sapiens* cystatin SA (CST2), mRNA. /PROD = cystatin SA /FL = gb: NM_001322.1 | −0.102178 | 5.21645 | 2.1671 | 2.40E−02 |
| Human mRNA for apolipoprotein AI (apo AI)=. /PROD = preproapolipoprotein AI | 0.215086 | 5.51109 | 2.49684 | 9.57E−03 |
| *Homo sapiens* MLL septin-like fusion (MSF), mRNA. /PROD = MLL septin-like fusion /FL = gb: AF123052.1 gb: NM_006640.1 | −3.29221 | 1.70902 | −1.49951 | 2.25E−03 |
| *Homo sapiens* cystatin S (CST4), mRNA. /PROD = cystatin S /FL = gb: NM_001899.1 | 0.92448 | 6.48842 | 3.87036 | 7.20E−03 |
| *Homo sapiens* phorbolin-like protein MDS019 (MDS019), mRNA. /PROD = phorbolin-like protein MDS019 /FL = gb: AF182420.1 gb: NM_021822.1 | −1.11883 | 4.73391 | 2.40782 | 7.86E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* apolipoprotein A-II (APOA2), mRNA. /PROD = apolipoprotein A-II precursor /FL = gb: M29882.1 gb: NM_001643.1 gb: BC005282.1 | −1.03333 | 5.80468 | 4.46856 | 3.23E−02 |
| ESTs | −1.55475 | 3.48278 | 0.420447 | 2.50E−02 |
| *Homo sapiens* glutamate decarboxylase 1 (brain, 67 kD) (GAD1), transcript variant GAD67, mRNA. /PROD = glutamate decarboxylase 1, isoform GAD67 /FL = gb: NM_000817.1 gb: M81883.1 gb: L16888.1 | −3.86752 | 1.56384 | −1.08675 | 2.52E−02 |
| ESTs | −0.731491 | 5.43249 | 3.52168 | 1.60E−02 |
| ESTs | −2.03591 | 3.38924 | 0.760984 | 2.34E−03 |
| *Homo sapiens* retinoid X receptor, gamma (RXRG), mRNA. /PROD = retinoid X receptor, gamma /FL = gb: NM_006917.1 gb: U38480.1 | −2.37496 | 2.62934 | −0.32035 | 8.83E−04 |
| ESTs | −0.648552 | 4.30576 | 1.43266 | 2.19E−03 |
| *Homo sapiens* cDNA FLJ11550 fis, clone HEMBA1002970 | −1.22228 | 5.37746 | 4.21644 | 1.68E−02 |
| ESTs | −1.782 | 3.50391 | 1.0501 | 1.85E−02 |
| *Homo sapiens* haptoglobin (HP), mRNA. /PROD = haptoglobin /FL = gb: K00422.1 gb: L29394.1 gb: NM_005143.1 | −1.10114 | 3.5449 | 0.477027 | 8.13E−03 |
| *Homo sapiens* hypothetical protein FLJ10970 (FLJ10970), mRNA. /PROD = hypothetical protein FLJ10970 /FL = gb: NM_018286.1 | −0.431989 | 5.14497 | 3.02045 | 2.62E−02 |
| *Homo sapiens* beta-site APP cleaving enzyme (BACE) mRNA, complete cds. /PROD = beta-site APP cleaving enzyme /FL = gb: AF200343.1 gb: AF204943.1 gb: AF190725.1 gb: AF201468.1 gb: NM_012104.1 | −2.0354 | 3.70648 | 1.75385 | 8.00E−03 |
| *Homo sapiens* hypothetical protein FLJ22252 similar to SRY-box containing gene 17 (FLJ22252), mRNA. /PROD = hypothetical protein FLJ22252 similar to SRY-boxcontaining gene 17 /FL = gb: NM_022454.1 | 1.36784 | 6.82571 | 4.5979 | 2.10E−02 |
| Cluster Incl. AB028021: *Homo sapiens* HNF-3beta mRNA for hepatocyte nuclear factor-3 beta, complete cds /cds = (196, 1569) /gb = AB028021 /gi = 4958949 /ug = Hs.155651 /len = 1944 | −1.5339 | 5.12418 | 4.11704 | 4.47E−02 |
| *Homo sapiens* gastrin-releasing peptide (GRP), mRNA. /PROD = gastrin-releasing peptide /FL = gb: NM_002091.1 gb: K02054.1 gb: BC004488.1 | −2.74071 | 2.70077 | 0.509757 | 2.49E−04 |
| *Homo sapiens* sema domain, seven thrombospondin repeats (type 1 and type 1-like), transmembrane domain (TM) and short cytoplasmic domain, (semaphorin) 5A (SEMA5A), mRNA. /PROD = sema domain, seven thrombospondin repeats (type1 and type 1-like), transmem | −1.53335 | 3.78503 | 1.48732 | 4.71E−02 |
| *Homo sapiens* mRNA; cDNA DKFZp586J0624 (from clone DKFZp586J0624); complete cds. /PROD = hypothetical protein /FL = gb: AF215636.1 gb: NM_014585.1 gb: AF231121.1 gb: AF226614.1 gb: AL136944.1 | −0.835182 | 5.22406 | 3.69882 | 2.08E−02 |
| Human mRNA for alpha-1 type II collagen. | −2.8736 | 2.155 | −0.38021 | 5.70E−03 |
| Rho GDP dissociation inhibitor (GDI) alpha | −1.54385 | 1.7147 | −2.58241 | 1.71E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| neuropilin 1 /FL = gb: AF016050.1 gb: NM_003873.1 gb: AF018956.1 | −1.62253 | 1.95432 | −1.9667 | 8.83E−04 |
| Human DNA sequence from clone RP1-181C24 on chromosome 6p11.1-12.2. Contains the 3 end of the BMP5 gene for bone morphogenetic protein 5, ESTs, STSs and GSSs /FL = gb: M60314.1 gb: NM_021073.1 | −3.72313 | 1.68755 | −0.37308 | 1.38E−03 |
| myristoylated alanine-rich protein kinase C substrate (MARCKS, 80K-L) /FL = gb: M68956.1 gb: D10522.1 gb: NM_002356.4 | −0.71724 | 3.51728 | 0.335725 | 4.29E−03 |
| hypothetical protein FLJ23403 /FL = gb: NM_022068.1 | −1.45618 | 1.81423 | −2.31327 | 1.20E−02 |
| hepatocyte nuclear factor 4, alpha | −4.26574 | 1.7879 | 0.445241 | 3.25E−02 |
| Homo sapiens cell adhesion molecule with homology to L1CAM (close homologue of L1) (CHL1), mRNA. /PROD = cell adhesion molecule with homology to L1CAM(close homologue of L1) /FL = gb: AF002246.1 gb: NM_006614.1 | −0.541188 | 2.1751 | −2.5002 | 1.16E−03 |
| matrix metalloproteinase 14 (membrane-inserted) /FL = gb: U41078.1 gb: NM_004995.2 | −2.05734 | 2.36236 | −0.5185 | 1.66E−02 |
| Homo sapiens glycophorin B (includes Ss blood group) (GYPB), mRNA. /PROD = glycophorin B precursor /FL = gb: J02982.1 gb: NM_002100.2 | −0.947308 | 3.26089 | 0.180293 | 4.83E−04 |
| WAS protein family, member 2 /FL = gb: NM_006990.1 gb: AB026542.1 | −2.18746 | 1.99129 | −1.05968 | 4.00E−03 |
| Homo sapiens frizzled-related protein (FRZB), mRNA. /PROD = frizzled-related protein /FL = gb: U24163.1 gb: U68057.1 gb: NM_001463.1 gb: U91903.1 | 0.56502 | 5.7261 | 3.67629 | 1.75E−02 |
| Homo sapiens glutamate decarboxylase 1 (brain, 67 kD) (GAD1), transcript variant GAD25, mRNA. /PROD = glutamate decarboxylase 1, isoform GAD25 /FL = gb: NM_013445.1 gb: AF178853.1 gb: BC002815.1 | −1.68495 | 2.27067 | −0.96944 | 8.02E−03 |
| ESTs | 0.812766 | 5.93144 | 3.91314 | 4.15E−02 |
| Homo sapiens clone 23736 mRNA sequence | −0.047182 | 5.79006 | 4.50744 | 1.74E−02 |
| Homo sapiens glycophorin E (GYPE), mRNA. /PROD = glycophorin E /FL = gb: NM_002102.1 gb: M29610.1 | −2.01601 | 1.79002 | −1.50134 | 1.97E−02 |
| ESTs | 1.06767 | 5.63319 | 3.12487 | 2.00E−02 |
| ESTs | −1.41162 | 2.5396 | −0.57029 | 1.29E−02 |
| Human Fritz mRNA, complete cds. /PROD = Fritz /FL = gb: U24163.1 gb: U68057.1 gb: NM_001463.1 gb: U91903.1 | 0.436589 | 5.69814 | 3.91514 | 1.99E−02 |
| Homo sapiens, clone MGC: 4655, mRNA, complete cds. /PROD = Unknown (protein for MGC: 4655) /FL = gb: BC004908.1 | 2.3772 | 5.9184 | 2.47596 | 1.20E−02 |
| KIAA0878 protein /FL = gb: NM_014899.1 gb: AB020685.1 | 1.1189 | 6.41747 | 4.78882 | 2.01E−02 |
| Homo sapiens sema domain, immunoglobulin domain (Ig), short basic domain, secreted, (semaphorin) 3E (SEMA3E), mRNA. /PROD = sema domain, immunoglobulin domain (Ig), shortbasic domain, secreted, (semaphorin) 3E /FL = gb: NM_012431.1 gb: AB002329.1 | −0.785987 | 3.69668 | 1.27624 | 2.10E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 1.48084 | 6.59709 | 4.81395 | 1.36E−02 |
| noggin /FL = gb: NM_005450.1 | −1.63627 | 3.28161 | 1.32958 | 2.53E−02 |
| *Homo sapiens* hypothetical protein FLJ11316 (FLJ11316), mRNA. /PROD = hypothetical protein FLJ11316 /FL = gb: NM_018388.1 | −0.904749 | 3.35854 | 0.755319 | 1.12E−04 |
| *Homo sapiens* angiopoietin 2 (ANGPT2), mRNA. /PROD = angiopoietin 2 /FL = gb: AB009865.1 gb: AF004327.1 gb: NM_001147.1 | −2.93044 | 2.23779 | 0.59685 | 3.43E−02 |
| *Homo sapiens* matrix metalloproteinase 14 (membrane-inserted) (MMP14), mRNA. /PROD = matrix metalloproteinase 14 preproprotein /FL = gb: U41078.1 gb: NM_004995.2 | −0.723489 | 2.97262 | −0.09689 | 5.44E−03 |
| G protein-coupled receptor | 1.50709 | 6.65228 | 5.05327 | 2.00E−02 |
| collagen, type IX, alpha 2 /FL = gb: NM_001852.1 | 1.27026 | 5.4659 | 2.93507 | 3.19E−03 |
| ESTs | 0.521638 | 3.93176 | 0.620223 | 0.00E+00 |
| KIAA1462 protein | −3.84563 | 1.65452 | 0.437064 | 3.27E−02 |
| *Homo sapiens* cartilage linking protein 1 (CRTL1), mRNA. /PROD = cartilage linking protein 1 /FL = gb: NM_001884.1 gb: U43328.1 | −1.31515 | 2.27271 | −0.80521 | 2.22E−02 |
| *Homo sapiens* solute carrier family 21 (prostaglandin transporter), member 2 (SLC21A2), mRNA. /PROD = solute carrier family 21 (prostaglandintransporter), member 2 /FL = gb: U70867.1 gb: NM_005630.1 | 0.711428 | 4.89808 | 2.43304 | 6.84E−03 |
| ESTs | 0.307173 | 4.78515 | 2.65653 | 1.72E−02 |
| 6-phosphofructo-2-kinasefructose-2,6-biphosphatase 4 | −0.242865 | 3.97929 | 1.59985 | 5.28E−03 |
| *Homo sapiens* dual specificity phosphatase 4 (DUSP4), mRNA. /PROD = dual specificity phosphatase 4 /FL = gb: NM_001394.2 gb: BC002671.1 gb: U48807.1 gb: U21108.1 | 0.953857 | 5.82811 | 4.12159 | 4.00E−03 |
| ESTs, Weakly similar to T00331 hypothetical protein KIAA0555 (*H. sapiens*) | −1.57372 | 2.70797 | 0.443622 | 6.74E−03 |
| ESTs | −3.57414 | 3.15167 | 3.37198 | 8.82E−03 |
| ESTs, Highly similar to IHH_HUMAN INDIAN HEDGEHOG PROTEIN PRECURSOR (*H. sapiens*) | −0.653989 | 3.22059 | 0.590533 | 5.18E−03 |
| ESTs, Weakly similar to FCE2 MOUSE LOW AFFINITY IMMUNOGLOBULIN EPSILON FC RECEPTOR (*M. musculus*) | 0.494192 | 5.22522 | 3.48031 | 1.97E−02 |
| homeo box HB9 /FL = gb: NM_005515.1 | −1.65563 | 3.2238 | 1.63092 | 5.58E−03 |
| *Homo sapiens* arylsulfatase E (chondrodysplasia punctata 1) (ARSE), mRNA. /PROD = arylsulfatase E precursor /FL = gb: X83573.1 gb: NM_000047.1 | 0.283004 | 4.95903 | 3.18424 | 9.22E−03 |
| ESTs | −0.05909 | 3.0455 | −0.29817 | 1.47E−02 |
| *Homo sapiens* hypothetical protein FLJ23403 (FLJ23403), mRNA. /PROD = hypothetical protein FLJ23403 /FL = gb: NM_022068.1 | −1.48452 | 1.97473 | −1.00431 | 5.72E−03 |
| ESTs | −0.182403 | 3.01548 | −0.18954 | 3.72E−03 |
| hypothetical protein FLJ23091 | 0.323388 | 5.25192 | 3.77987 | 3.57E−02 |
| Human dipeptidyl peptidase IV (CD26) mRNA, complete cds. /PROD = dipeptidyl peptidase IV /FL = gb: M74777.1 | −3.61145 | 0.760585 | −1.25595 | 3.07E−02 |
| hypothetical protein FLJ21032 | 0.355672 | 4.67756 | 2.61753 | 4.59E−02 |
| *Homo sapiens* Kell blood group (KEL), mRNA. /PROD = Kell blood group antigen /FL = gb: BC003135.1 gb: NM_000420.1 | −2.20519 | 1.89439 | −0.38393 | 1.91E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| splicing factor, arginineserine-rich 5 | 0.7481 | 5.68934 | 4.27169 | 2.97E−03 |
| Human prostatic secretory protein 57 mRNA, complete cds. /PROD = PSP57 /FL = gb: U22178.1 | −3.01313 | 1.46338 | −0.40767 | 1.97E−02 |
| Homo sapiens KIAA0878 protein (KIAA0878), mRNA. /PROD = KIAA0878 protein /FL = gb: NM_014899.1 gb: AB020685.1 | 2.0265 | 7.00937 | 5.65368 | 2.85E−02 |
| Homo sapiens cryptic mRNA, complete cds. /PROD = cryptic /FL = gb: AF312769.1 | 0.104874 | 2.87319 | −0.67353 | 1.61E−03 |
| Homo sapiens cDNA FLJ13221 fis, clone NT2RP4002075 | 0.355743 | 3.98782 | 1.30963 | 1.38E−03 |
| phorbolin-like protein MDS019 | −1.11756 | 2.83853 | 0.503523 | 1.59E−02 |
| Homo sapiens mRNA for KIAA1409 protein, partial cds. /PROD = KIAA1409 protein | 0.368334 | 2.8009 | −1.03191 | 1.78E−02 |
| Homo sapiens mRNA; cDNA DKFZp434D0818 (from clone DKFZp434D0818) | −2.63427 | 1.64513 | −0.3056 | 2.52E−02 |
| ESTs | 0.35393 | 5.14775 | 3.74875 | 3.16E−02 |
| Homo sapiens TBX3-iso protein (TBX3-iso), mRNA. /PROD = TBX3-iso protein /FL = gb: NM_016569.1 gb: AF216750.1 | −2.34566 | 2.45238 | 1.07038 | 1.31E−02 |
| Homo sapiens chromosome 19, cosmid R31181 | −0.258871 | 3.0636 | 0.223926 | 1.58E−03 |
| Homo sapiens mRNA for GATA-6, complete cds. /PROD = GATA-6 /FL = gb: U66075.1 gb: NM_005257.1 gb: D87811.1 | 2.21862 | 6.8609 | 5.34263 | 4.29E−02 |
| Homo sapiens ankyrin-like with transmembrane domains 1 (ANKTM1), mRNA | −1.10879 | 3.93484 | 2.81939 | 1.29E−02 |
| G protein-coupled receptor 49 | 0.265509 | 4.46257 | 2.50537 | 2.19E−02 |
| Homo sapiens growth differentiation factor 3 (GDF3), mRNA. /PROD = growth differentiation factor 3 precursor /FL = gb: NM_020634.1 gb: AF263538.1 | 1.67253 | 5.34944 | 2.87486 | 8.62E−05 |
| Human (clone HSY3RR) neuropeptide Y receptor (NPYR) mRNA, complete cds. /PROD = neuropeptide Y receptor /FL = gb: L06797.1 gb: NM_003467.1 gb: AF025375.1 gb: AF147204.1 gb: M99293.1 gb: L01639.1 | 1.77461 | 6.70301 | 5.47995 | 3.00E−02 |
| Homo sapiens type VI collagen alpha 2 chain precursor (COL6A2) mRNA, complete cds, alternatively spliced. /PROD = type VI collagen alpha 2 chain precursor /FL = gb: AY029208.1 | 1.7011 | 5.33126 | 2.84458 | 5.91E−03 |
| ESTs | −0.349726 | 3.29119 | 0.824929 | 4.11E−03 |
| ESTs | −0.903317 | 1.89777 | −1.36429 | 6.84E−03 |
| Homo sapiens hypothetical protein FLJ10718 (FLJ10718), mRNA. /PROD = hypothetical protein FLJ10718 /FL = gb: NM_018192.1 | 2.60483 | 7.10633 | 5.55242 | 1.41E−02 |
| Homo sapiens Rho GTPase activating protein 6 (ARHGAP6), transcript variant 2, mRNA. /PROD = Rho GTPase activating protein 6 isoform 2 /FL = gb: AF022212.2 gb: NM_001174.2 | −1.10389 | 1.83053 | −1.28521 | 1.28E−02 |
| stanniocalcin 1 /FL = gb: U25997.1 gb: NM_003155.1 gb: U46768.1 | 2.41135 | 7.29563 | 6.14284 | 2.51E−02 |
| Human glycophorin HeP2 mRNA, partial cds. /PROD = glycophorin HeP2 | −0.843493 | 2.71108 | 0.233547 | 2.98E−04 |
| Homo sapiens cDNA FLJ12993 fis, clone NT2RP3000197 | 0.147259 | 4.12241 | 2.06949 | 6.84E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* presenilin stabilization factor b (PSF) mRNA, complete cds; alternatively spliced. /PROD = presenilin stabilization factor b /FL = gb: AY113699.1 | −0.86173 | 2.85614 | 0.56745 | 6.09E−03 |
| *Homo sapiens* glycophorin Erik STA (GPErik) gene complete cds. /PROD = glycophorin Erik (STA) /FL = gb: U00178.1 | −1.19362 | 2.17108 | −0.45439 | 1.45E−04 |
| bromodomain and PHD finger containing, 3 | −2.8472 | 1.75573 | 0.369397 | 8.62E−05 |
| ESTs | 0.784344 | 4.74104 | 2.71543 | 7.55E−03 |
| ESTs | −1.26251 | 3.4693 | 2.27614 | 3.80E−03 |
| ESTs | −1.71713 | 1.23763 | −1.71122 | 2.99E−02 |
| *Homo sapiens* microsomal glutathione S-transferase 2 (MGST2), mRNA. /PROD = microsomal glutathione S-transferase 2 /FL = gb: NM_002413.1 gb: U77604.1 | 2.06233 | 6.81536 | 5.6918 | 3.79E−02 |
| *Homo sapiens* eomesodermin (*Xenopus laevis*) homolog (EOMES), mRNA. /PROD = eomesodermin (*Xenopus laevis*) homolog /FL = gb: AB031038.1 gb: NM_005442.1 | 2.65926 | 6.71627 | 4.89839 | 2.76E−02 |
| *Homo sapiens* mRNA for MSX-2, complete cds. /PROD = MSX-2 /FL = gb: D89377.1 | 0.407211 | 4.11145 | 1.94529 | 1.35E−02 |
| *Homo sapiens* apolipoprotein A-II (APOA2), mRNA. /PROD = apolipoprotein A-II precursor /FL = gb: M29882.1 gb: NM_001643.1 gb: BC005282.1 | −1.10237 | 5.10066 | 4.75899 | 1.34E−02 |
| *Homo sapiens* adenylate cyclase 8 (brain) (ADCY8), mRNA. /PROD = adenylate cyclase 8 /FL = gb: NM_001115.1 | −1.3408 | 1.12773 | −2.26149 | 1.07E−02 |
| *Homo sapiens* glucose-6-phosphate transporter (G6PT) gene, G6PT-Dt allele, complete cds | −0.193516 | 3.03064 | 0.407738 | 1.38E−03 |
| *Homo sapiens* glutathione S-transferase A2 (GSTA2), mRNA. /PROD = glutathione S-transferase A2 /FL = gb: BC002895.1 gb: M25627.1 gb: M16594.1 gb: M14777.1 gb: M15872.1 gb: M21758.1 gb: NM_000846.1 | −3.10645 | 1.11704 | −0.4221 | 5.37E−04 |
| *Homo sapiens* sodium dependent phosphate transporter isoform NaPi-IIb mRNA, complete cds. /PROD = sodium dependent phosphate transporter isoformNaPi-IIb /FL = gb: AF111856.1 gb: NM_006424.1 gb: AF146796.1 | −0.397133 | 2.78341 | 0.231961 | 1.11E−02 |
| ESTs | 2.77413 | 7.19192 | 5.906 | 3.17E−02 |
| *Homo sapiens* partial LHX9 gene for LIM-homeobox 9, 3UTR. | −2.2486 | 1.64952 | −0.13424 | 7.89E−03 |
| *Homo sapiens* LYST-interacting protein LIP3 mRNA, partial cds. /PROD = LYST-interacting protein LIP3 | −0.682149 | 2.34271 | −0.31253 | 9.87E−03 |
| putative 47 kDa protein | −0.123937 | 3.2914 | 1.05247 | 3.72E−03 |
| *Homo sapiens* protein S (alpha) (PROS1), mRNA. /PROD = protein S (alpha) /FL = gb: M15036.1 gb: NM_000313.1 | 0.577604 | 4.00035 | 1.7883 | 7.89E−03 |
| ESTs | −1.63711 | 0.915477 | −2.15328 | 1.83E−02 |
| protocadherin 10 | 1.76718 | 5.1503 | 2.98569 | 2.52E−02 |
| KIAA1511 protein | 0.620278 | 3.86886 | 1.57543 | 1.86E−03 |
| *Homo sapiens* cDNA FLJ13221 fis, clone NT2RP4002075 | 0.282785 | 3.44178 | 1.08178 | 1.31E−03 |
| *Homo sapiens* fibroblast growth factor receptor 4, soluble-form splice variant (FGFR4) mRNA, complete cds. | −1.72385 | 2.26674 | 0.747239 | 6.86E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| /PROD = fibroblast growth factor receptor 4, soluble-form splice variant /FL = gb: NM_022963.1 gb: AF202063.1 | | | | |
| X75208 /FEATURE = cds /DEFINITION = HSPTKR *H. sapiens* HEK2 mRNA for protein tyrosine kinase receptor | −1.36729 | 2.60456 | 1.08204 | 1.58E−02 |
| *Homo sapiens* chemokine receptor CXCR4 mRNA, complete cds. /PROD = chemokine receptor CXCR4 /FL = gb: AF348491.1 | 2.30557 | 6.72969 | 5.66933 | 3.31E−02 |
| KIAA1415 protein | 0.185854 | 3.70346 | 1.74255 | 7.78E−04 |
| ESTs | −0.048335 | 3.11786 | 0.836448 | 1.29E−02 |
| *Homo sapiens* stanniocalcin 1 (STC1), mRNA. /PROD = stanniocalcin 1 /FL = gb: U25997.1 gb: NM_003155.1 gb: U46768.1 | 2.39435 | 6.55737 | 5.28007 | 2.19E−02 |
| *Homo sapiens* high mobility group protein-R mRNA, complete cds. /PROD = high mobility group protein-R /FL = gb: AF176039.1 | 1.04695 | 3.2786 | 0.095286 | 2.11E−02 |
| ESTs, Moderately similar to ALU4_HUMAN ALU SUBFAMILY SB2 SEQUENCE CONTAMINATION WARNING ENTRY (*H. sapiens*) | −1.10358 | 1.66331 | −0.98371 | 3.37E−02 |
| *Homo sapiens* arrestin, beta 1 (ARRB1), transcript variant 1, mRNA. /PROD = arrestin beta 1, isoform A /FL = gb: BC003636.1 gb: AF084040.1 gb: NM_004041.2 | −0.158844 | 2.41791 | −0.40915 | 1.12E−02 |
| ESTs | −1.34399 | 1.80279 | −0.44529 | 1.60E−03 |
| Human mRNA for pro-alpha 1 (II) collagen 3end C-term. triple helical and C-terminal non-helical domain. /PROD = pro-alpha 1 (II) collagen (313 AA; AA 975-271c) /FL = gb: NM_001844.2 | 0.85982 | 4.1935 | 2.15657 | 1.09E−02 |
| *Homo sapiens* hypothetical protein DKFZp564B052 (DKFZp564B052), mRNA. /PROD = hypothetical protein DKFZp564B052 /FL = gb: NM_030820.1 | 1.47773 | 4.42479 | 2.00326 | 1.16E−03 |
| testis enhanced gene transcript (BAX inhibitor 1) | −0.695228 | 2.99328 | 1.31679 | 1.17E−03 |
| *Homo sapiens* fasciculation and elongation protein zeta 1 (zygin I) (FEZ1), transcript variant 1, mRNA. /PROD = zygin 1, isoform 1 /FL = gb: U60060.1 gb: U69139.1 gb: NM_005103.2 | 1.86433 | 4.71354 | 2.20315 | 8.62E−05 |
| *Homo sapiens* matrix metalloproteinase 15 (membrane-inserted) (MMP15), mRNA. /PROD = matrix metalloproteinase 15 preproprotein /FL = gb: D86331.1 gb: NM_002428.1 | −0.298504 | 3.44582 | 1.8336 | 4.80E−03 |
| heparan sulfate proteoglycan 2 (perlecan) /FL = gb: M85289.1 gb: NM_005529.2 | −2.53327 | 0.924726 | −0.97212 | 4.31E−02 |
| *Homo sapiens* dickkopf (*Xenopus laevis*) homolog 1 (DKK1), mRNA. /PROD = dickkopf (*Xenopus laevis*) homolog 1 /FL = gb: AF177394.1 gb: NM_012242.1 gb: AF127563.1 | 0.981469 | 3.70716 | 1.09014 | 1.76E−03 |
| ESTs | −0.801487 | 3.37342 | 2.21393 | 1.22E−02 |
| ESTs | −2.57626 | 1.40231 | 0.050493 | 6.60E−03 |
| ESTs | 0.499579 | 4.10541 | 2.39934 | 4.29E−03 |
| *Homo sapiens* bone morphogenetic protein 2 (BMP2), mRNA. /PROD = bone morphogenetic protein 2 precursor /FL = gb: NM_001200.1 | 2.04506 | 6.19114 | 5.02927 | 4.98E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Human extracellular matrix protein 1 (ECM1) mRNA, complete cds. /PROD = extracellular matrix protein 1 /FL = gb: NM_004425.2 gb: U65932.1 gb: U68186.1 | 0.634778 | 3.65829 | 1.37564 | 6.11E−04 |
| Homo sapiens nuclear receptor subfamily 0, group B, member 1 (NR0B1), mRNA. /PROD = adrenal hypoplasia protein /FL = gb: NM_000475.2 | −1.92783 | 2.32456 | 1.27907 | 2.99E−02 |
| Homo sapiens cDNA: FLJ23067 fis, clone LNG04993. | −2.25626 | 1.95987 | 0.882498 | 6.62E−03 |
| Homo sapiens ADP-ribosylation factor 4-like (ARF4L), mRNA. /PROD = ADP-ribosylation factor 4-like /FL = gb: U25771.1 gb: L38490.1 gb: NM_001661.1 gb: BC000043.1 | 1.63466 | 5.70351 | 4.48037 | 1.90E−02 |
| Homo sapiens HT016 mRNA, complete cds. /PROD = HT016 /FL = gb: AF225426.1 | 0.218762 | 3.97514 | 2.45222 | 3.37E−02 |
| Homo sapiens, tropomodulin, clone MGC: 3643, mRNA, complete cds. /PROD = tropomodulin /FL = gb: NM_003275.1 gb: M77016.1 gb: BC002660.1 | 0.348796 | 3.54199 | 1.46427 | 1.29E−03 |
| Homo sapiens hypothetical protein FLJ22471 (FLJ22471), mRNA. /PROD = hypothetical protein FLJ22471 /FL = gb: NM_025140.1 | 0.903825 | 4.65366 | 3.1349 | 2.48E−02 |
| ESTs | −0.120583 | 2.94229 | 0.738304 | 7.20E−03 |
| ESTs, Moderately similar to JC4969 pig-c protein (H. sapiens) | −2.39713 | 0.906454 | −1.04495 | 1.69E−02 |
| Homo sapiens LIM homeobox protein 1 (LHX1), mRNA. /PROD = LIM homeobox protein 1 /FL = gb: NM_005568.1 gb: U14755.1 | −0.77166 | 2.27746 | 0.085559 | 4.26E−02 |
| Homo sapiens, hypothetical protein MGC2865, clone MGC: 20246 IMAGE: 4635389, mRNA, complete cds. /FL = gb: BC016043.1 | −2.43105 | 0.646883 | −1.50617 | 8.27E−03 |
| ESTs | −2.01523 | 2.16773 | 1.12403 | 1.99E−02 |
| Homo sapiens oxoglutarate dehydrogenase (lipoamide) (OGDH), mRNA. /PROD = oxoglutarate dehydrogenase (lipoamide) /FL = gb: D10523.1 gb: BC004964.1 gb: NM_002541.1 | −0.032595 | 2.3997 | −0.38533 | 1.45E−02 |
| ESTs, Weakly similar to T32252 hypothetical protein T15B7.2 - Caenorhabditis elegans (C. elegans) | 2.20966 | 5.35974 | 3.33255 | 1.12E−04 |
| Homo sapiens, cleft lip and palate associated transmembrane protein 1, clone MGC: 10593, mRNA, complete cds. /PROD = cleft lip and palate associated transmembraneprotein 1 /FL = gb: BC004865.1 | 1.31578 | 3.52357 | 0.556735 | 2.92E−03 |
| Homo sapiens clone TUA8 Cri-du-chat region mRNA | 0.09218 | 3.37126 | 1.49746 | 6.46E−03 |
| Homo sapiens transcriptional activator of the c-fos promoter (CROC4), mRNA. /PROD = transcriptional activator of the c-fos promoter /FL = gb: NM_006365.1 gb: U49857.1 | 0.666391 | 4.50481 | 3.22532 | 5.80E−03 |
| Homo sapiens hypothetical protein FLJ21195 similar to protein related to DAC and cerberus (FLJ21195), mRNA. /PROD = hypothetical protein FLJ21195 similar to proteinrelated to DAC and cerberus /FL = gb: NM_022469.1 | −1.38519 | 2.23626 | 0.763963 | 7.36E−03 |

TABLE VI-continued

MEAN NORMALIZED INTENSITY VALUES (IN LOG
FORMAT) OF GENES FOR H9 EMBRYONIC STEM CELLS
DERIVED DEFINITIVE ENDODERM STAGE CELLS CULTURED
ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ras homolog gene family, member B /FL = gb: AF498971.1 gb: NM_004040.1 | −0.123101 | 2.52093 | 0.071885 | 1.86E−02 |
| cartilage linking protein 1 | 0.879449 | 3.47789 | 0.987243 | 1.03E−03 |
| Homo sapiens BCL2adenovirus E1B 19 kD-interacting protein 3 (BNIP3) mRNA, complete cds. /PROD = BCL2adenovirus E1B 19 kD-interacting protein 3 /FL = gb: AF002697.1 gb: NM_004052.2 gb: U15174.1 | 3.30506 | 6.91803 | 5.44746 | 1.79E−03 |
| Homo sapiens polycythemia rubra vera 1; cell surface receptor (PRV1), mRNA. /PROD = polycythemia rubra vera 1; cell surfacereceptor /FL = gb: NM_020406.1 gb: AF146747.1 | −1.19629 | 2.40987 | 0.93741 | 9.40E−03 |
| Homo sapiens hypothetical protein FLJ11560 (FLJ11560), mRNA. /PROD = hypothetical protein FLJ11560 /FL = gb: NM_025182.1 | −0.044112 | 3.42017 | 1.80688 | 3.77E−03 |
| plexin A2 | 0.930527 | 4.36203 | 2.74167 | 1.52E−02 |
| Homo sapiens mRNA; cDNA DKFZp547H236 (from clone DKFZp547H236). /PROD = hypothetical protein | 1.37193 | 4.24502 | 2.08129 | 5.37E−04 |
| Homo sapiens cystatin C (amyloid angiopathy and cerebral hemorrhage) (CST3), mRNA. /PROD = cystatin C (amyloid angiopathy and cerebralhemorrhage) /FL = gb: NM_000099.1 | 2.08601 | 5.30525 | 3.51965 | 2.20E−03 |
| ESTs, Moderately similar to NFY-C (H. sapiens) | −0.749407 | 2.00148 | −0.24268 | 2.34E−03 |
| ESTs | 2.54243 | 5.75201 | 3.97307 | 2.60E−02 |
| Homo sapiens sialyltransferase (STHM), mRNA. /PROD = sialyltransferase /FL = gb: U14550.1 gb: NM_006456.1 | −0.68709 | 2.89586 | 1.50348 | 3.70E−02 |
| Homo sapiens SG2NA beta isoform mRNA, partial cds. /PROD = SG2NA beta isoform | −1.15566 | 1.13989 | −1.53439 | 1.55E−02 |
| Homo sapiens hypothetical protein FLJ12838 (FLJ12838), mRNA. /PROD = hypothetical protein FLJ12838 /FL = gb: NM_024641.1 | 1.49091 | 4.80138 | 3.15205 | 2.63E−02 |
| Homo sapiens solute carrier (SLC25A18) mRNA, complete cds; nuclear gene for mitochondrial product. /PROD = solute carrier /FL = gb: AY008285.1 | 0.403706 | 2.12385 | −1.10043 | 1.78E−02 |
| KIAA0346 protein | −1.34736 | 2.49605 | 1.41497 | 3.90E−03 |
| Human clone 23826 mRNA sequence | 1.80782 | 4.07112 | 1.44315 | 2.28E−04 |
| Homo sapiens receptor tyrosine kinase-like orphan receptor 2 (ROR2), mRNA. /PROD = receptor tyrosine kinase-like orphan receptor 2 /FL = gb: M97639.1 gb: NM_004560.1 | 1.53333 | 4.73839 | 3.05612 | 1.63E−02 |
| Homo sapiens MYC-associated zinc finger protein (purine-binding transcription factor) (MAZ), mRNA. /PROD = MYC-associated zinc finger protein(purine-binding transcription factor) /FL = gb: D85131.1 gb: NM_002383.1 | −0.055569 | 2.67075 | 0.511292 | 2.63E−02 |
| Homo sapiens cDNA FLJ30081 fis, clone BGGI12000693, weakly similar to POLYHOMEOTIC-PROXIMAL CHROMATIN PROTEIN. | 0.677905 | 3.33728 | 1.12499 | 1.12E−04 |
| Homo sapiens elongation of very long chain fatty acids (FEN1Elo2, SUR4Elo3, yeast)-like 2 (ELOVL2), mRNA. | 0.099979 | 3.23372 | 1.50802 | 2.59E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| /PROD = elongation of very long chain fatty acids(FEN1Elo2, SUR4Elo3, yeast)-like 2 /FL = gb: NM_017770.1 | | | | |
| Homo sapiens thyrotropin-releasing hormone (TRH), mRNA. /PROD = thyrotropin-releasing hormone /FL = gb: NM_007117.1 | −1.65672 | 1.46994 | −0.25839 | 3.02E−02 |
| ESTs, Weakly similar to A46302 PTB-associated splicing factor, long form (H. sapiens) | 0.894051 | 4.21835 | 2.69535 | 1.57E−02 |
| Human MLC1emb gene for embryonic myosin alkaline light chain, promoter and exon 1 | 1.3489 | 5.11354 | 4.03961 | 1.61E−02 |
| Homo sapiens microseminoprotein, beta-(MSMB), mRNA. /PROD = microseminoprotein, beta- /FL = gb: NM_002443.1 | −2.37904 | 1.3101 | 0.169915 | 2.46E−02 |
| Homo sapiens cDNA FLJ11390 fis, clone HEMBA1000561, weakly similar to ZINC FINGER PROTEIN 91. | −1.12944 | 2.02889 | 0.364373 | 0.00E+00 |
| ESTs, Weakly similar to ALU8_HUMAN ALU SUBFAMILY SX SEQUENCE CONTAMINATION WARNING ENTRY (H. sapiens) | 2.76608 | 6.07949 | 4.57766 | 1.93E−02 |
| Homo sapiens cDNA FLJ13810 fis, clone THYRO1000279 | −2.92389 | 0.51764 | −0.85322 | 8.08E−03 |
| Homo sapiens, aminolevulinate, delta-, dehydratase, clone MGC: 5057, mRNA, complete cds. /PROD = aminolevulinate, delta-, dehydratase /FL = gb: BC000977.1 gb: M13928.1 gb: NM_000031.1 | 1.3099 | 4.44525 | 2.76918 | 7.69E−03 |
| Homo sapiens kidney-specific membrane protein NX-17 mRNA, complete cds. /PROD = kidney-specific membrane protein NX-17 /FL = gb: AF229179.1 | 1.91929 | 5.08917 | 3.44968 | 6.91E−03 |
| Homo sapiens alpha 2,8-sialyltransferase mRNA, complete cds. /PROD = alpha 2,8-sialyltransferase /FL = gb: L43494.1 gb: D26360.1 gb: L32867.1 gb: NM_003034.1 | −1.10548 | 2.36359 | 1.05469 | 4.63E−03 |
| tyrosine 3-monooxygenasetryptophan 5-monooxygenase activation protein, eta polypeptide | 2.98486 | 6.17918 | 4.60758 | 8.01E−03 |
| Homo sapiens cardiac ankyrin repeat protein (CARP), mRNA. /PROD = cardiac ankyrin repeat protein /FL = gb: NM_014391.1 | −0.002291 | 3.35645 | 1.98688 | 3.44E−02 |
| Homo sapiens porcupine (MG61), mRNA. /PROD = porcupine /FL = gb: AF317059.1 gb: AF317058.1 gb: NM_022825.1 | 1.51754 | 4.96311 | 3.68103 | 9.86E−03 |
| collagen, type V, alpha 1 /FL = gb: D90279.1 gb: NM_000093.1 gb: M76729.1 | 1.5875 | 3.98844 | 1.66569 | 1.17E−03 |
| Homo sapiens forkhead box F2 (FOXF2), mRNA. /PROD = forkhead box F2 /FL = gb: U13220.1 gb: NM_001452.1 | −1.54469 | 1.02305 | −1.11517 | 6.95E−03 |
| PTPRF interacting protein, binding protein 2 (liprin beta 2) | −1.92021 | 3.74378 | 2.77277 | 2.10E−02 |
| Homo sapiens PRO1957 mRNA, complete cds. /PROD = PRO1957 /FL = gb: AF116676.1 | 1.68941 | 5.30311 | 4.22705 | 1.43E−02 |
| Homo sapiens hypothetical protein FLJ23514 (FLJ23514), mRNA. /PROD = hypothetical protein FLJ23514 /FL = gb: NM_021827.1 | 0.564613 | 5.98527 | 5.24692 | 2.85E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Homo sapiens mRNA; cDNA DKFZp586G2120 (from clone DKFZp586G2120); complete cds. /PROD = hypothetical protein /FL = gb: AL136924.1 | −1.80897 | 1.69722 | 0.523009 | 2.47E−02 |
| Cluster Incl. L37033: Human FK-506 binding protein homologue (FKBP38) mRNA, complete cds /cds = (140, 1207) /gb = L37033 /gi = 965469 /ug = Hs.173464 /len = 1613 | 0.615619 | 3.478 | 1.66132 | 1.54E−02 |
| ESTs | −0.004009 | 3.63657 | 2.61352 | 4.29E−02 |
| Homo sapiens apolipoprotein C-I (APOC1), mRNA. /PROD = apolipoprotein C-I precursor /FL = gb: NM_001645.2 | 3.24954 | 6.71073 | 5.50997 | 2.16E−02 |
| ESTs | 1.38635 | 4.93112 | 3.83641 | 1.39E−02 |
| Homo sapiens cDNA FLJ34035 fis, clone FCBBF2004788. | −3.58002 | −0.48718 | −2.00751 | 1.46E−02 |
| Homo sapiens, clone IMAGE: 3509274, mRNA, partial cds | 0.493686 | 2.94923 | 0.794513 | 1.82E−02 |
| Homo sapiens putative sterol reductase SR-1 (TM7SF2) mRNA, complete cds. /PROD = putative sterol reductase SR-1 /FL = gb: AF096304.1 | 1.66857 | 4.3767 | 2.47833 | 5.37E−04 |
| nuclear factor of kappa light polypeptide gene enhancer in B-cells inhibitor, alpha /FL = gb: NM_020529.1 gb: BC002601.1 gb: BC004983.1 gb: M69043.1 | 2.91463 | 6.48938 | 5.47812 | 1.97E−02 |
| hypothetical protein FLJ12666 | 0.215767 | 3.10249 | 1.40459 | 1.91E−02 |
| Homo sapiens ectodermal dysplasia 1, anhidrotic (ED1), mRNA. /PROD = ectodermal dysplasia 1, anhidrotic /FL = gb: AF060999.1 gb: NM_001399.1 gb: AF040628.1 gb: AF061189.1 | 0.796627 | 4.22895 | 3.07833 | 1.01E−02 |
| glycoprotein M6A /FL = gb: D49958.1 | 0.274378 | 3.59045 | 2.3278 | 2.64E−02 |
| ESTs | 1.04714 | 3.87608 | 2.12752 | 3.75E−02 |
| ESTs | −1.48489 | 1.371 | −0.35043 | 1.88E−03 |
| ESTs, Weakly similar to KIAA1330 protein (H. sapiens) | −0.925232 | 2.41149 | 1.18187 | 2.65E−03 |
| putative 47 kDa protein | 0.156484 | 2.78771 | 0.861726 | 2.60E−02 |
| Homo sapiens hypothetical protein FLJ32835 (FLJ32835), mRNA. /FL = gb: NM_152506.1 | −0.595622 | 4.84785 | 3.94683 | 3.34E−02 |
| Homo sapiens GS1999full mRNA, complete cds. /FL = gb: AB048286.1 | 0.137029 | 2.75189 | 0.849942 | 0.00E+00 |
| Homo sapiens hexabrachion (tenascin C, cytotactin) (HXB), mRNA. /PROD = hexabrachion (tenascin C, cytotactin) /FL = gb: M55618.1 gb: NM_002160.1 | 3.96862 | 5.66572 | 2.85391 | 1.39E−02 |
| Homo sapiens Pig10 (PIG10) mRNA, complete cds. /PROD = Pig10 /FL = gb: AF059611.1 gb: AF010314.1 gb: NM_003633.1 gb: BC000418.1 gb: AF005381.1 | 0.129454 | 2.86013 | 1.09765 | 1.16E−03 |
| Homo sapiens annexin A6 (ANXA6), transcript variant 1, mRNA. /PROD = annexin VI isoform 1 /FL = gb: D00510.1 gb: J03578.1 gb: NM_001155.2 | 3.89026 | 6.43752 | 4.49981 | 8.81E−04 |
| Homo sapiens c-mer proto-oncogene tyrosine kinase (MERTK), mRNA. /PROD = c-mer proto-oncogene tyrosine kinase /FL = gb: NM_006343.1 gb: U08023.1 | 1.78994 | 4.92901 | 3.61665 | 1.84E−02 |
| Homo sapiens caspase-like apoptosis regulatory protein 2 (clarp) mRNA, alternatively spliced, complete cds. | 0.434199 | 5.04863 | 5.2167 | 2.46E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| /PROD = caspase-like apoptosis regulatory protein 2 /FL = gb: AF005775.1 Human embryonic myosin alkali light chain (MLC1) mRNA, complete cds. /FL = gb: M36172.1 gb: M24121.1 gb: NM_002476.1 | 1.94171 | 5.24959 | 4.11475 | 2.11E−02 |
| Homo sapiens phosphatidylinositol-4-phosphate 5-kinase, type I, beta (PIP5K1B), mRNA. /PROD = phosphatidylinositol-4-phosphate 5-kinase, typeI, beta /FL = gb: NM_003558.1 | 1.34876 | 4.12788 | 2.46657 | 3.66E−03 |
| Homo sapiens mRNA; cDNA DKFZp434E082 (from clone DKFZp434E082) | 1.36443 | 4.34866 | 2.94283 | 2.92E−03 |
| Homo sapiens dystrophin (muscular dystrophy, Duchenne and Becker types), includes DXS142, DXS164, DXS206, DXS230, DXS239, DXS268, DXS269, DXS270, DXS272 (DMD), transcript variant Dp427p2, mRNA. /PROD = dystrophin Dp427p2 isoform /FL = gb: NM_004010.1 | 1.40427 | 4.41881 | 3.04441 | 1.83E−02 |
| Homo sapiens, clone MGC: 14801, mRNA, complete cds. /PROD = Unknown (protein for MGC: 14801) /FL = gb: BC005997.1 | 2.03928 | 3.96694 | 1.51059 | 5.65E−04 |
| Homo sapiens hypothetical protein BC017868 (LOC159091), mRNA. /FL = gb: BC017868.1 gb: NM_138819.1 | −0.290244 | 2.2418 | 0.40157 | 6.04E−03 |
| ESTs, Highly similar to AF229172 1 class III myosin (H. sapiens) | −0.475471 | 1.94826 | 0.002417 | 5.28E−03 |
| Homo sapiens solute carrier family 9 (sodiumhydrogen exchanger), isoform 5 (SLC9A5), mRNA. /PROD = solute carrier family 9 (sodiumhydrogenexchanger), isoform 5 /FL = gb: AF111173.1 gb: NM_004594.1 | 0.047487 | 2.80601 | 1.19645 | 2.80E−03 |
| Homo sapiens F37Esophageal cancer-related gene-coding leucine-zipper motif (FEZ1), mRNA. /PROD = F37Esophageal cancer-related gene-codingleucine-zipper motif /FL = gb: AF123659.1 gb: NM_021020.1 | −0.128814 | 3.17069 | 2.10422 | 1.54E−02 |
| Homo sapiens deiodinase, iodothyronine, type III (DIO3), mRNA. /PROD = thyroxine deiodinase type III /FL = gb: NM_001362.1 gb: S79854.1 | −0.136937 | 5.08366 | 4.22897 | 1.41E−02 |
| Homo sapiens insulin-like growth factor binding protein 6 (IGFBP6), mRNA. /PROD = insulin-like growth factor binding protein 6 /FL = gb: BC005007.1 gb: M62402.1 gb: BC003507.1 gb: NM_002178.1 | 2.6126 | 5.13945 | 3.30402 | 9.72E−04 |
| Homo sapiens U2 small nuclear ribonucleoprotein auxiliary factor (65 kD) (U2AF65), mRNA. /PROD = U2 small nuclear ribonucleoprotein auxiliaryfactor (65 kD) /FL = gb: NM_007279.1 | −0.821533 | 1.81533 | 0.096512 | 4.72E−02 |
| Homo sapiens hypothetical protein DKFZp434F0318 (DKFZP434F0318), mRNA. /PROD = hypothetical protein DKFZp434F0318 /FL = gb: NM_030817.1 | −1.11464 | 1.81375 | 0.394686 | 9.09E−03 |
| Homo sapiens BACE mRNA for beta-site APP cleaving enzyme I-476, complete cds. /PROD = beta-site APP cleaving enzyme I-476 /FL = gb: AB050436.1 | 0.48553 | 3.13284 | 1.44588 | 4.99E−04 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs, Weakly similar to ALUC_HUMAN !!!! ALU CLASS C WARNING ENTRY !!! (*H. sapiens*) | 1.07951 | 4.06134 | 2.7193 | 2.11E−02 |
| *Homo sapiens* mRNA for KIAA0876 protein, partial cds. /PROD = KIAA0876 protein | −0.432037 | 1.97736 | 0.073246 | 3.37E−02 |
| *Homo sapiens* mRNA for protein-tyrosine kinase, complete cds. /PROD = protein-tyrosine kinase /FL = gb: U05682.1 gb: D17517.1 gb: D50479.1 | 0.160986 | 2.75713 | 1.04172 | 2.11E−02 |
| KIAA0418 gene product | −0.677643 | 1.83134 | 0.034385 | 1.45E−04 |
| *Homo sapiens* phosphofructokinase, liver (PFKL), mRNA. /PROD = phosphofructokinase, liver /FL = gb: NM_002626.1 gb: BC004920.1 gb: X15573.1 | 2.039 | 4.51747 | 2.70388 | 1.28E−03 |
| *Homo sapiens* enolase 2, (gamma, neuronal) (ENO2), mRNA. /PROD = enolase 2, (gamma, neuronal) /FL = gb: NM_001975.1 gb: BC002745.1 gb: M22349.1 | 2.60624 | 5.37458 | 3.92621 | 3.17E−03 |
| *Homo sapiens* AD036 mRNA, complete cds. /PROD = AD036 /FL = gb: AF260333.1 | −0.503334 | 2.65787 | 1.60278 | 3.61E−02 |
| ESTs | −2.07933 | 1.00157 | −0.1307 | 2.39E−02 |
| *Homo sapiens* keratin 19 (KRT19), mRNA. /PROD = keratin 19 /FL = gb: NM_002276.1 gb: BC002539.1 | 3.80582 | 6.96535 | 5.91937 | 2.11E−02 |
| pleiomorphic adenoma gene-like 1 /FL = gb: U72621.3 | −0.646793 | 1.88692 | 0.221481 | 4.21E−03 |
| *Homo sapiens*, Similar to lipase protein, clone MGC: 2843, mRNA, complete cds. /PROD = Similar to lipase protein /FL = gb: NM_020676.1 gb: BC001698.1 | −1.16073 | 1.9994 | 0.961706 | 1.89E−02 |
| Cluster Incl. AB002344: Human mRNA for KIAA0346 gene, partial cds /cds = (0, 4852) /gb = AB002344 /gi = 2280479 /ug = Hs.103915 /len = 6121 | 2.15679 | 4.91332 | 3.47797 | 7.39E−03 |
| Cluster Incl. N80935: zb07g06.s1 Homo sapiens cDNA, 3 end /clone = IMAGE-301402 /clone_end = 3 /gb = N80935 /gi = 1243636 /ug = Hs.22483 /len = 527 | 2.12419 | 4.48236 | 2.66555 | 1.50E−02 |
| tryptase, alpha | 2.99108 | 5.46095 | 3.76442 | 1.31E−03 |
| ESTs, Weakly similar to Z132_HUMAN ZINC FINGER PROTEIN 13 (*H. sapiens*) | 1.04865 | 3.65906 | 2.12166 | 2.43E−02 |
| *Homo sapiens* core histone macroH2A2.2 (MACROH2A2), mRNA. /PROD = core histone macroH2A2.2 /FL = gb: AF151534.1 gb: NM_018649.1 | 1.67293 | 4.73906 | 3.66212 | 3.62E−02 |
| ESTs | −0.146413 | 2.69334 | 1.39451 | 1.02E−02 |
| Human rho GDI mRNA, complete cds. /PROD = human rho GDI /FL = gb: M97579.1 gb: D13989.1 gb: NM_004309.1 | 0.019358 | 1.75075 | −0.65155 | 1.85E−02 |
| heat shock 90 kD protein 1, alpha | 1.69225 | 4.20576 | 2.60887 | 2.10E−02 |
| *Homo sapiens* BTB (POZ) domain containing 2 (BTBD2), mRNA. /PROD = BTB (POZ) domain containing 2 /FL = gb: NM_017797.1 | 1.10085 | 3.7628 | 2.32464 | 1.85E−02 |
| *Homo sapiens* mandaselin long form mRNA, complete cds. /PROD = mandaselin long form /FL = gb: AY048775.1 | −0.148053 | 2.58361 | 1.2296 | 1.57E−02 |
| signal transducer and activator of transcription 3 (acute-phase response factor) | −0.837261 | 1.90254 | 0.560225 | 8.83E−04 |
| *Homo sapiens* lymphocyte antigen 6 complex, locus E (LY6E), mRNA. | 0.866364 | 4.91832 | 4.92642 | 2.78E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| /PROD = lymphocyte antigen 6 complex, locus E /FL = gb: U42376.1 gb: NM_002346.1 gb: U56145.1 | | | | |
| ESTs | −1.24632 | 1.09042 | −0.61316 | 4.05E−02 |
| Homo sapiens, clone IMAGE: 4047715, mRNA. | −2.50816 | 1.81 | 1.52693 | 2.63E−02 |
| Cluster Incl. AB002344: Human mRNA for KIAA0346 gene, partial cds /cds = (0, 4852) /gb = AB002344 /gi = 2280479 /ug = Hs.103915 /len = 6121 | 1.89578 | 4.61333 | 3.31717 | 1.12E−02 |
| Homo sapiens singed (Drosophila)-like (sea urchin fascin homolog like) (SNL), mRNA. /PROD = singed (Drosophila)-like (sea urchin fascinhomolog like) /FL = gb: BC000521.1 gb: NM_003088.1 gb: U03057.1 gb: U09873.1 | 4.23317 | 6.74774 | 5.25403 | 5.12E−03 |
| Homo sapiens mRNA; cDNA DKFZp586L0120 (from clone DKFZp586L0120). | −2.72593 | 1.58998 | 1.27994 | 4.54E−02 |
| Homo sapiens mitogen-activated protein kinase 10 (MAPK10), mRNA. /PROD = mitogen-activated protein kinase 10 /FL = gb: U07620.1 gb: U34819.1 gb: U34820.1 gb: NM_002753.1 | 0.647994 | 3.46459 | 2.28644 | 6.65E−03 |
| Homo sapiens transmembrane tyrosine kinase mRNA, complete cds. /PROD = tyrosine kinase /FL = gb: L08961.1 | −0.006089 | 2.96035 | 1.93237 | 7.69E−03 |
| Homo sapiens mRNA; cDNA DKFZp762H185 (from clone DKFZp762H185) | 2.83663 | 5.30784 | 3.79206 | 6.22E−03 |
| tyrosine 3-monooxygenasetryptophan 5-monooxygenase activation protein, eta polypeptide | 3.48271 | 6.19368 | 4.92556 | 2.11E−02 |
| Homo sapiens mRNA; cDNA DKFZp434K0621 (from clone DKFZp434K0621); partial cds | 0.581419 | 3.38088 | 2.21428 | 3.89E−02 |
| ESTs, Weakly similar to ALUF_HUMAN !!!! ALU CLASS F WARNING ENTRY !!! (H. sapiens) | −1.03247 | 1.75349 | 0.587598 | 2.11E−02 |
| tudor repeat associator with PCTAIRE 2 | 2.15771 | 4.69127 | 3.27451 | 2.63E−02 |
| Homo sapiens mRNA; cDNA DKFZp564K1672 (from clone DKFZp564K1672); partial cds. /PROD = hypothetical protein | 4.49405 | 7.38448 | 6.33474 | 1.39E−02 |
| ESTs | −0.184212 | 2.15367 | 0.554696 | 1.15E−02 |
| Homo sapiens bHLH factor Hes4 (LOC57801), mRNA. /PROD = bHLH factor Hes4 /FL = gb: NM_021170.1 gb: AB048791.1 | 0.47816 | 3.40725 | 2.40001 | 3.16E−02 |
| Homo sapiens guanylate cyclase activator 1B (retina) (GUCA1B), mRNA. /PROD = guanylate cyclase activator 1B (retina) /FL = gb: M95174.1 gb: NM_002098.1 gb: M97496.1 | −0.714216 | 1.95339 | 0.684983 | 3.38E−03 |
| KIAA0918 protein | −1.39708 | 0.961939 | −0.57499 | 1.40E−02 |
| Homo sapiens mRNA for KIAA1161 protein, partial cds. /PROD = KIAA1161 protein | 0.781796 | 3.32846 | 1.98143 | 6.60E−03 |
| Homo sapiens, Similar to B9 protein, clone MGC: 11339, mRNA, complete cds. /PROD = Similar to B9 protein /FL = gb: BC002944.1 | 1.43881 | 3.80457 | 2.29205 | 8.62E−05 |
| hypothetical protein FLJ12666 | 2.34087 | 5.11201 | 4.02837 | 1.97E−02 |
| Homo sapiens FLICE-like inhibitory protein short form mRNA, complete cds. /PROD = FLICE-like inhibitory protein short form /FL = gb: U97075.1 | 0.135783 | 4.45631 | 4.92758 | 1.96E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* olfactory receptor, family 52, subfamily A, member 1 (OR52A1), mRNA. /PROD = olfactory receptor, family 52, subfamily A, member 1 /FL = gb: NM_012375.1 | −0.309574 | 2.08723 | 0.636487 | 4.36E−03 |
| Human DNA sequence from clone RP4-781L3 on chromosome 1p34.3-36.11 Contains a pseudogene similar to IFITM3 (interferon inducedntransmembrane protein 3 (1-8U)), STSs and GSSs | 2.82768 | 5.54517 | 4.43909 | 2.04E−03 |
| *Homo sapiens* KIAA0127 gene product (KIAA0127), mRNA. /PROD = KIAA0127 gene product /FL = gb: D50917.1 gb: NM_014755.1 | 2.05236 | 4.43794 | 3.00216 | 3.12E−02 |
| *Homo sapiens* clone HB-2 mRNA sequence | −0.503949 | 2.27896 | 1.25171 | 3.01E−02 |
| hypothetical protein FLJ23091 | −0.76092 | 3.70916 | 3.04154 | 2.45E−02 |
| ESTs | −0.403665 | 2.01868 | 0.643615 | 5.11E−04 |
| ESTs | 2.14401 | 4.70353 | 3.47114 | 3.15E−03 |
| *Homo sapiens* regulator of G protein signalling 5 (RGS5) mRNA, complete cds. /PROD = regulator of G protein signalling 5 /FL = gb: AF493929.1 | 3.0091 | 5.37511 | 3.95132 | 1.29E−03 |
| endothelin receptor type A /FL = gb: NM_001957.1 gb: L06622.1 | −1.83423 | 2.54948 | 1.95432 | 1.51E−02 |
| H. sapiens skeletal embryonic myosin light chain 1 (MLC1) mRNA. /PROD = myosin light chain 1 | 0.690058 | 3.3896 | 2.36018 | 3.27E−02 |
| *Homo sapiens* Kruppel-like factor 8 (KLF8), mRNA. /PROD = Kruppel-like factor 8 /FL = gb: U28282.1 gb: NM_007250.1 | 0.326119 | 2.825 | 1.63929 | 3.92E−02 |
| hypothetical protein DKFZp434F2322 | 0.070576 | 2.58185 | 1.42121 | 5.81E−03 |
| *Homo sapiens* transcription factor 2, hepatic; LF-B3; variant hepatic nuclear factor (TCF2), transcript variant a, mRNA. /PROD = transcription factor 2, isoform a /FL = gb: NM_000458.1 | −1.12537 | 3.45355 | 2.54347 | 1.15E−02 |
| H2A histone family, member X | 1.37085 | 2.48515 | −0.04057 | 1.34E−02 |
| *Homo sapiens* H1 histone family, member X (H1FX), mRNA. /PROD = H1 histone family, member X /FL = gb: D64142.1 gb: BC000426.1 gb: NM_006026.1 | 3.21701 | 5.68105 | 4.50969 | 4.29E−03 |
| ESTs, Weakly similar to KIAA1399 protein (*H. sapiens*) | −0.831241 | 2.82364 | 2.79997 | 4.18E−02 |
| *Homo sapiens* PNAS-145 mRNA, complete cds. /PROD = PNAS-145 /FL = gb: U03105.1 gb: NM_006813.1 gb: AF279899.1 | 2.84962 | 5.38084 | 4.2868 | 8.61E−03 |
| *Homo sapiens* erythrocyte membrane protein band 4.9 (dematin) (EPB49), mRNA. /PROD = erythrocyte membrane protein band 4.9 (dematin) /FL = gb: NM_001978.1 gb: U28389.1 | −0.306603 | 2.11391 | 0.923806 | 4.81E−03 |
| ESTs | 0.783545 | 3.23146 | 2.07738 | 2.13E−02 |
| ESTs | 1.17515 | 3.61815 | 2.46265 | 1.56E−03 |
| nudix (nucleoside diphosphate linked moiety X)-type motif 4 | 2.09472 | 5.82355 | 5.68859 | 3.63E−02 |
| Novel human mRNA from chromosome 22. /PROD = hypothetical protein | −0.533665 | 3.44679 | 3.05803 | 3.99E−02 |
| *Homo sapiens* partial mRNA for putative nuclear factor. /PROD = putative nuclear factor /FL = gb: NM_017688.1 | 1.55224 | 3.89366 | 2.67866 | 1.53E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* BCL2adenovirus E1B 19 kD-interacting protein 3 (BNIP3), nuclear gene encoding mitochondrial protein, mRNA. /PROD = BCL2adenovirus E1B 19 kD-interacting protein 3 /FL = gb: AF002697.1 gb: NM_004052.2 gb: U15174.1 | 4.51142 | 6.99506 | 5.92755 | 2.25E−03 |
| *Homo sapiens* bone morphogenetic protein 5 (BMP5), mRNA. /PROD = bone morphogenetic protein 5 /FL = gb: M60314.1 gb: NM_021073.1 | −0.6099 | 1.76351 | 0.614791 | 6.46E−03 |
| *Homo sapiens* nuclear receptor subfamily 0, group B, member 1 (NR0B1), mRNA. /PROD = adrenal hypoplasia protein /FL = gb: NM_000475.2 | −0.213822 | 4.14059 | 3.29782 | 3.42E−02 |
| *Homo sapiens* mRNA; cDNA DKFZp434P228 (from clone DKFZp434P228) | 1.76846 | 4.196 | 3.11284 | 1.23E−02 |
| *Homo sapiens* pilin-like transcription factor (PILB), mRNA. /PROD = pilin-like transcription factor /FL = gb: AF122004.1 gb: NM_012228.1 | 3.14467 | 5.51066 | 4.38212 | 3.80E−03 |
| *Homo sapiens* complement component 5 (C5), mRNA. /PROD = complement component 5 /FL = gb: M57729.1 gb: NM_001735.1 | −1.89639 | 1.65637 | 1.59643 | 1.74E−02 |
| *Homo sapiens* adaptor-related protein complex 3, beta 2 subunit (AP3B2), mRNA. /PROD = adaptor-related protein complex 3, beta 2subunit /FL = gb: AF022152.1 gb: NM_004644.1 gb: U37673.1 | −0.208283 | 2.17404 | 1.07398 | 1.39E−02 |
| *Homo sapiens* dynein, axonemal, light polypeptide 4 (DNAL4), mRNA. /PROD = dynein, axonemal, light polypeptide 4 /FL = gb: BC002968.1 gb: NM_005740.1 | 0.458271 | 2.88755 | 1.8494 | 3.66E−03 |
| *Homo sapiens*, Similar to RIKEN cDNA C330013D18 gene, clone MGC: 11226, mRNA, complete cds | 0.087468 | 2.45867 | 1.42701 | 3.35E−03 |
| *Homo sapiens* cDNA: FLJ22731 fis, clone HSI15841. | −2.30948 | 1.62817 | 2.24143 | 4.15E−02 |
| ESTs | 0.532996 | 4.6172 | 3.79228 | 2.76E−02 |
| *Homo sapiens* CXCR4 gene encoding receptor CXCR4 | 3.11086 | 7.24917 | 6.36084 | 3.13E−02 |
| stanniocalcin 1 | 2.48686 | 6.20245 | 5.70081 | 4.94E−02 |
| KIAA0761 protein | −2.09591 | 1.57935 | 1.05907 | 1.86E−02 |
| ESTs | −1.16374 | 2.24964 | 2.52108 | 3.83E−02 |
| *Homo sapiens* cDNA FLJ36116 fis, clone TESTI2022338. | 3.02587 | 6.7146 | 6.15456 | 3.88E−02 |
| *Homo sapiens*, clone MGC: 24252 IMAGE: 3932604, mRNA, complete cds. /PROD = Unknown (protein for MGC: 24252) /FL = gb: BC014364.1 | −1.53346 | 2.53854 | 1.59251 | 3.91E−03 |
| *Homo sapiens* cDNA FLJ13392 fis, clone PLACE1001280 | −1.90184 | 1.76129 | 1.16856 | 1.47E−02 |
| *Homo sapiens* hypothetical protein FLJ12538 similar to ras-related protein RAB17 (FLJ12538), mRNA. /PROD = hypothetical protein FLJ12538 similar toras-related protein RAB17 /FL = gb: AL136645.1 gb: NM_022449.1 | 1.70617 | 5.11419 | 4.73391 | 2.71E−02 |
| Human DNA sequence from clone RP11-446H13 on chromosome 10. Contains the 3 end of the gene for a novel protein similar to KIAA1059 (ortholog of mouse VPS10 domain receptor protein SORCS), an RPL23A | −0.889422 | 2.90076 | 2.11955 | 3.52E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| (60S ribosmal protein 23A) pseudogene, ESTs, STSs an | | | | |
| Homo sapiens calmegin (CLGN), mRNA. /PROD = calmegin /FL = gb: NM_004362.1 gb: D86322.1 | −0.104278 | 2.97817 | 3.11092 | 1.89E−02 |
| Homo sapiens testican 3 (HSAJ1454), mRNA. /PROD = testican 3 /FL = gb: NM_016950.1 gb: BC000460.1 gb: BC003017.1 | −2.81226 | 0.7939 | 1.55068 | 3.99E−02 |
| Homo sapiens gelsolin (amyloidosis, Finnish type) (GSN), mRNA. /PROD = gelsolin (amyloidosis, Finnish type) /FL = gb: NM_000177.1 | 1.6198 | 4.54047 | 4.45008 | 1.07E−02 |
| Homo sapiens endothelin receptor type A (EDNRA), mRNA. /PROD = endothelin receptor type A /FL = gb: NM_001957.1 gb: L06622.1 | 0.763007 | 4.05983 | 3.55203 | 3.99E−02 |
| Homo sapiens cDNA: FLJ22808 fis, clone KAIA2925. | −0.367449 | 2.7584 | 2.41394 | 4.31E−02 |
| Homo sapiens hypothetical protein FLJ10312 (FLJ10312), mRNA. /PROD = hypothetical protein FLJ10312 /FL = gb: NM_030672.1 | 1.59498 | 4.6335 | 4.89157 | 4.85E−02 |
| Homo sapiens lipase mRNA, complete cds. /PROD = lipase /FL = gb: AF225418.1 | −2.2131 | 1.0208 | 0.55849 | 3.57E−02 |
| Homo sapiens clone FLC1492 PRO3121 mRNA, complete cds. /PROD = PRO3121 /FL = gb: AF130082.1 | −0.300037 | −0.46894 | −3.39203 | 1.80E−02 |
| protease, serine, 4 (trypsin 4, brain) | −0.345569 | 2.86256 | 3.35886 | 4.65E−02 |
| Homo sapiens ret finger protein-like 2 (RFPL2), mRNA. /PROD = ret finger protein-like 2 /FL = gb: NM_006605.1 | −2.15511 | 1.1797 | 0.503917 | 1.94E−02 |
| Homo sapiens beta3GalNAcT-1 mRNA for globoside synthase, complete cds, clone: type 2. /PROD = globoside synthase /FL = gb: AB050856.1 | −2.73257 | 0.21269 | −0.0984 | 2.48E−02 |
| Homo sapiens hypothetical protein FLJ11155 (FLJ11155), mRNA. /PROD = hypothetical protein FLJ11155 /FL = gb: NM_018342.1 | −3.34565 | −0.42738 | −0.71255 | 3.07E−02 |
| Homo sapiens, dual specificity phosphatase 4, clone MGC: 3713, mRNA, complete cds. /PROD = dual specificity phosphatase 4 /FL = gb: NM_001394.2 gb: BC002671.1 gb: U48807.1 gb: U21108.1 | 2.11487 | 5.16681 | 5.60057 | 3.11E−02 |
| Homo sapiens MAD (mothers against decapentaplegic, Drosophila) homolog 6 (MADH6), mRNA. /PROD = MAD (mothers against decapentaplegic, Drosophila) homolog 6 /FL = gb: U59914.1 gb: NM_005585.1 | 0.917516 | 4.29847 | 3.5309 | 2.44E−02 |
| secreted frizzled-related protein 1 /FL = gb: AF056087.1 gb: NM_003012.2 gb: AF017987.1 gb: AF001900.1 | 1.64933 | 4.41286 | 4.21799 | 4.12E−02 |
| Homo sapiens secreted apoptosis related protein 2 (SARP2) mRNA, complete cds. /PROD = secreted apoptosis related protein 2 /FL = gb: AF056087.1 gb: NM_003012.2 gb: AF017987.1 gb: AF001900.1 | 3.18446 | 5.9316 | 5.74251 | 3.31E−02 |
| KIAA0882 protein | 2.05587 | 4.63577 | 4.67451 | 4.89E−02 |
| Homo sapiens nudix (nucleoside diphosphate linked moiety X)-type motif 4 (NUDT4), mRNA. /PROD = nudix (nucleoside diphosphate linked moietyX)-type motif 4 | 3.91519 | 6.54632 | 6.42767 | 4.63E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| /FL = gb: NM_019094.1 gb: AF191653.1 gb: AF191649.1 gb: AF191650.1 | | | | |
| *Homo sapiens* cDNA FLJ31061 fis, clone HSYRA2000927. | −1.30452 | 2.06218 | 1.20749 | 1.72E−02 |
| *Homo sapiens* diphosphoinositol polyphosphate phosphohydrolase type 2 beta (NUDT4) mRNA, complete cds. /PROD = diphosphoinositol polyphosphate phosphohydrolasetype 2 beta /FL = gb: NM_019094.1 gb: AF191653.1 gb: AF191649.1 gb: AF191650.1 | 2.62612 | 5.53515 | 5.12935 | 3.96E−02 |
| *Homo sapiens* titin (TTN), mRNA. /PROD = titin /FL = gb: NM_003319.1 | −0.466154 | 2.46856 | 2.00309 | 4.18E−03 |
| carboxypeptidase E /FL = gb: NM_001873.1 | 2.72316 | 5.80072 | 5.15668 | 2.99E−02 |
| ESTs | −1.80443 | 0.692933 | 0.613229 | 1.46E−03 |
| *Homo sapiens* hypothetical protein FLJ39502 (FLJ39502), mRNA. /FL = gb: NM_173648.1 | −1.60435 | 1.6149 | 2.4204 | 2.10E−02 |
| *Homo sapiens* renal tumor antigen (RAGE), mRNA. /PROD = renal tumor antigen /FL = gb: NM_014226.1 gb: AB022694.1 | −0.305406 | 2.4556 | 2.09136 | 3.30E−02 |
| T-box 3 (ulnar mammary syndrome) | −1.70952 | 1.31576 | 0.679584 | 1.29E−02 |
| *Homo sapiens* mitogen-activated protein kinase kinase kinase 8 (MAP3K8), mRNA. /PROD = mitogen-activated protein kinase kinase kinase8 /FL = gb: NM_005204.1 gb: D14497.1 | −1.14241 | 1.82177 | 1.23928 | 2.48E−02 |
| *Homo sapiens* enoyl-Coenzyme A, hydratase3-hydroxyacyl Coenzyme A dehydrogenase (EHHADH), nuclear gene encoding mitochondrial protein, mRNA. /PROD = enoyl-Coenzyme A, hydratase3-hydroxyacylCoenzyme A dehydrogenase /FL = gb: NM_001966.1 gb: L07077.1 | 0.226733 | 3.18231 | 2.59938 | 6.22E−03 |
| ESTs | 1.65525 | 3.9984 | 3.98375 | 1.97E−02 |
| *Homo sapiens* secreted frizzled-related protein 1 (SFRP1), mRNA. /PROD = secreted frizzled-related protein 1 /FL = gb: AF056087.1 gb: NM_003012.2 gb: AF017987.1 gb: AF001900.1 | 3.91678 | 7.18429 | 6.24313 | 2.35E−02 |
| ESTs | 2.28659 | 5.21675 | 4.59884 | 3.11E−02 |
| *Homo sapiens* selenoprotein P, plasma, 1 (SEPP1), mRNA. /PROD = selenoprotein P precursor /FL = gb: NM_005410.1 | 2.73332 | 5.13625 | 5.04138 | 1.75E−02 |
| hypothetical protein FLJ12838 /FL = gb: NM_024641.1 | 2.21522 | 5.4785 | 4.50835 | 4.55E−02 |
| *Homo sapiens* mRNA; cDNA DKFZp761M1216 (from clone DKFZp761M1216) | −2.59761 | 0.092924 | −0.31569 | 4.19E−02 |
| *Homo sapiens* KPL1 (KPL1) mRNA, complete cds. /PROD = KPL1 /FL = gb: AF081583.1 gb: U89715.1 gb: NM_021200.1 | −0.08886 | 2.51294 | 2.15967 | 1.97E−02 |
| *Homo sapiens*, synovial sarcoma, X breakpoint 1, clone MGC: 5162, mRNA, complete cds. /PROD = synovial sarcoma, X breakpoint 1 /FL = gb: BC001003.2 gb: NM_005635.1 | −1.57209 | 1.39869 | 2.12662 | 6.84E−03 |
| *Homo sapiens*, Similar to testican 3, clone MGC: 8506, mRNA, complete cds. /PROD = Similar to testican 3 /FL = gb: NM_016950.1 gb: BC000460.1 gb: BC003017.1 | −2.778 | 0.563149 | 1.66935 | 1.87E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 0.502949 | 3.0682 | 2.72874 | 2.02E−02 |
| *Homo sapiens* cDNA FLJ32963 fis, clone TESTI2008405. | 1.49644 | 3.87336 | 3.68478 | 6.89E−03 |
| triadin /FL = gb: U18985.1 gb: NM_006073.1 | −1.61408 | 0.713083 | 0.566175 | 1.87E−02 |
| *Homo sapiens* adlican mRNA, complete cds. /PROD = adlican /FL = gb: AF245505.1 | 0.872786 | 3.20404 | 3.02406 | 4.21E−02 |
| Human midkine mRNA, complete cds. /PROD = midkine /FL = gb: NM_002391.1 gb: M69148.1 | 3.55275 | 5.93819 | 5.68363 | 1.89E−02 |
| *Homo sapiens*, synovial sarcoma, X breakpoint 4, clone MGC: 12411, mRNA, complete cds. /PROD = synovial sarcoma, X breakpoint 4 /FL = gb: BC005325.1 | −0.806785 | 1.90972 | 2.5215 | 4.17E−02 |
| ESTs | −3.61193 | −0.9408 | −1.53439 | 2.43E−03 |
| ESTs | −0.619714 | 1.93617 | 1.44843 | 4.14E−02 |
| ESTs | 0.446983 | 3.14315 | 2.48676 | 1.98E−02 |
| *Homo sapiens* flavin containing monooxygenase 5 (FMO5), mRNA. /PROD = flavin containing monooxygenase 5 /FL = gb: L37080.1 gb: NM_001461.1 | −0.476203 | 1.99948 | 1.55491 | 3.73E−02 |
| *Homo sapiens* aminopeptidase A mRNA, complete cds. /PROD = aminopeptidase A /FL = gb: L12468.1 gb: NM_001977.1 gb: L14721.1 | −0.758987 | 2.07596 | 1.20831 | 3.00E−02 |
| *Homo sapiens* hypothetical protein DKFZp761H1710 (DKFZP761H1710), mRNA. /PROD = hypothetical protein DKFZp761H1710 /FL = gb: NM_031297.1 | −0.713164 | 2.03145 | 1.24823 | 2.17E−03 |
| ESTs | −1.94194 | 0.608912 | 0.013238 | 1.72E−02 |
| *Homo sapiens* sialyltransferase 8 (alpha-2,8-polysialytransferase) D (SIAT8D), mRNA. /PROD = sialyltransferase 8 (alpha-2,8-polysialytransferase) D /FL = gb: NM_005668.1 gb: L41680.1 | −1.07243 | 1.83889 | 0.855205 | 2.16E−02 |
| *Homo sapiens*, clone IMAGE: 5194204, mRNA. | −2.13256 | 0.383746 | 1.02639 | 4.55E−02 |
| hypothetical protein MGC4342 /FL = gb: NM_024329.1 gb: BC003033.1 | −0.403018 | 2.01722 | 1.41263 | 1.97E−02 |
| *Homo sapiens* PHD finger protein 1 (PHF1), transcript variant 2, mRNA. /PROD = PHD finger protein 1, isoform b /FL = gb: NM_024165.1 gb: AF052205.1 | 0.620171 | 2.95191 | 2.42296 | 2.32E−02 |
| actinin, alpha 4 | 0.436893 | 3.11051 | 2.23625 | 5.44E−03 |
| *Homo sapiens* PCTAIRE protein kinase 1 (PCTK1), mRNA. /PROD = PCTAIRE protein kinase 1 /FL = gb: NM_006201.1 | 2.38171 | 4.87071 | 4.16957 | 2.90E−03 |
| Human DNA sequence from clone RP11-165F24 on chromosome 9. Contains the 3 end of the gene for a novel protein (similar to *Drosophila* CG6630 and CG11376, KIAA1058, rat TRG), an RPL12 (60S ribosomal protein L12) pseudogene, ESTs, STSs, GSSs and a C . . . | 0.167347 | 2.56439 | 1.93736 | 3.93E−02 |
| insulin-like growth factor binding protein 3 /FL = gb: NM_000598.1 | 0.921068 | 3.60279 | 2.67905 | 4.80E−02 |
| *Homo sapiens*, clone IMAGE: 3840937, mRNA, partial cds. /PROD = Unknown (protein for IMAGE: 3840937) | 3.59778 | 6.12936 | 6.92649 | 8.62E−05 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* phosphoglucomutase 1 (PGM1), mRNA. /PROD = phosphoglucomutase 1 /FL = gb: NM_002633.1 gb: BC001756.1 gb: M83088.1 | 4.74364 | 7.09524 | 6.43056 | 2.21E−02 |
| apolipoprotein C-I | 2.77701 | 5.23054 | 4.44049 | 3.39E−02 |
| *Homo sapiens* insulin induced gene 1 (INSIG1), mRNA. /PROD = insulin induced gene 1 /FL = gb: NM_005542.1 | 2.11462 | 4.44128 | 3.77765 | 3.21E−02 |
| Human a6(IV) collagen (COL4A6) mRNA, complete cds. /PROD = A type IV collagen /FL = gb: U04845.1 | 0.798849 | 3.23623 | 2.41372 | 1.38E−03 |
| *Homo sapiens* mRNA for alpha 1,6-fucosyltransferase, complete cds. /PROD = alpha 1,6-fucosyltransferase /FL = gb: AB049740.2 | 1.31479 | 3.6699 | 2.90742 | 3.48E−02 |
| ESTs, Moderately similar to Six5 (*M. musculus*) | 0.434259 | 2.81512 | 1.9556 | 1.23E−02 |
| solute carrier family 2 (facilitated glucose transporter), member 3 /FL = gb: NM_006931.1 gb: M20681.1 | 5.23156 | 7.63734 | 6.74444 | 1.99E−02 |
| Human acid sphingomyelinase (ASM) mRNA, complete cds. /PROD = acid sphingomyelinase /FL = gb: NM_000543.1 gb: M59916.1 | 1.03965 | 3.45689 | 2.52125 | 2.62E−02 |
| ESTs, Weakly similar to unnamed protein product (*H. sapiens*) | 3.0131 | 5.41021 | 4.46614 | 4.79E−03 |
| *Homo sapiens* cDNA FLJ33178 fis, clone ADRGL2002753. | 0.137476 | −1.9718 | −4.73502 | 2.23E−03 |
| *Homo sapiens*, parathyroid hormone-like hormone, clone MGC: 14611, mRNA, complete cds. /PROD = parathyroid hormone-like hormone /FL = gb: BC005961.1 | 2.46289 | −0.34647 | −1.96791 | 3.05E−02 |
| *Homo sapiens* colon carcinoma related protein (LOC51159), mRNA. /PROD = colon carcinoma related protein /FL = gb: NM_016206.1 gb: AF099505.1 | 2.50614 | −0.01889 | −1.04926 | 2.52E−02 |
| KIAA0036 gene product | 3.05174 | −0.66523 | −2.2068 | 2.62E−02 |
| *Homo sapiens* cDNA FLJ13536 fis, clone PLACE1006521 | 4.27968 | 1.86625 | 1.70965 | 1.11E−02 |
| *Homo sapiens* cDNA: FLJ22463 fis, clone HRC10126 | 3.68063 | 1.24806 | 1.39728 | 1.42E−02 |
| *Homo sapiens* UDP-N-acetylglucosamine:a-1,3-D-mannoside beta-1,4-N-acetylglucosaminyltransferase IV-homolog (HGNT-IV-H), mRNA. /PROD = UDP-N-acetylglucosamine:a-1,3-D-mannosidebeta-1,4-N-acetylglucosaminyltransferase IV-homolog /FL = gb: AB024729.1 gb: NM_0 | 2.71164 | 0.270906 | 0.433883 | 1.98E−02 |
| tissue factor pathway inhibitor 2 /FL = gb: D29992.1 gb: L27624.1 gb: NM_006528.1 gb: BC005330.1 | 4.19529 | 1.63281 | 1.58393 | 7.53E−03 |
| ESTs | 2.8924 | 0.521234 | 0.762594 | 2.82E−02 |
| putative gene product | −0.518738 | −0.66615 | 1.82038 | 4.91E−02 |
| *Homo sapiens* mRNA for KIAA1758 protein, partial cds. /PROD = KIAA1758 protein | 2.42082 | −0.03923 | 0.213473 | 1.25E−02 |
| prostaglandin E receptor 4 (subtype EP4) /FL = gb: L25124.1 gb: D28472.1 gb: NM_000958.1 gb: L28175.1 | 2.58497 | 0.196846 | 0.527172 | 1.42E−02 |
| *Homo sapiens* cDNA: FLJ22463 fis, clone HRC10126 | 2.85068 | 0.473875 | 0.830447 | 1.97E−02 |
| *Homo sapiens* heparan sulfate (glucosamine) 3-O-sulfotransferase 2 (HS3ST2), mRNA. /PROD = heparan | 3.18462 | 0.571052 | 0.709206 | 4.54E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| sulfate D-glucosaminyl3-O-sulfotransferase 2 /FL = gb: AF105375.1 gb: AF105374.1 gb: NM_006043.1 | | | | |
| Homo sapiens schwannomin interacting protein 1 (SCHIP-1), mRNA. /PROD = schwannomin interacting protein 1 /FL = gb: AF145713.1 gb: NM_014575.1 | 5.5957 | 3.21054 | 3.57915 | 2.11E−02 |
| Human lysyl oxidase (LOX) gene, exon 7 | 2.11886 | −0.24936 | 0.138069 | 2.55E−03 |
| Human nephropontin mRNA, complete cds. /PROD = nephropontin /FL = gb: M83248.1 | 7.82555 | 5.27856 | 5.06542 | 4.61E−02 |
| Human mRNA for KIAA0386 gene, complete cds. /FL = gb: AB002384.1 | 3.9213 | 1.56305 | 1.13663 | 1.93E−02 |
| ESTs | 3.22146 | 0.851355 | 0.404487 | 3.41E−03 |
| Human glioma pathogenesis-related protein (GliPR) mRNA, complete cds. /PROD = glioma pathogenesis-related protein /FL = gb: NM_006851.1 gb: U16307.1 | 3.20187 | 0.502872 | 0.348681 | 1.34E−02 |
| ESTs | 2.96697 | 0.440894 | 0.773495 | 1.97E−02 |
| Homo sapiens cDNA FLJ13384 fis, clone PLACE1001062, highly similar to Homo sapiens mRNA for lysine-ketoglutarate reductasesaccharopine dehydrogenase. | 5.9221 | 3.48419 | 3.9531 | 3.38E−02 |
| Homo sapiens mRNA; cDNA DKFZp761I1912 (from clone DKFZp761I1912) | 6.06894 | 3.31919 | 3.4798 | 4.97E−02 |
| ESTs | 4.12419 | 1.53997 | 1.88239 | 5.68E−03 |
| Homo sapiens fibroblast growth factor 2 (basic) (FGF2), mRNA. /PROD = fibroblast growth factor 2 (basic) /FL = gb: NM_002006.1 gb: M27968.1 | 5.49297 | 2.64534 | 2.76054 | 4.71E−02 |
| ribosomal protein L34 pseudogene 1 | 3.45116 | 2.78236 | 5.10812 | 2.42E−02 |
| HIV-1 rev binding protein 2 | 4.4245 | 1.47599 | 1.52824 | 2.10E−02 |
| H. sapiens FGF gene, exon 3 /FL = gb: NM_000800.1 gb: M13361.1 | 2.04849 | −0.34703 | −0.95745 | 3.33E−02 |
| ESTs | 2.03304 | −0.9164 | −0.83676 | 4.19E−02 |
| ESTs | 2.87393 | 0.428858 | 1.02011 | 9.72E−04 |
| Homo sapiens clone 23700 mRNA sequence | 4.60148 | 1.64243 | 1.72052 | 4.74E−02 |
| ESTs, Highly similar to S21424 nestin (H. sapiens) | 3.08579 | 0.725853 | 1.40345 | 1.99E−02 |
| Homo sapiens actin, gamma 2, smooth muscle, enteric (ACTG2), mRNA. /PROD = actin, gamma 2 propeptide /FL = gb: NM_001615.2 | 7.17155 | 4.15208 | 4.18551 | 4.72E−02 |
| hypothetical protein FLJ22833 | 2.80785 | 0.480636 | 1.25154 | 2.43E−02 |
| Homo sapiens LIM homeobox protein 6 (LHX6), mRNA. /PROD = LIM homeobox protein 6 /FL = gb: AB031041.1 gb: NM_014368.1 gb: AL136570.1 | 2.52571 | −0.06036 | 0.459727 | 4.37E−02 |
| Homo sapiens, clone IMAGE: 5271039, mRNA. | 3.05576 | 0.189935 | 0.452681 | 4.05E−02 |
| Homo sapiens cAMP response element-binding protein CRE-BPa (H_GS165L15.1), mRNA. /PROD = cAMP response element-binding protein CRE-BPa /FL = gb: NM_004904.1 gb: L05911.1 | 2.90971 | 0.487264 | 1.21334 | 4.24E−02 |
| G protein-coupled receptor 1 /FL = gb: NM_005279.1 | 1.15804 | −1.24345 | −0.49352 | 2.28E−03 |
| Homo sapiens neuropilin (NRP) and tolloid (TLL)-like 1 (NETO1), transcript variant 3, mRNA. /PROD = neuropilin- and tolloid-like protein 1 isoform 3precursor /FL = gb: AF448838.1 gb: NM_138966.2 | 3.25525 | 0.20233 | 0.301354 | 2.83E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* mRNA for KIAA0559 protein, partial cds. /PROD = KIAA0559 protein | 2.37088 | −0.29358 | 0.199028 | 2.81E−02 |
| Human 65-kilodalton phosphoprotein (p65) mRNA, complete cds. /PROD = phosphoprotein p65 /FL = gb: M22300.1 gb: NM_002298.2 gb: J02923.1 | 3.25522 | 0.620942 | 1.15317 | 2.88E−02 |
| Human DNA sequence from clone RP11-31K16 on chromosome 9. Contains a snoRNA binding domain pseudogene, the ELAVL2 gene for ELAV (embryonic lethal, abnormal vision, *Drosophila*)-like 2, ESTs, STSs, GSSs and a CpG island | 4.77522 | 2.18971 | 2.77459 | 4.04E−02 |
| hypothetical protein FLJ11006 | 1.75389 | −0.66646 | 0.100591 | 7.78E−04 |
| *Homo sapiens* mRNA; cDNA DKFZp566A1046 (from clone DKFZp566A1046) | 3.97344 | 1.32598 | 1.8683 | 3.19E−02 |
| ESTs | 4.13356 | 1.60769 | 2.27415 | 1.85E−02 |
| H. sapiens gene from PAC 106H8. | 3.05906 | −0.08711 | −0.13845 | 4.34E−02 |
| Human T-cell receptor rearranged beta-chain V-region (V-D-J) mRNA, complete cds. /FL = gb: M15564.1 | 3.43862 | 0.94127 | 1.64514 | 5.31E−03 |
| peptidylprolyl isomerase A (cyclophilin A) | 1.76352 | 0.908832 | 3.26124 | 2.19E−02 |
| *Homo sapiens* mRNA for KIAA1597 protein, partial cds. /PROD = KIAA1597 protein | 6.20675 | 3.06104 | 3.12403 | 1.78E−02 |
| HIV-1 rev binding protein 2 | 3.54001 | 0.617783 | 0.325316 | 3.52E−02 |
| *Homo sapiens* nidogen 2 (NID2), mRNA. /PROD = nidogen 2 /FL = gb: NM_007361.1 gb: D86425.1 | 3.39549 | 0.915898 | 1.65422 | 4.70E−03 |
| *Homo sapiens* mRNA; cDNA DKFZp566A1046 (from clone DKFZp566A1046) | 3.49826 | 0.859233 | 1.46022 | 3.01E−02 |
| *Homo sapiens* muscleblind (*Drosophila*)-like (MBNL), mRNA. /PROD = muscleblind (*Drosophila*)-like /FL = gb: NM_021038.1 gb: AB007888.1 | 3.53962 | 0.508166 | 0.298438 | 3.90E−02 |
| hypothetical protein FLJ20163 | 5.26708 | 2.17148 | 2.01643 | 3.33E−02 |
| KIAA0455 gene product | 3.25374 | 0.057742 | −0.01612 | 2.66E−02 |
| hypothetical protein FLJ22833 /FL = gb: NM_022837.1 | 2.93229 | 0.533105 | 1.40606 | 3.19E−02 |
| ESTs | 2.19313 | −0.32822 | 0.427128 | 1.87E−02 |
| *Homo sapiens* NADPH oxidase 4 (NOX4), mRNA. /PROD = NADPH oxidase 4 /FL = gb: AF261943.1 gb: NM_016931.1 gb: AF254621.1 gb: AB041035.1 | 5.57794 | 2.61602 | 2.28462 | 4.04E−02 |
| ESTs | 3.3266 | 0.840887 | 1.69605 | 0.00E+00 |
| ESTs | 1.99635 | −0.56359 | 0.236236 | 1.39E−02 |
| *Homo sapiens* serumglucocorticoid regulated kinase (SGK), mRNA. /PROD = serumglucocorticoid regulated kinase /FL = gb: BC001263.1 gb: NM_005627.1 gb: AF153609.1 | 4.81433 | 2.46478 | 3.47797 | 2.02E−02 |
| A kinase (PRKA) anchor protein 2 | 6.03149 | 3.65135 | 4.63469 | 1.17E−02 |
| ESTs | 3.8522 | 1.17894 | 0.483367 | 3.08E−02 |
| *Homo sapiens* similar to rat tricarboxylate carrier-like protein (BA108L7.2), mRNA. /PROD = similar to rat tricarboxylate carrier-likeprotein /FL = gb: NM_030971.1 | 1.74077 | −1.45032 | −1.24979 | 5.69E−04 |
| *Homo sapiens*, lectin, galactoside-binding, soluble, 3 (galectin 3), clone MGC: 2058, mRNA, complete cds. /PROD = lectin, galactoside-binding, | 4.53668 | 1.85893 | 2.59596 | 3.84E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| soluble, 3(galectin 3) /FL = gb: NM_002306.1 gb: M35368.1 gb: BC001120.1 gb: M36682.1 gb: M57710.1 gb: AB006780.1 | | | | |
| ESTs | 1.06738 | −1.51321 | −0.67814 | 7.68E−03 |
| Homo sapiens heptacellular carcinoma novel gene-3 protein (LOC51339), mRNA. /PROD = heptacellular carcinoma novel gene-3 protein /FL = gb: NM_016651.2 gb: AF251079.2 | 5.55437 | 3.02649 | 3.91576 | 2.22E−02 |
| Homo sapiens, Similar to transforming growth factor beta 1 induced transcript 1, clone MGC: 4078, mRNA, complete cds. /PROD = Similar to transforming growth factor beta 1induced transcript 1 /FL = gb: NM_015927.1 gb: BC001830.1 gb: AF116343.1 | 4.82642 | 2.07249 | 2.74019 | 1.03E−02 |
| ESTs, Highly similar to FXD3_HUMAN FORKHEAD BOX PROTEIN D3 (H. sapiens) | 3.81523 | 1.18624 | 1.98102 | 4.17E−02 |
| ESTs | 4.52094 | 1.70664 | 2.3196 | 2.78E−02 |
| Homo sapiens potassium intermediatesmall conductance calcium-activated channel, subfamily N, member 2 (KCNN2), mRNA. /PROD = potassium intermediatesmall conductancecalcium-activated channel, subfamily N, member 2 /FL = gb: NM_021614.1 gb: AF239613.1 | 3.68048 | 0.897369 | 1.5433 | 1.32E−02 |
| Homo sapiens transporter similar to yeast MRS2 (MRS2L), mRNA. /PROD = transporter similar to yeast MRS2 /FL = AF288288.1 gb: NM_020662.1 | 5.68324 | 3.35483 | 4.46553 | 3.00E−03 |
| Homo sapiens a disintegrin-like and metalloprotease (reprolysin type) with thrombospondin type 1 motif, 5 (aggrecanase-2) (ADAMTS5), mRNA. /PROD = a disintegrin and metalloprotease withthrombospondin motifs-5 preproprotein /FL = gb: NM_007038.1 gb: AF14209 | 4.54713 | 2.07152 | 1.10726 | 5.91E−03 |
| HIV-1 rev binding protein 2 | 3.85003 | 0.823769 | 0.407316 | 3.76E−02 |
| Human, parathyroid-like protein (associated with humoral hypercalcemia of malignancy) mRNA, complete cds. /FL = gb: J03580.1 | 1.73564 | −1.5631 | −1.41799 | 4.04E−02 |
| ESTs | 5.27633 | 2.76577 | 3.71542 | 1.39E−02 |
| ESTs | 1.7022 | −1.29085 | −0.81236 | 1.72E−02 |
| pyruvate dehydrogenase phosphatase /FL = gb: NM_018444.1 gb: AF155661.1 | 6.62966 | 4.26189 | 5.37384 | 1.04E−03 |
| ESTs | 3.90566 | 1.11378 | 1.80307 | 1.57E−02 |
| Homo sapiens DRM (DRM) mRNA, complete cds. /PROD = DRM /FL = gb: NM_013372.1 gb: AF110137.2 gb: AF045800.1 gb: AF154054.1 | 6.16645 | 3.12369 | 3.57831 | 1.59E−02 |
| Homo sapiens cDNA: FLJ22769 fis, clone KAIA1316 | 2.36483 | −0.5543 | 0.025213 | 1.45E−04 |
| ESTs | 4.31647 | 1.44801 | 2.11226 | 2.19E−02 |
| ESTs | 1.24891 | −1.42983 | −0.57145 | 1.29E−02 |
| Homo sapiens mRNA; cDNA DKFZp586N012 (from clone DKFZp586N012) | 2.85031 | 0.231102 | 1.16439 | 1.08E−02 |
| jagged 1 (Alagille syndrome) | 2.54951 | 0.151382 | 1.31733 | 4.46E−03 |
| ESTs, Weakly similar to I38588 reverse transcriptase homolog (H. sapiens) | 1.16209 | −1.26828 | −0.1187 | 3.40E−02 |
| KIAA1339 protein | 4.41803 | 2.09451 | 3.35786 | 3.90E−02 |
| ESTs | 3.83407 | 0.892884 | 1.56759 | 8.98E−03 |
| DKFZP434D156 protein | 4.42983 | 2.05154 | 3.28988 | 1.60E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* mRNA expressed only in placental villi, clone SMAP41. | 3.84408 | 0.705031 | 1.20856 | 2.25E−02 |
| RAS guanyl releasing protein 2 (calcium and DAG-regulated) | 2.7724 | 0.235409 | 1.34452 | 1.96E−02 |
| KIAA0164 gene product /FL = gb: NM_014739.1 gb: D79986.1 | 4.99867 | 2.5327 | 3.72535 | 2.85E−02 |
| *Homo sapiens* mRNA; cDNA DKFZp761M0111 (from clone DKFZp761M0111) | 5.14752 | 2.61217 | 3.76652 | 3.78E−02 |
| *Homo sapiens* NPD009 mRNA, complete cds. /PROD = NPD009 /FL = gb: NM_020686.1 gb: AF237813.1 | 2.15383 | −0.27664 | 0.990295 | 2.09E−03 |
| muscleblind (*Drosophila*)-like /FL = gb: NM_021038.1 gb: AB007888.1 | 3.23823 | 0.467215 | 1.39628 | 7.60E−03 |
| ESTs | 4.49318 | 1.35004 | 1.91395 | 3.79E−02 |
| muscleblind (*Drosophila*)-like /FL = gb: NM_021038.1 gb: AB007888.1 | 1.84877 | −0.57315 | 0.732468 | 8.06E−03 |
| ESTs | 6.068 | 3.42334 | 4.51189 | 1.89E−02 |
| ESTs, Weakly similar to unnamed protein product (*H. sapiens*) | 3.24528 | 0.740266 | 1.98306 | 3.89E−04 |
| Human complement cytolysis inhibitor (CLI) mRNA, complete cds. /FL = gb: J02908.1 gb: NM_001831.1 gb: M64722.1 gb: M25915.1 | 6.50766 | 4.03647 | 5.33533 | 1.77E−02 |
| ESTs | 5.36759 | 2.42249 | 3.24765 | 3.23E−03 |
| ESTs | 0.957239 | −1.43055 | −0.04796 | 5.55E−04 |
| transporter similar to yeast MRS2 | 3.77395 | 1.18311 | 2.36844 | 1.83E−02 |
| *Homo sapiens*, Similar to regulator for ribosome resistance homolog (*S. cerevisiae*), clone MGC: 2755, mRNA, complete cds. /PROD = Similar to regulator for ribosome resistancehomolog (*S. cerevisiae*) /FL = gb: BC001811.1 | 5.09957 | 2.72179 | 4.14116 | 2.72E−02 |
| SWISNF related, matrix associated, actin dependent regulator of chromatin, subfamily a, member 2 /FL = gb: NM_003070.1 gb: D26155.1 | 2.54229 | −0.29226 | 0.695255 | 1.89E−02 |
| *Homo sapiens* mRNA; cDNA DKFZp586L2424 (from clone DKFZp586L2424) | 3.34446 | 0.795373 | 2.07147 | 1.03E−02 |
| ESTs | 4.63117 | 2.08252 | 3.36946 | 2.25E−03 |
| *Homo sapiens* bicarbonate transporter-related protein BTR1 mRNA, complete cds. /PROD = bicarbonate transporter-related protein BTR1 /FL = gb: AF336127.1 | 3.17407 | 0.745852 | 2.17046 | 1.71E−03 |
| ESTs | 1.08377 | −1.27197 | 0.228305 | 4.76E−02 |
| ESTs | 2.94657 | 0.127188 | 1.20032 | 1.43E−02 |
| *Homo sapiens* mRNA; cDNA DKFZp434B2016 (from clone DKFZp434B2016). | 2.47798 | −0.26439 | 0.894731 | 4.51E−03 |
| ESTs | 2.39983 | −1.04089 | −0.57976 | 3.37E−02 |
| *Homo sapiens* synaptotagmin interacting protein STIP1 mRNA, partial cds. /PROD = synaptotagmin interacting protein STIP1 | 2.11009 | −0.57109 | 0.653181 | 1.78E−02 |
| *Homo sapiens* connexin 26 (GJB2) mRNA, complete cds. /PROD = connexin 26 /FL = gb: NM_004004.1 gb: M86849.2 | 2.86049 | −0.57377 | −0.09328 | 4.27E−04 |
| *Homo sapiens* brain-derived neurotrophic factor (BDNF), mRNA. /PROD = brain-derived neurotrophic factor /FL = gb: NM_001709.1 | 1.71599 | −0.79412 | 0.616733 | 3.09E−02 |
| ESTs, Weakly similar to unknown (*H. sapiens*) | 2.33677 | −0.04066 | 1.5217 | 1.87E−03 |
| ESTs | 2.57265 | 0.177794 | 1.74876 | 2.74E−04 |
| ESTs | 2.6809 | 0.209095 | 1.70624 | 1.21E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Homo sapiens DKC1 gene, exons 1 to 11 | 4.18307 | 1.70283 | 3.20863 | 2.00E−02 |
| Homo sapiens T cell receptor beta chain (TCRBV13S1-TCRBJ2S1) mRNA, complete cds. /PROD = T cell receptor beta chain /FL = gb: AF043179.1 | 4.45228 | 1.38318 | 2.30031 | 3.27E−03 |
| Homo sapiens PRO0066 mRNA, complete cds. /PROD = PRO0066 /FL = gb: AF113007.1 | 0.466715 | −1.87679 | −0.22665 | 4.25E−03 |
| axonal transport of synaptic vesicles | 5.20385 | 2.74124 | 4.27648 | 3.33E−03 |
| Homo sapiens, Similar to cyclin M2, clone MGC: 12933 IMAGE: 4308662, mRNA, complete cds. /PROD = Similar to cyclin M2 /FL = gb: BC021222.1 | 0.139313 | −2.31405 | −0.76333 | 1.46E−02 |
| Homo sapiens clone CDABP0095 mRNA sequence | 3.87201 | 2.7936 | 5.73958 | 9.63E−03 |
| H. sapiens mRNA for ribosomal protein L18a homologue. /PROD = ribosomal protein L18a homologue | 2.00401 | 0.354674 | 2.73013 | 4.70E−04 |
| ESTs, Weakly similar to ALU7_HUMAN ALU SUBFAMILY SQ SEQUENCE CONTAMINATION WARNING ENTRY (H. sapiens) | 3.43639 | 0.843826 | 2.28468 | 3.37E−02 |
| Homo sapiens, clone IMAGE: 5242616, mRNA. | −0.525567 | −2.07832 | 0.406964 | 2.23E−02 |
| Homo sapiens C1orf24 mRNA, complete cds. /PROD = C1orf24 /FL = gb: AF288391.1 gb: AB050477.1 gb: NM_022083.1 | 5.17968 | 2.58724 | 4.04213 | 1.98E−04 |
| Homo sapiens clone IMAGE: 451939, mRNA sequence | 5.15776 | 2.22786 | 3.40438 | 2.60E−02 |
| Homo sapiens cDNA FLJ14942 fis, clone PLACE1011185, highly similar to INSERTION ELEMENT IS1 PROTEIN INSB. | 0.682724 | −2.08716 | −0.74074 | 1.45E−02 |
| hypothetical protein FLJ20425 /FL = gb: NM_017816.1 gb: AL136750.1 | 4.23689 | 1.90847 | 3.69988 | 1.15E−02 |
| Homo sapiens matrix metalloproteinase 10 (stromelysin 2) (MMP10), mRNA. /PROD = matrix metalloproteinase 10 preproprotein /FL = gb: BC002591.1 gb: NM_002425.1 | 2.28308 | −0.65903 | 0.521586 | 8.87E−03 |
| ESTs | 3.67167 | 2.20619 | 4.86553 | 3.16E−03 |
| Homo sapiens prominin (mouse)-like 1 (PROML1), mRNA. /PROD = prominin (mouse)-like 1 /FL = gb: NM_006017.1 gb: AF027208.1 | 5.46002 | 2.79737 | 4.29571 | 1.38E−03 |
| Homo sapiens mRNA; cDNA DKFZp434M2415 (from clone DKFZp434M2415). | 2.40278 | −0.68409 | 0.399469 | 1.48E−02 |
| Homo sapiens hypothetical protein FLJ20701 (FLJ20701), mRNA. /PROD = hypothetical protein FLJ20701 /FL = gb: NM_017933.1 | 2.1471 | 0.312211 | 2.65409 | 2.28E−04 |
| Homo sapiens cDNA FLJ35259 fis, clone PROST2004251. | 6.79033 | 3.86627 | 5.12737 | 1.23E−03 |
| Homo sapiens hypothetical protein FLJ39553 (FLJ39553), mRNA. /FL = gb: NM_173549.1 | 4.0369 | 1.34318 | 2.84336 | 7.69E−03 |
| Human microfibril-associated glycoprotein-2 MAGP-2 mRNA, complete cds. /PROD = microfibril-associated glycoprotein-2 MAGP-2 /FL = gb: NM_003480.1 gb: U37283.1 | 3.89326 | 0.527618 | 1.35764 | 1.81E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* proprotein convertase subtilisinkexin type 5 (PCSK5), mRNA. /PROD = proprotein convertase subtilisinkexin type 5 /FL = gb: U56387.2 gb: NM_006200.1 | 3.76897 | 0.368734 | 1.17396 | 1.38E−02 |
| Cluster Incl. AI735391:at10e09.x1 Homo sapiens cDNA, 3 end /clone = IMAGE-2354728 /clone_end = 3 /gb = AI735391 /gi = 5056915 /ug = Hs.20137 /len = 567 | 2.59941 | 0.203564 | 2.03637 | 1.12E−04 |
| ESTs | 2.30031 | −1.01596 | −0.08964 | 1.46E−02 |
| Kruppel-like factor 4 (gut) | 3.50041 | 1.09954 | 2.95915 | 1.22E−02 |
| *Homo sapiens* full length insert cDNA YI25A03 | −1.40946 | −3.04877 | −0.39378 | 3.32E−02 |
| ESTs | 0.806666 | −2.01081 | −0.53076 | 1.91E−02 |
| *Homo sapiens* mRNA; cDNA DKFZp761G02121 (from clone DKFZp761G02121); partial cds | 3.1892 | 0.012768 | 1.13562 | 1.35E−03 |
| *Homo sapiens* TMEFF2 mRNA, complete cds. /FL = gb: AB017269.1 gb: NM_016192.2 gb: AF179274.2 gb: AF242222.1 | 2.28638 | −0.89508 | 0.225546 | 1.21E−03 |
| *Homo sapiens*, clone MGC: 3328, mRNA, complete cds. /PROD = Unknown (protein for MGC: 3328) /FL = gb: BC001745.1 gb: NM_014392.1 | 3.54625 | 0.772486 | 2.30168 | 4.16E−02 |
| ESTs | 2.18149 | −0.58303 | 0.984522 | 2.68E−02 |
| synaptojanin 2 | 4.166 | 1.83143 | 3.84199 | 0.00E+00 |
| KIAA0367 protein | 1.5999 | −1.50555 | −0.26286 | 1.58E−02 |
| ESTs, Moderately similar to ALU8_HUMAN ALU SUBFAMILY SX SEQUENCE CONTAMINATION WARNING ENTRY (*H. sapiens*) | 0.868185 | −1.46804 | 0.573078 | 1.69E−02 |
| bromodomain adjacent to zinc finger domain, 1B | 1.60872 | −1.12544 | 0.518361 | 2.11E−02 |
| Human complement cytolysis inhibitor (CLI) mRNA, complete cds. /FL = gb: J02908.1 gb: NM_001831.1 gb: M64722.1 gb: M25915.1 | 6.61592 | 3.91665 | 5.596 | 1.66E−02 |
| forkhead box O1A (rhabdomyosarcoma) /FL = gb: NM_002015.2 gb: AF032885.1 gb: U02310.1 | 5.04975 | 2.59802 | 4.53545 | 1.60E−03 |
| *Homo sapiens* cDNA: FLJ22727 fis, clone HSI15054 | 4.88391 | 2.09093 | 3.68875 | 1.91E−02 |
| cadherin 6, type 2, K-cadherin (fetal kidney) /FL = gb: D31784.1 gb: NM_004932.1 | 3.27371 | 0.243335 | 1.61199 | 2.74E−04 |
| ESTs | 3.97749 | 0.786845 | 1.99803 | 1.73E−02 |
| endonuclease G-like 1 /FL = gb: AB020523.1 gb: NM_005107.1 | 1.11519 | −2.09018 | −0.88324 | 1.69E−02 |
| *Homo sapiens* cDNA FLJ13034 fis, clone NT2RP3001232 | 4.59641 | 0.64328 | 1.1121 | 1.66E−02 |
| Human DNA sequence from clone RP4-614O4 on chromosome 20q11.1-12 Contains the 3 part of the MMP24 (matrix metalloproteinase 24 (membrane-inserted)) gene, the ITGB4BP (integrin beta 4 binding protein) gene, the 3 end of a novel gene, the 3 end o . . . | 2.91607 | 0.209555 | 1.92644 | 1.93E−02 |
| *Homo sapiens*, collapsin response mediator protein-5; CRMP3-associated molecule, clone MGC: 11247, mRNA, complete cds. /PROD = collapsin response mediator protein-5; CRMP3-associated molecule /FL = gb: BC002874.1 | 0.672753 | −1.75265 | 0.250803 | 8.65E−03 |
| ESTs, Moderately similar to ALU7_HUMAN ALU SUBFAMILY SQ | 2.91576 | 0.289656 | 2.10334 | 2.57E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| SEQUENCE CONTAMINATION WARNING ENTRY (*H. sapiens*) ESTs, Moderately similar to CA1C RAT COLLAGEN ALPHA 1(XII) CHAIN (R. norvegicus) | 6.2681 | 1.94518 | 1.82747 | 4.12E−02 |
| *Homo sapiens* alpha-aminoadipate semialdehyde synthase mRNA, complete cds. /PROD = alpha-aminoadipate semialdehyde synthase /FL = gb: AF229180.1 | 5.2604 | 2.72549 | 4.6685 | 4.33E−03 |
| *Homo sapiens* Wnt inhibitory factor-1 (WIF-1), mRNA. /PROD = Wnt inhibitory factor-1 /FL = gb: AF122922.1 gb: NM_007191.1 | 1.03265 | −1.51207 | 0.433159 | 8.62E−05 |
| ribosomal protein S11 | 4.95358 | 2.25158 | 4.04683 | 2.98E−04 |
| *Homo sapiens* tumor necrosis factor, alpha-induced protein 6 (TNFAIP6), mRNA. /PROD = tumor necrosis factor, alpha-induced protein 6 /FL = gb: NM_007115.1 | 2.42729 | −0.73843 | 0.613222 | 1.93E−02 |
| *Homo sapiens* hairyenhancer-of-split related with YRPW motif 2 (HEY2), mRNA. /PROD = hairyenhancer-of-split related with YRPW motif2 /FL = gb: NM_012259.1 gb: AF311884.1 gb: AB044755.1 gb: AF232238.1 gb: AF237949.1 gb: AF173901.1 | 2.3848 | −0.44154 | 1.27956 | 3.16E−03 |
| *Homo sapiens* semenogelin I (SEMG1), mRNA. /PROD = semenogelin I /FL = gb: J04440.1 gb: NM_003007.1 | 0.585816 | −2.46893 | −0.95223 | 3.05E−02 |
| *Homo sapiens*, Similar to cadherin 6, type 2, K-cadherin (fetal kidney), clone MGC: 1470, mRNA, complete cds. /PROD = Similar to cadherin 6, type 2, K-cadherin (fetalkidney) /FL = gb: BC000019.1 | 2.38648 | −0.02212 | 2.14359 | 2.59E−03 |
| *Homo sapiens* mRNA; cDNA DKFZp434H0350 (from clone DKFZp434H0350); partial cds. /PROD = hypothetical protein | 2.16899 | −0.56794 | 1.27546 | 3.16E−03 |
| *Homo sapiens* growth factor receptor-bound protein 14 (GRB14), mRNA. /PROD = growth factor receptor-bound protein 14 /FL = gb: L76687.1 gb: NM_004490.1 | 4.2346 | 1.17569 | 2.73613 | 4.80E−03 |
| *Homo sapiens*, Similar to TAF5-like RNA polymerase II, p300CBP-associated factor (PCAF)-associated factor, 65 kDa, clone MGC: 46101 IMAGE: 5551246, mRNA, complete cds. /PROD = Similar to TAF5-like RNA polymerase II, p300CBP-associated factor (PCAF)-associat | 2.10954 | −0.1313 | 2.24853 | 8.24E−04 |
| *Homo sapiens* mRNA; cDNA DKFZp761J1324 (from clone DKFZp761J1324) | 1.42404 | −1.99222 | −0.77126 | 3.21E−02 |
| solute carrier family 30 (zinc transporter), member 1 | 2.82535 | 0.288493 | 2.38889 | 0.00E+00 |
| antizyme inhibitor | 3.65887 | 0.37346 | 1.74912 | 1.86E−02 |
| *Homo sapiens* GRO1 oncogene (melanoma growth stimulating activity, alpha) (GRO1), mRNA. /PROD = GRO1 oncogene (melanoma growth stimulatingactivity, alpha) /FL = gb: NM_001511.1 | 2.51473 | 0.107263 | 2.38874 | 7.16E−04 |

TABLE VI-continued

MEAN NORMALIZED INTENSITY VALUES (IN LOG
FORMAT) OF GENES FOR H9 EMBRYONIC STEM CELLS
DERIVED DEFINITIVE ENDODERM STAGE CELLS CULTURED
ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* proprotein convertase subtilisinkexin type 5 (PCSK5), mRNA. /PROD = proprotein convertase subtilisinkexin type 5 /FL = gb: U56387.2 gb: NM_006200.1 | 4.90999 | 0.871309 | 1.52441 | 1.71E−02 |
| ESTs | 0.254736 | −1.96122 | 0.51777 | 4.00E−02 |
| G-protein gamma-12 subunit /FL = gb: NM_018841.1 gb: AF119663.1 | 3.93653 | 1.06178 | 2.88889 | 5.11E−04 |
| platelet-derived growth factor alpha polypeptide | 3.50343 | 0.651246 | 2.50207 | 3.99E−03 |
| clusterin (complement lysis inhibitor, SP-40,40, sulfated glycoprotein 2, testosterone-repressed prostate message 2, apolipoprotein J) | 2.88196 | −0.42677 | 0.9712 | 8.48E−03 |
| ESTs | 2.82081 | −1.69816 | −1.89985 | 4.10E−02 |
| *Homo sapiens* insulinoma-associated 1 (INSM1), mRNA. /PROD = insulinoma-associated 1 /FL = gb: NM_002196.1 gb: M93119.1 | 2.94347 | 0.120494 | 2.02248 | 1.43E−03 |
| LBP protein 32 /FL = gb: NM_014552.1 gb: AF198489.1 | 2.68546 | −0.16678 | 1.70626 | 1.87E−03 |
| ESTs, Highly similar to T42654 hypothetical protein DKFZp434G1115.1 (*H. sapiens*) | 2.84504 | 0.515703 | 2.95379 | 7.92E−04 |
| *Homo sapiens* Friend leukemia virus integration 1 (FLI1), mRNA. /PROD = Friend leukemia virus integration 1 /FL = gb: BC001670.1 gb: NM_002017.2 gb: M98833.3 | 1.7744 | −2.28064 | −1.56765 | 3.14E−02 |
| ESTs | 0.846429 | −2.42046 | −0.91891 | 1.57E−02 |
| *Homo sapiens* oxidative 3 alpha hydroxysteroid dehydrogenase; retinol dehydrogenase; 3-hydroxysteroid epimerase (RODH), mRNA. /PROD = oxidative 3 alpha hydroxysteroid dehydrogenase;retinol dehydrogenase; 3-hydroxysteroid epimerase /FL = gb: AF016509.1 gb: A | 1.30153 | −1.64227 | 0.196394 | 3.20E−03 |
| minor histocompatibility antigen HA-1 | 1.89498 | −0.37136 | 2.15157 | 4.61E−02 |
| UDP-glucose pyrophosphorylase 2 | 4.26327 | 0.968939 | 2.4776 | 6.20E−03 |
| *Homo sapiens* regulator of G-protein signalling 2, 24 kD (RGS2), mRNA. /PROD = regulator of G-protein signalling 2, 24 kD /FL = gb: L13463.1 gb: NM_002923.1 | 5.42952 | 3.05504 | 5.49711 | 1.21E−03 |
| ESTs | 4.49987 | 1.01623 | 2.35659 | 1.86E−03 |
| ESTs | 0.623422 | −1.94907 | 0.317138 | 8.95E−04 |
| ESTs | 0.326084 | −1.69499 | 1.13586 | 1.10E−02 |
| ESTs | 3.82952 | 0.673296 | 2.37112 | 3.92E−02 |
| *Homo sapiens* cDNA FLJ10160 fis, clone HEMBA1003545, highly similar to INSULIN GENE ENHANCER PROTEIN ISL-2. | 2.80876 | −0.24405 | 1.56853 | 1.39E−02 |
| thyroid hormone receptor-associated protein, 150 kDa subunit /FL = gb: NM_005119.1 gb: AF117756.1 | 4.66717 | 2.01883 | 4.2391 | 4.63E−03 |
| ESTs | 2.4548 | −0.3811 | 1.65212 | 4.08E−03 |
| *Homo sapiens* mRNA; cDNA DKFZp667D095 (from clone DKFZp667D095) | 3.13835 | 0.605922 | 2.95511 | 1.53E−03 |
| *Homo sapiens* synaptojanin 2 mRNA, complete cds. /PROD = synaptojanin 2 /FL = gb: AF318616.1 | 2.94452 | 0.23595 | 2.4148 | 3.63E−04 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Homo sapiens procollagen C-endopeptidase enhancer (PCOLCE), mRNA. /PROD = procollagen C-endopeptidase enhancer /FL = gb: BC000574.1 gb: NM_002593.2 gb: AB008549.1 gb: L33799.1 | 3.37999 | 0.343624 | 2.21149 | 1.46E−02 |
| ESTs | 3.24495 | 0.925809 | 3.52818 | 1.70E−04 |
| Homo sapiens mRNA for KIAA0930 protein, partial cds. /PROD = KIAA0930 protein | 3.65772 | 0.911608 | 3.09513 | 8.62E−05 |
| Homo sapiens forkhead transcription factor FOXL2 (BPES), mRNA. /PROD = forkhead transcription factor FOXL2 /FL = gb: AF301906.1 gb: NM_023067.1 | 1.51993 | −2.14186 | −0.86243 | 3.75E−02 |
| ESTs | 1.9867 | −1.5948 | −0.2171 | 2.81E−03 |
| ESTs, Highly similar to AF174600 1 F-box protein Fbx20 (H. sapiens) | 3.06175 | 0.202953 | 2.35691 | 2.45E−02 |
| Homo sapiens ankyrin 3, node of Ranvier (ankyrin G) (ANK3), transcript variant 2, mRNA. /PROD = ankyrin 3, isoform 2 /FL = gb: NM_001149.1 gb: U43965.1 | 3.11644 | 0.101116 | 2.09865 | 2.90E−03 |
| Homo sapiens tumor necrosis factor receptor superfamily, member 6 (TNFRSF6), mRNA. /PROD = apoptosis (APO-1) antigen 1 /FL = gb: NM_000043.1 gb: M67454.1 | 2.39086 | −1.04254 | 0.558779 | 1.62E−02 |
| Homo sapiens thyrotropin-releasing hormone degrading ectoenzyme (TRHDE), mRNA. /PROD = thyrotropin-releasing hormone degradingectoenzyme /FL = gb: AF126372.1 gb: NM_013381.1 | 1.30849 | −1.50688 | 0.822517 | 4.91E−02 |
| ESTs | 4.65711 | 0.915563 | 2.32327 | 6.29E−03 |
| Homo sapiens mRNA; cDNA DKFZp564N1116 (from clone DKFZp564N1116) | 2.36072 | −2.02594 | −1.25286 | 1.50E−02 |
| Homo sapiens placental protein 13-like protein (LOC56891), mRNA. /PROD = placental protein 13-like protein /FL = gb: NM_020129.1 gb: AF267852.1 | 3.55894 | 0.434263 | 2.47085 | 3.48E−03 |
| Homo sapiens, Similar to receptor tyrosine kinase-like orphan receptor 1, clone MGC: 12687, mRNA, complete cds. /PROD = Similar to receptor tyrosine kinase-like orphanreceptor 1 /FL = gb: BC006374.1 | 2.05578 | 0.178992 | 3.5007 | 4.46E−04 |
| ESTs | 0.159066 | −2.96514 | −0.84976 | 3.25E−02 |
| Homo sapiens, Similar to v-ets avian erythroblastosis virus E26 oncogene homolog 1, clone MGC: 29755 IMAGE: 3946751, mRNA, complete cds. /PROD = Similar to v-ets avian erythroblastosis virusE26 oncogene homolog 1 /FL = gb: BC017314.1 | 2.22285 | −1.58562 | −0.1074 | 2.63E−02 |
| ESTs, Highly similar to dedicator of cyto-kinesis 1 (H. sapiens) | 0.83871 | −2.29829 | −0.12951 | 1.85E−02 |
| ESTs | 1.1465 | −1.7403 | 0.682768 | 3.99E−02 |
| ESTs | 1.7466 | −1.67509 | 0.283174 | 2.97E−03 |
| ESTs, Weakly similar to PMXB_HUMAN PAIRED MESODERM HOMEOBOX PROTEIN 2B (H. sapiens) | 1.03192 | −2.44485 | −0.51457 | 1.87E−03 |
| ESTs | 3.22222 | −0.29339 | 1.59904 | 7.36E−03 |
| Homo sapiens cDNA FLJ10561 fis, clone NT2RP2002672 | 2.295 | −1.60823 | −0.08369 | 3.93E−03 |
| Homo sapiens, Similar to KIAA0441 gene product, clone MGC: 45124 | 1.38545 | −1.60426 | 0.86909 | 2.33E−03 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| IMAGE: 5578893, mRNA, complete cds. /PROD = Similar to KIAA0441 gene product /FL = gb: BC036731.1 | | | | |
| Homo sapiens, clone IMAGE: 4067166, mRNA | 0.195869 | −2.50507 | 0.276993 | 1.16E−03 |
| ESTs | 1.5857 | −2.61787 | −1.30022 | 1.12E−02 |
| Homo sapiens methyl-CpG binding protein MBD2 (MBD2) mRNA, complete cds. /PROD = methyl-CpG binding protein MBD2 /FL = gb: NM_003927.2 gb: AF072242.1 | 0.490598 | −3.45465 | −1.70163 | 3.90E−03 |
| KIAA1151 protein | 0.642527 | −2.04288 | 1.00885 | 4.09E−03 |
| H. sapiens mRNA for B-HLH DNA binding protein. /PROD = B-HLH DNA binding protein /FL = gb: NM_000474.1 | 5.43034 | 1.56039 | 3.45122 | 1.12E−04 |
| Homo sapiens, Similar to hypothetical protein FLJ32001, clone MGC: 39559 IMAGE: 4828136, mRNA, complete cds. /PROD = Similar to hypothetical protein FLJ32001 /FL = gb: BC036200.1 | 0.520711 | −1.99011 | 1.26899 | 2.63E−02 |
| Homo sapiens Wilms tumor 1 (WT1), transcript variant D, mRNA. /PROD = Wilms tumor 1 isoform D /FL = gb: NM_024424.1 gb: NM_024426.1 | 2.40462 | −2.96375 | −2.43546 | 1.41E−02 |
| ESTs | 1.53104 | −1.54553 | 1.37309 | 8.14E−03 |
| Homo sapiens, Similar to cadherin 6, type 2, K-cadherin (fetal kidney), clone MGC: 1470, mRNA, complete cds. /PROD = Similar to cadherin 6, type 2, K-cadherin (fetalkidney) /FL = gb: BC000019.1 | 2.54746 | −0.69811 | 2.13419 | 1.45E−04 |
| ESTs | 0.133612 | −3.77953 | −1.56636 | 1.40E−02 |
| paternally expressed 3 | 2.87581 | −1.67669 | −0.0118 | 2.17E−02 |
| Homo sapiens Charot-Leyden crystal protein (CLC), mRNA. /PROD = Charot-Leyden crystal protein /FL = gb: NM_001828.3 gb: L01664.1 | 3.30086 | −0.41644 | 2.1096 | 2.08E−02 |
| ESTs | 3.26198 | −0.72777 | 1.5682 | 3.16E−03 |
| Homo sapiens tachykinin, precursor 1 (substance K, substance P, neurokinin 1, neurokinin 2, neuromedin L, neurokinin alpha, neuropeptide K, neuropeptide gamma) (TAC1), transcript variant beta, mRNA. /PROD = tachykinin 2 precursor, isoform beta /FL = gb: U3 | 2.77265 | −1.02081 | 1.48319 | 4.07E−04 |
| Homo sapiens PNAS-123 mRNA, complete cds | 1.59659 | −1.46656 | 1.84663 | 3.90E−03 |
| Homo sapiens hypothetical protein FLJ20075 (FLJ20075), mRNA. /PROD = hypothetical protein FLJ20075 /FL = gb: NM_017655.1 | −0.359245 | −3.46654 | −0.06528 | 2.55E−03 |
| Human platelet-derived growth factor alpha-receptor (PDGFRA) mRNA, exons 13-16 | 2.44464 | −0.5846 | 2.90484 | 3.63E−04 |
| Homo sapiens cDNA: FLJ22547 fis, clone HSI00356 | 4.29365 | −0.10882 | 2.09548 | 1.54E−02 |
| Homo sapiens HSPC156 protein (HSPC156), mRNA. /PROD = HSPC156 protein /FL = gb: NM_014178.1 gb: AF161505.1 | 0.786188 | −2.32161 | 1.29619 | 8.62E−05 |
| Homo sapiens mRNA; cDNA DKFZp586P1124 (from clone DKFZp586P1124) | 0.485642 | −4.8524 | −3.09356 | 2.02E−02 |
| caldesmon 1 /FL = gb: M64110.1 gb: NM_004342.2 | 7.09236 | 2.67863 | 5.63436 | 7.47E−03 |
| Homo sapiens, Similar to hypothetical protein FLJ10058, clone MGC: 34305 | 1.69808 | −2.74939 | 0.215566 | 1.92E−02 |

TABLE VI-continued

MEAN NORMALIZED INTENSITY VALUES (IN LOG
FORMAT) OF GENES FOR H9 EMBRYONIC STEM CELLS
DERIVED DEFINITIVE ENDODERM STAGE CELLS CULTURED
ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| IMAGE: 5167647, mRNA, complete cds. /PROD = Similar to hypothetical protein FLJ10058 /FL = gb: BC034293.1 | | | | |
| *Homo sapiens*, Similar to LIM homeobox protein 8, clone IMAGE: 4839343, mRNA. | −0.062884 | −4.30121 | −1.10961 | 1.16E−02 |
| *Homo sapiens* chorionic somatomammotropin hormone 2 (CSH2), transcript variant 4, mRNA. /PROD = chorionic somatomammotropin hormone 2, isoform4 /FL = gb: NM_022646.1 | 0.812166 | −2.21846 | 2.21843 | 3.60E−03 |
| *Homo sapiens* HES-related repressor protein 1 HERP1 mRNA, complete cds. /PROD = HES-related repressor protein 1 HERP1 /FL = gb: NM_012259.1 gb: AF311884.1 gb: AB044755.1 gb: AF232238.1 gb: AF237949.1 gb: AF173901.1 | 2.80599 | −1.19396 | 2.40562 | 2.44E−03 |
| *Homo sapiens* cadherin 6, type 2, K-cadherin (fetal kidney) (CDH6), mRNA. /PROD = cadherin, type 2, K-cadherin (fetal kidney) /FL = gb: D31784.1 gb: NM_004932.1 | 0.824752 | −3.83509 | −0.87634 | 2.49E−02 |
| paternally expressed 3 | 2.87398 | −4.12925 | −3.49232 | 2.19E−02 |
| *Homo sapiens* cDNA FLJ11398 fis, clone HEMBA1000637. | 2.5268 | −1.71619 | 1.84868 | 4.46E−04 |
| *Homo sapiens* BCL2-interacting killer (apoptosis-inducing) (BIK), mRNA. /PROD = BCL2-interacting killer /FL = gb: NM_001197.2 gb: BC001599.1 gb: U34584.1 gb: U49730.1 | 4.30042 | 0.023414 | 3.56237 | 1.94E−03 |
| *Homo sapiens* testis expressed sequence 14 (TEX14), mRNA. /PROD = testis expressed sequence 14 /FL = gb: NM_031272.1 | 3.51154 | −2.84891 | −1.3824 | 2.18E−02 |
| *Homo sapiens* growth hormone 2 (GH2), transcript variant 2, mRNA. /PROD = growth hormone 2, isoform 2 precursor /FL = gb: J03756.1 gb: NM_022557.1 | 0.922569 | −2.77587 | 1.4679 | 1.60E−03 |
| *Homo sapiens*, clone IMAGE: 4828836, mRNA. | 0.972907 | −4.24111 | −1.48398 | 1.63E−02 |
| *Homo sapiens* galanin receptor 1 (GALR1), mRNA. /PROD = galanin receptor 1 /FL = gb: NM_001480.2 gb: U23854.1 gb: L34339.1 gb: U53511.1 | 2.50745 | −3.13141 | −0.33802 | 3.38E−03 |
| *Homo sapiens*, serine (or cysteine) proteinase inhibitor, clade B (ovalbumin), member 3, clone MGC: 12244, mRNA, complete cds. /PROD = serine (or cysteine) proteinase inhibitor, cladeB (ovalbumin), member 3 /FL = gb: NM_006919.1 gb: U19556.1 gb: BC005224.1 | 1.96851 | −4.13943 | −1.56568 | 3.06E−02 |
| DKFZP566K1924 protein | 2.88225 | −2.59632 | 1.39062 | 0.00E+00 |
| ESTs, Moderately similar to ALU2_HUMAN ALU SUBFAMILY SB SEQUENCE CONTAMINATION WARNING ENTRY (*H. sapiens*) | 4.24074 | −0.69782 | 3.87444 | 1.12E−04 |
| Human mRNA upregulated during camptothecin-induced apoptosis of U937 cells. | 0.494505 | −4.62912 | −0.18915 | 4.38E−02 |
| nuclear receptor subfamily 1, group I, member 3 | 1.77902 | −4.02806 | −0.19682 | 4.34E−02 |
| ESTs | −1.3795 | −6.08172 | −0.94606 | 6.91E−04 |
| *Homo sapiens* chorionic somatomammotropin hormone 2 | 1.12437 | −3.12138 | 2.61605 | 1.12E−04 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| (CSH2), transcript variant 1, mRNA. /PROD = chorionic somatomammotropin hormone 2, isoform 1precursor /FL = gb: NM_020991.2 gb: BC002717.1 | | | | |
| Homo sapiens mRNA for SCCA2b, complete cds. /PROD = SCCA2b /FL = gb: AB046400.1 | 3.32911 | −3.16288 | 0.568045 | 1.93E−02 |
| Homo sapiens KIAA0469 gene product (KIAA0469), mRNA. /PROD = KIAA0469 gene product /FL = gb: AB007938.1 gb: NM_014851.1 | 4.03097 | −1.94826 | 2.56518 | 2.49E−04 |
| ESTs | 4.45389 | −2.40636 | 5.33359 | 5.65E−04 |

TABLE VII

THE EFFECT OF WNT-3A TREATMENT ON CYTOKINE EXPRESSION IN POPULATIONS OF CELLS FROM THE HUMAN EMBRYONIC STEM CELL LINE H9.

| | Cell lysate | | | | Cell conditioned media | | | |
|---|---|---|---|---|---|---|---|---|
| | w/o wnt 1 | w/o wnt 2 | w/wnt 1 | w/wnt 2 | w/o wnt 1 | w/o wnt 2 | w/wnt 1 | w/wnt 2 |
| POS | 62,842.33 | 67,606.06 | 49,758.34 | 50,702.57 | 96,585.15 | 109,721.82 | 199,709.04 | 195,889.94 |
| NEG | 23.38 | 34.49 | 370.82 | 400.66 | 58.06 | 34.45 | 216.90 | 105.20 |
| Angiogenin | 38.50 | 132.91 | 619.40 | 750.85 | 13,726.35 | 11,749.55 | 57,442.48 | 54,969.04 |
| BDNF | 167.50 | 167.82 | 763.51 | 951.45 | 689.22 | 563.39 | 770.08 | 715.86 |
| BLC | 2.00 | 48.99 | 742.24 | 476.36 | 107.69 | 512.77 | 337.12 | 249.80 |
| BMP-4 | 247.00 | 273.70 | 348.44 | 304.48 | 583.40 | 541.83 | 1,158.54 | 771.19 |
| BMP-6 | 8.50 | 141.92 | 571.23 | 641.05 | 354.91 | 355.28 | 985.70 | 670.60 |
| CK beta 8-1 | 1.00 | 1.13 | 22.48 | 21.54 | 17.79 | 25.31 | 42.78 | 75.44 |
| CNTF | 1.00 | 55.19 | 1,382.51 | 1,060.82 | 282.81 | 211.86 | 787.19 | 541.51 |
| EGF | 32.50 | 82.22 | 742.24 | 984.39 | 1,681.85 | 1,406.12 | 23,331.57 | 22,768.53 |
| Eotaxin | 1.00 | 7.32 | 301.87 | 253.80 | 207.89 | 199.67 | 622.91 | 291.71 |
| Eotaxin-2 | 262.00 | 336.77 | 1,155.31 | 960.31 | 890.56 | 744.31 | 2,156.21 | 1,445.14 |
| Eotaxin-3 | 184.50 | 284.96 | 934.12 | 847.56 | 975.77 | 665.56 | 2,140.81 | 1,480.35 |
| FGF-6 | 629.00 | 379.57 | 1,327.92 | 964.54 | 1,239.85 | 947.73 | 3,283.94 | 2,519.78 |
| FGF-7 | 31.00 | 222.45 | 1,075.02 | 941.73 | 449.49 | 352.47 | 1,086.66 | 861.72 |
| Flt-3 Ligand | 44.00 | 180.21 | 857.45 | 795.19 | 315.58 | 277.47 | 511.67 | 792.98 |
| Fractalkine | 23.50 | 62.51 | 792.02 | 456.51 | 120.80 | 145.30 | 359.37 | 367.15 |
| GCP-2 | 1.00 | 45.05 | 593.71 | 538.86 | 203.21 | 166.86 | 451.78 | 362.12 |
| GDNF | 84.00 | 292.84 | 436.75 | 444.68 | 176.99 | 194.98 | 443.22 | 509.66 |
| GM-CSF | 433.00 | 636.37 | 1,343.17 | 1,161.75 | 777.25 | 722.75 | 1,808.82 | 1,446.82 |
| I-309 | 152.50 | 246.10 | 708.52 | 743.25 | 1,828.87 | 179.05 | 318.30 | 288.36 |
| IFN-gamma | 349.00 | 441.52 | 1,202.67 | 1,037.60 | 283.74 | 559.64 | 1,238.97 | 1,435.08 |
| IGFBP-1 | 1.50 | 3.38 | 59.41 | 85.73 | 33.71 | 24.37 | 227.60 | 155.91 |
| IGFBP-2 | 3,785.50 | 5,554.45 | 2,671.90 | 2,414.72 | 27,656.85 | 28,473.95 | 42,215.53 | 43,934.33 |
| IGFBP-4 | 5,553.00 | 6,043.27 | 4,459.85 | 4,173.19 | 10,091.09 | 6,029.45 | 18,988.34 | 13,380.14 |
| IGF-I | 1.00 | 2.25 | 558.38 | 208.19 | 88.96 | 148.11 | 254.98 | 187.77 |
| IL-10 | 158.00 | 422.93 | 1,222.75 | 1,096.30 | 722.93 | 564.32 | 1,625.71 | 1,129.96 |
| IL-13 | 428.50 | 555.84 | 1,486.89 | 1,407.96 | 1,114.36 | 786.49 | 2,522.42 | 1,807.27 |
| IL-15 | 599.50 | 808.13 | 1,677.16 | 1,601.79 | 1,140.59 | 858.67 | 2,495.04 | 1,981.62 |
| IL-16 | 2.00 | 137.97 | 651.11 | 668.50 | 259.39 | 214.67 | 436.38 | 405.71 |
| IL-1alpha | 1,236.00 | 1,216.99 | 1,612.93 | 1,421.89 | 10,155.70 | 5,842.90 | 3,999.26 | 3,545.79 |
| IL-1beta | 1.00 | 1.13 | 352.05 | 312.08 | 117.99 | 75.93 | 316.59 | 278.30 |
| IL-1ra | 33.00 | 25.91 | 302.68 | 198.48 | 142.34 | 93.74 | 354.23 | 581.75 |
| IL-2 | 210.50 | 681.99 | 966.23 | 1,133.88 | 188.22 | 363.72 | 758.10 | 881.84 |
| IL-3 | 3,146.50 | 1,976.13 | 2,119.94 | 1,497.48 | 4,598.86 | 5,260.77 | 11,345.78 | 12,174.73 |
| IL-4 | 17.50 | 74.34 | 625.42 | 638.94 | 357.72 | 239.04 | 804.30 | 673.95 |
| IL-5 | 400.50 | 555.84 | 1,245.23 | 1,167.24 | 1,056.31 | 791.18 | 2,120.27 | 1,713.38 |
| IL-6 | 828.50 | 516.98 | 1,121.19 | 842.07 | 7,377.28 | 9,527.88 | 9,774.82 | 9,991.93 |
| IL-7 | 190.00 | 313.12 | 1,212.31 | 531.68 | 456.98 | 430.27 | 681.09 | 1,017.63 |
| Leptin | 900.50 | 617.79 | 1,234.39 | 1,091.65 | 2,999.42 | 2,016.38 | 7,238.71 | 4,886.99 |
| LIGHT | 10.50 | 232.02 | 1,081.04 | 888.10 | 619.92 | 453.71 | 1,346.78 | 1,108.17 |
| MCP-1 | 242.50 | 282.71 | 1,022.03 | 1,076.03 | 572.17 | 500.58 | 2,015.89 | 1,567.53 |
| MCP-2 | 24.00 | 109.25 | 909.63 | 1,152.46 | 129.23 | 351.53 | 694.78 | 694.07 |

TABLE VII-continued

THE EFFECT OF WNT-3A TREAMENT ON CYTOKINE EXPRESSION IN POPULATIONS
OF CELLS FROM THE HUMAN EMBRYONIC STEM CELL LINE H9.

| | Cell lysate | | | | Cell conditioned media | | | |
|---|---|---|---|---|---|---|---|---|
| | w/o wnt 1 | w/o wnt 2 | w/wnt 1 | w/wnt 2 | w/o wnt 1 | w/o wnt 2 | w/wnt 1 | w/wnt 2 |
| MCP-3 | 1.00 | 168.38 | 1,184.61 | 1,255.50 | 401.73 | 169.67 | 701.62 | 583.42 |
| MCP-4 | 7.50 | 46.74 | 1,380.51 | 1,606.86 | 123.61 | 61.87 | 231.02 | 276.62 |
| M-CSF | 1.00 | 63.64 | 852.63 | 867.83 | 529.09 | 269.04 | 740.98 | 684.01 |
| MDC | 1.00 | 2.25 | 269.36 | 280.41 | 157.32 | 52.50 | 280.65 | 132.44 |
| MIG | 291.00 | 226.39 | 1,113.16 | 1,137.26 | 272.50 | 486.52 | 617.77 | 1,222.17 |
| MIP-1-delta | 1.50 | 1.13 | 491.75 | 322.22 | 144.21 | 66.56 | 474.02 | 291.71 |
| MIP-3-alpha | 1.00 | 5.63 | 1,602.09 | 1,399.93 | 55.25 | 0.00 | 208.78 | 184.41 |
| NAP-2 | 1.00 | 6.19 | 465.66 | 177.37 | 97.39 | 110.61 | 371.35 | 343.68 |
| NT-3 | 1.00 | 1.13 | 316.73 | 275.76 | 97.39 | 171.55 | 571.57 | 427.51 |
| PARC | 1.00 | 2.25 | 352.85 | 353.04 | 170.43 | 81.56 | 474.02 | 363.80 |
| PDGF-BB | 437.00 | 1,644.99 | 517.84 | 597.56 | 4,729.96 | 8,521.09 | 2,635.37 | 2,005.09 |
| RANTES | 1.00 | 89.54 | 724.98 | 637.25 | 393.31 | 347.78 | 682.80 | 855.01 |
| SCF | 74.50 | 148.67 | 1,152.50 | 1,021.13 | 691.09 | 487.46 | 1,394.69 | 2,155.98 |
| SDF-1 | 23.50 | 51.25 | 940.14 | 1,294.78 | 382.07 | 123.74 | 326.85 | 616.95 |
| TARC | 1.50 | 5.07 | 372.93 | 343.33 | 206.95 | 71.24 | 277.23 | 1,642.97 |
| TGF-beta 1 | 362.00 | 230.33 | 1,426.67 | 1,240.30 | 752.90 | 740.56 | 1,827.65 | 1,849.18 |
| TGF-beta 3 | 3.00 | 25.91 | 377.74 | 1,130.93 | 111.44 | 115.30 | 294.34 | 343.68 |
| TNF-alpha | 431.00 | 579.49 | 2,851.74 | 1,285.91 | 1,205.20 | 929.91 | 2,609.70 | 2,167.71 |
| TNF-beta | 241.00 | 342.40 | 1,049.33 | 1,026.62 | 675.17 | 671.19 | 1,701.01 | 1,637.94 |
| Internal Control | 18,642.67 | 18,642.67 | 18,642.67 | 18,642.67 | 18,642.67 | 18,642.67 | 18,642.67 | 18,642.67 |
| POS | 60,794.83 | 48,106.85 | 35,652.42 | 47,391.58 | 94,013.71 | 90,889.16 | 141,321.30 | 149,125.43 |
| NEG | 11.13 | 5.53 | 11.22 | 30.45 | 24.93 | 17.75 | 36.22 | 33.27 |
| Acrp30 | 1,036.00 | 744.50 | 601.61 | 690.66 | 1,797.52 | 1,319.88 | 2,795.71 | 2,302.99 |
| AgRP | 11.00 | 153.99 | 77.82 | 89.00 | 378.17 | 195.90 | 651.26 | 482.21 |
| Angiopoietin-2 | 28.50 | 10.43 | 357.97 | 771.04 | 655.82 | 632.60 | 65,959.24 | 71,664.21 |
| Amphiregulin | 17.50 | 15.44 | 73.63 | 154.62 | 250.52 | 151.01 | 619.07 | 782.60 |
| Axl | 637.50 | 795.83 | 88.59 | 139.03 | 401.31 | 324.05 | 610.40 | 748.34 |
| bFGF | 59,820.50 | 54,057.29 | 11,722.95 | 21,398.52 | 7,948.03 | 4,993.83 | 1,226.99 | 1,241.09 |

The invention claimed is:

1. A method for producing pancreatic endoderm cells expressing NKX2.2 and PDX1, comprising:
   (i) obtaining definitive endoderm cells;
   (ii) culturing the definitive endoderm cells in a first culture medium comprising a transforming growth factor (TGF)-β receptor agonist, retinoic acid or a retinoic acid analog, and fibroblast growth factor (FGF)-2;
   (iii) removing the first culture medium; and
   (iv) culturing the cells from step (ii) in a second culture medium comprising retinoic acid or a retinoic acid analog,
   thereby producing pancreatic endoderm cells expressing NKX2.2 and PDX1.

2. The method of claim 1, wherein the TGF-β receptor agonist is activin A.

3. The method of claim 2, wherein the first culture medium comprises 100 ng/mL activin A.

4. The method of claim 1, wherein the first culture medium comprises 1 µM retinoic acid.

5. The method of claim 1, wherein the first culture medium comprises 50 ng/mL FGF-2.

6. The method of claim 1, wherein obtaining definitive endoderm cells comprises differentiating pluripotent stem cells into definitive endoderm cells by treating the pluripotent stem cells with a TGF-β receptor agonist.

7. The method of claim 6, wherein the TGF-β receptor agonist is activin A.

8. A composition comprising an isolated human pancreatic endoderm cell population expressing NKX2.2 and PDX1, activin A at a concentration of about 50 ng/ml to about 100 ng/ml, retinoic acid at a concentration of about 1 nM to about 1 µM, and fibroblast growth factor (FGF)-2 at a concentration of about 50 pg/ml to about 50 ng/ml.

9. The composition of claim 8, comprising 100 ng/mL activin A.

10. The composition of claim 8, comprising 1 µM retinoic acid.

11. The composition of claim 8, comprising 50 ng/mL FGF-2.

12. The composition of claim 8, comprising 50 ng/mL activin A.

13. The method of claim 2, wherein the first culture medium comprises 50 ng/ml activin A.

14. The method of claim 1, wherein the second culture medium further comprises FGF-2.

15. The method of claim 14, wherein the second culture medium comprises 50 ng/mL FGF-2.

16. The method of claim 1, wherein the second culture medium comprises 1 µM retinoic acid.

17. The method of claim 1, wherein the definitive endoderm cells are cultured in the first culture medium for 3 to 5 days.

18. The method of claim 1, wherein the cells are cultured in the second culture medium for 3 to 5 days.

* * * * *